US010115925B2

(12) United States Patent
Park et al.

(10) Patent No.: US 10,115,925 B2
(45) Date of Patent: Oct. 30, 2018

(54) ORGANIC OPTOELECTRONIC DEVICE AND DISPLAY APPARATUS

(71) Applicant: SAMSUNG SDI CO., LTD., Yongin-si, Gyeonggi-do (KR)

(72) Inventors: Jae-Han Park, Suwon-si (KR); Young-Kwon Kim, Suwon-si (KR); Jin-Hyun Lui, Suwon-si (KR); Eun-Sun Yu, Suwon-si (KR); Han-Ill Lee, Suwon-si (KR); Ho-Kuk Jung, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 0 days.

(21) Appl. No.: 15/522,437

(22) PCT Filed: Jul. 21, 2015

(86) PCT No.: PCT/KR2015/007572
§ 371 (c)(1),
(2) Date: Apr. 27, 2017

(87) PCT Pub. No.: WO2016/068451
PCT Pub. Date: May 6, 2016

(65) Prior Publication Data
US 2017/0331067 A1 Nov. 16, 2017

(30) Foreign Application Priority Data
Oct. 28, 2014 (KR) ........................ 10-2014-0147558

(51) Int. Cl.
*H01L 21/00* (2006.01)
*H01L 51/50* (2006.01)
(Continued)

(52) U.S. Cl.
CPC ........ *H01L 51/5056* (2013.01); *C07D 498/12* (2013.01); *H01L 51/5072* (2013.01); *H01L 27/14* (2013.01); *H01L 51/5004* (2013.01)

(58) Field of Classification Search
CPC ............ H01L 51/5056; H01L 51/5072; H01L 51/5004; C07D 498/12
(Continued)

(56) References Cited

U.S. PATENT DOCUMENTS 8,420,230 B2 4/2013 Yang et al.
8,945,728 B2 2/2015 Ishibashi et al.
(Continued)

FOREIGN PATENT DOCUMENTS

KR 10-2007-0030759 3/2007
KR 10-2009-0105072 A 10/2009
(Continued)

*Primary Examiner* — Anthony Ho
(74) *Attorney, Agent, or Firm* — Lee & Morse, P.C.

(57) ABSTRACT

The present invention relates to an organic optoelectronic device and a display apparatus comprising same, the organic optoelectronic device comprising: an anode and a cathode facing each other; a light-emitting layer located between the anode and cathode; a hole transport layer located between the anode and light-emitting layer; an auxiliary hole transport layer located between the hole transport layer and light-emitting layer; an electron transport layer located between the cathode and light-emitting layer; and an auxiliary electron transport layer between the electron transport layer and light-emitting layer, wherein the auxiliary electron transport layer comprises at least one type of a first compound expressed by a particular Chemical Formula, and the auxiliary hole transport layer comprises at least one type of a second compound expressed by a particular Chemical Formula.

14 Claims, 2 Drawing Sheets

(51) Int. Cl.
*C07D 498/12* (2006.01)
*H01L 27/14* (2006.01)

(58) Field of Classification Search
USPC .............................................................. 438/7
See application file for complete search history.

(56) References Cited

U.S. PATENT DOCUMENTS

| | | | |
|---|---|---|---|
| 2007/0190355 | A1 | 8/2007 | Ikeda et al. |
| 2014/0203272 | A1 | 7/2014 | Hong et al. |

FOREIGN PATENT DOCUMENTS

| | | |
|---|---|---|
| KR | 10-2010-0021908 | 2/2010 |
| KR | 10-2013-0098226 A | 9/2013 |
| KR | 10-2013-0106255 | 9/2013 |
| KR | 10-2014-0010133 | 1/2014 |

ORGANIC OPTOELECTRONIC DEVICE AND DISPLAY APPARATUS

CROSS REFERENCE TO RELATED APPLICATIONS

This is the U.S. national phase application based on PCT Application No. PCT/KR 2015/007572, filed Jul. 21, 2015, which is based on Korean Patent Application No. 10-2014-0147558filed on Oct. 28, 2014, the entire contents of all of which are hereby incorporated by reference.

BACKGROUND OF THE INVENTION (a) Field of the Invention

An organic optoelectronic device and a display apparatus are disclosed.

(b) Description of the Related Art

An organic optoelectronic device (organic optoelectric diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and has a structure in which an organic layer is disposed between an anode and a cathode.

A blue organic light emitting diode having a long life-span is considered to be one of the critical factors for realizing a full color display having a long life-span. Accordingly, development of a blue organic light emitting diode having a long life-span is being actively researched. In order to solve this problem, a blue organic light emitting diode having a long life-span is provided in this invention.

SUMMARY OF THE INVENTION

Technical Object

An embodiment provides an organic optoelectronic device capable of realizing high efficiency characteristics.

Another embodiment provides a display apparatus including the organic optoelectronic device.

Technical Solution

According to an embodiment, an organic optoelectronic device includes an anode and a cathode facing each other, a light-emitting layer located between the anode and cathode, a hole transport layer located between the anode and light-emitting layer, an auxiliary hole transport layer located between the hole transport layer and light-emitting layer, an electron transport layer located between the cathode and light-emitting layer and an auxiliary electron transport layer between the electron transport layer and light-emitting layer, wherein the auxiliary electron transport layer includes at least one type of a first compound expressed by Chemical Formula 1 and the auxiliary hole transport layer includes at least one type of a second compound expressed by Chemical Formula 2.

[Chemical Formula 1]

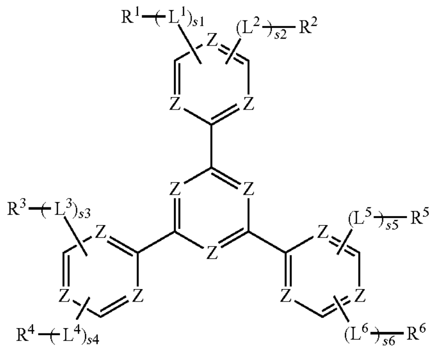

In Chemical Formula 1,

Z is independently N, C, or $CR^a$, at least one of Z is N, $R^1$ to $R^6$ and $R^a$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof, $L^1$ to $L^6$ are independently a single bond, a substituted or unsubstituted C6 to C30 arylene group, a substituted or unsubstituted heteroarylene group, or a combination thereof, and s1 to s6 are independently an integer ranging from 0 to 5,

[Chemical Formula 2]

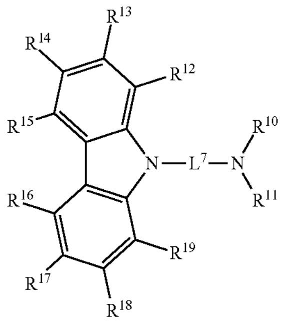

wherein, in Chemical Formula 2, $R^{10}$ to $R^{19}$ are independently hydrogen, deuterium, a substituted or unsubstituted C6 to C30 aryl group, a substituted or unsubstituted C2 to C30 heteroarylene group, or a combination thereof, and $L^7$ is a substituted or unsubstituted C2 to C10 alkenylene group, a substituted or unsubstituted C6 to C30 arylene group, a substituted or unsubstituted C2 to C30 heteroarylene group, or a combination thereof.

The “substituted” refers to replacement of at least one hydrogen by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, a fluorenyl group, or a cyano group.

According to another embodiment, a display apparatus including the organic optoelectronic device is provided.

Advantageous Effect

An organic optoelectronic device having high efficiency may be realized.

DETAILED DESCRIPTION

Figure 1:
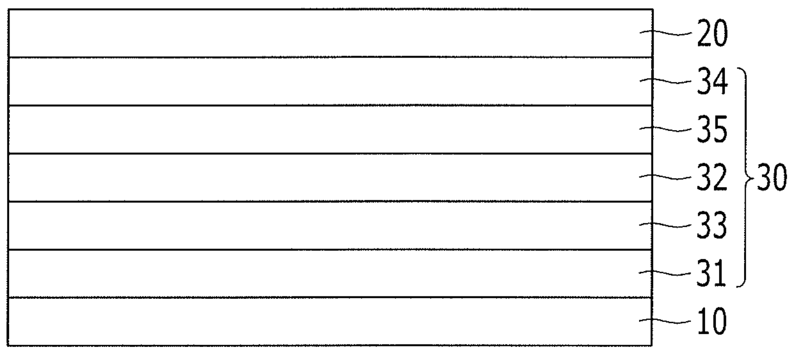
FIGS. 1 and 2 are schematic cross-sectional views showing organic optoelectronic devices according to embodiments.

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group such as a trifluoromethyl group, or a cyano group.

In addition, two adjacent substituents of the substituted halogen, hydroxy group, amino group, substituted or unsubstituted C1 to C20 amine group, a nitro group, substituted or unsubstituted C3 to C40 silyl group, C1 to C30 alkyl group, C1 to C10 alkylsilyl group, C3 to C30 cycloalkyl group, C2 to C30 heterocycloalkyl group, C6 to C30 aryl group, C2 to C30 heteroaryl group, C1 to C20 alkoxy group, fluoro group, C1 to C10 trifluoroalkyl group such as trifluoromethyl group, or cyano group may be fused with each other to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including one to three heteroatoms selected from the group consisting of N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a substituent including all element of the cycle having p-orbitals which form conjugation, and may be monocyclic, polycyclic or fused ring polycyclic (i.e., rings sharing adjacent pairs of carbon atoms) functional group.

In the present specification, "heteroaryl group" may refer to an aryl group including 1 to 3 heteroatoms selected from N, O, S, P, and Si and remaining carbon. When the heteroaryl group is a fused ring, each ring may include 1 to 3 heteroatoms.

More specifically, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazolyl group, or a combination thereof, but are not limited thereto.

In the specification, hole characteristics refer to an ability to donate an electron to form a hole when an electric field is applied and that a hole formed in the anode may be easily injected into a light-emitting layer and transported in the light-emitting layer due to conductive characteristics according to a highest occupied molecular orbital (HOMO) level.

In addition, electron characteristics refer to an ability to accept an electron when an electric field is applied and that electron formed in the cathode may be easily injected into the light-emitting layer and transported in the light-emitting layer due to conductive characteristics according to a lowest unoccupied molecular orbital (LUMO) level.

Hereinafter, an organic optoelectronic device according to an embodiment is described.

The organic optoelectronic device may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectronic device is described, but the present invention can be applied to other organic optoelectronic devices in the same way.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Figure 2:
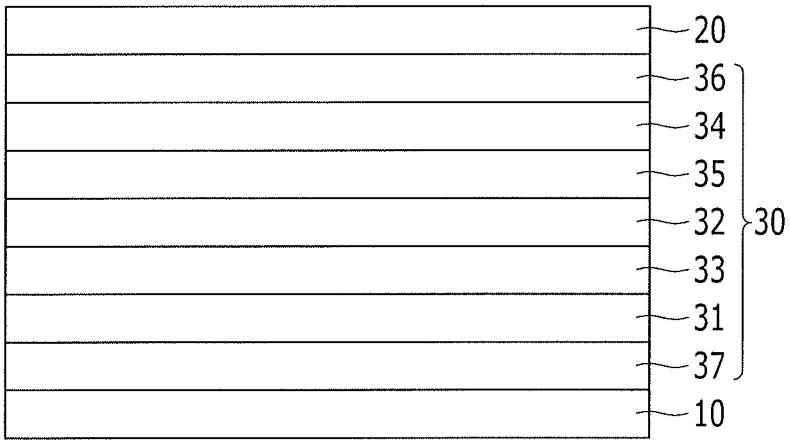

FIGS. 1 and 2 are schematic cross-sectional views showing organic optoelectronic devices according to embodiments.

Referring to FIG. 1, an organic optoelectronic device according to an embodiment includes an anode 10 and a cathode 20 facing each other and an organic layer 30 between the anode 10 and the cathode 20.

The anode 10 may be made of a conductor having a large work function to help hole injection, and may be for example metal, metal oxide and/or a conductive polymer. The anode 10 may be, for example a metal such as nickel, platinum, vanadium, chromium, copper, zinc, and gold or an alloy thereof; metal oxide such as zinc oxide, indium oxide, indium tin oxide (ITO), indium zinc oxide (IZO), and the like; a combination of metal and an oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 20 may be made of a conductor having a small work function to help electron injection, and may be for example a metal, a metal oxide and/or a conductive polymer. The cathode 20 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 30 includes a hole transport layer 31, a light-emitting layer 32, and an auxiliary hole transport layer 33 between the hole transport layer 31 and the light-emitting layer 32.

In addition, the organic layer 30 includes an electron transport layer 34 and an auxiliary electron transport layer 35 between the electron transport layer 34 and the light-emitting layer 32.

In addition, the organic layer 30 may further include a hole injection layer 37 between the hole transport layer 31 and the anode 10 and an electron injection layer 36 between the electron transport layer 34 and the cathode 20.

The hole injection layer 37 between the hole transport layer 31 and the anode 10 may improve interface characteristics between ITO used as the anode and an organic material used as the hole transport layer 31 and may smooth a surface of the ITO by being coated on the ITO having coating the surface of uneven ITO. For example, the hole injection layer 37 may select a material having a median value of a work function level of the ITO and a HOMO level of the hole transport layer 31, particularly a material having an appropriate conductivity in order to adjust a difference the work function level of the ITO as an anode and the HOMO level of the hole transport layer 31. In connection with the present invention, the material of the hole injection layer 37 may be N4,N4'-diphenyl-N4,N4'-bis(9-phenyl-9H-carbazol-3-yl)biphenyl-4,4'-diamine, but is not limited thereto. In addition, a conventional material constituting the hole injection layer 37 may be also used together, and may be for example, aromatic amines such as copper phthlalocyanine (CuPc), N,N'-dinaphthyl-N,N'-phenyl-(1,1'-biphenyl)-4,4'-diamine (NPD), 4,4',4"-tris[methylphenyl(phenyl)amino] triphenyl amine (m-MTDATA), 4,4',4"-tris[1-naphthyl(phenyl)amino]triphenyl amine (1-TNATA), 4,4',4"-tris[2-naphthyl(phenyl)amino]triphenyl amine (2-TNATA), 1,3,5-tris[N-(4-diphenylaminophenyl)phenylamino]benzene(p-DPA-TDAB), and the like, a compound such as 4,4'-bis[N-[4-{N,N-bis(3-methylphenyl)amino}phenyl]-N-phenylamino]biphenyl (DNTPD), hexaazatriphenylene-hexacarbonitrile (HAT-CN) and the like, poly(3,4-ethylenedioxythiophene)-poly(styrnesulfonate) (PEDOT) that is a polythiophene derivative as conductive polymer. The hole injection layer 37 may be coated in a thickness, for example 10 to 300 Å on the ITO used as an anode.

The electron injection layer 36 is staked on the electron transport layer, makes electron injection from a cathode and as a result improves power efficiency, and may include generally used materials without particular limit, for example, a material such as LiF, Liq, NaCl, CsF, $Li_2O$, BaO, and the like.

The hole transport layer 31 is a layer that makes hole transport from the anode 10 into the light-emitting layer 32, and may include, for example an amine compound but is not limited thereto.

The amine compound may include, for example at least one aryl group and/or heteroaryl group. The amine compound may be expressed by, for example Chemical Formula a or b, but is not limited thereto.

[Chemical Formula a]

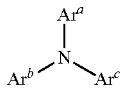

[Chemical Formula b]

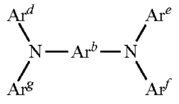

In Chemical Formula a or Chemical Formula b, $Ar^a$ to $Ar^g$ are independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof, at least one of $Ar^a$ to $Ar^c$ and at least one of $Ar^d$ to $Ar^g$ are a substituted or unsubstituted C6 to C30 aryl group, a substituted or unsubstituted C2 to C30 heteroaryl group, or a combination thereof, and $Ar^h$ is a single bond, a substituted or unsubstituted C1 to C20 alkylene group, a substituted or unsubstituted C6 to C30 arylene group, a substituted or unsubstituted C2 to C30 heteroarylene group, or a combination thereof.

The electron transport layer 34 is a layer that makes electron transport from the cathode 20 into the light-emitting layer 32, and may include an organic compound having an electron accepting functional group (an electron withdrawing group), a metal compound capable of accepting electrons well, or a mixture thereof. For example, as an electron transport layer material, it may include aluminum trihydroxyquinoline ($Alq_3$), 2-(4-biphenylyl)-5-phenyl-1,3,4-oxadiazole (PBD) that is a 1,3,4-oxadiazole derivative, 1,3,4-tris[(3-penyl-6-trifluoromethyl)quinoxaline-2-yl] benzene (TPQ) that is a quinoxaline derivative, a triazole derivative, and 8-(4-(4-(naphthalen-2-yl)-6-(naphthalen-3-yl)-1,3,5-triazin-2-yl)phenyl)quinoline) that is a triazine derivative, and the like, but is not limited thereto.

In addition, the electron transport layer may use an organometallic compound expressed by Chemical Formula c alone or as a mixture with the electron transport layer material.

$Y_m$-M-$(OA)_n$ [Chemical Formula c]

In Chemical Formula c,

Y includes a moiety consisting a single bond by a direct bond between one of C, N, O, and S and M and a moiety consisting a coordination bond between one of C, N, O, and S, and M and is a ligand chelated by the single bond and the coordination bond, M is an alkali metal, an alkali earth metal, aluminum (Al), or a boron (B) atom, OA is a monovalent ligand capable of single-bonding or coordination-bonding with M, O is oxygen, A is one of a substituted or unsubstituted C1 to C30 alkyl group, a substituted or unsubstituted C5 to C50 aryl group, a substituted or unsubstituted C2 to C30 alkenyl group, a substituted or unsubstituted C2 to C20 alkynyl group, a substituted or unsubstituted C3 to C30 cycloalkyl group, a substituted or unsubstituted C5 to C30 cycloalkenyl group and a substituted or unsubstituted C2 to C50 heteroaryl group having O, N, or S as a heteroatom, when M is one metal selected from the alkali metal, m=1 and n=0, when M is one metal selected from the alkali earth metal, m=1 and n=1 or m=2 and n=0, when M is boron or aluminum, m is an integer ranging from 1 to 3 and n is an integer of 0 to 2, and m+n=3, and 'substituted' in the 'substituted or unsubstituted' refers to substitution with one or more a substituent selected from deuterium, a cyano group, a halogen, a hydroxy group, a nitro group, an alkyl group, an alkoxy group, an alkylamino group, an arylamino group, a heteroarylamino group, an alkylsilyl group, an arylsilyl group, an aryloxy group, an aryl group, a heteroaryl group, germanium, phosphorus, and boron.

In the present invention, Y is the same or different and is independently selected from Chemical Formula c1 to Chemical Formula c39, but is not limited thereto.

[Chemical Formula c1]

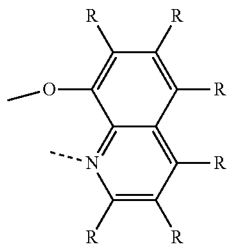

-continued

[Chemical Formula c2]

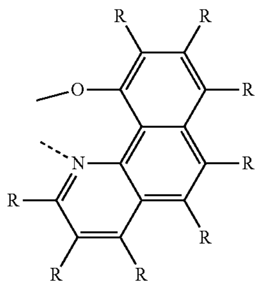

[Chemical Formula c3]

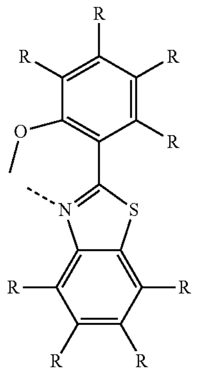

[Chemical Formula c4]

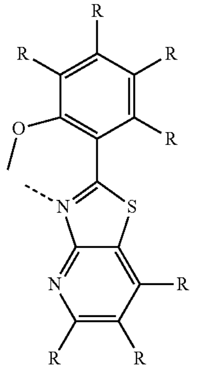

[Chemical Formula c5]

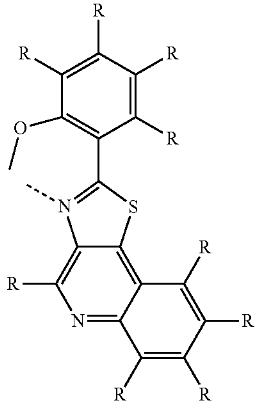

-continued
[Chemical Formula c6]
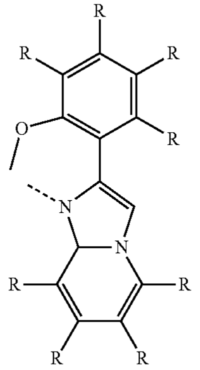
[Chemical Formula c7]
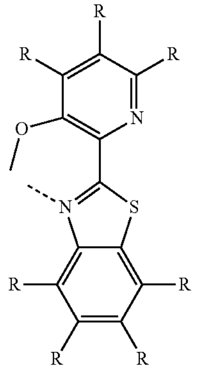
[Chemical Formula c8]
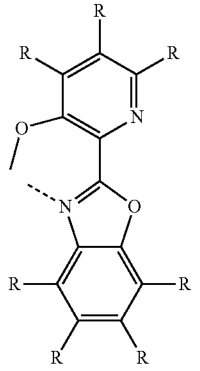
[Chemical Formula c9]
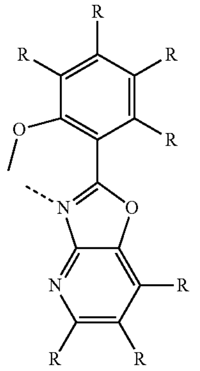
-continued
[Chemical Formula c10]
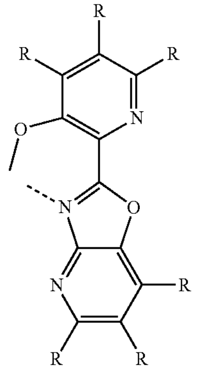
[Chemical Formula c11]
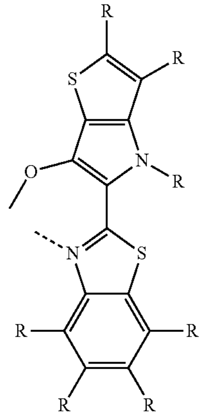
[Chemical Formula c12]
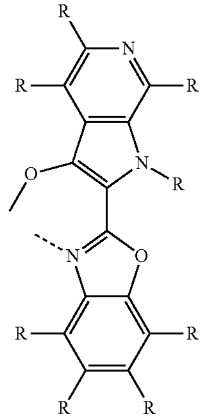
[Chemical Formula c13]
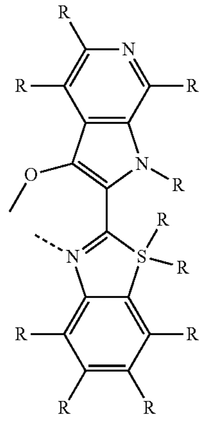

-continued
[Chemical Formula c14]
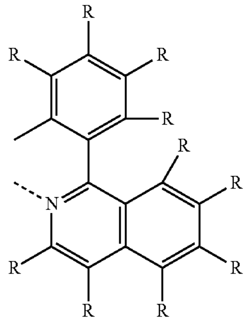
[Chemical Formula c15]
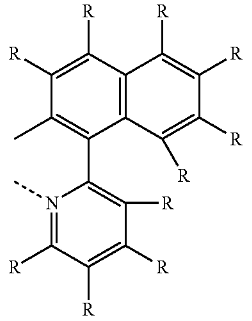
[Chemical Formula c16]
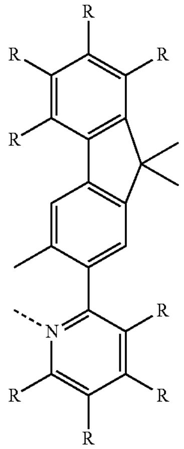
[Chemical Formula c17]
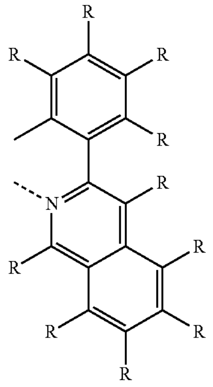
-continued
[Chemical Formula c18]
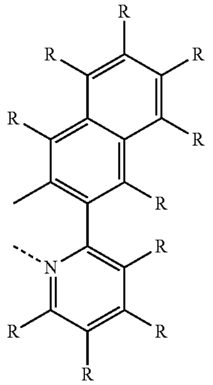
[Chemical Formula c19]
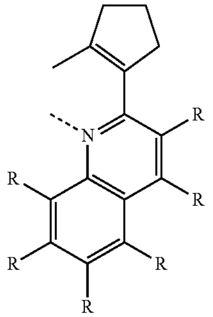
[Chemical Formula c20]
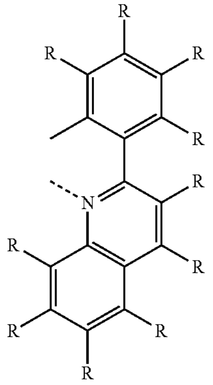
[Chemical Formula c21]
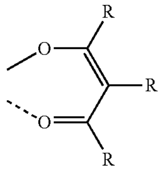
[Chemical Formula c22]
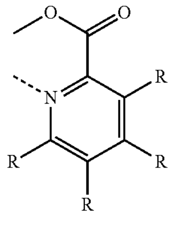

-continued
[Chemical Formula c23]
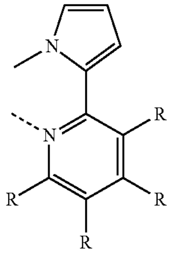
[Chemical Formula c24]
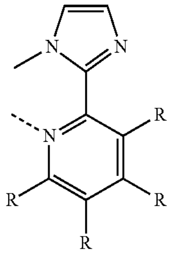
[Chemical Formula c25]
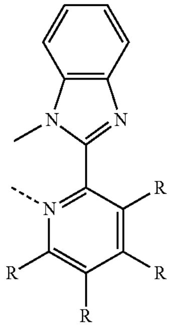
[Chemical Formula c26]
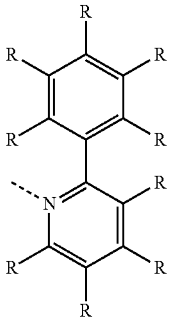
[Chemical Formula c27]
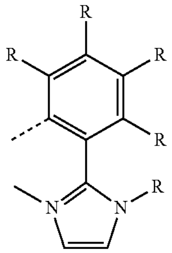
-continued
[Chemical Formula c28]
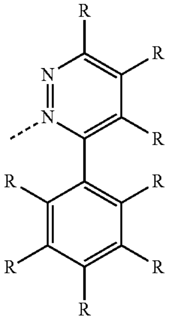
[Chemical Formula c29]
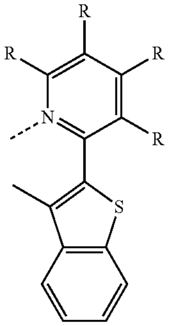
[Chemical Formula c30]
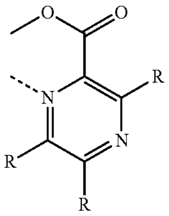
[Chemical Formula c31]
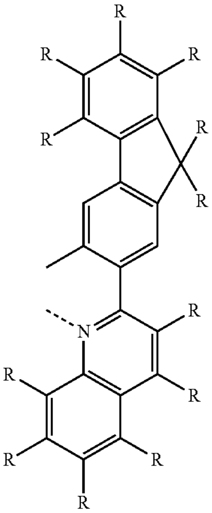

-continued

[Chemical Formula c32]

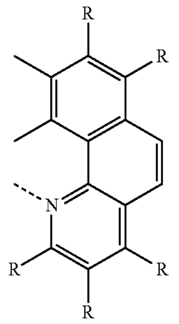

[Chemical Formula c33]

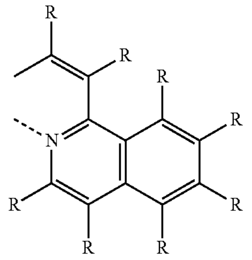

[Chemical Formula c34]

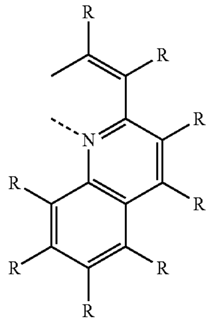

[Chemical Formula c35]

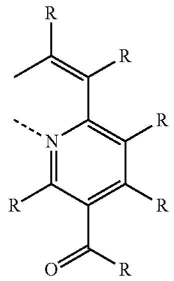

[Chemical Formula c36]

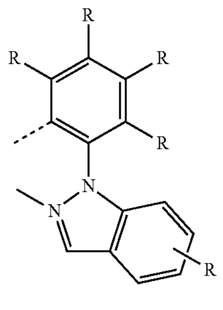

-continued

[Chemical Formula c37]

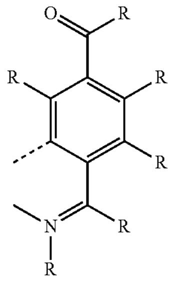

[Chemical Formula c38]

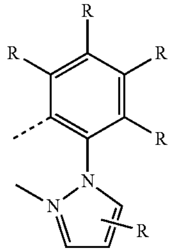

[Chemical Formula c39]

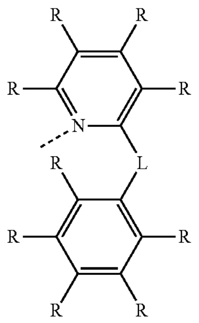

In Chemical Formula c1 to Chemical Formula c39,

R is the same or different and is independently selected from hydrogen, deuterium, a halogen, a cyano group, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C30 alkoxy group, a substituted or unsubstituted C3 to C30 cycloalkyl group, a substituted or unsubstituted C2 to C30 alkenyl group, a substituted or unsubstituted C1 to C30 alkylamino group, a substituted or unsubstituted C1 to C30 alkylsilyl group, a substituted or unsubstituted C6 to C30 arylamino group, and a substituted or unsubstituted C6 to C30 arylsilyl group, or is linked to an adjacent substitutent with alkylene or alkenylene to from a spiroring or a fused ring.

The light-emitting layer 32 is an organic layer emitting light and includes a host and a dopant when a doping system is adopted. Herein, the host mainly promotes a recombination of electrons and holes and holds excitons in an light-emitting layer, while the dopant efficiently emits light from the excitons obtained from the recombination.

The light-emitting layer may include a known host and dopant.

The known host may be, for example, Alq3, CBP (4,4'-N,N'-dicarbazole-biphenyl), PVK (poly(n-vinylcarbazole)), 9,10-di(naphthalen-2-yl)anthracene (ADN), TCTA, TPBI (1,3,5-tris(N-phenylbenzimidazol-2-yl)benzene), TBADN (3-tert-butyl-9,10-di(naph-2-yl) anthracene), mCP, OXD-7, and the like, but is not limited thereto.

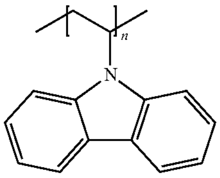

PVK

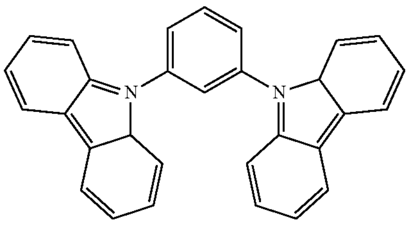

mCP

-continued

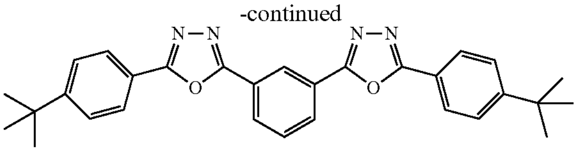

OXD-7

The dopant may be at least one of a fluorescent dopant and a phosphorescent dopant. The phosphorescent dopant may be an organometal complex including Ir, Pt, Os, Re, Ti, Zr, Hf, or a combination of two or more, but is not limited thereto.

Examples of known blue dopants may be $F_2$Irpic, $(F_2ppy)_2$Ir(tmd), Ir$(dfppz)_3$, ter-fluorene(fluorene), 4,4'-bis(4-diphenylaminostyryl)biphenyl (DPAVBi), 2,5,8,11-tetra-tert-butyl perylene (TBPe), DPVBi, a pyrene derivative (KR0525408, LG Electronics Inc.), and the like, but are not limited thereto.

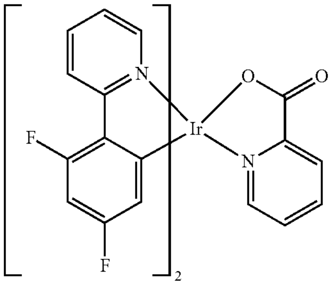

$F_2$Irpic

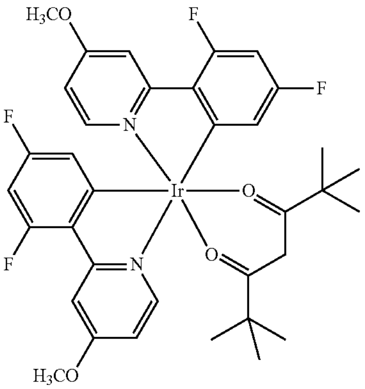

$(F_2ppy)_2$Ir(tmd)

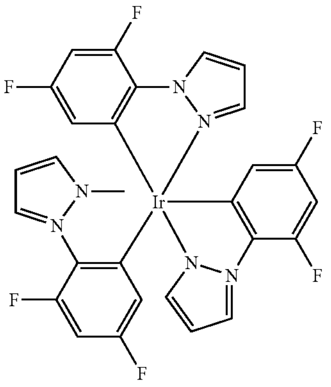

Ir$(dfppz)_3$

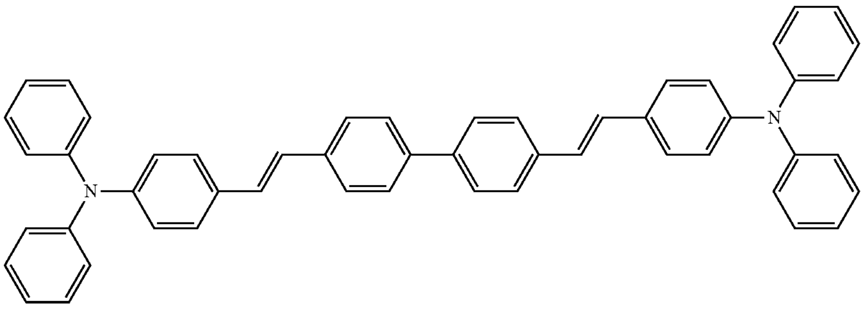

DPAVBi

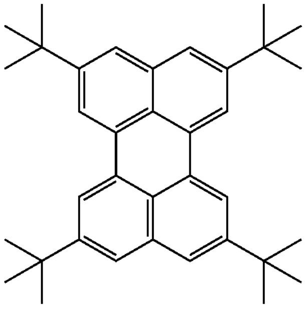

TBPe

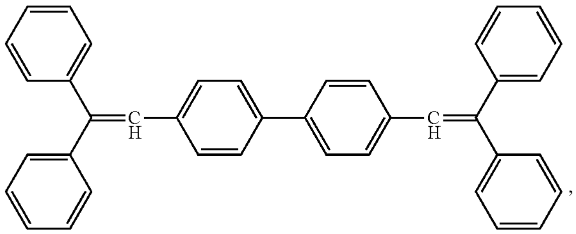

DPVBi

-continued

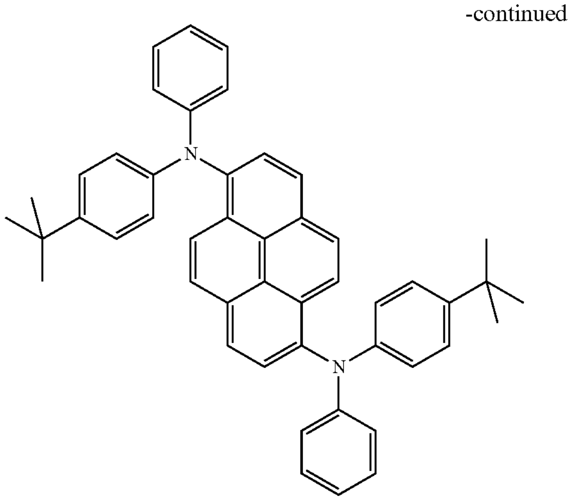

Examples of known red dopants may include, PtOEP, $Ir(piq)_3$, BtpIr, and the like, but are not limited thereto.

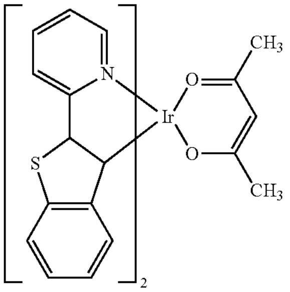

BtpIr

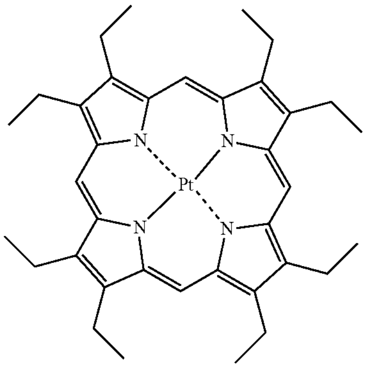

PtOEP

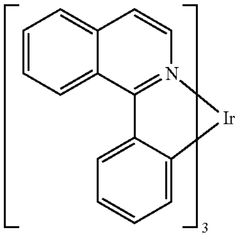

$Ir(piq)_3$

Examples of known green dopant may be $Ir(ppy)_3$ (ppy=phenylpyridine), $Ir(ppy)_2(acac)$, $Ir(mpyp)_3$, and the like, but are not limited thereto.

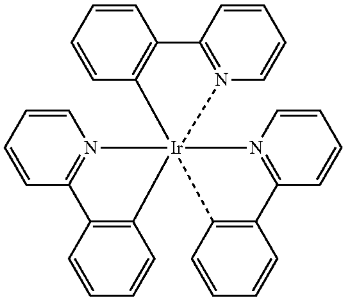

$Ir(ppy)_3$

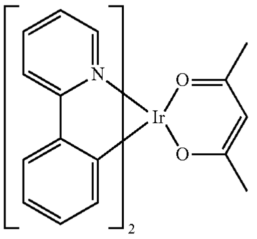

$Ir(ppy)_2(acac)$

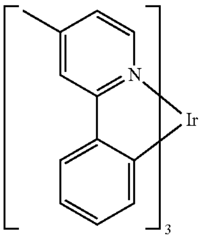

$Ir(mpyp)_3$

When the light-emitting layer includes hosts and dopants, an amount of the dopants may be generally about 0.01 to about 15 wt % based on 100 wt % of the light-emitting layer, without limitation.

The light-emitting layer may have a thickness of about 200 Å to about 700 Å.

The auxiliary electron transport layer 35 includes a first compound having relatively strong electron characteristics and a second compound having relatively strong hole characteristics.

The first compound is a compound having relatively strong electron characteristics and may be expressed by Chemical Formula 1.

[Chemical Formula 1]

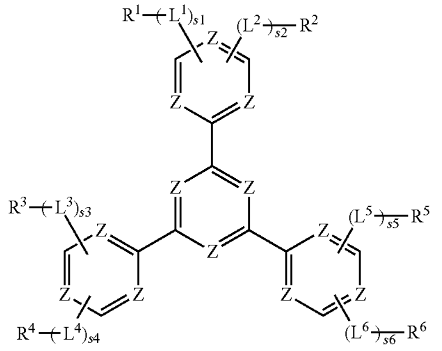

In Chemical Formula 1,

Z is independently N, C, or $CR^a$, at least one of Z is N, $R^1$ to $R^6$ and $R^a$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof, $L^1$ to $L^6$ are independently a single bond, a substituted or unsubstituted C6 to C30 arylene group, a substituted or unsubstituted heteroarylene group, or a combination thereof, and s1 to s6 are independently an integer ranging from 0 to 5, The first compound may be, for example expressed by one of Chemical Formula 1-i to Chemical Formula 1-ix according to the presence of a substituent and a bonding position.

[Chemical Formula 1-i]

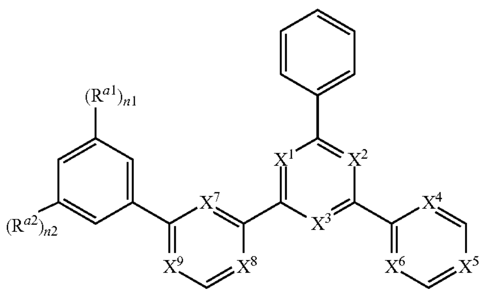

[Chemical Formula 1-ii]

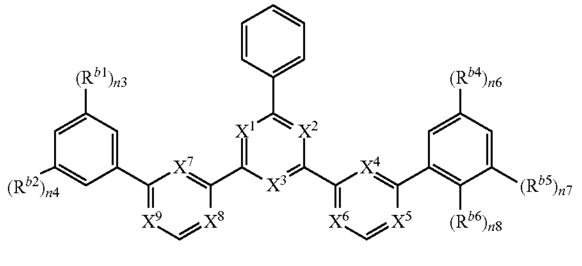

-continued

[Chemical Formula 1-iii]

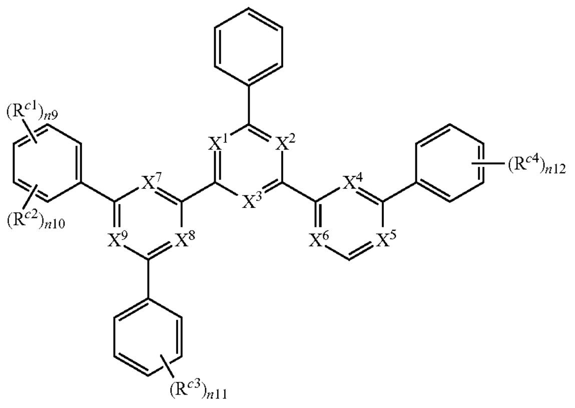

[Chemical Formula 1-iv]

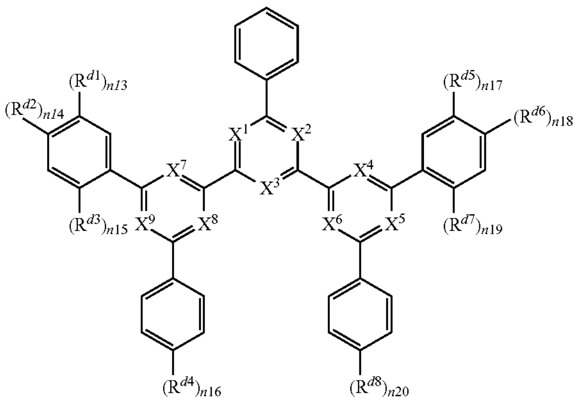

[Chemical Formula 1-v]

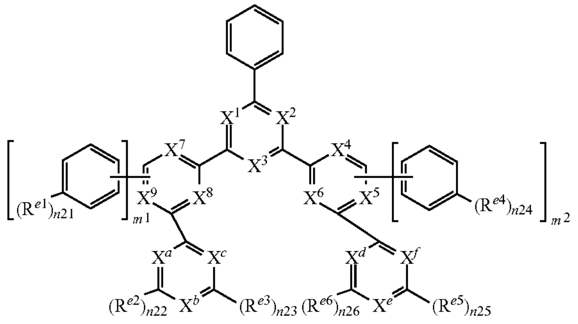

[Chemical Formula 1-vi]

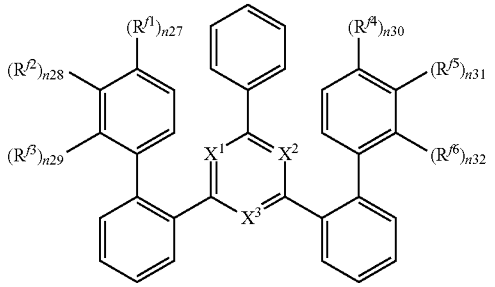

-continued

[Chemical Formula 1-vii]

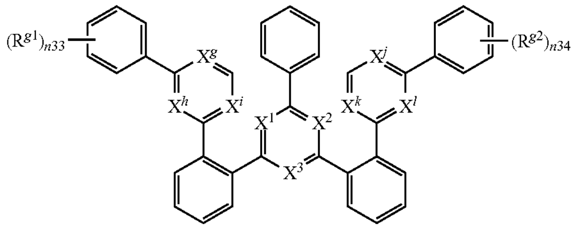

[Chemical Formula 1-viii]

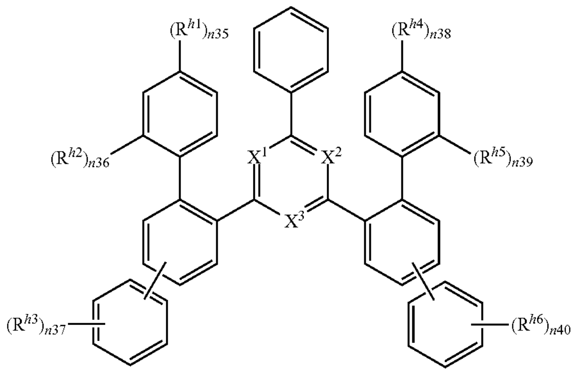

[Chemical Formula 1-ix]

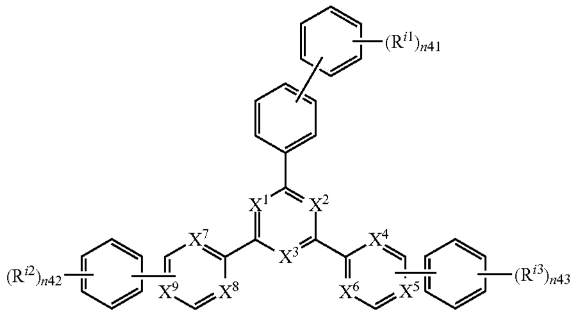

In Chemical Formula 1-i, $R^{a1}$ and $R^{a2}$ are independently a substituted or unsubstituted C1 to C10 alkyl group, a substituted or unsubstituted C6 to C30 aryl group, a substituted or unsubstituted C2 to C30 heteroaryl group, or a combination thereof, and n1 and n2 are independently an integer of 0 or 1, but n1 and n2 are not 0 simultaneously.

In Chemical Formula 1-ii, $R^{b1}$ to $R^{b6}$ are independently a substituted or unsubstituted C1 to C10 alkyl group, a substituted or unsubstituted C6 to C30 aryl group, a substituted or unsubstituted C2 to C30 heteroaryl group, or a combination thereof, and n3 to n8 are independently an integer of 0 or 1, but n3 to n5 are not 0 simultaneously and n6 to n8 are not 0 simultaneously.

In Chemical Formula 1-iii, $R^{c1}$ to $R^{c4}$ are independently a substituted or unsubstituted C1 to C10 alkyl group, a substituted or unsubstituted C6 to C30 aryl group, a substituted or unsubstituted C2 to C30 heteroaryl group, or a combination thereof, and n9 to n12 are independently an integer of 0 or 1. DeletedTexts일 수

In Chemical Formula 1-iv, $R^{d1}$ to $R^{d8}$ are independently a substituted or unsubstituted C1 to C10 alkyl group, a substituted or unsubstituted C6 to C30 aryl group or a substituted or unsubstituted C2 to C30 heteroaryl group, or a combination thereof, and n13 to n20 are independently an integer of 0 or 1.

In Chemical Formula 1-v, $X^a$ to $X^f$ are independently N or CH, at least one of $X^a$ to $X^c$ is N, at least one of $X^d$ to $X^f$ is N, $R^{e1}$ to $R^{e6}$ are independently a substituted or unsubstituted C1 to C10 alkyl group, a substituted or unsubstituted C6 to C30 aryl group or a substituted or unsubstituted C2 to C30 heteroaryl group, or a combination thereof, and n21 to n26, m1, and m2 are independently an integer of 0 or 1.

In Chemical Formula 1-vi, $R^{f1}$ to $R^{f6}$ are independently a substituted or unsubstituted C1 to C10 alkyl group, a substituted or unsubstituted C6 to C30 aryl group, a substituted or unsubstituted C2 to C30 heteroaryl group, or a combination thereof, n27 to n32 are independently an integer of 0 or 1, but n27 to n29 are not 0 simultaneously and n30 to n32 are not 0 simultaneously.

In Chemical Formula 1-vii, $X^g$ to $X^l$ are independently N or CH, at least one of $X^g$ to $X^i$ is N, at least one of $X^j$ to $X^l$ is N, $R^{g1}$ and $R^{g2}$ are independently a substituted or unsubstituted C1 to C10 alkyl group, a substituted or unsubstituted C6 to C30 aryl group, a substituted or unsubstituted C2 to C30 heteroaryl group, or a combination thereof, and n33 and n34 are independently an integer of 0 or 1.

In Chemical Formula 1-viii, $R^{h1}$ to $R^{h6}$ are independently a substituted or unsubstituted C1 to C10 alkyl group, a substituted or unsubstituted C6 to C30 aryl group, a substituted or unsubstituted C2 to C30 heteroaryl group, or a combination thereof, and n35 to n40 are independently an integer of 0 or 1.

In Chemical Formula 1-ix, $R^{i1}$ to $R^{i3}$ are independently a substituted or unsubstituted C1 to C10 alkyl group, a substituted or unsubstituted C6 to C30 aryl group, a substituted or unsubstituted C2 to C30 heteroaryl group, or a combination thereof, and n41 to n43 are independently an integer of 0 or 1.

In Chemical Formulae 1-i to 1-ix, $X^1$ to $X^9$ may be the same as described above. For example, in Chemical Formulae 1-i to 1-v, and 1-ix, $X^1$ to $X^9$ are CH or N and at least one of $X^1$ to $X^9$ is N, in Chemical Formulae 1-vi 1-vii, and 1-viii, $X^1$ to $X^3$ are CH or N and at least one of $X^1$ to $X^3$ is N.

In one example of the present invention, in Chemical Formulae 1-i to 1-ix, at least two of $X^1$ to $X^3$ may be N. In one example of the present invention, in Chemical Formulae 1-i to 1-ix, $X^1$ to $X^3$ may be all N.

The first compound includes a hetero hexagonal cyclic compound including at least one nitrogen atom (a hexagonal nitrogen-containing ring) as a core compound. The first compound has a structure easily receiving electrons when an electric field is applied thereto and accordingly, may increase the injection amount of electrons, decrease a driving voltage of an organic optoelectronic device including the first compound, and improves efficiency due to the hetero hexagonal cyclic compound including at least one nitrogen atom (a hexagonal nitrogen-containing ring) as the core compound.

The first compound expressed by Chemical Formula 1 has at least one of kink structure in the center of an arylene group and/or a heteroarylene group.

The kink structure indicates a structure that an arylene group and/or a heteroarylene group are not linked straight at the linking point. For example, as for phenylene, ortho-phenylene (o-phenylene) and meta phenylene (m-phenylene) have the kink structure in which their linking point are not straight, while para phenylene (p-phenylene) has no kink structure.

In Chemical Formula 1, the kink structure may be formed in the center of a linking group, that is an arylene group/heteroarylene group.

For example, n1 of Chemical Formula 1-I may be 0, that is $(R^{a1})_{n1}$ may be hydrogen, and n2 of $(R^{a2})_{n2}$ is may be 0, that is $(R^{a2})_{n2}$ may be hydrogen. In the same way, n3 of $(R^{b1})_{n3}$ of Chemical Formula 1-ii may be 0 and n9 of $(R^{c1})_{n9}$ of Chemical Formula 1-iii may be 0.

In addition, when three Z's of the center 6-membered ring in Chemical Formula 1 are all nitrogen atoms, the hexagonal nitrogen-containing ring becomes a triazine structure, Chemical Formula 1 is a structure wherein three hexangonal rings linked to triazine, and all the three hexangonal rings may consist of an arylene group or an heteroarylene group. This is one planar structure that maximizes surfaces contacting homogeneous other molecules during formation of a thin film, and particularly is efficient for electron transport.

For example, the first compound may be expressed by Chemical Formula Y.

[Chemical Formula Y]

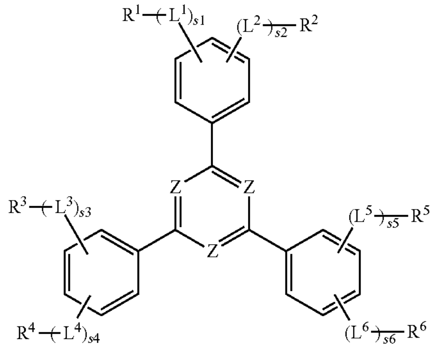

In Chemical Formula Y,

Z is independently N or CH, at least one of Z is N, $R^1$ to $R^6$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof, $L^1$ to $L^6$ are independently a single bond, a substituted or unsubstituted C6 to C30 arylene group, a substituted or unsubstituted heteroarylene group, or a combination thereof, and s1 to s6 are independently an integer ranging from 0 to 5.

For example, the first compound may be expressed by Chemical Formula Z.

[Chemical Formula Z]

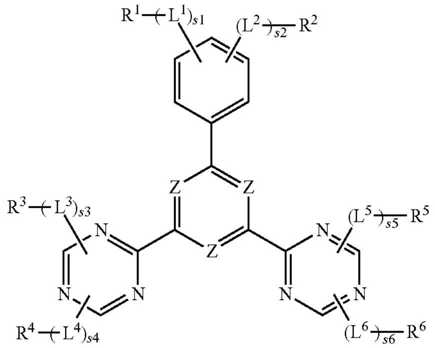

In Chemical Formula Z,

Z is independently N or CH, at least one of Z is N, $R^1$ to $R^6$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof, $L^1$ to $L^6$ are independently a single bond, a substituted or unsubstituted C6 to C30 arylene group, a substituted or unsubstituted heteroarylene group, or a combination thereof, and s1 to s6 are independently an integer ranging from 0 to 5.

For example, $R^1$ to $R^6$ may independently be selected from hydrogen and groups of Group B, but are not limited thereto.

[Group B]

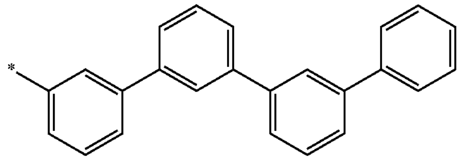

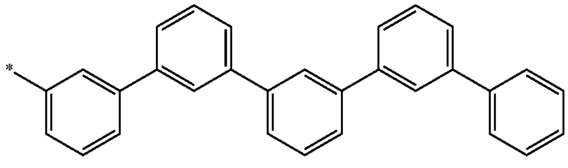

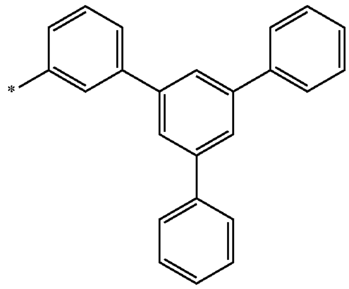

-continued
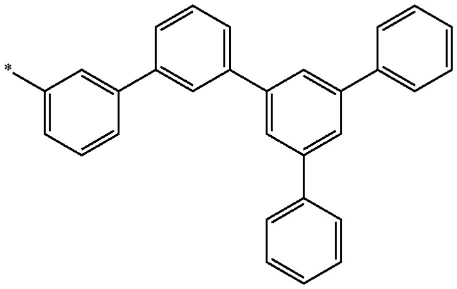
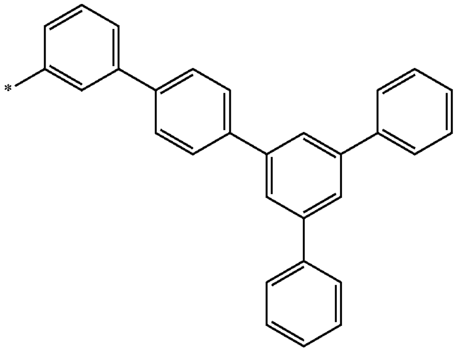
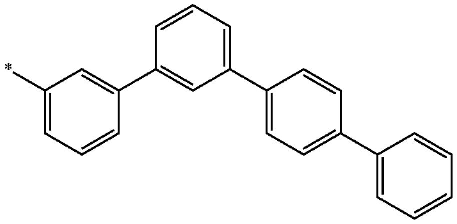
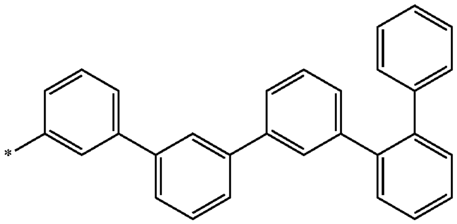
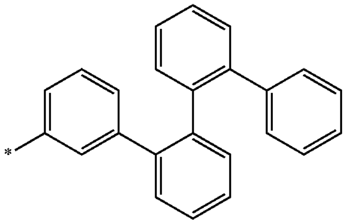
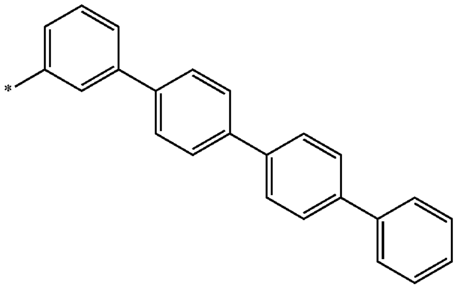
-continued
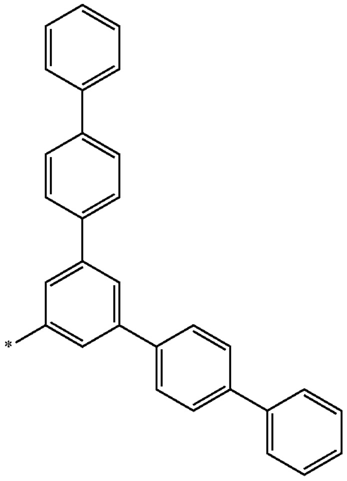
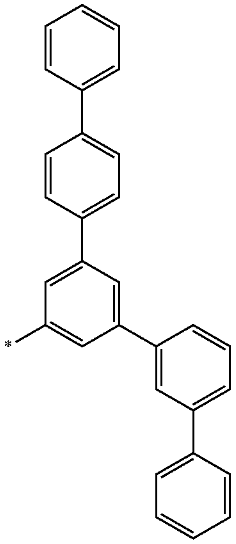
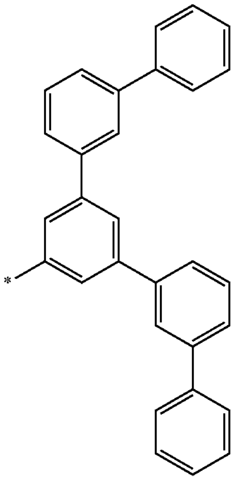
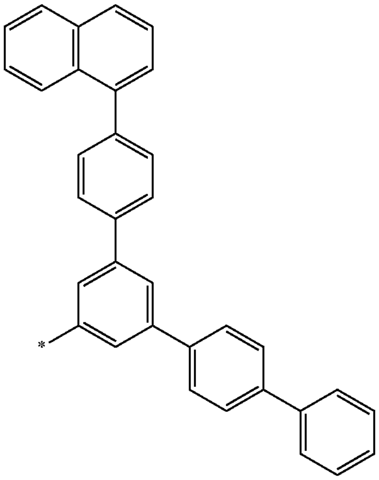

-continued
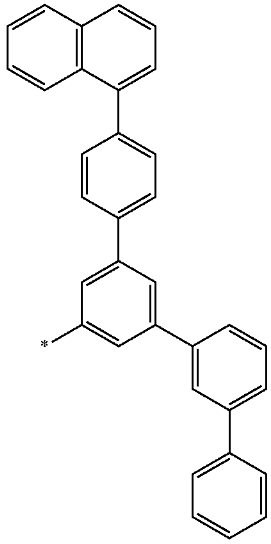
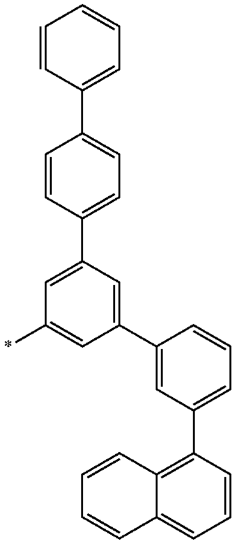
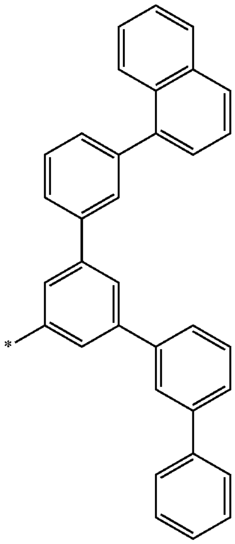
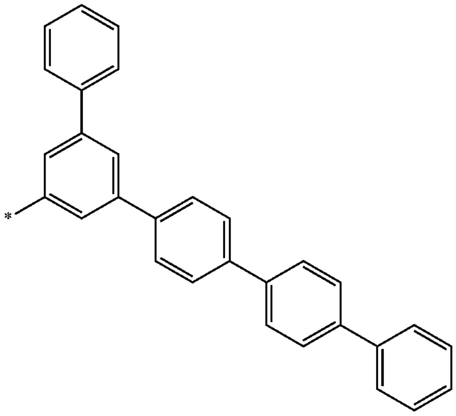
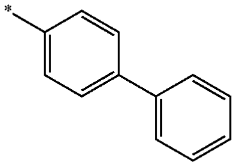
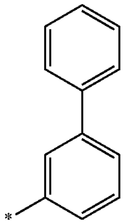
-continued
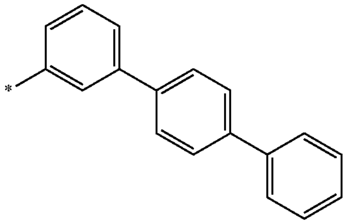
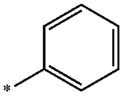
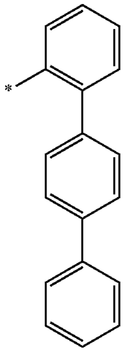
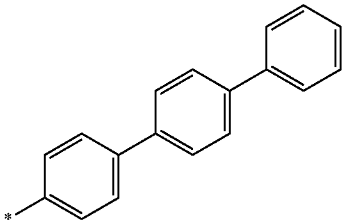
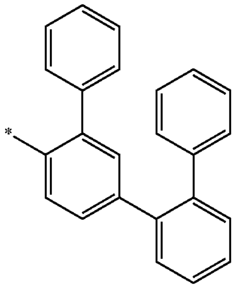
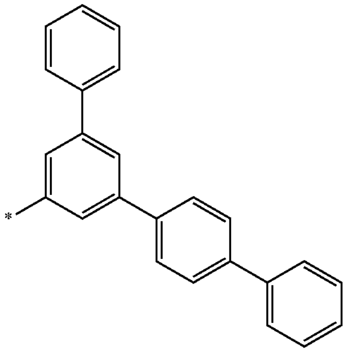
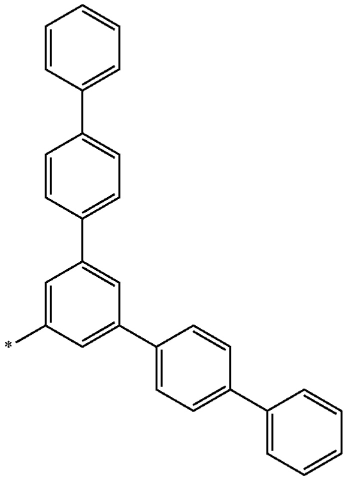

-continued
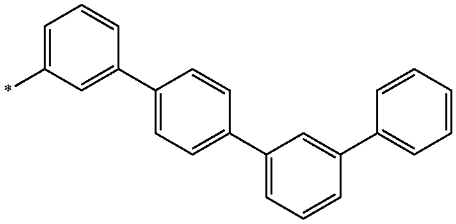
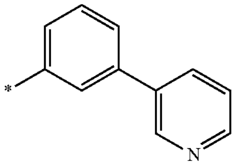
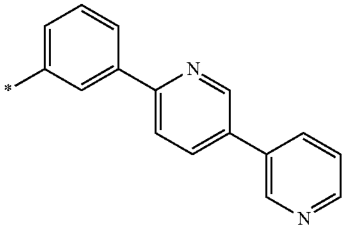
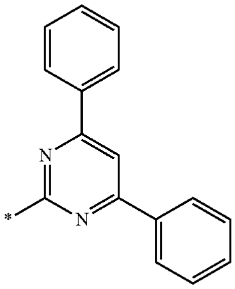
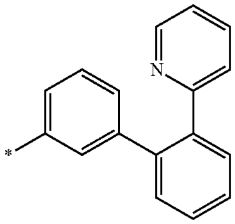
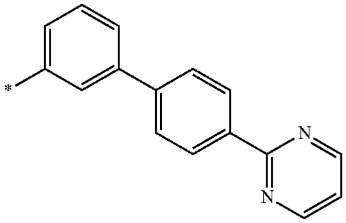
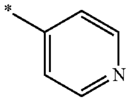
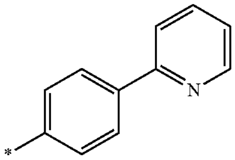
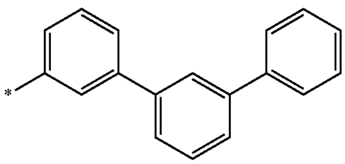
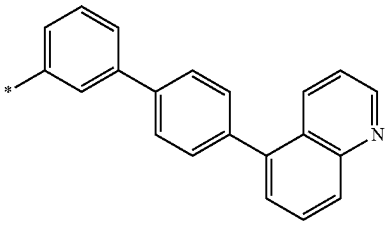
-continued
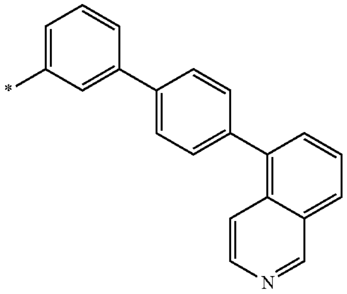
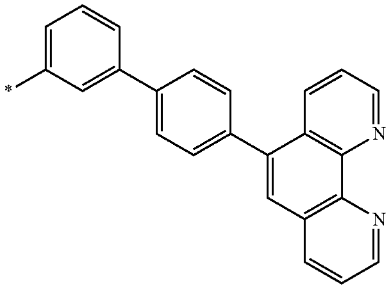
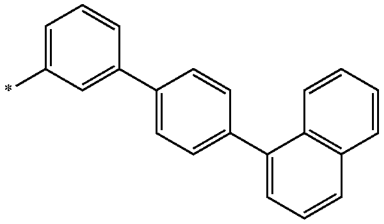
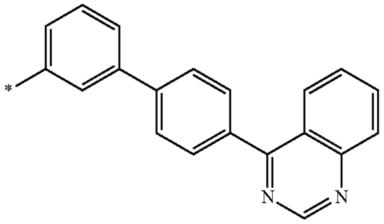
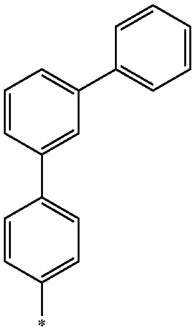
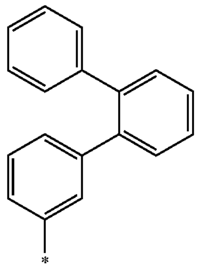
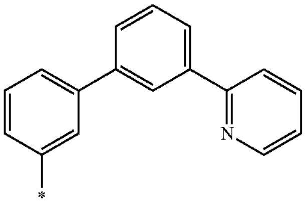

-continued
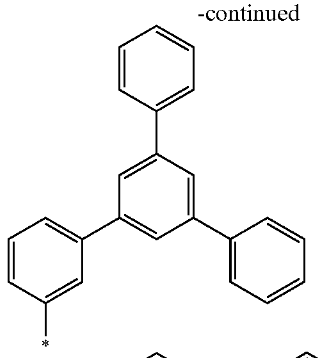
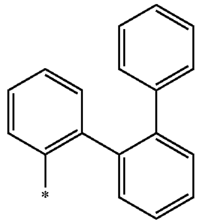
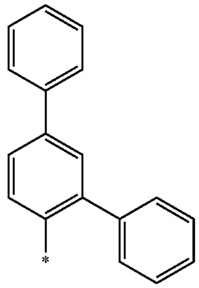
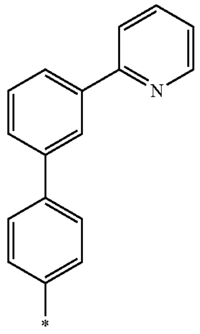
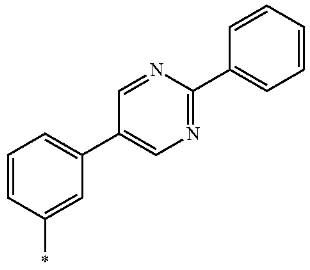
-continued
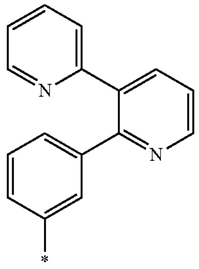
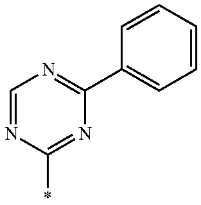
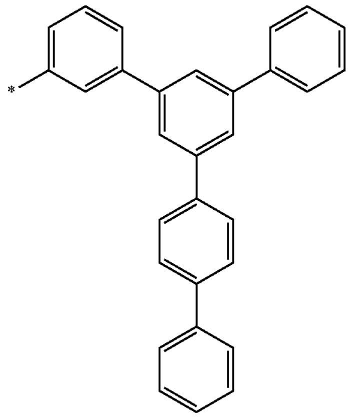
In addition, the first compound may be one of compounds of Group 1, but is not limited thereto.
[Group 1]
[A-1]
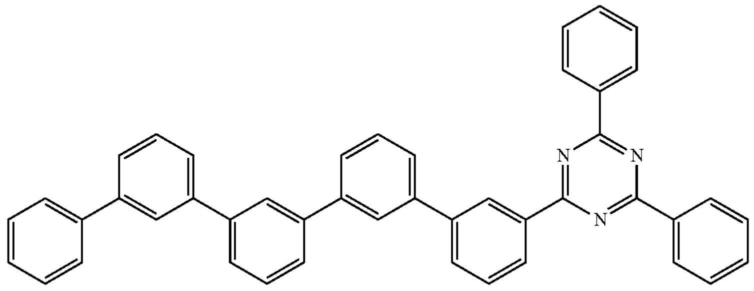
[A-2]
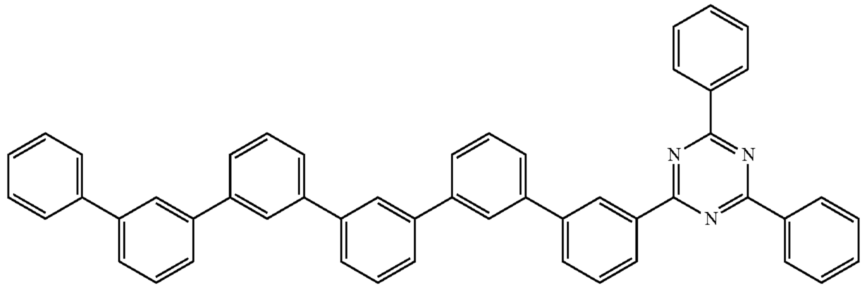

-continued
[A-3]
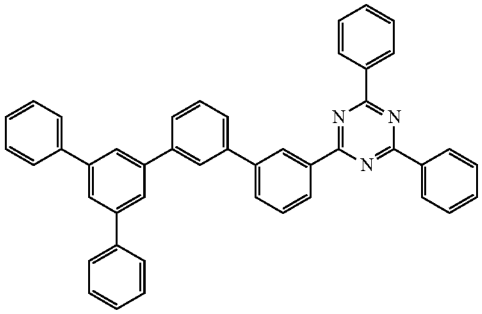
[A-4]
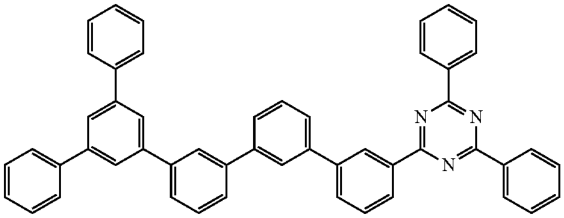
[A-5]
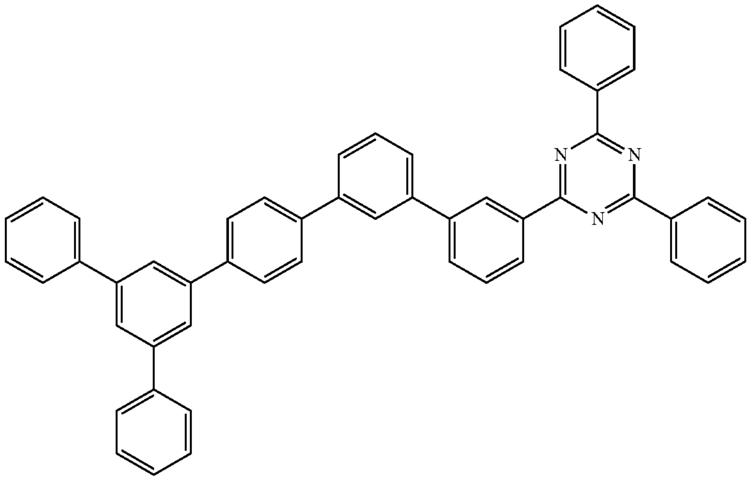
[A-6]
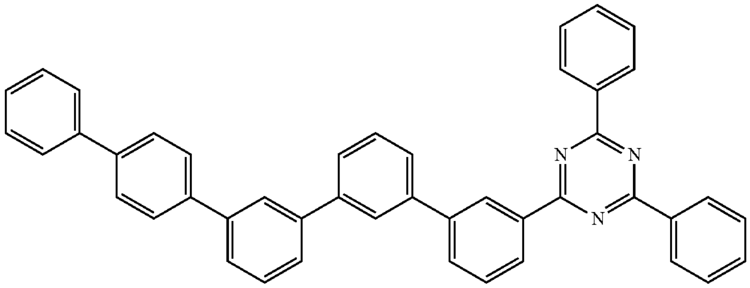
[A-7]
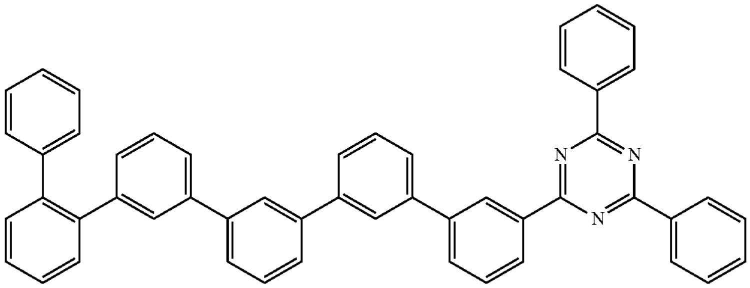

-continued
[A-8]
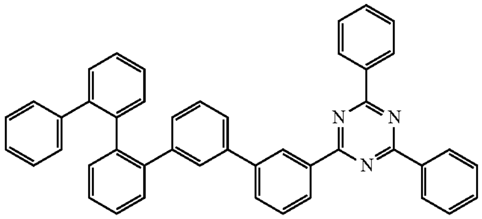
[A-9]
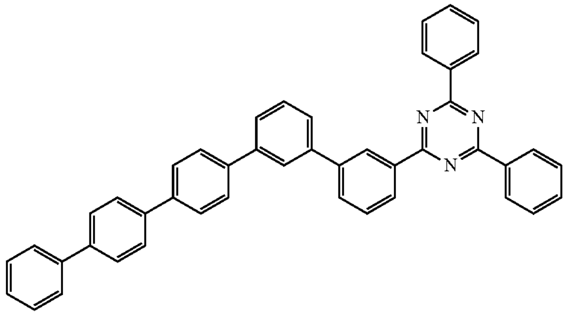
[A-10]
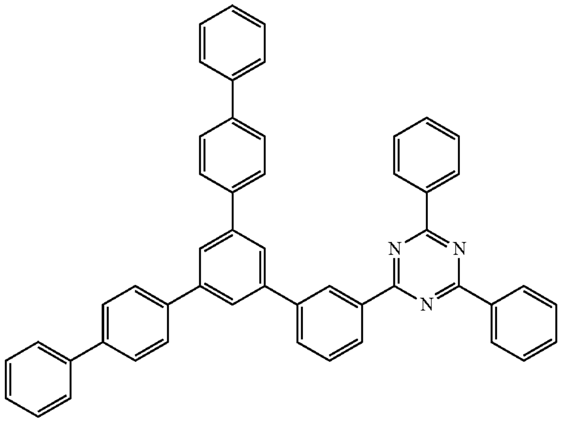
[A-11]
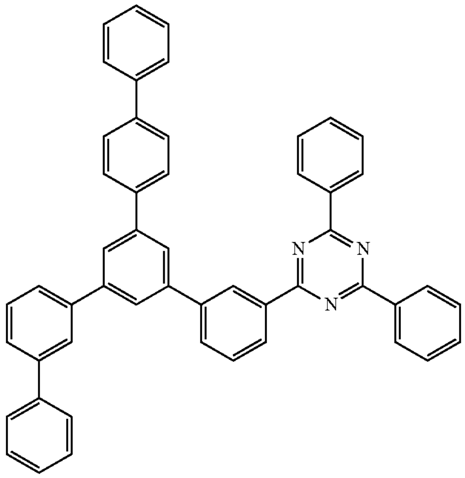
[A-12]
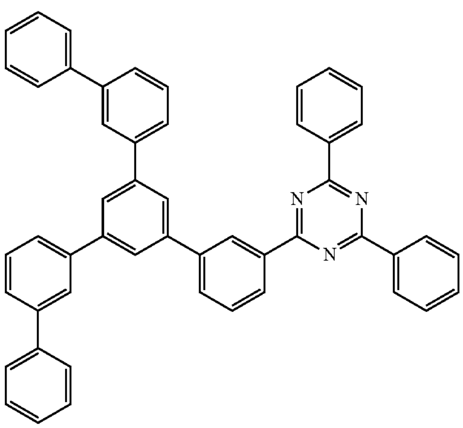
[A-13]
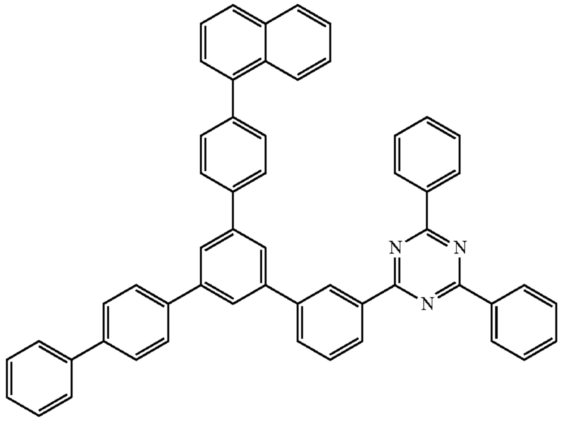

-continued
[A-14]
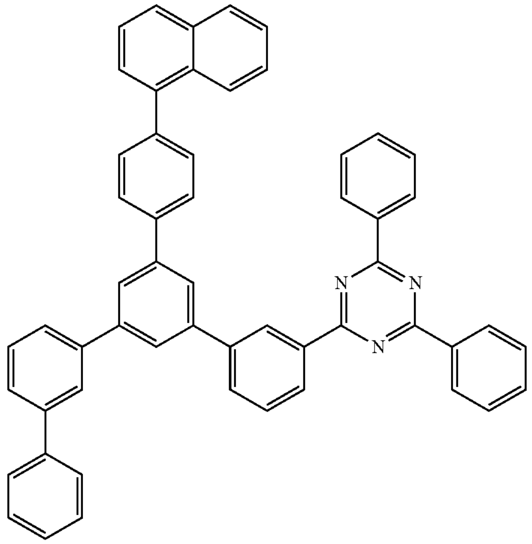
[A-15]
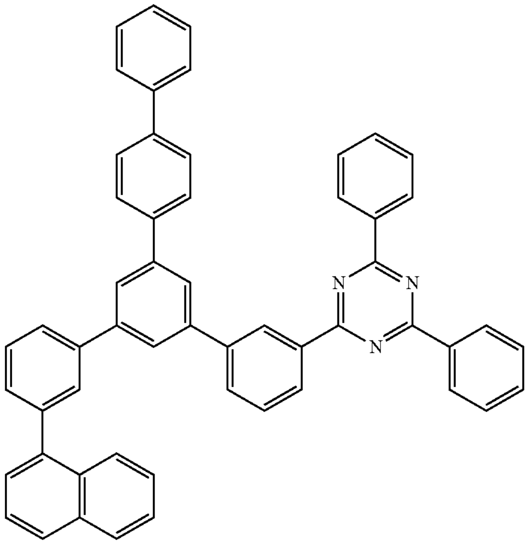
[A-16]
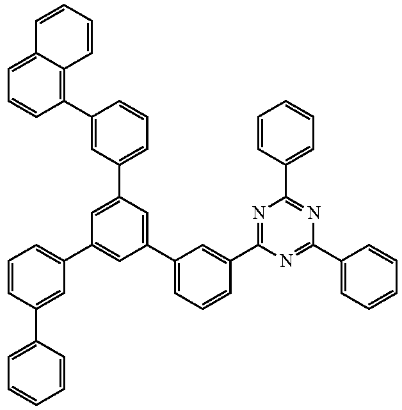
[A-17]
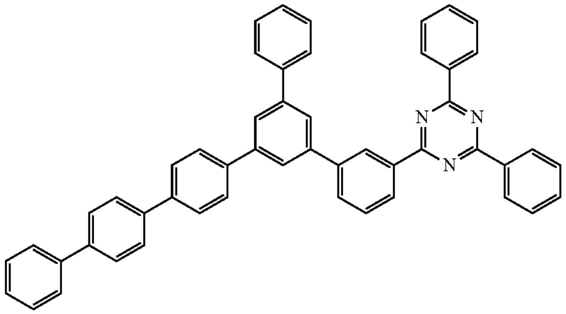
[A-18]
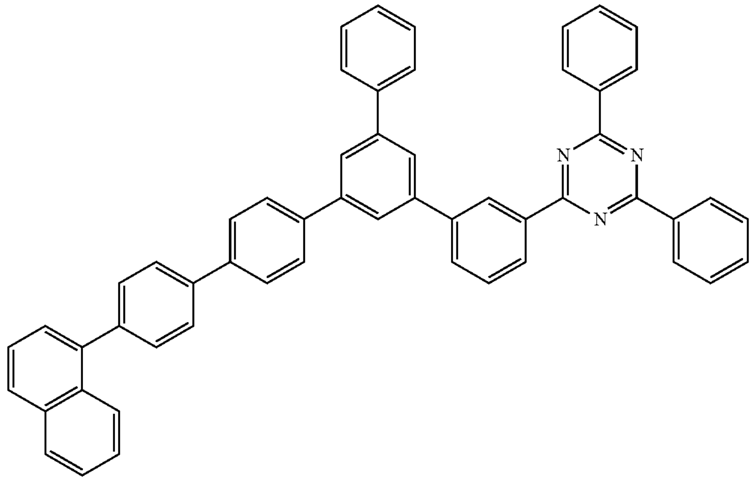

-continued
[A-19]
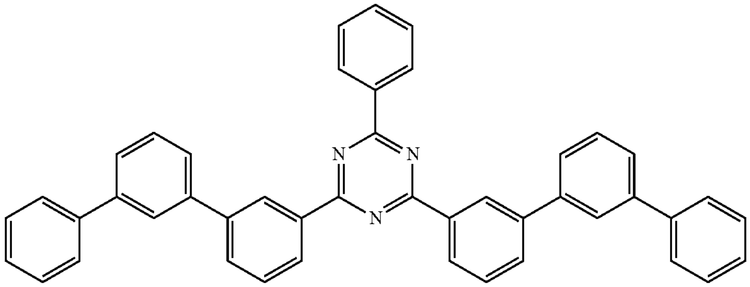
[A-20]
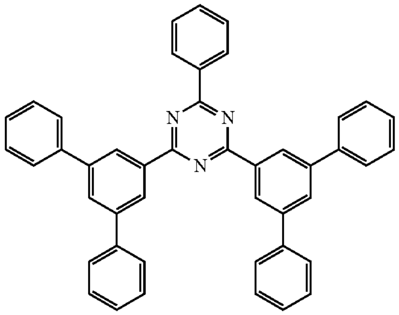
[A-21]
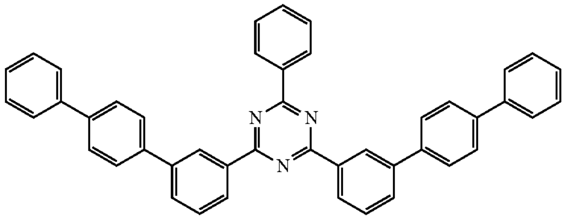
[A-22]
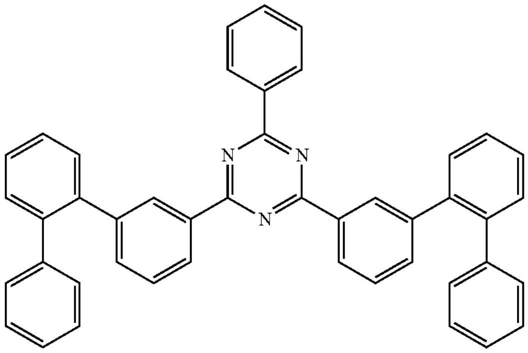
[A-23]
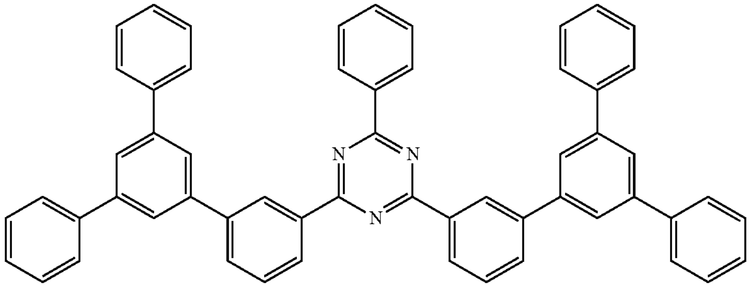
[A-24]
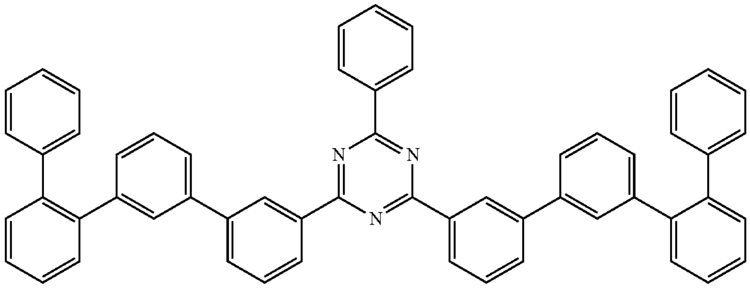

-continued
[A-25]
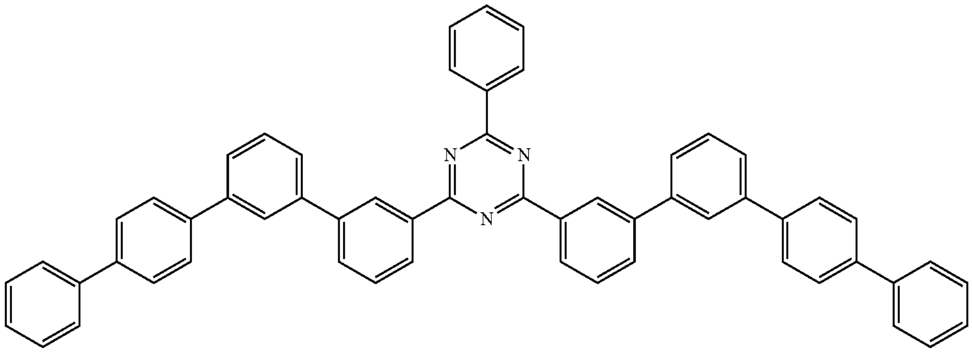
[A-26]
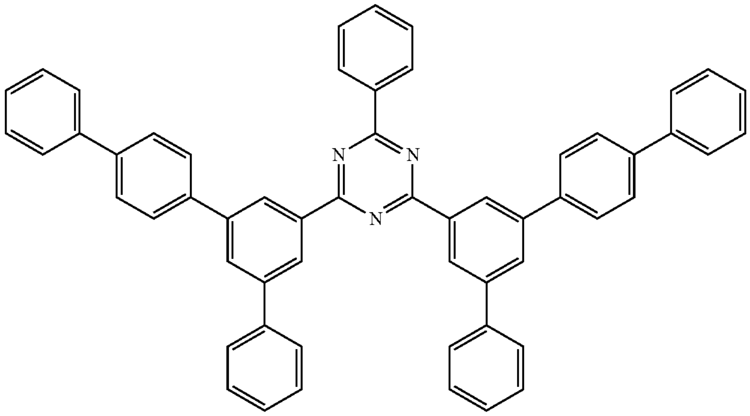
[A-27]
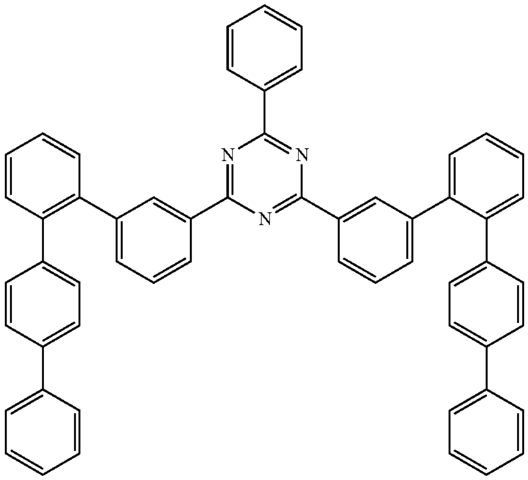
[A-28]
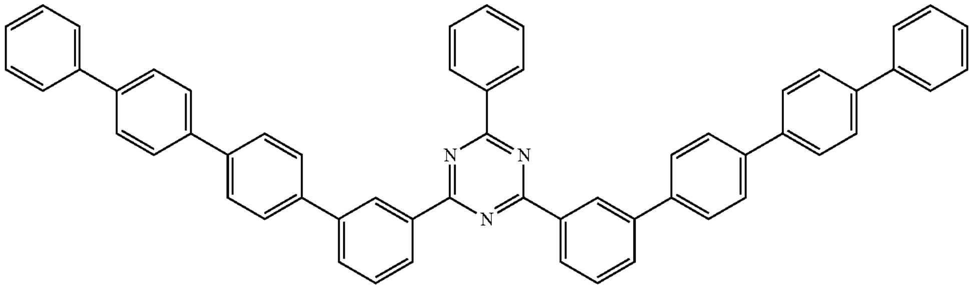

-continued
[A-29]
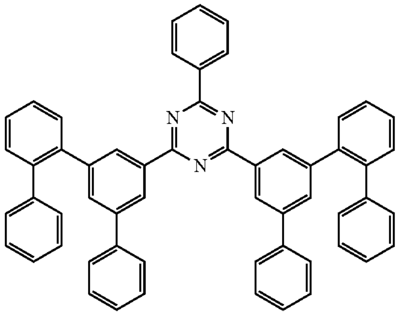
[A-30]
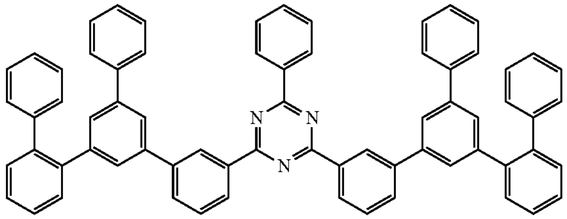
[A-31]
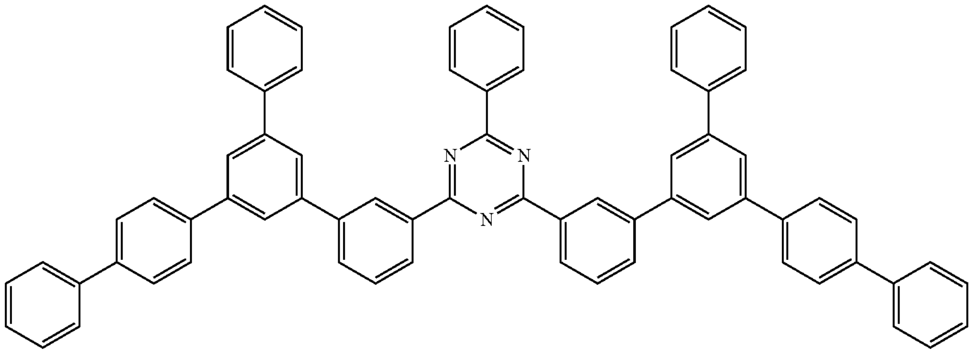
[A-32]
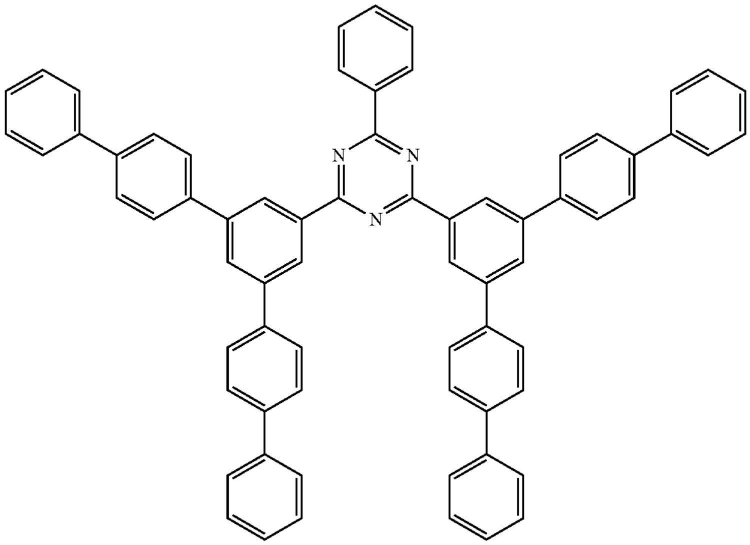
[A-33]
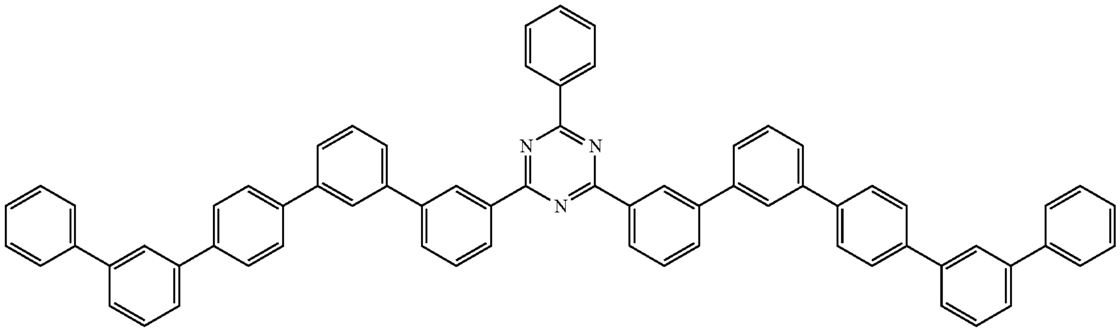

-continued
[A-34]
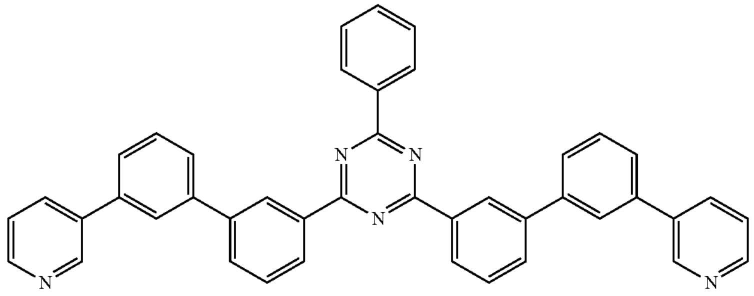
[A-35]
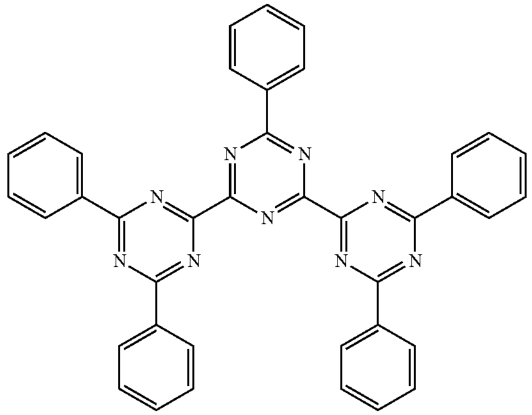
[A-36]
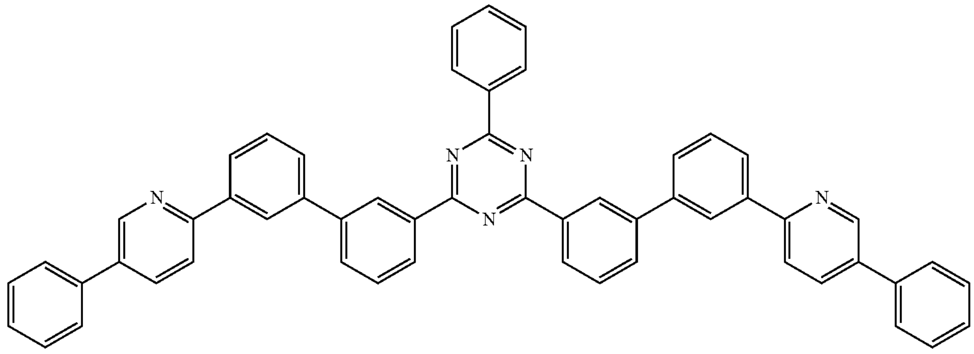
[A-37]
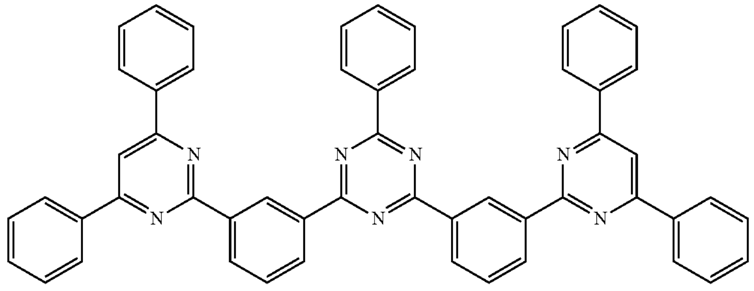

-continued
[A-38]
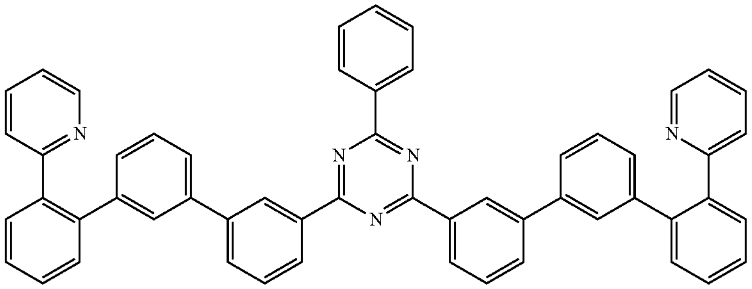
[A-39]
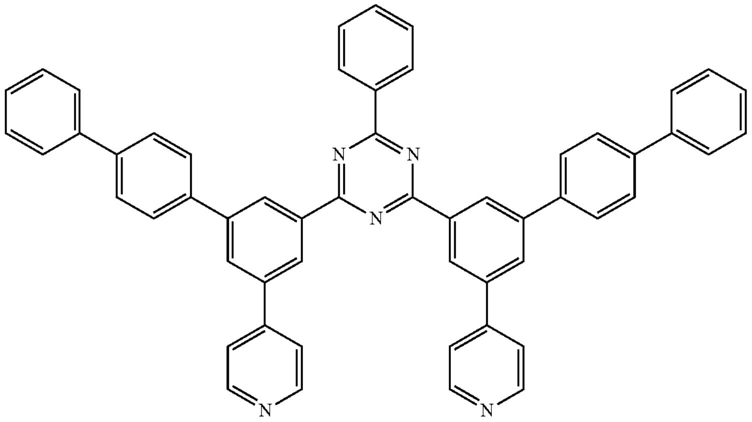
[A-40]
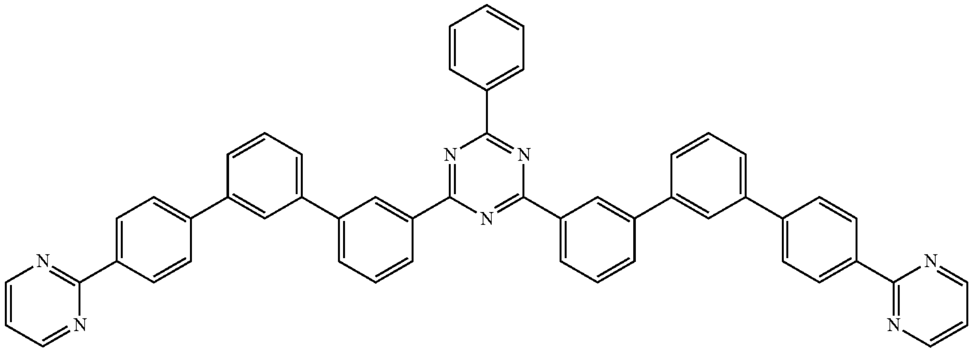
[A-41]
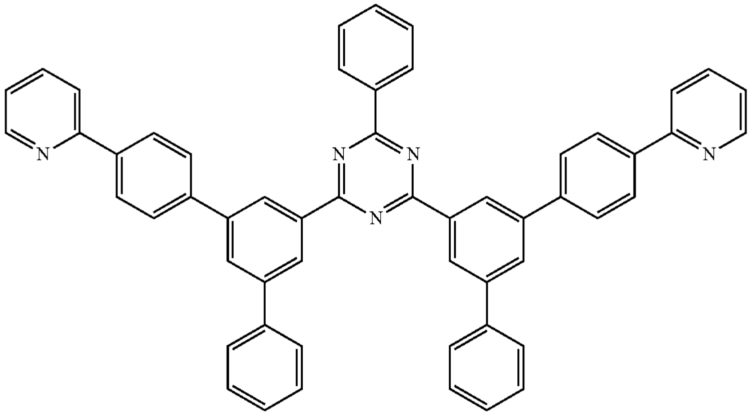

-continued
[A-42]
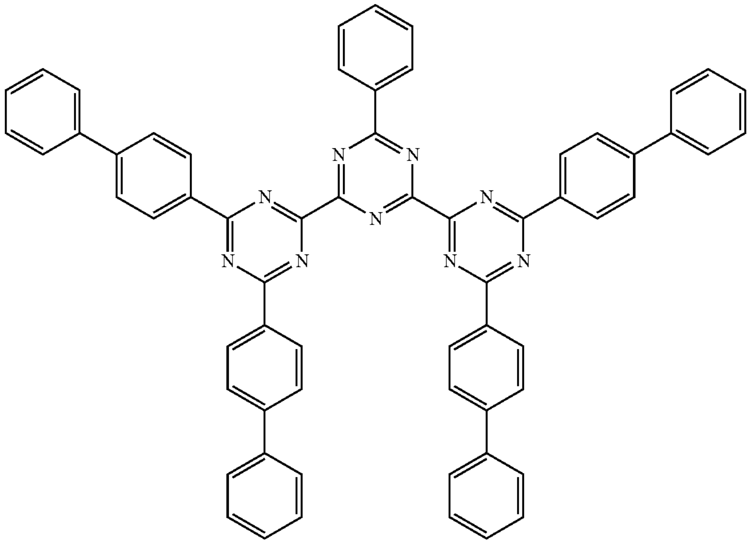
[A-43]
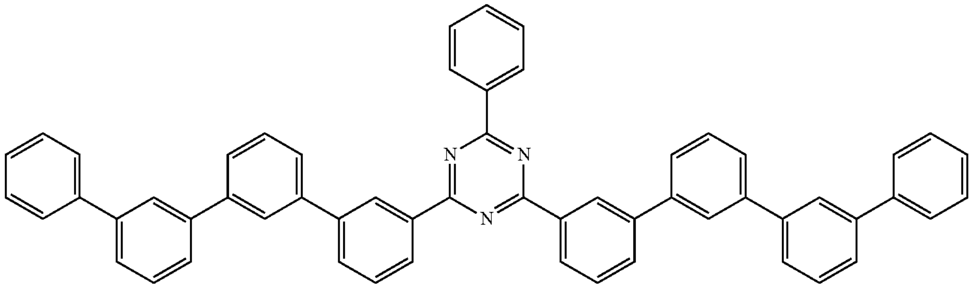
[A-44]
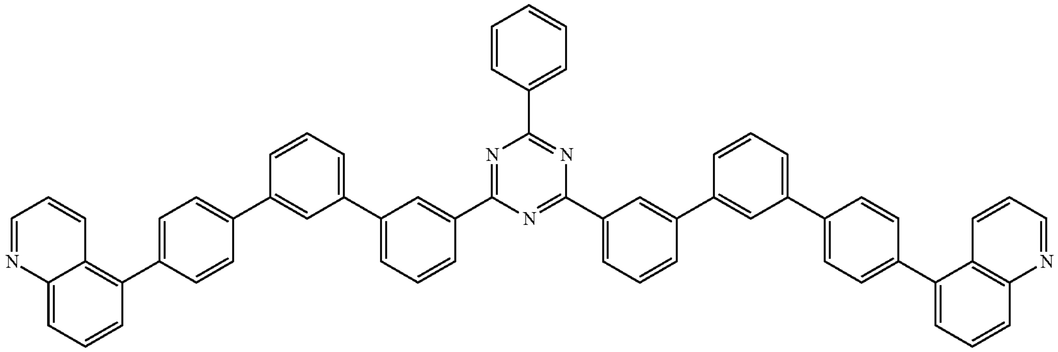
[A-45]
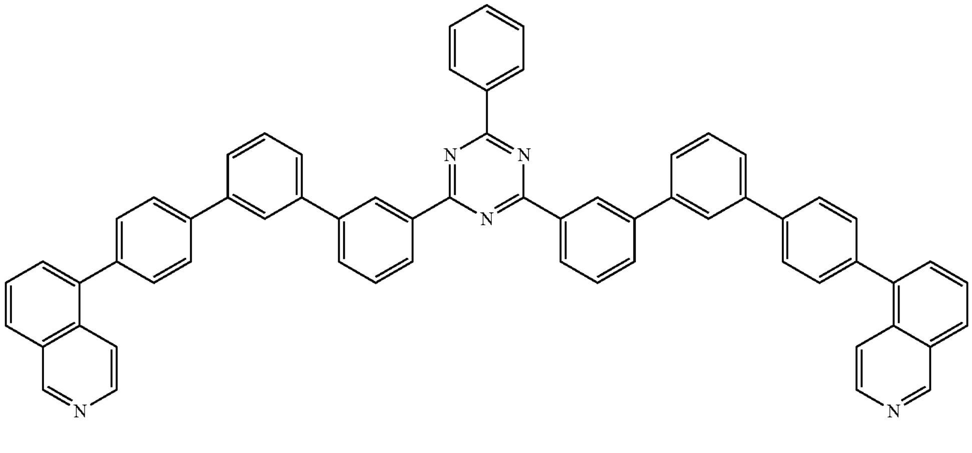

-continued
[A-46]
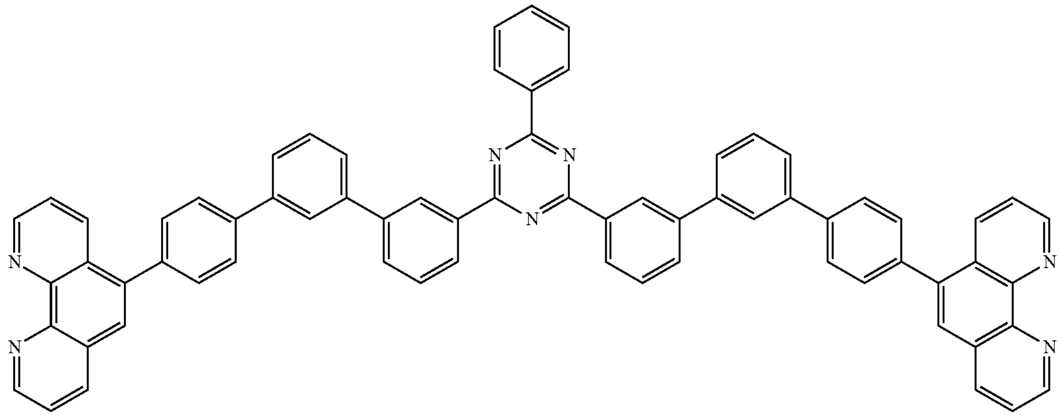
[A-47]
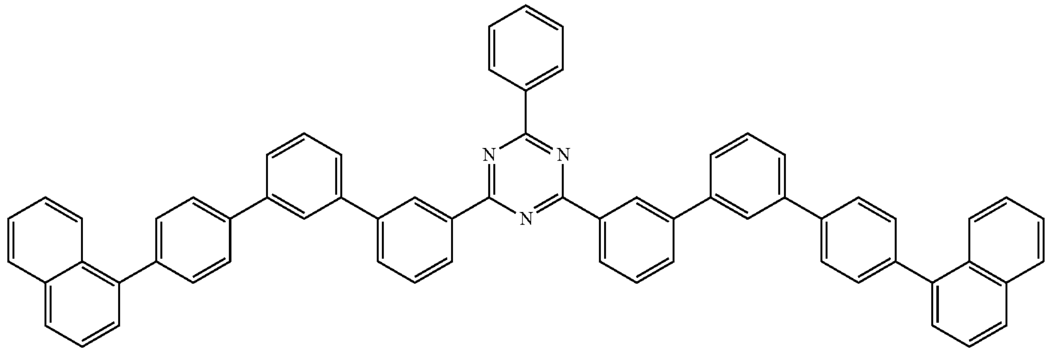
[A-48]
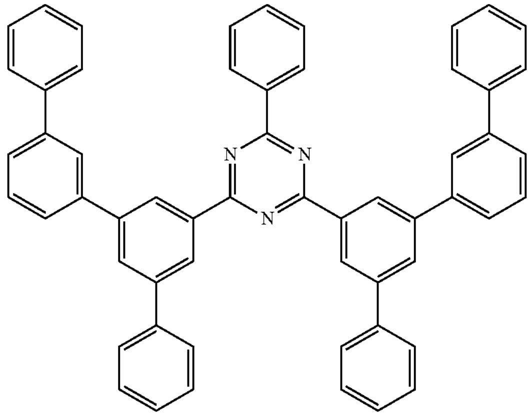

-continued
[A-49]
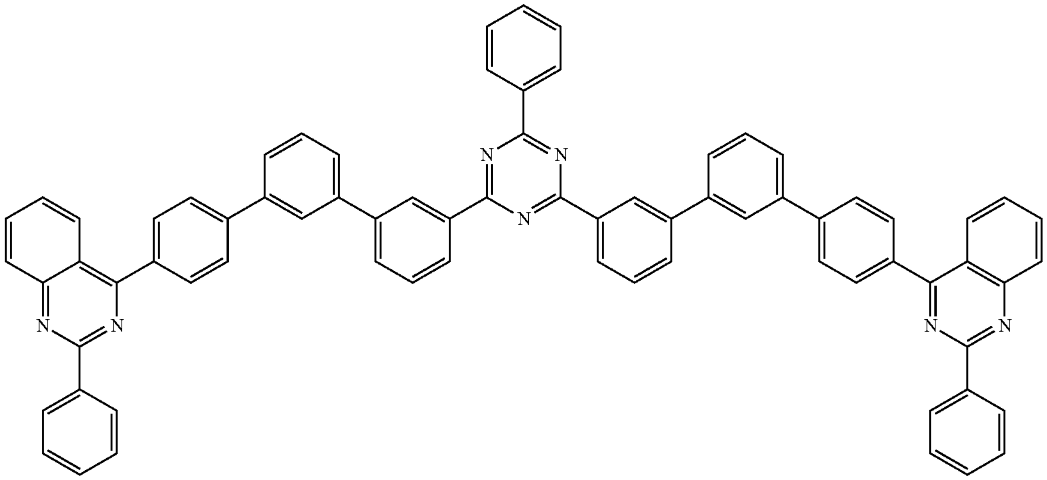
[A-50]
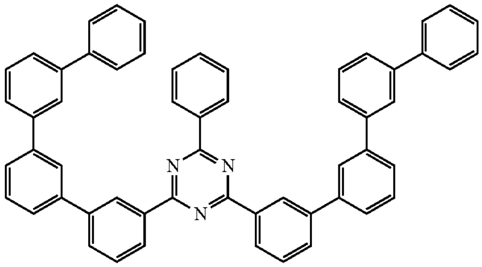
[A-51]
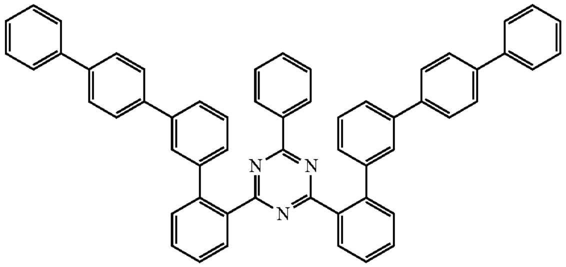
[A-52]
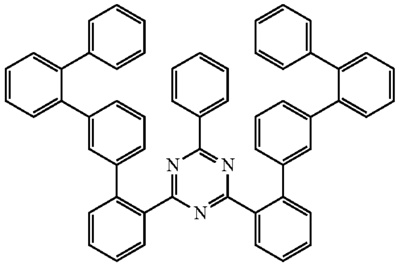
[A-53]
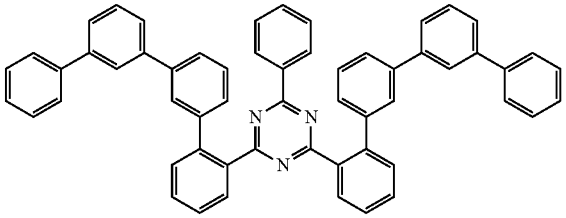
[A-54]
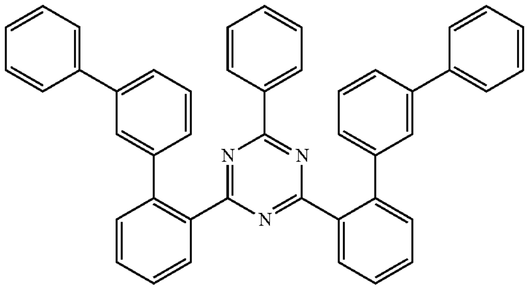
[A-55]
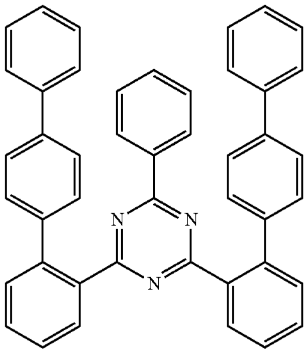

-continued
[A-56]
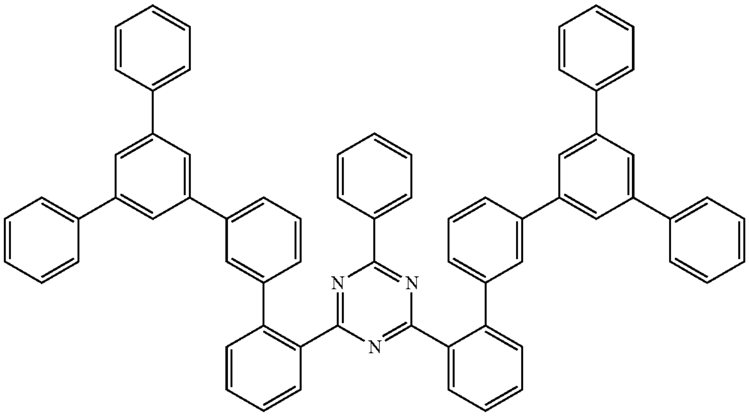
[A-57]
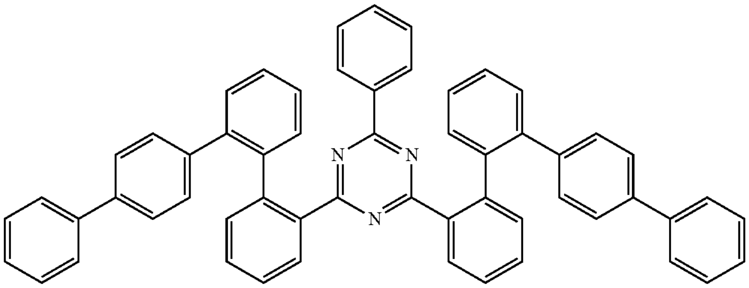
[A-58]
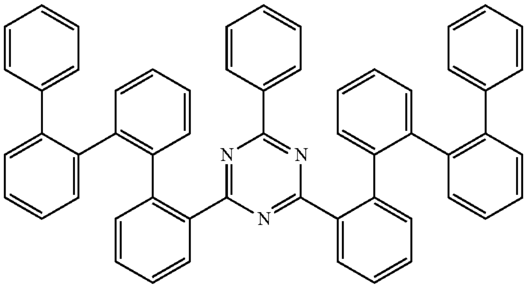
[A-59]
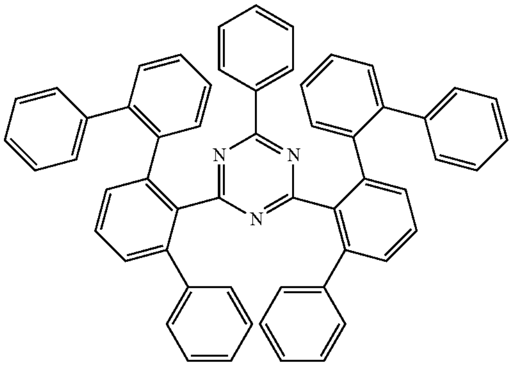
[A-60]
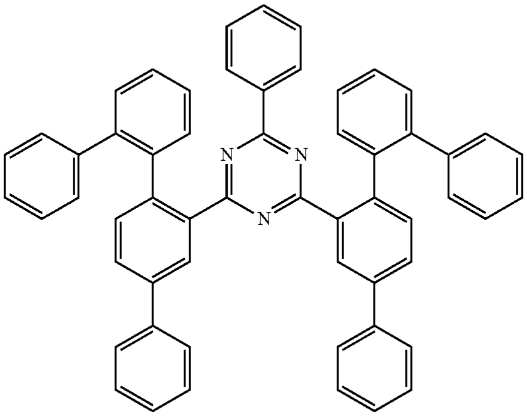
[A-61]
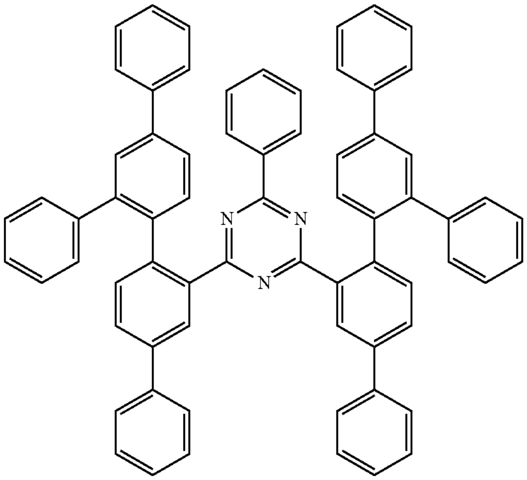

-continued
[A-62]
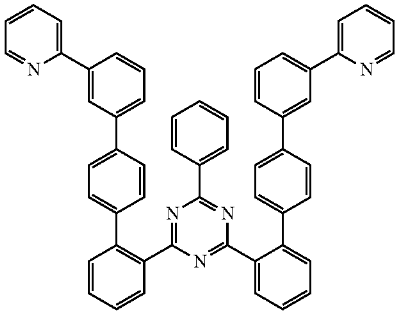
[A-63]
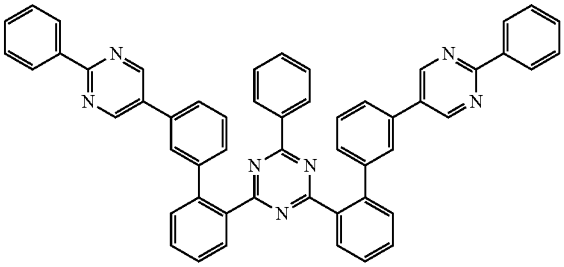
[A-64]
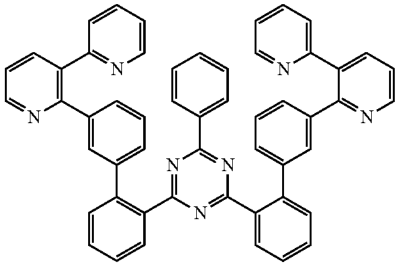
[A-65]
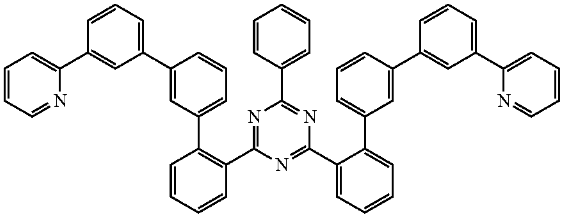
[A-66]
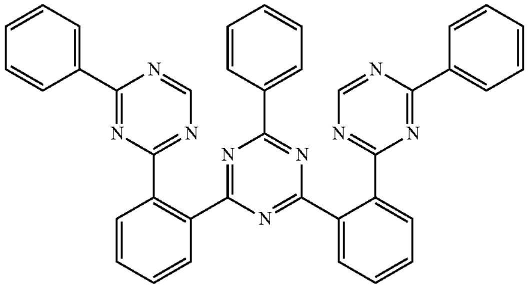
[A-67]
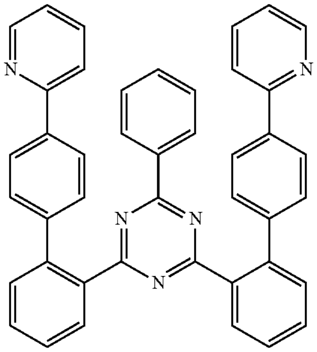
[A-68]
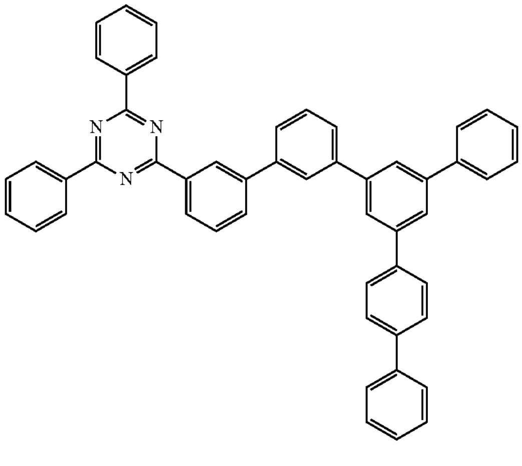
[A-69]
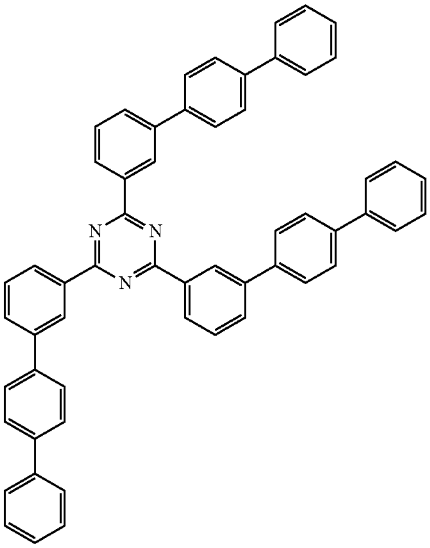

-continued
[A-70]
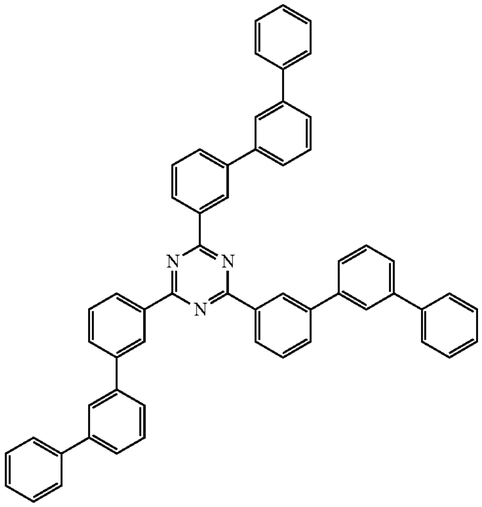
[A-71]
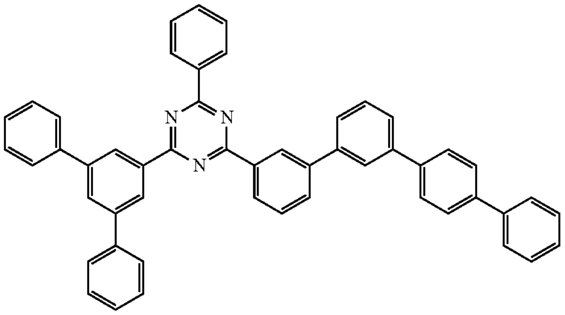
[A-72]
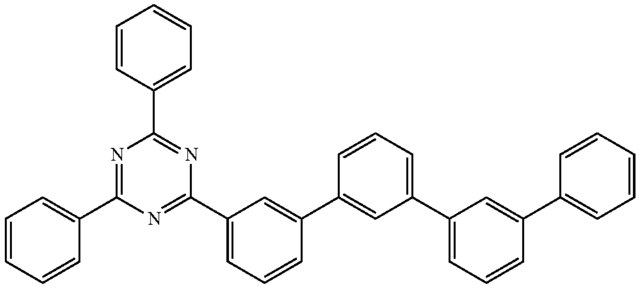
[A-73]
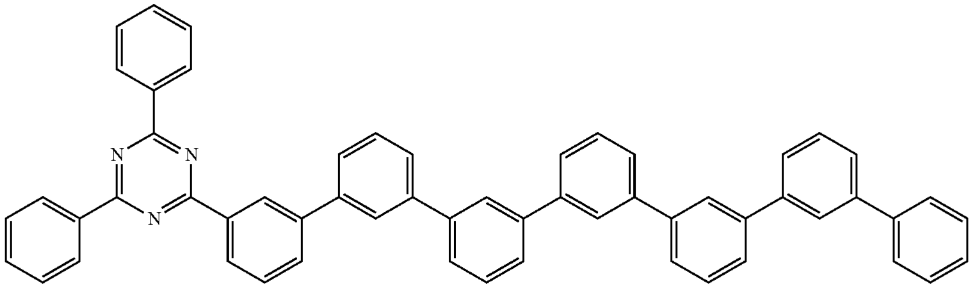

-continued
[A-74]
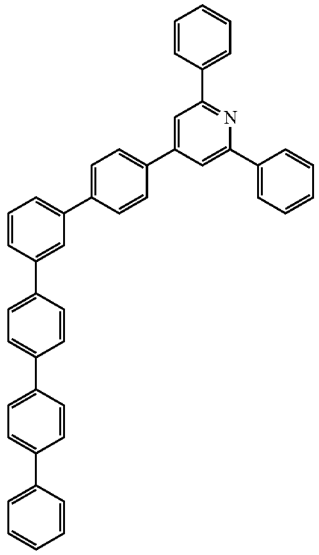
[B-1]
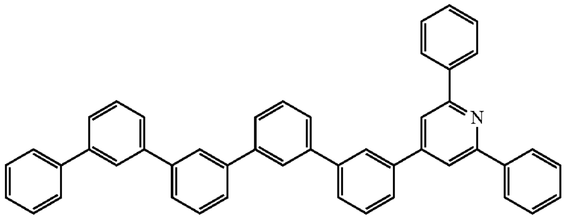
[B-2]
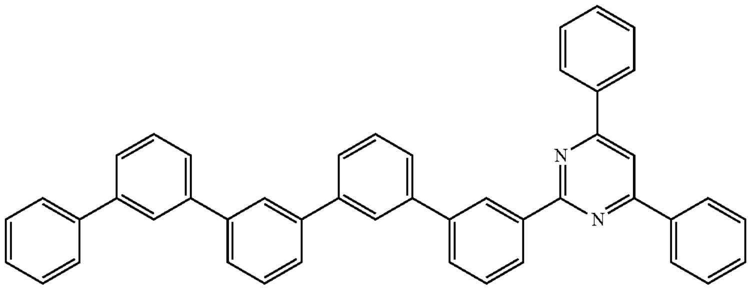
[B-3]
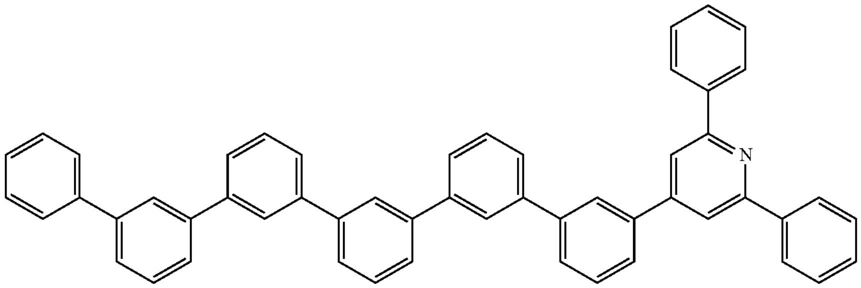
[B-4]
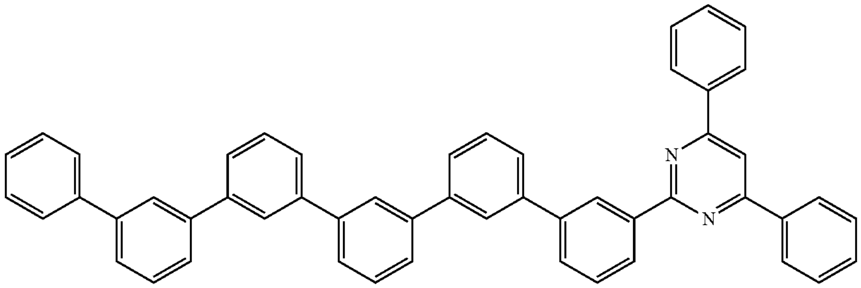

-continued
[B-5]
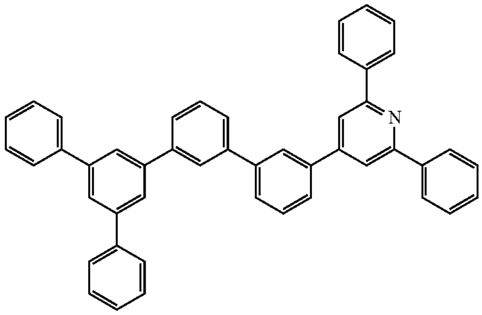
[B-6]
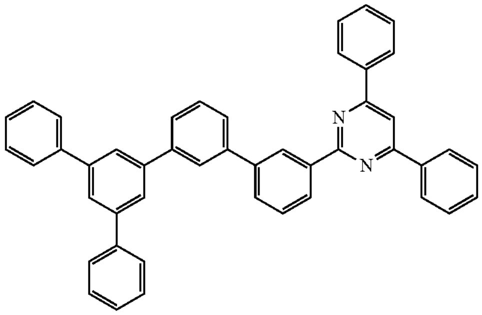
[B-7]
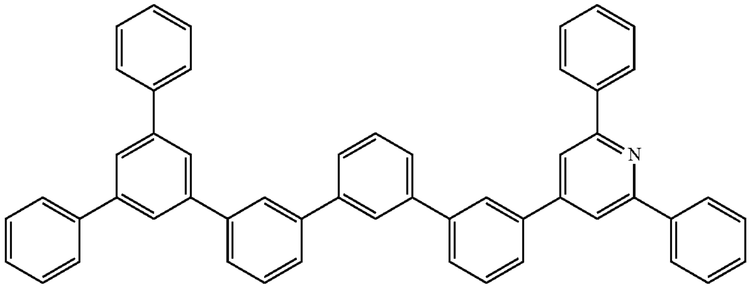
[B-8]
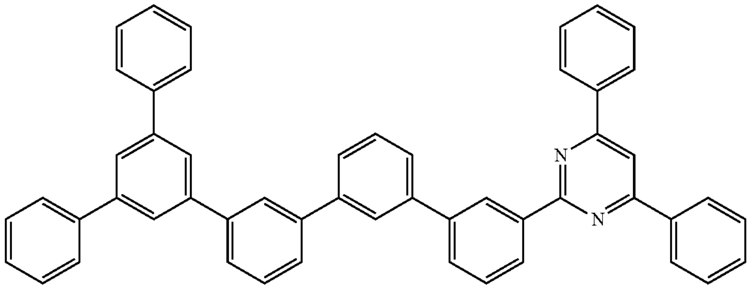
[B-9]
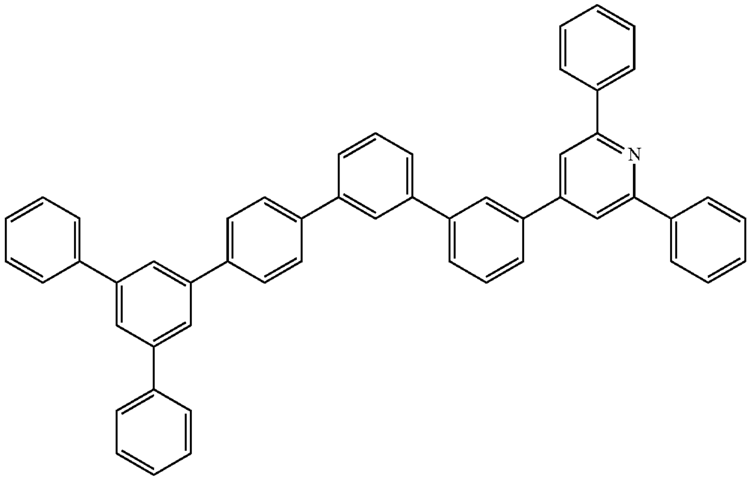

-continued
[B-10]
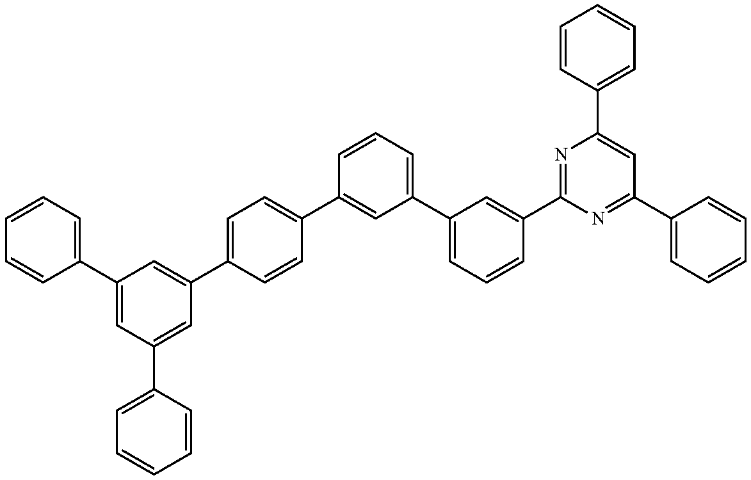
[B-11]
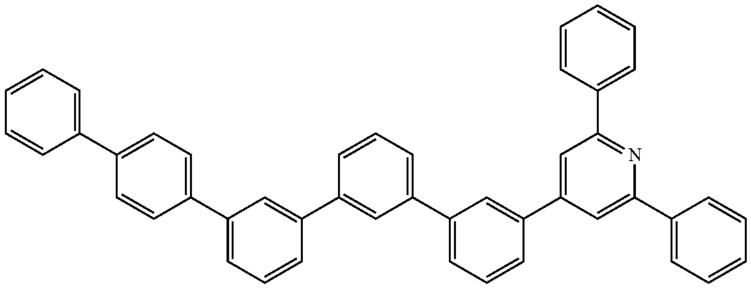
[B-12]
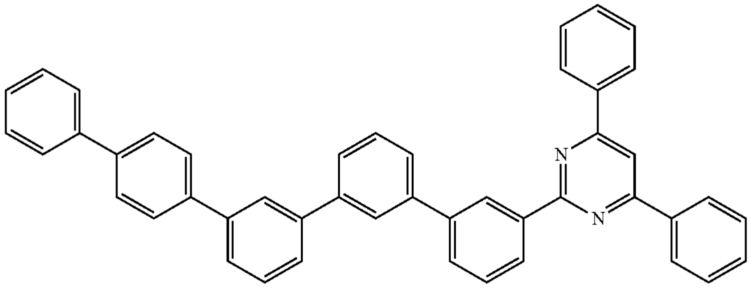
[B-13]
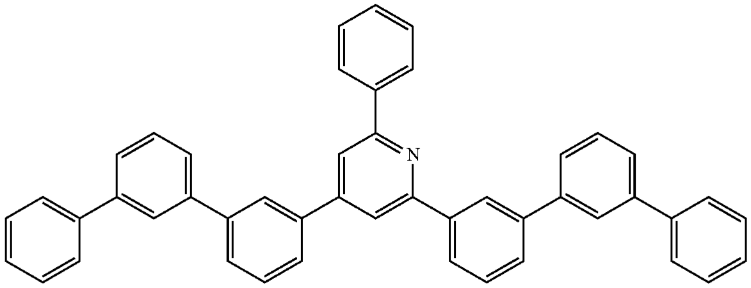

-continued
[B-14]
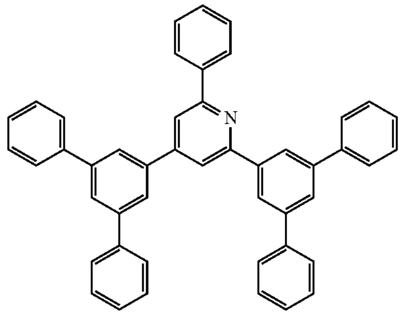
[B-15]
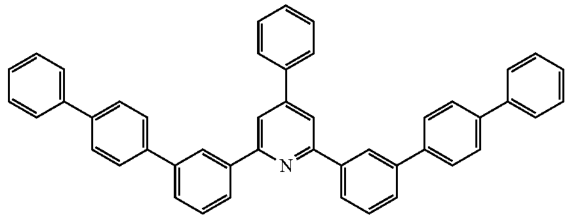
[B-16]
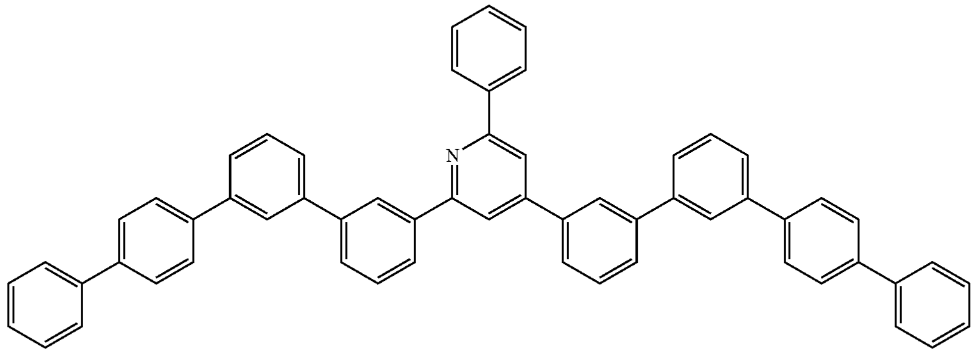
[B-17]
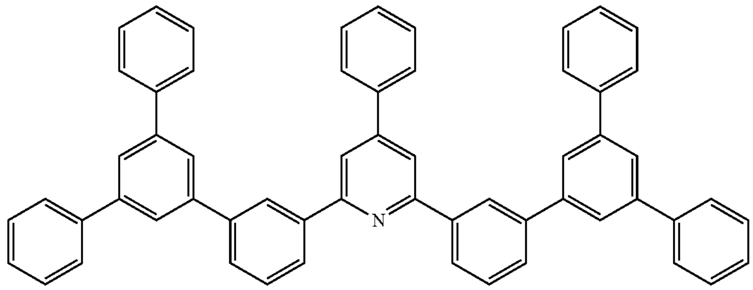
[B-18]
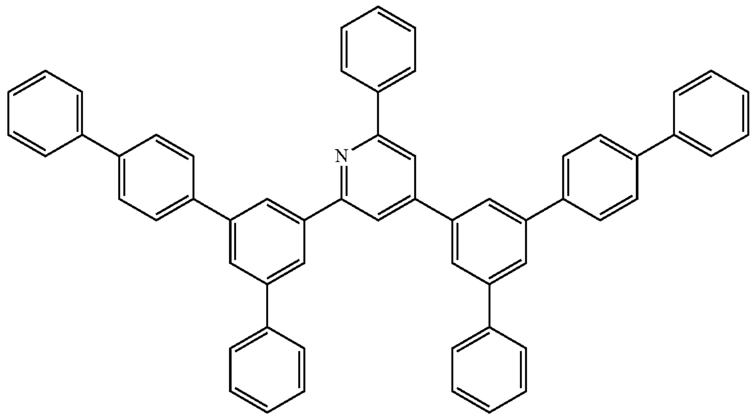

-continued
[B-19]
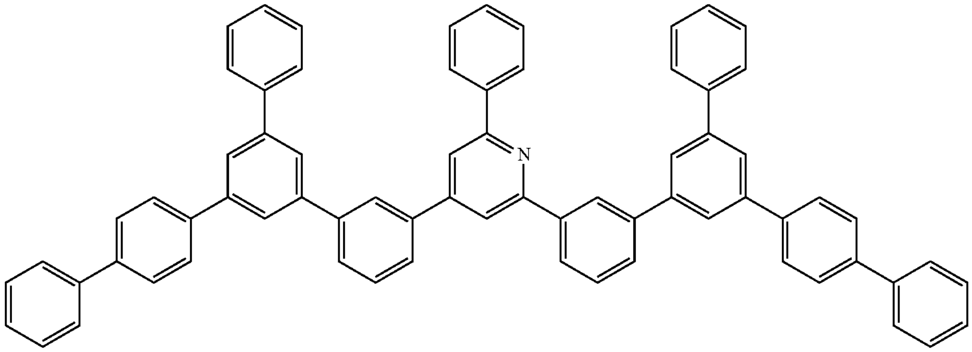
[B-20]
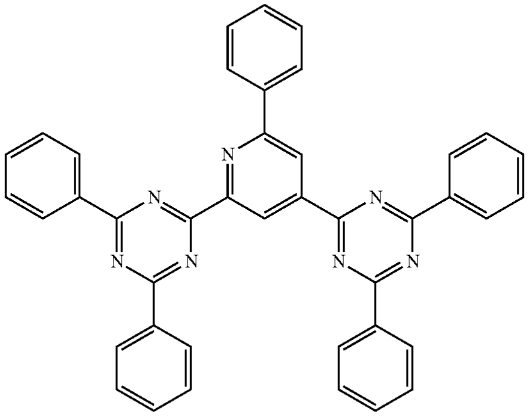
[B-21]
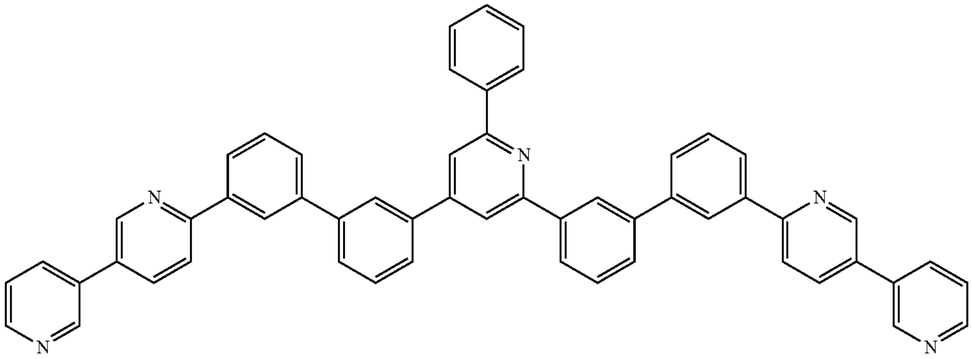
[B-22]
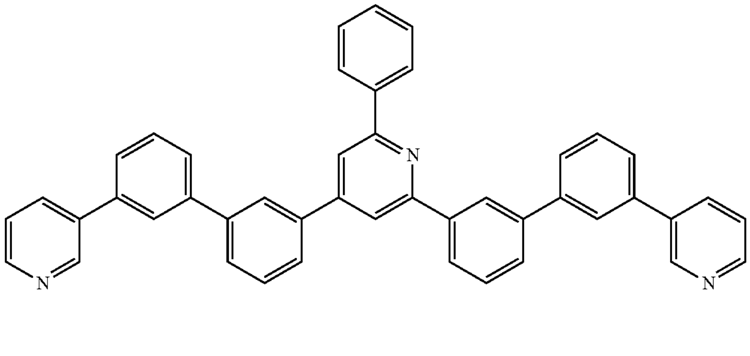

-continued
[B-23]
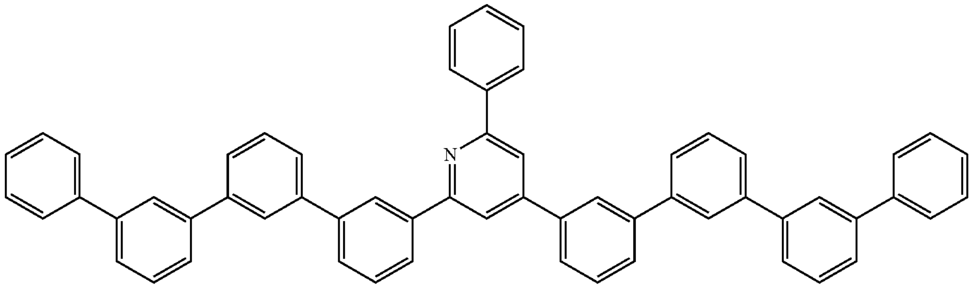
[B-24]
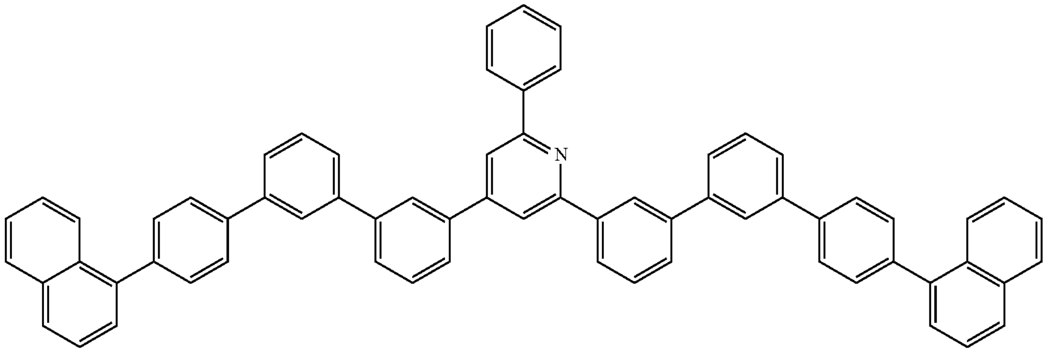
[B-25]
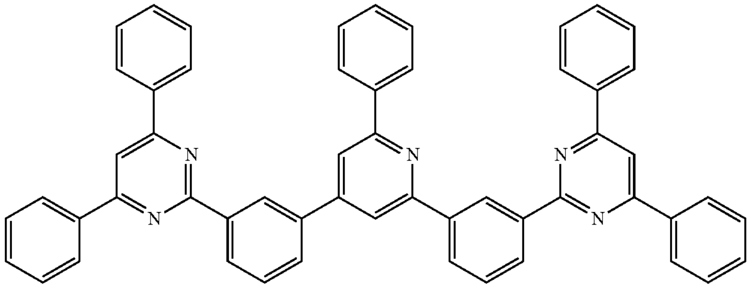
[B-26]
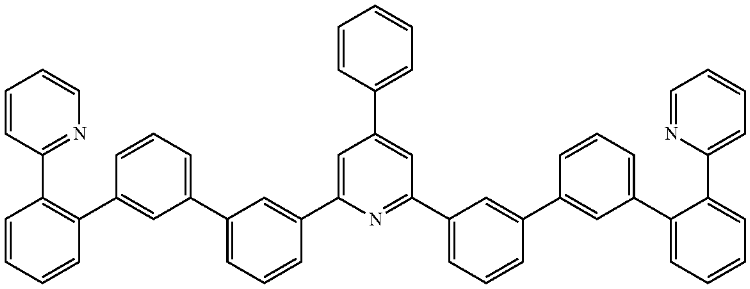

-continued
[B-27]
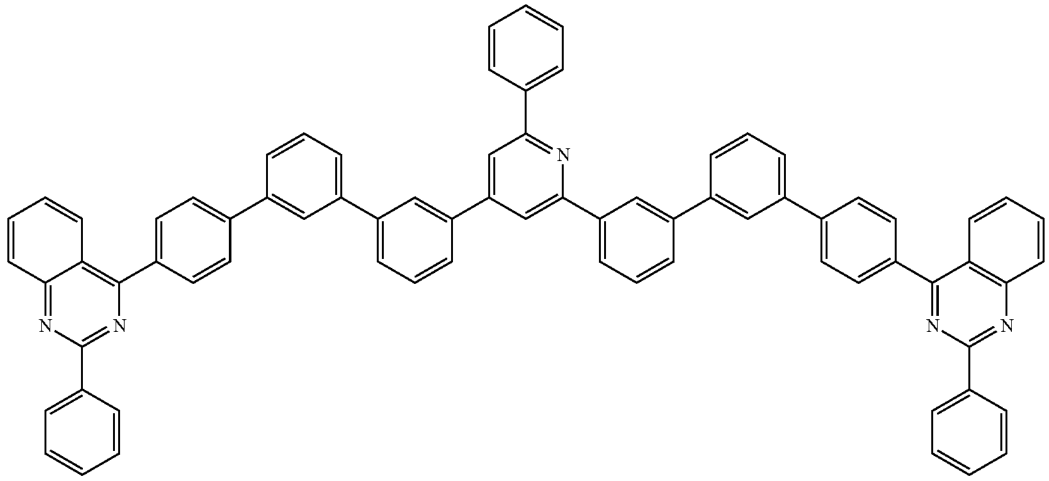
[B-28]
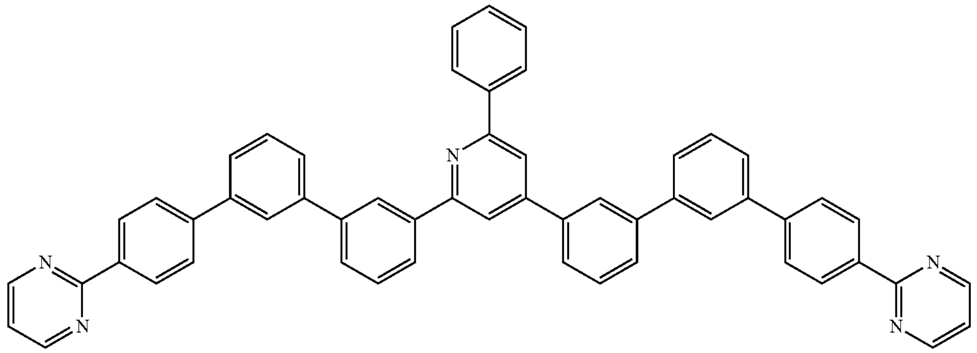
[B-29]
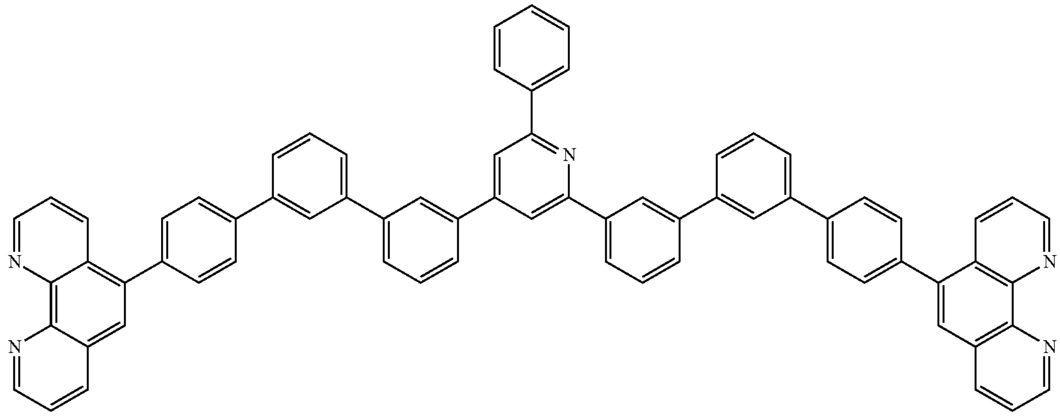
[B-30]
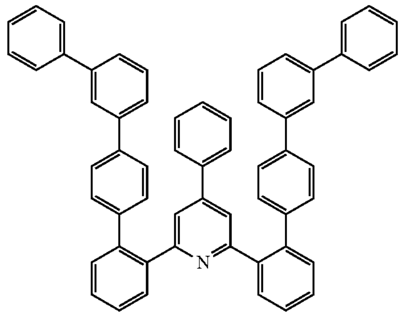
[B-31]
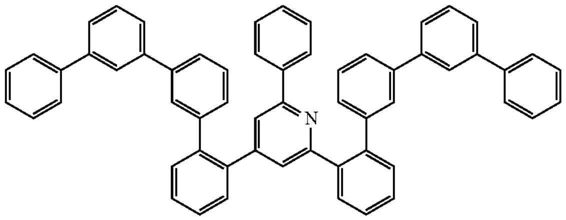

-continued
[B-32]
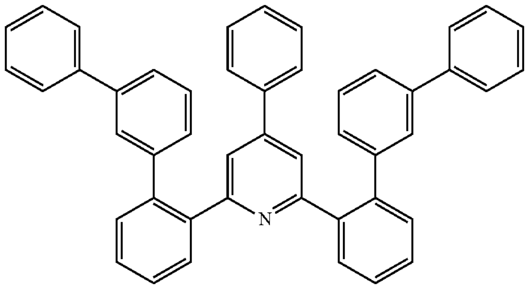
[B-33]
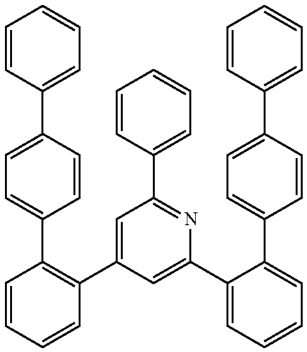
[B-34]
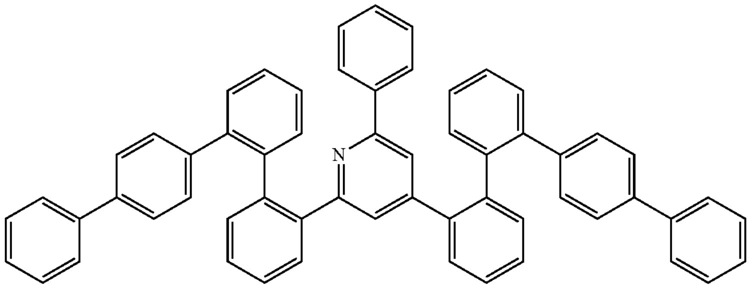
[B-35]
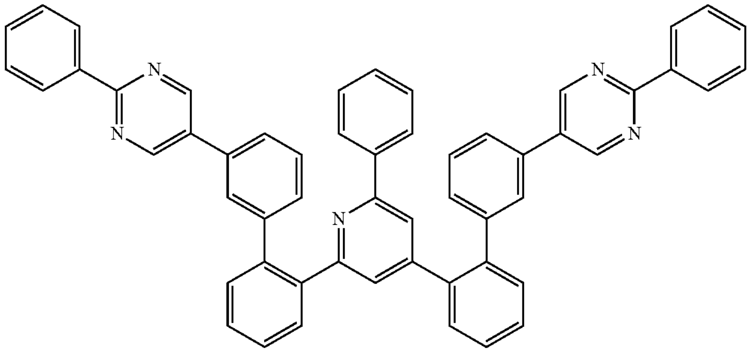
[B-36]
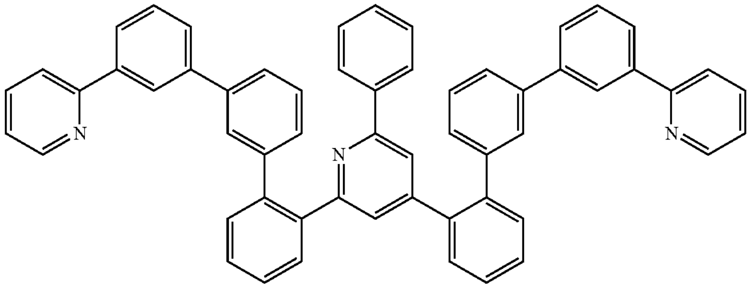
[B-37]
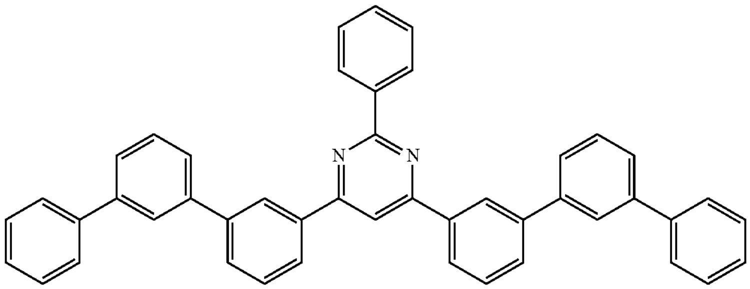

-continued
[B-38]
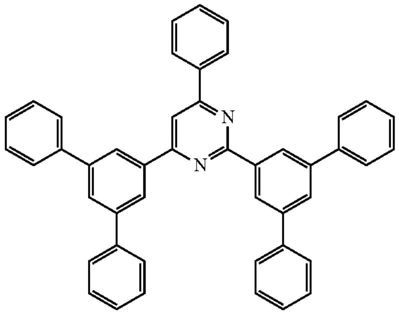
[B-39]
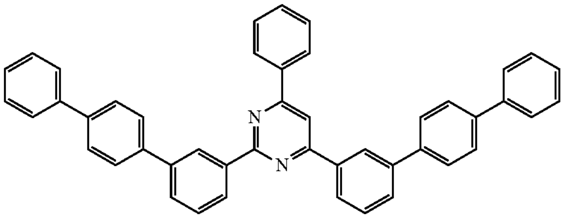
[B-40]
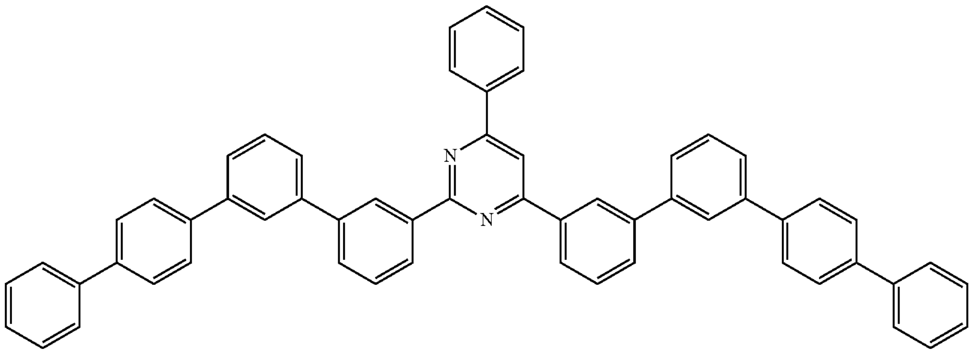
[B-41]
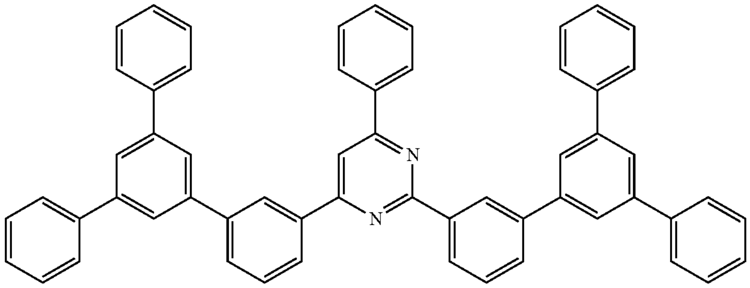
[B-42]
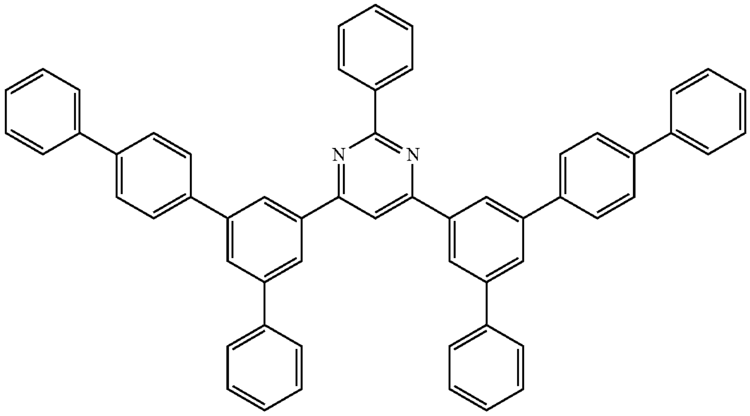

-continued
[B-43]
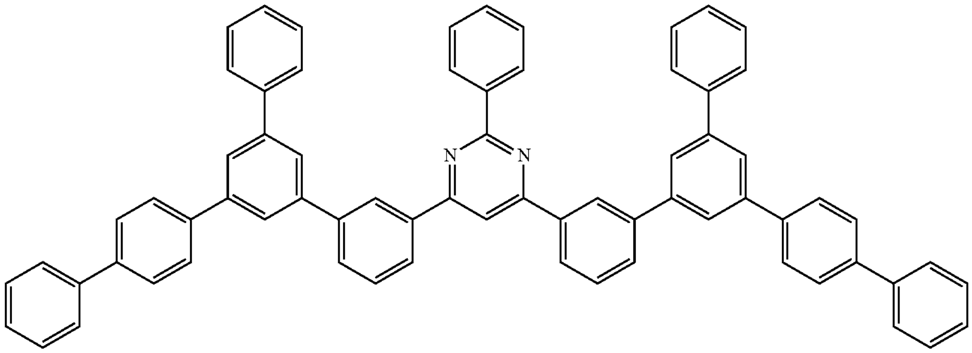
[B-44]
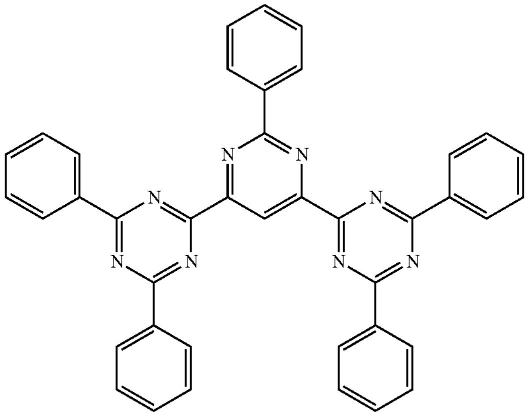
[B-45]
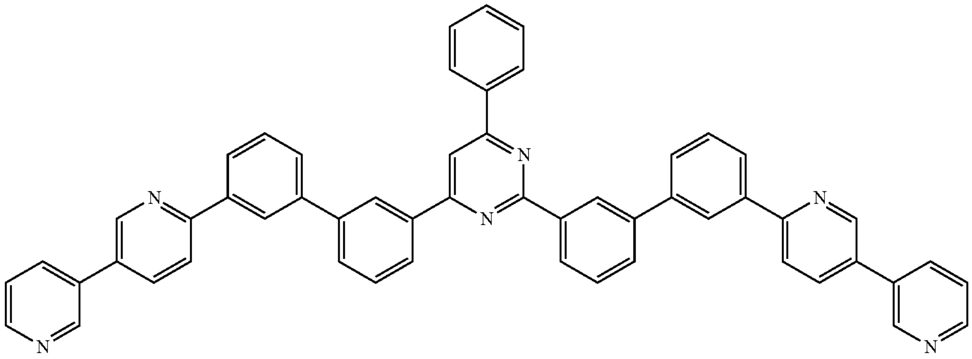
[B-46]
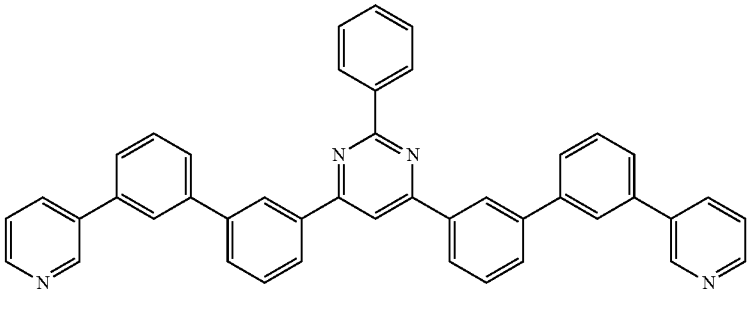

-continued
[B-47]
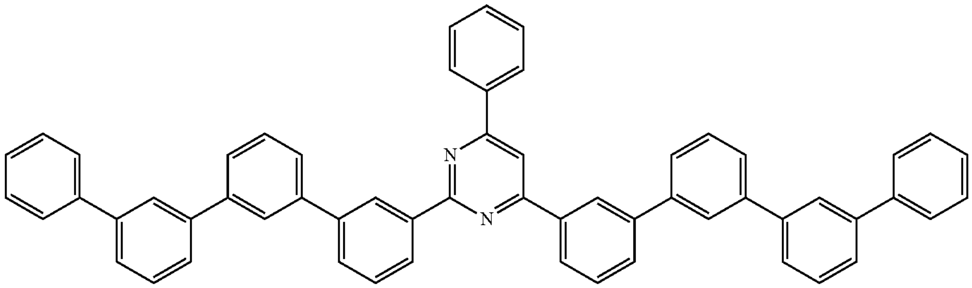
[B-48]
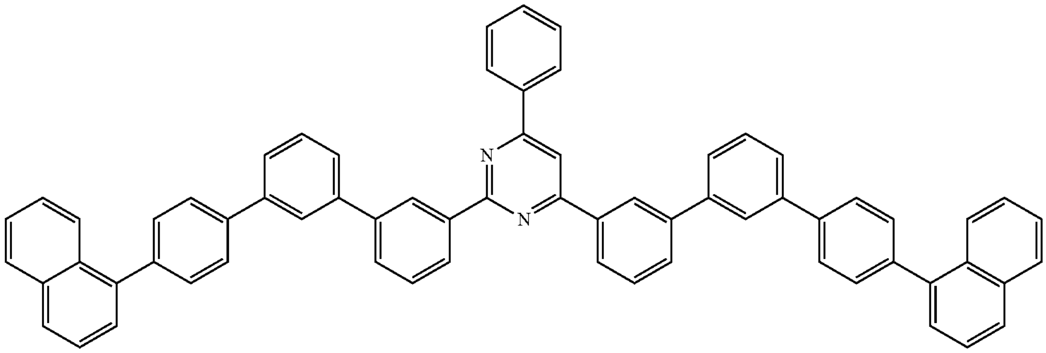
[B-49]
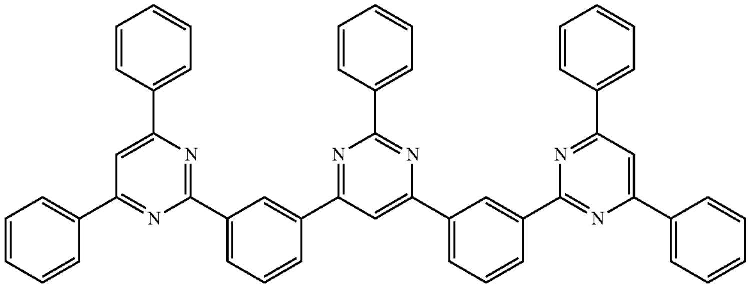
[B-50]
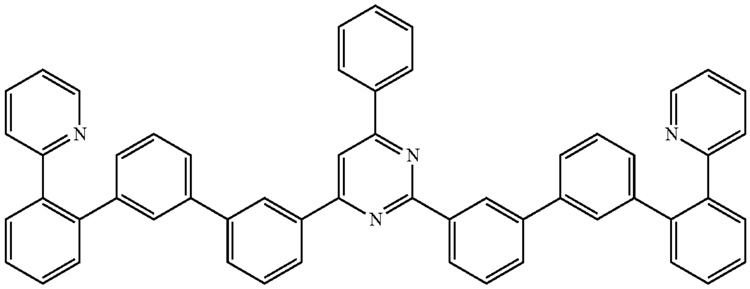

-continued
[B-51]
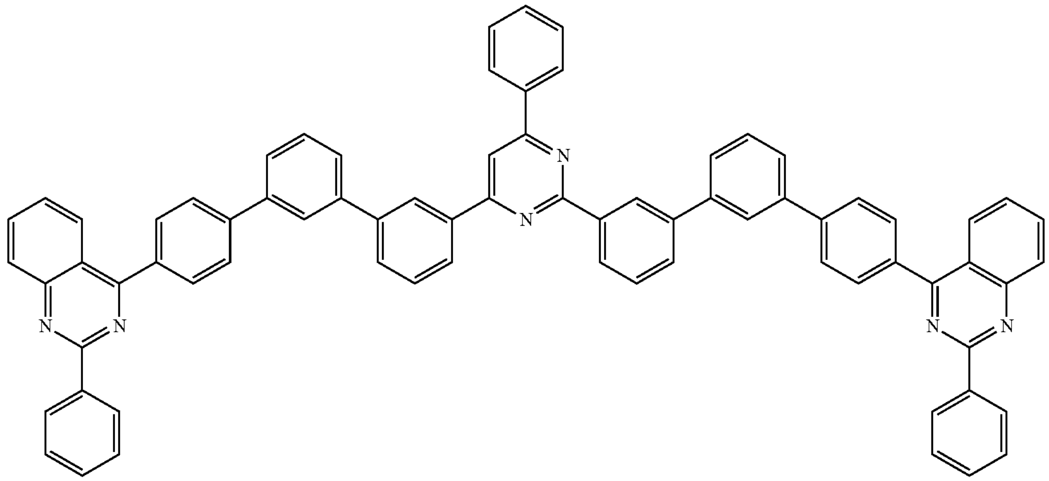
[B-52]
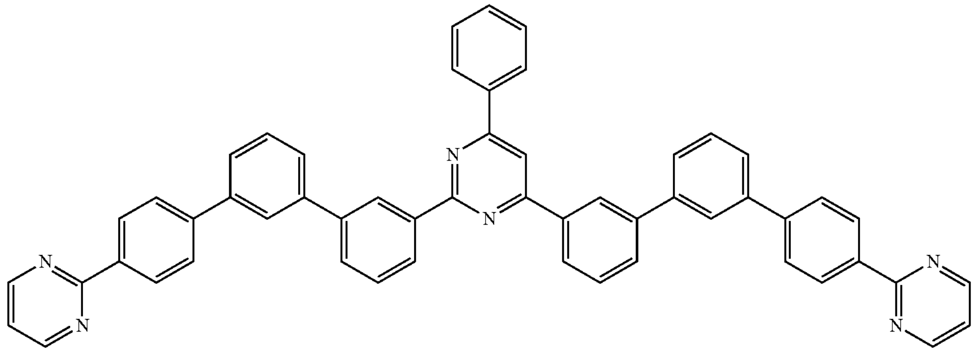
[B-53]
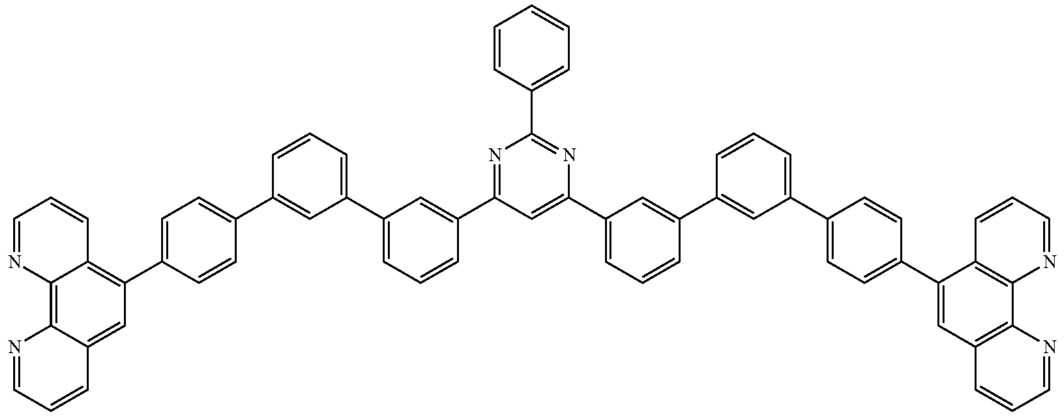
[B-54]
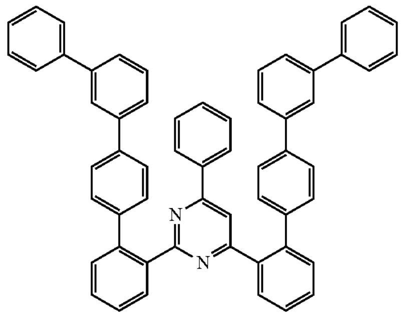
[B-55]
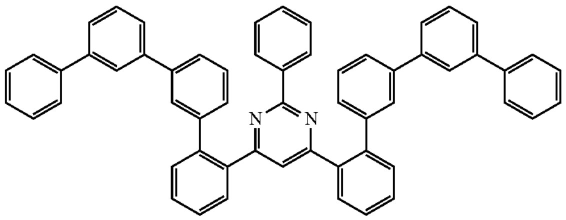

-continued
[B-56]
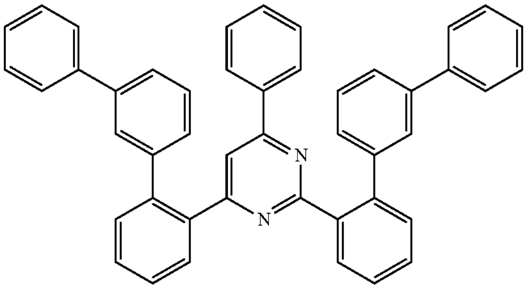
[B-57]
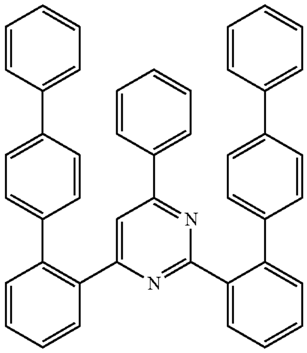
[B-58]
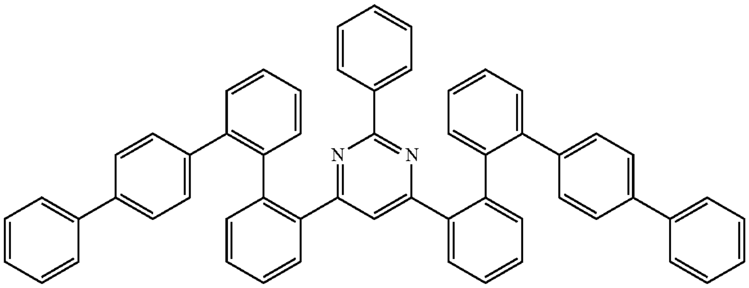
[B-59]
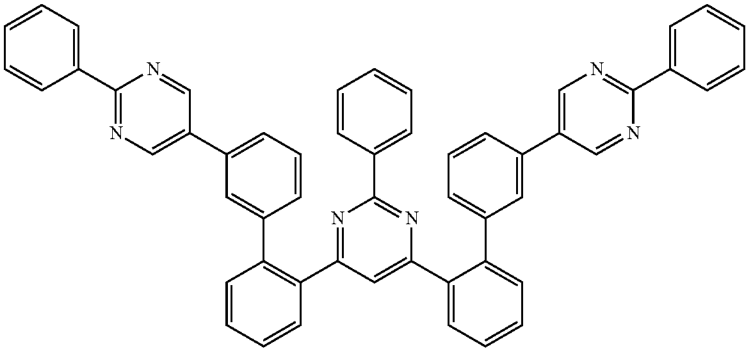
[B-60]
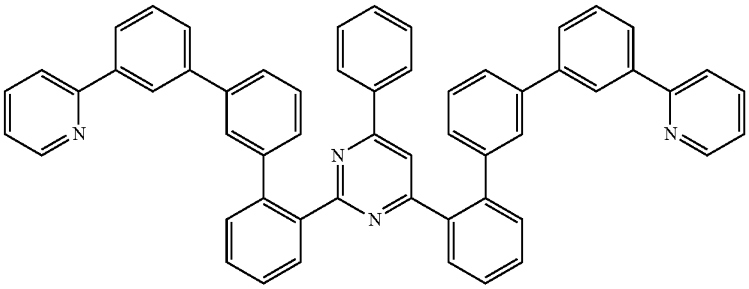

-continued
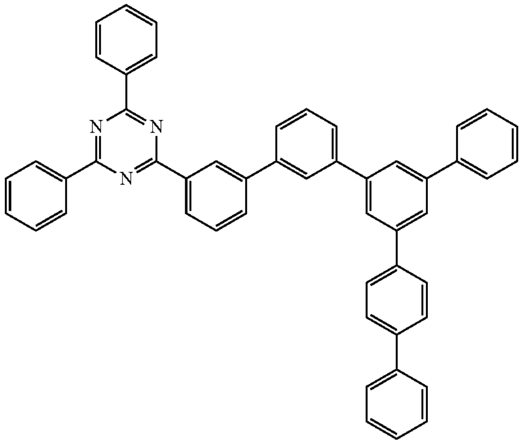
[B-61]
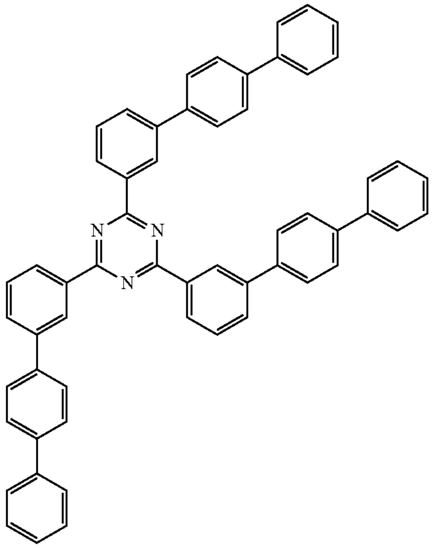
[B-62]
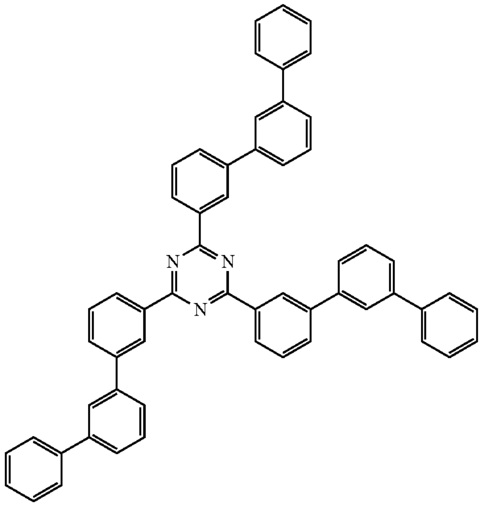
[B-63]
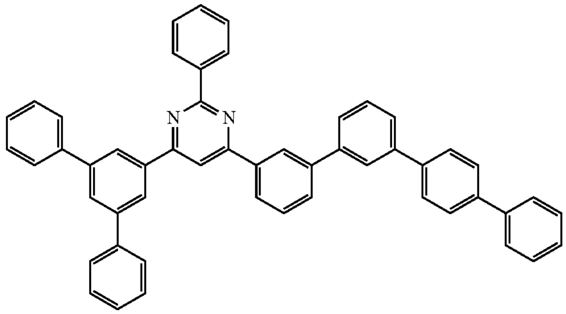
[B-64]
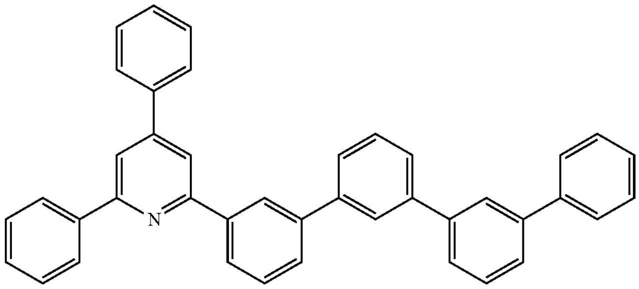
[B-65]

-continued

[B-66]

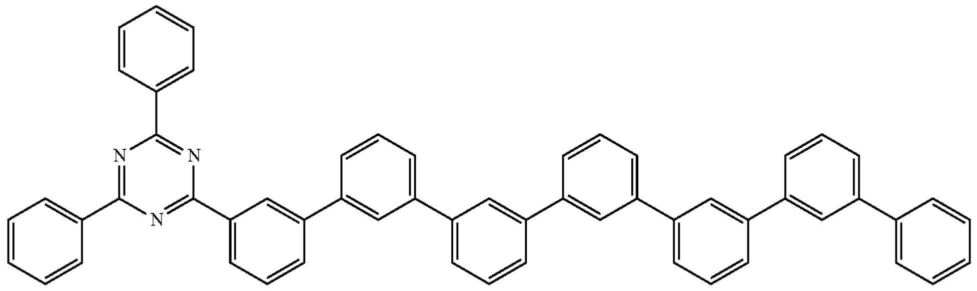

The first compound has the above kink structure and thus, may appropriately localize charges and effectively control a flow of a conjugation system and resultantly, improve efficiency of an organic optoelectronic device manufactured by using the compound.

The auxiliary hole transport layer 33 includes a second compound having excellent hole transport characteristics and thus, may reduce a HOMO energy level difference between the hole transport layer 31 and the light-emitting layer 32, and adjust hole injection characteristics and resultantly, decrease accumulation of holes on the interface of the auxiliary hole transport is layer 33 and the light-emitting layer 32 and thus, a quenching phenomenon that excitons disappear on the interface due to polaron. Accordingly, the device may be less deteriorated and stabilized and thus, have improved efficiency and life-span.

The second compound may be a compound expressed by Chemical Formula 2.

[Chemical Formula 2]

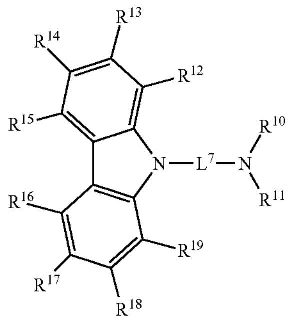

In Chemical Formula 2, $R^{10}$ to $R^{19}$ are independently hydrogen, deuterium, a substituted or unsubstituted C6 to C30 aryl group, a substituted or unsubstituted fluorenyl group, or a combination thereof, $L^1$ is a substituted or unsubstituted C2 to C10 alkenylene group, a substituted or unsubstituted C6 to C30 arylene group, a substituted or unsubstituted C2 to C30 heteroarylene group, or a combination thereof.

The second compound may be, for example expressed by one of Chemical Formula 2-i to Chemical Formula 2-iii.

[Chemical Formula 2-i]

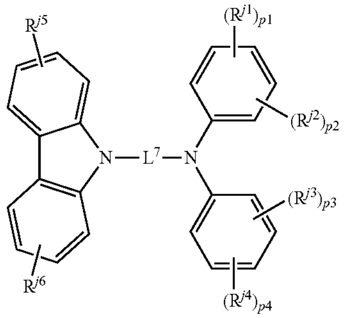

[Chemical Formula 2-ii]

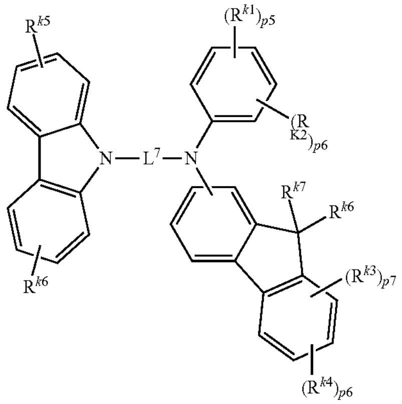

[Chemical Formula 2-iii]

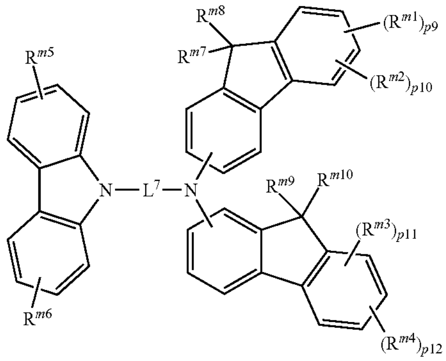

In Chemical Formula 2-i, $L^7$ is a substituted or unsubstituted C6 to C30 arylene group, a substituted or unsubstituted C2 to C30 heteroarylene group, or a combination thereof, $R^{j1}$ to $R^{j6}$ are independently a substituted or unsubstituted C1 to C10 alkyl group, a substituted or unsubstituted C1 to C30 aryl group, a C2 to C30 heteroarylene group, or a combination thereof, and p1 to p4 are independently an integer of 0 to 5, provided that $0 \leq p1+p2 \leq 5$, and $0 \leq p3+p4 \leq 5$.

In Chemical Formula 2-ii, $L^7$ is a substituted or unsubstituted C6 to C30 arylene group, a substituted or unsubstituted C2 to C30 heteroarylene group, or a combination thereof, $R^{k1}$ to $R^{k6}$ are independently a substituted or unsubstituted C1 to C10 alkyl group, a substituted or unsubstituted C1 to C30 aryl group, a substituted or unsubstituted C2 to C30 heteroarylene group, or a combination thereof, $R^{k7}$ and $R^{k8}$ are independently hydrogen or a substituted or unsubstituted C1 to C10 alkyl group substituted or unsubstituted C1 to C30 aryl group, a substituted or unsubstituted C2 to C30 heteroarylene group, or a combination thereof, p5 and p6 are independently an integer of 0 to 5, provided that $0 \leq p5+p6 \leq 5$, and p7 and p8 are independently an integer of 0 to 4, provided that $0 \leq p7+p8 \leq 4$.

In Chemical Formula 2-iii, $L^7$ is a substituted or unsubstituted C6 to C30 arylene group, a substituted or unsubstituted C2 to C30 heteroarylene group, or a combination thereof, $R^{m1}$ to $R^{m6}$ are independently a substituted or unsubstituted C1 to C10 alkyl group, a substituted or unsubstituted C1 to C30 aryl group, or a combination thereof $R^{m7}$ to $R^{m10}$ are independently hydrogen or a substituted or unsubstituted C1 to C10 alkyl group, a substituted or unsubstituted C1 to C30 aryl group, a substituted or unsubstituted C2 to C30 heteroarylene group, or a combination thereof, and p9 to p12 are independently an integer of 0 to 4, provided that $0 \leq p9+p10 \leq 4$ and $0 \leq p11+p12 \leq 4$.

For example, $L^7$ may be one of linking groups of Group A, but is not limited thereto.

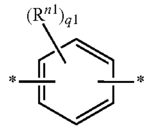

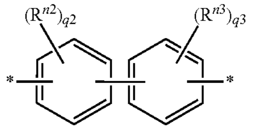

-continued

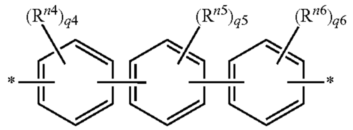

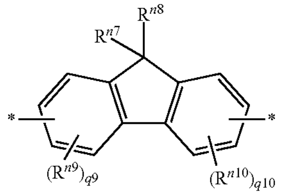

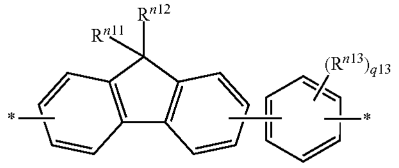

In Group A, $R^{n1}$ to $R^{n13}$ are independently hydrogen, a substituted or unsubstituted C1 to C10 alkyl group, or a substituted or unsubstituted C6 to C20 aryl group, q1 to q6 and q13 are independently an integer of 0 to 4, and q9 and q10 are independently an integer of 0 to 3.

For example, $R^{n1}$ to $R^{n6}$, $R^{n9}$, $R^{n10}$, and $R^{n13}$ may independently be hydrogen or a substituted or unsubstituted C6 to C20 aryl group.

For example, $R^{n7}$, $R^{n8}$, $R^{n11}$, and $R^{n12}$ may independently be hydrogen or a substituted or unsubstituted C1 to C10 alkyl group.

As one example of the present invention, in [Chemical Formula 2], $R^{10}$ to $R^{19}$ may independently be hydrogen, deuterium, a substituted or unsubstituted C6 to C30 aryl group, or a combination thereof, and $L^7$ may be a substituted or unsubstituted C6 to C30 arylene group.

As one example of the present invention, in [Chemical Formula 2], [Chemical Formula 2-i], [Chemical Formula 2-ii] and [Chemical Formula 2-iii], the C6 to C30 arylene group may be a phenylene group, a biphenylene group, a terphenylene group, a tetraphenylene group, a fluorenylene group, or a combination thereof, and the C6 to C30 aryl group may be a phenyl group, a biphenyl group, a terphenyl group, a tetraphenyl group, a fluorenyl group, or a combination thereof.

The second compound may be, for example expressed by one of Chemical Formula P-1 to Chemical Formula P-117, but is not limited thereto.

P-1

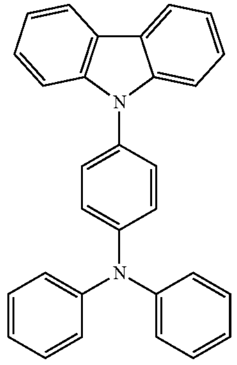

P-2

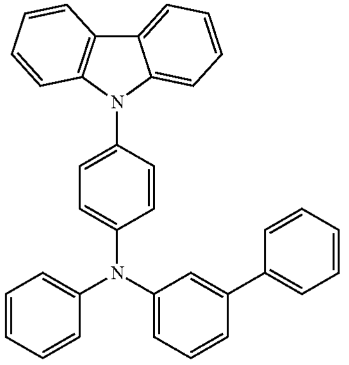

-continued
P-3
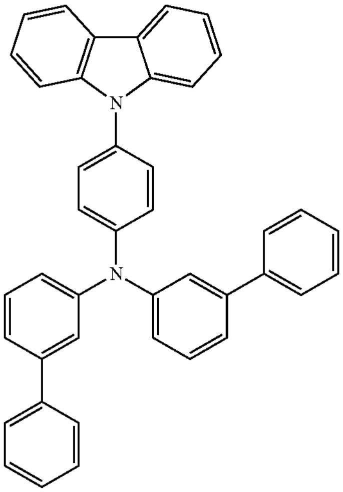
P-4
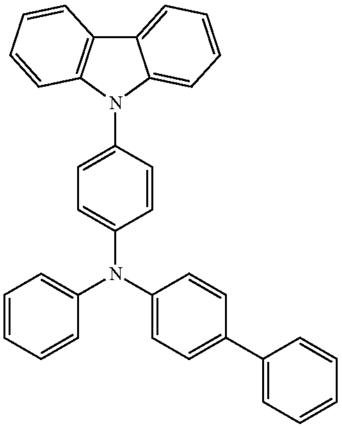
P-5
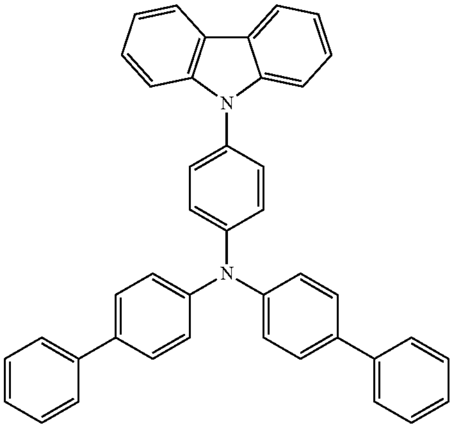
P-6
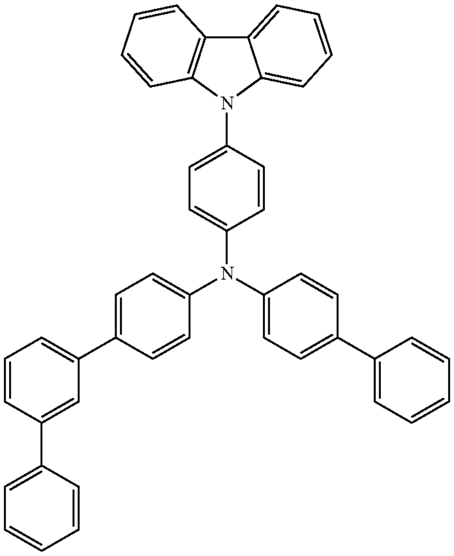
P-7
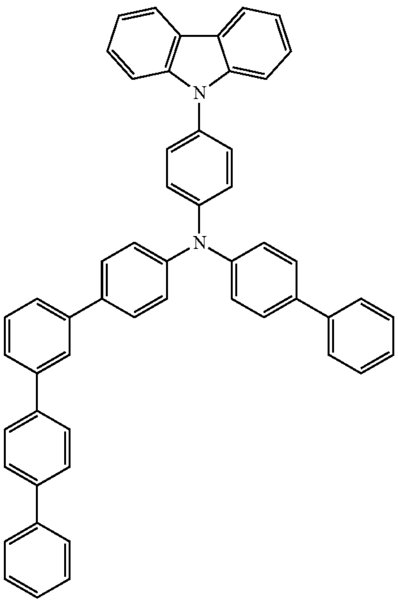
P-8
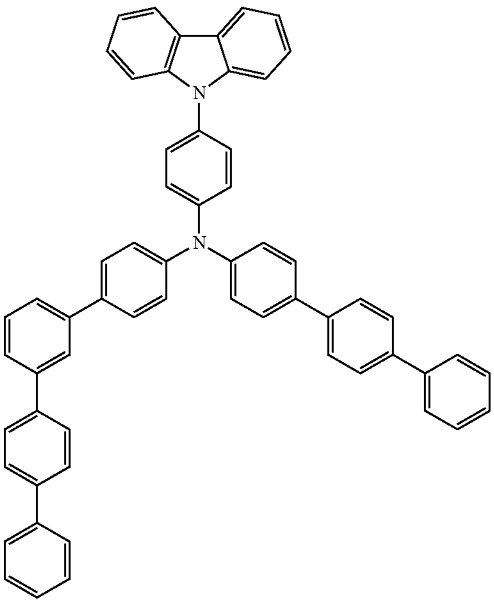

-continued
P-9
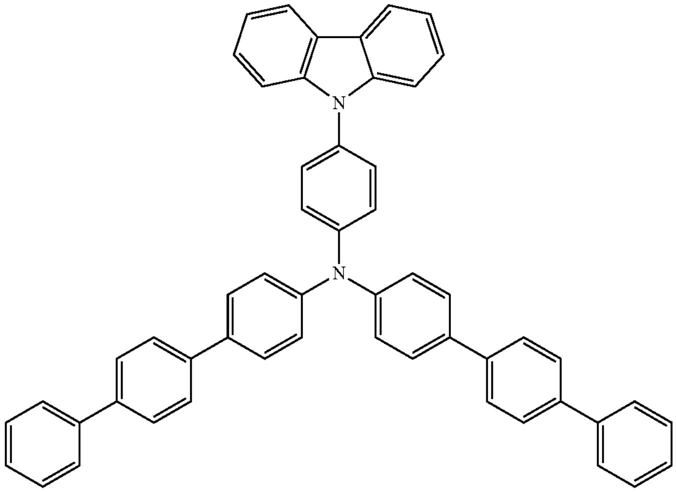
P-10
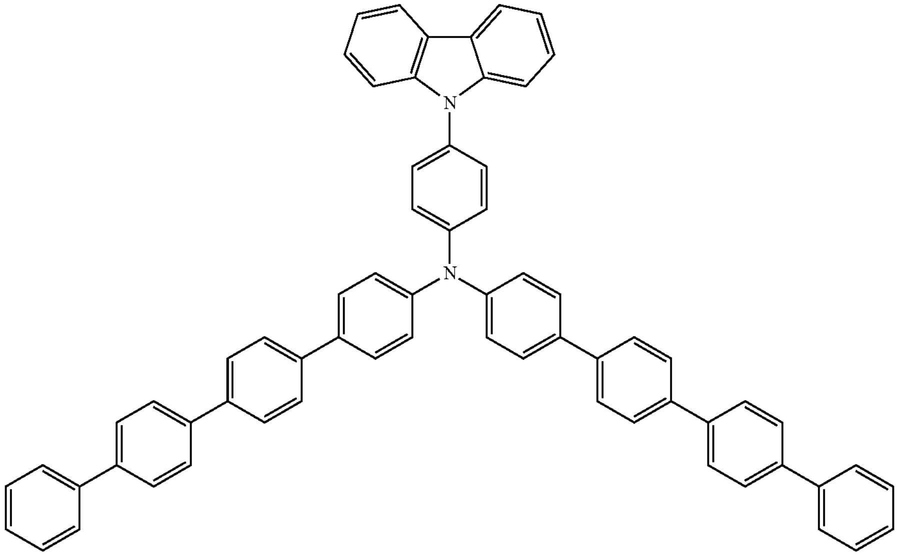
P-11
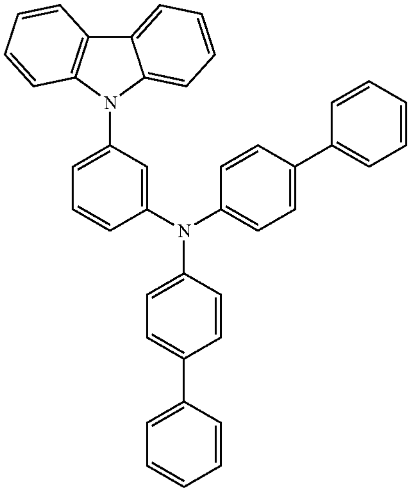
P-12
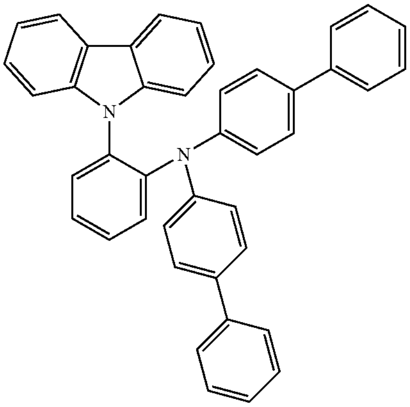

-continued
P-13
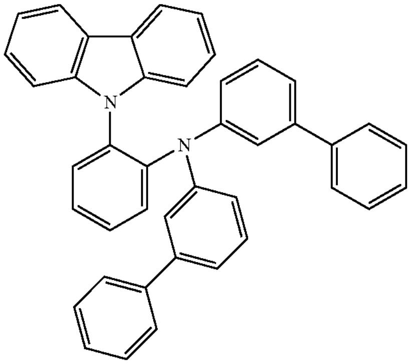
P-14
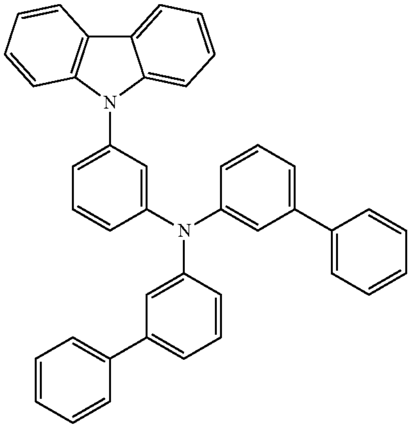
P-15
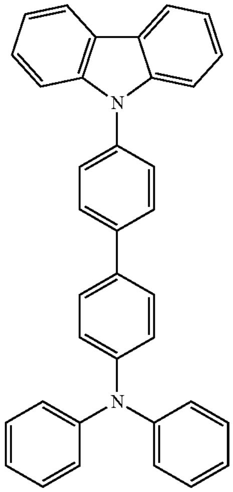
P-16
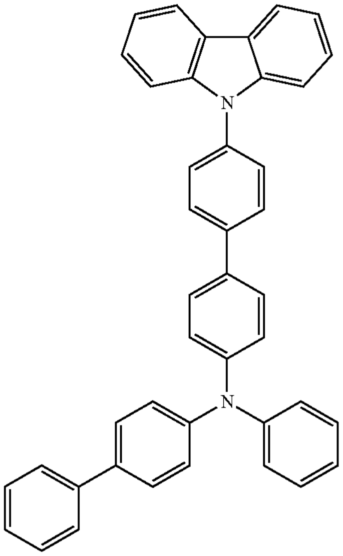
P-17
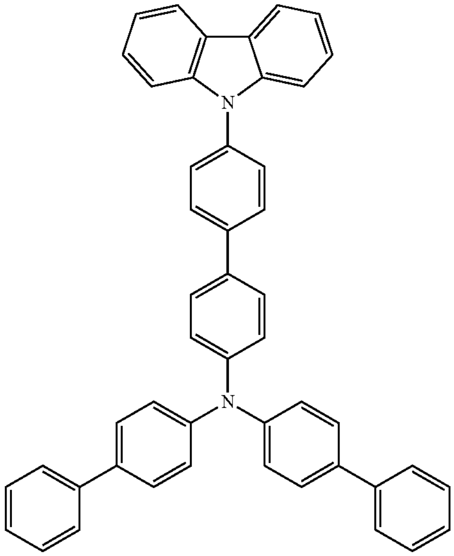
P-18
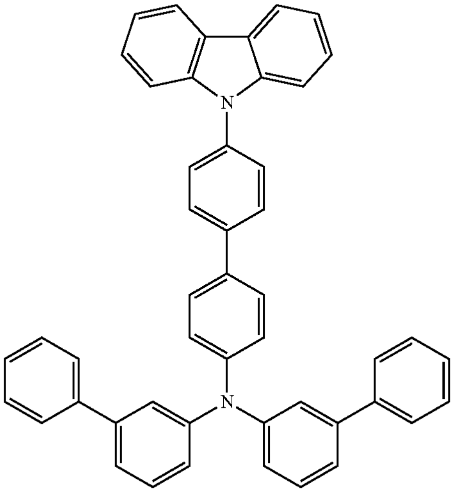

-continued
P-19
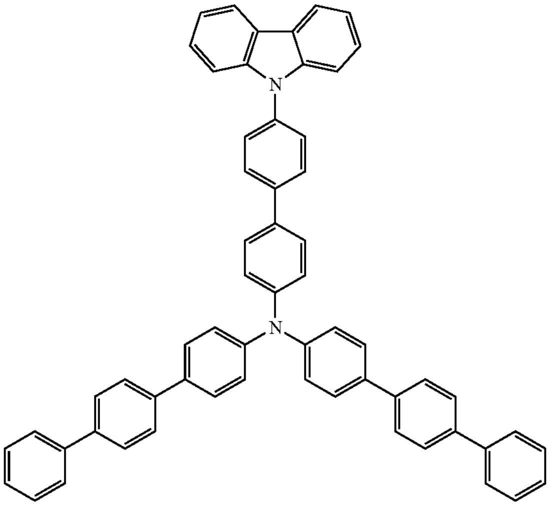
P-20
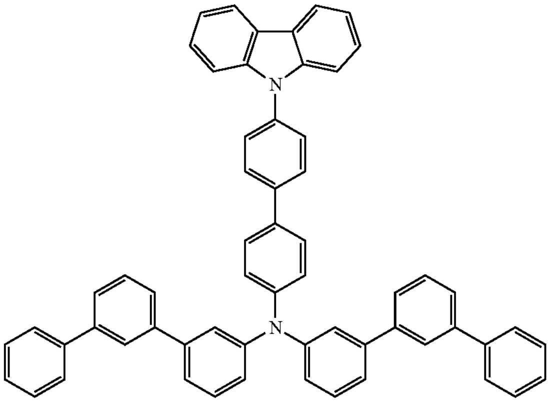
P-21
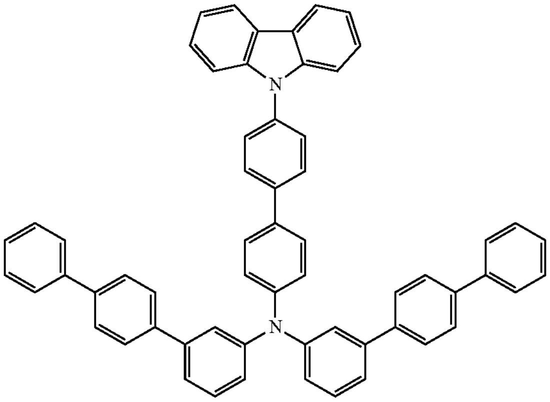
P-22
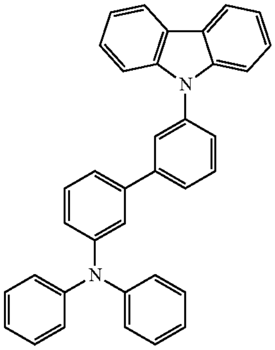
P-23
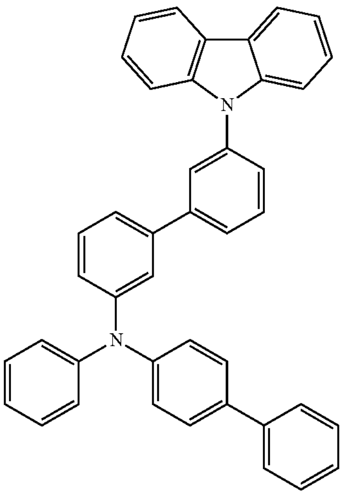
P-24
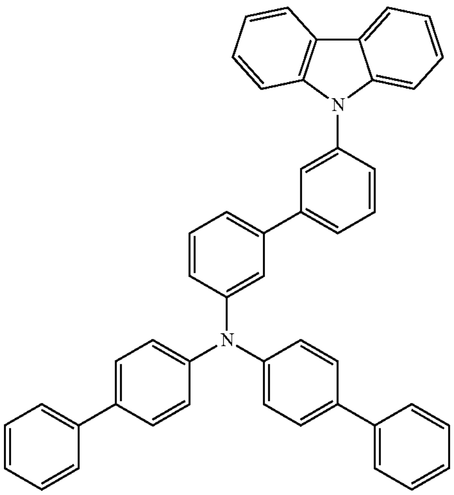

-continued
P-25
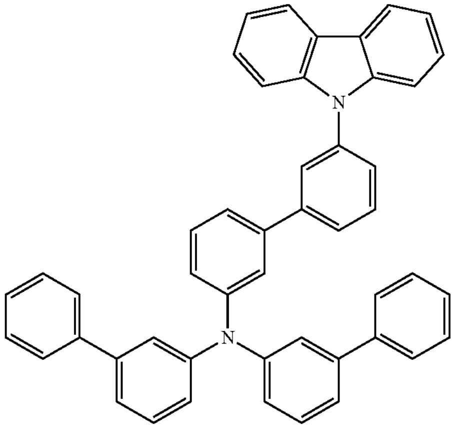
P-26
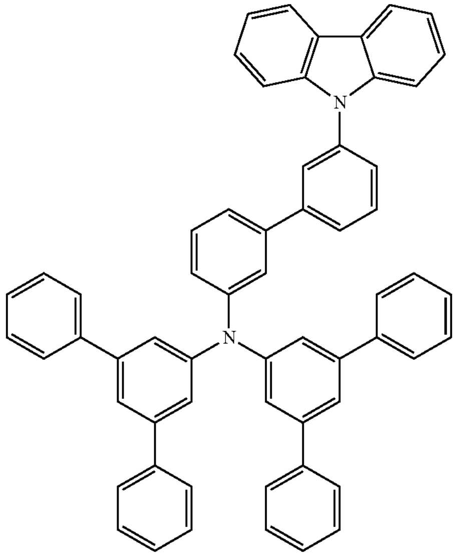
P-27
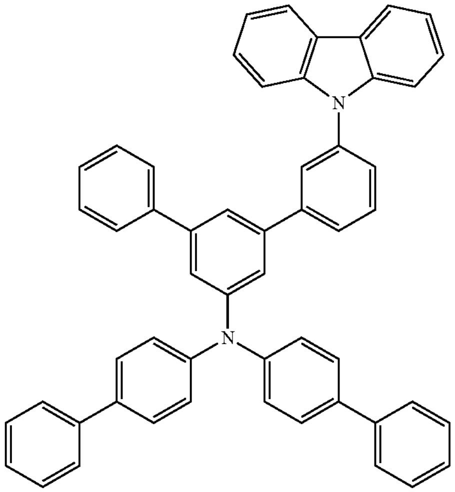
P-28
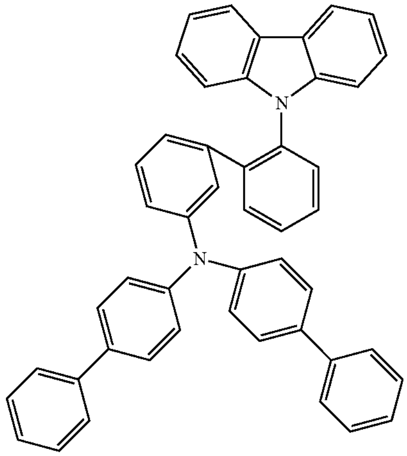
P-29
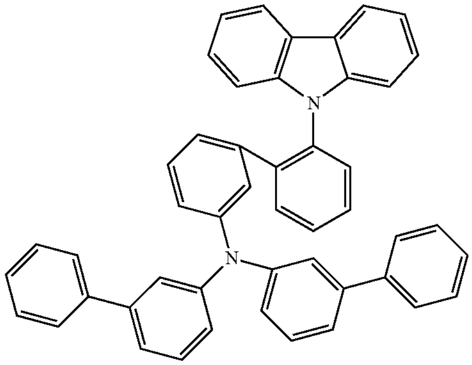
P-30
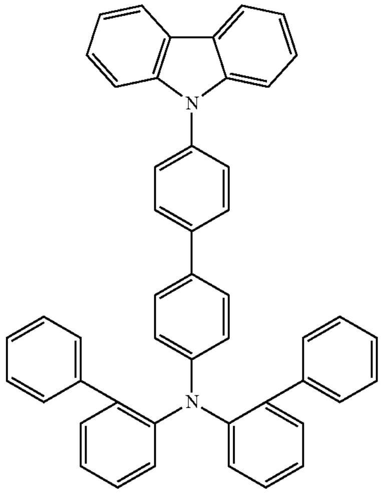

-continued
P-31
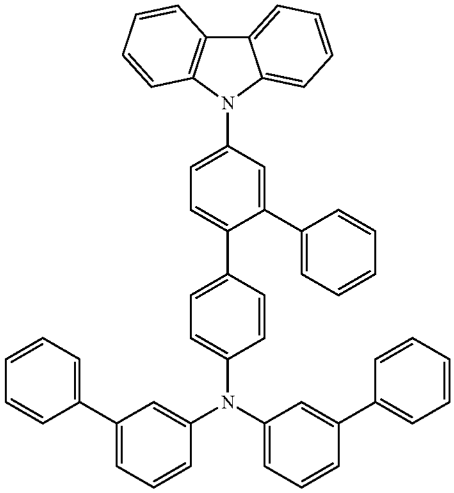
P-32
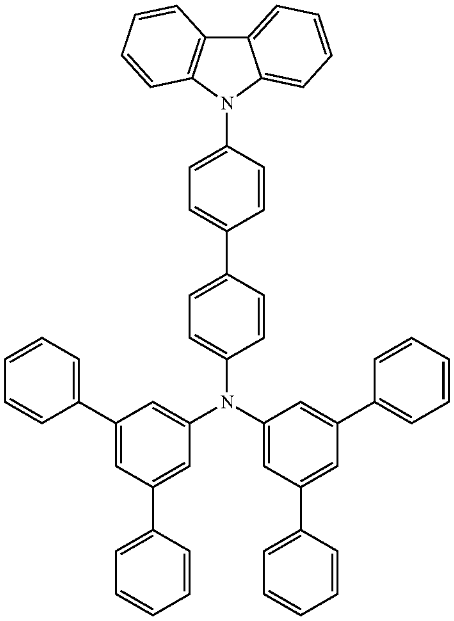
P-33
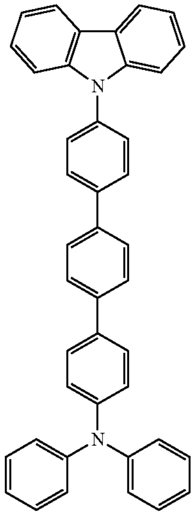
P-34
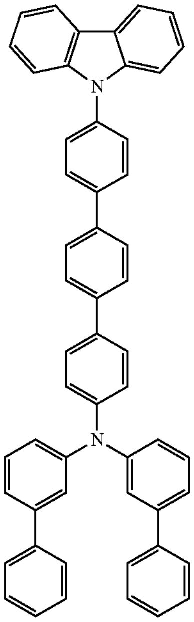

-continued
P-35
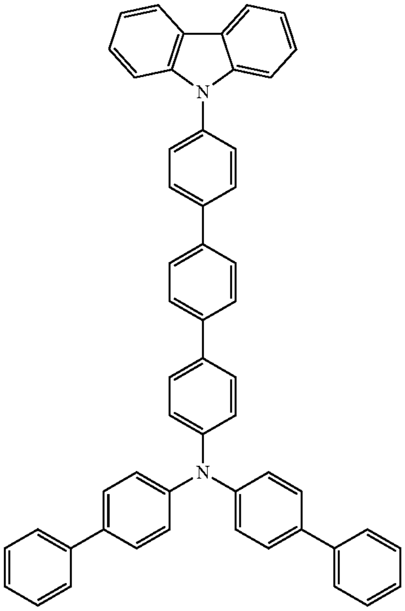
P-36
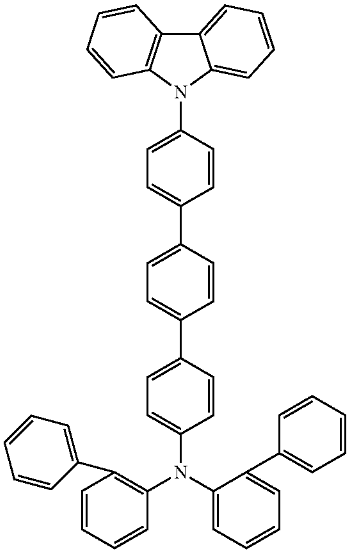
P-37
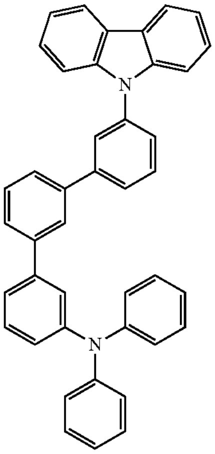
P-38
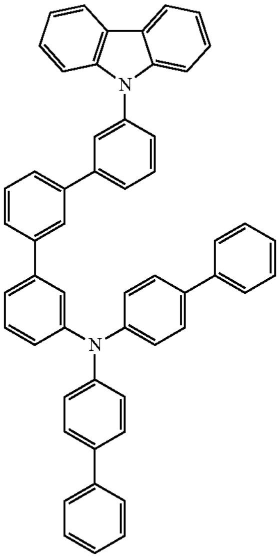

-continued
P-39
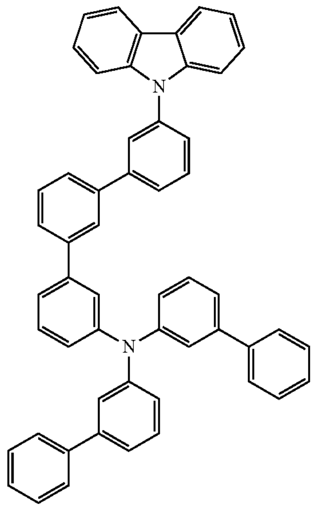
P-40
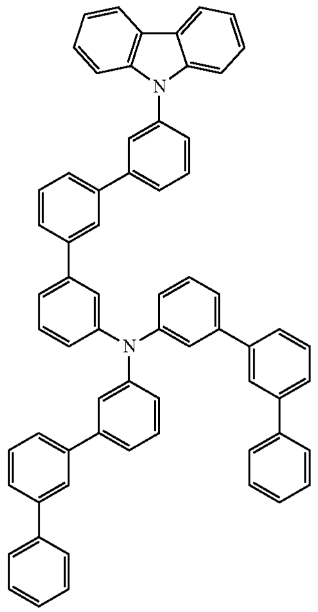
P-41
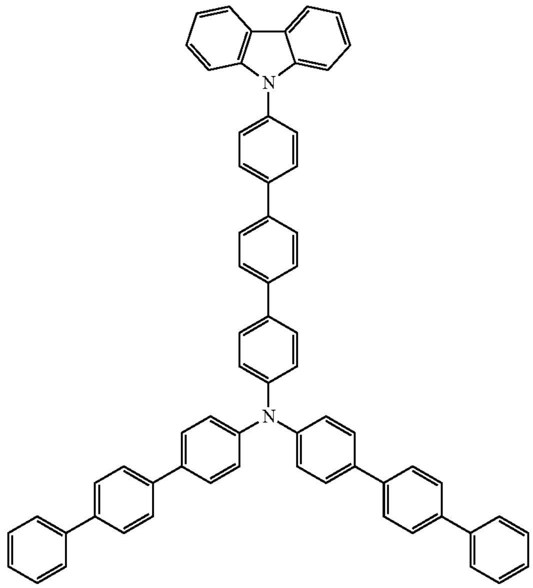
P-42
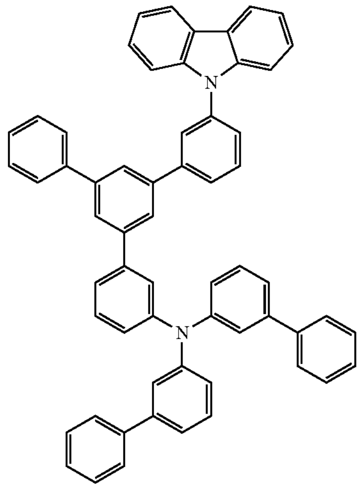

-continued
P-43
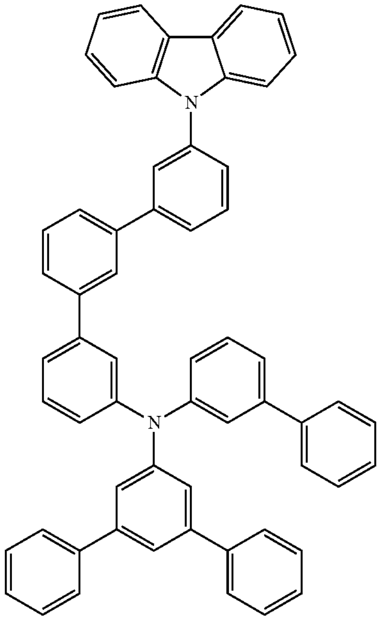
P-44
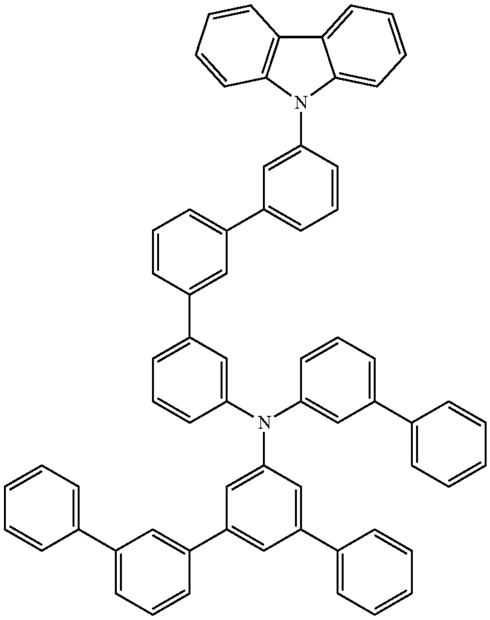
P-45
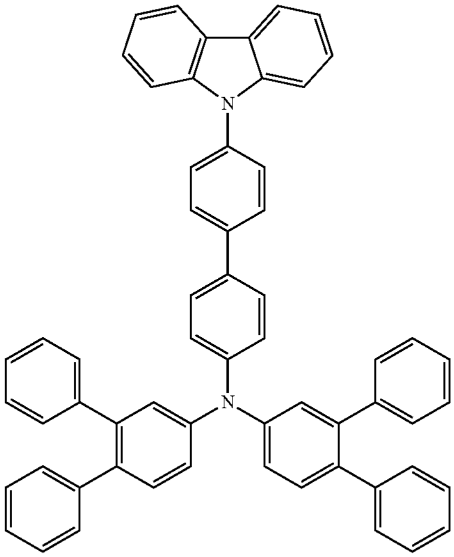
P-46
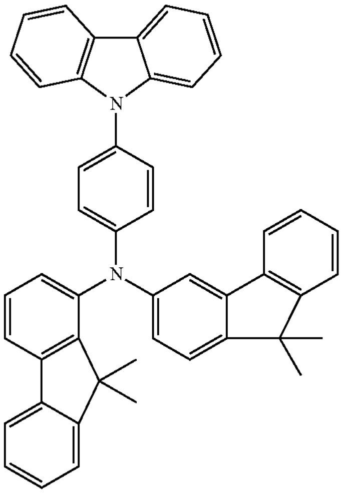
P-47
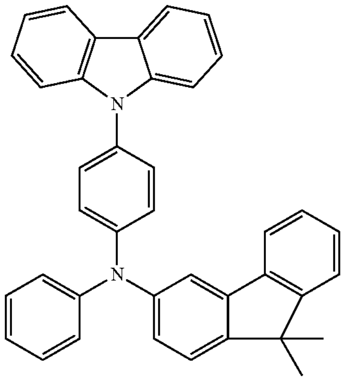
P-48
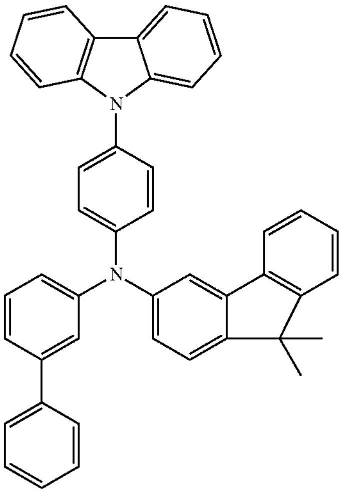

-continued
P-49
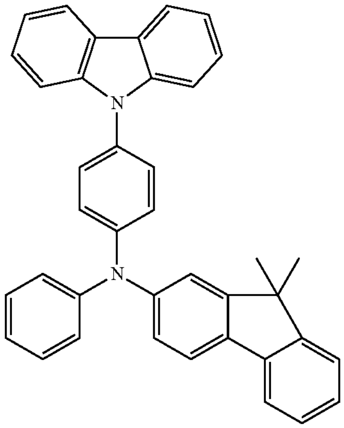
P-50
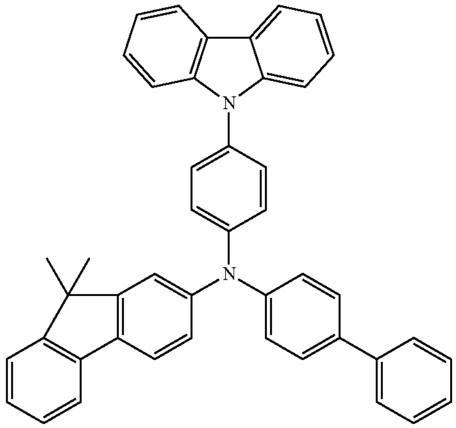
P-51
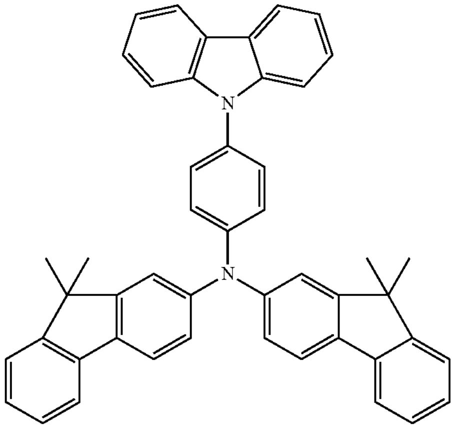
P-52
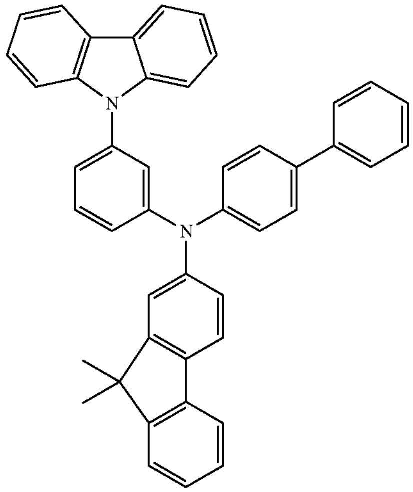
P-53
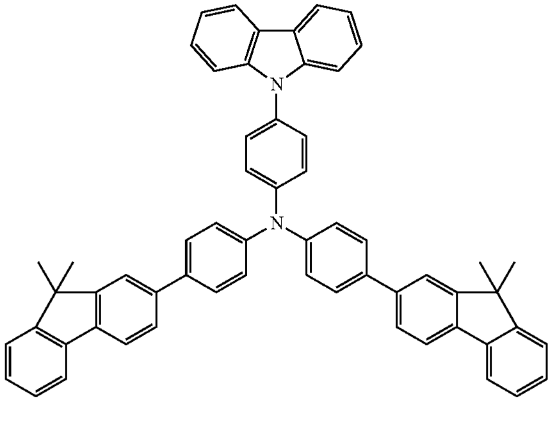
P-54
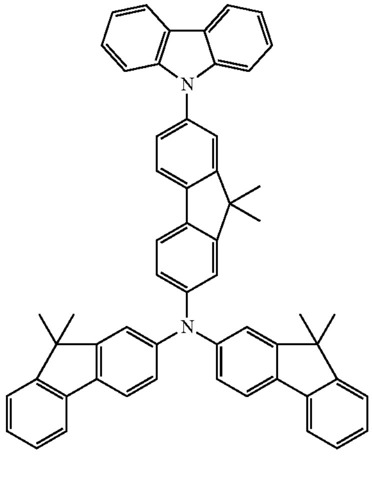

-continued
P-55
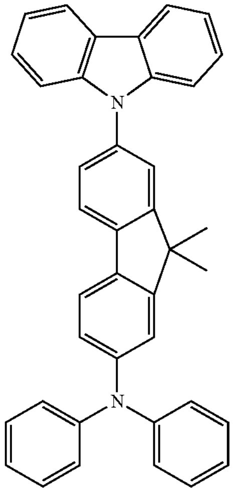
P-56
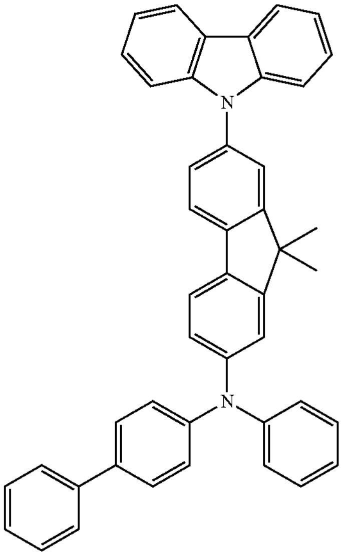
P-57
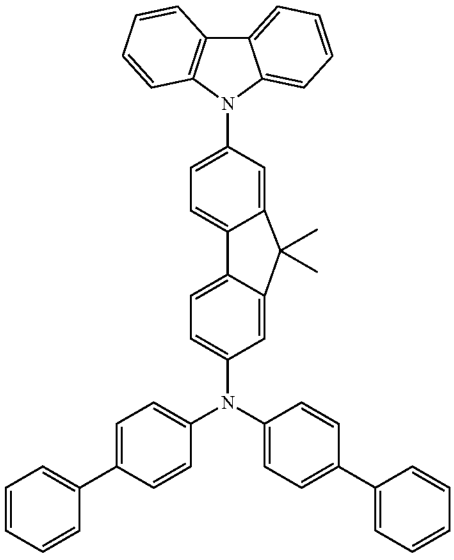
P-58
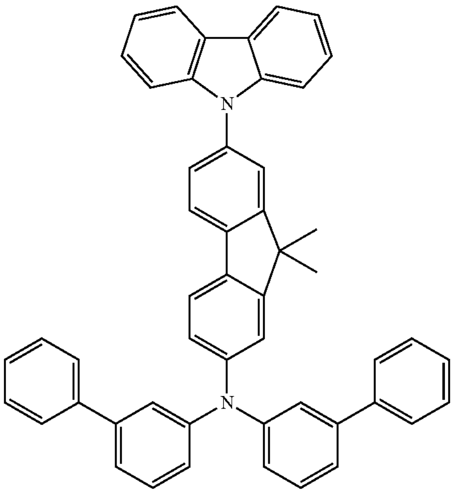
P-59
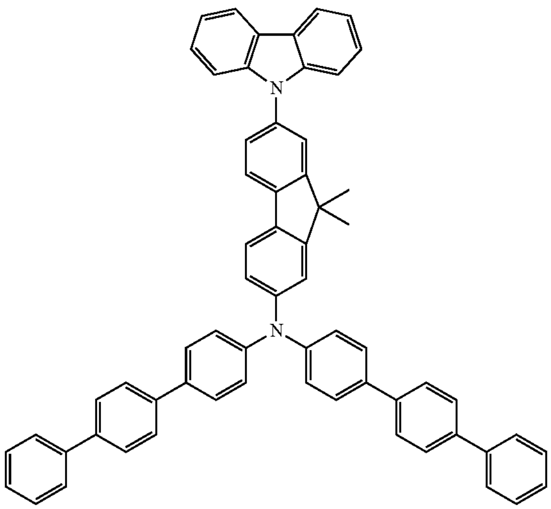
P-60
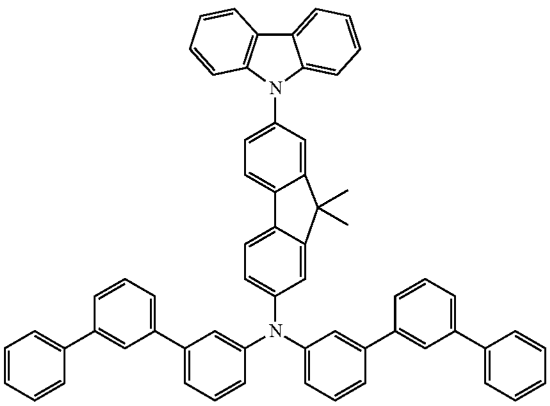

-continued
P-61
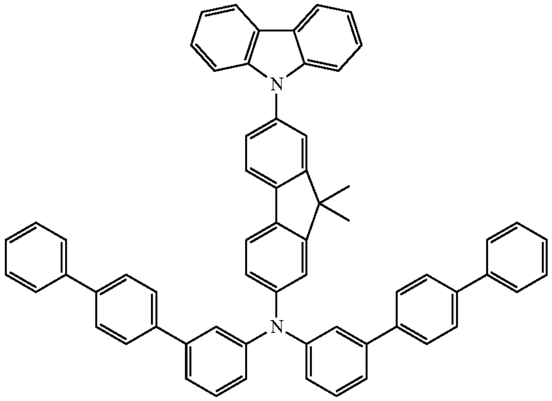
P-62
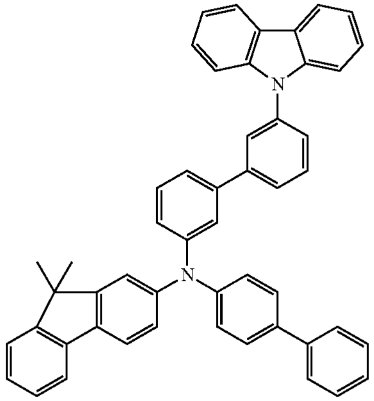
P-63
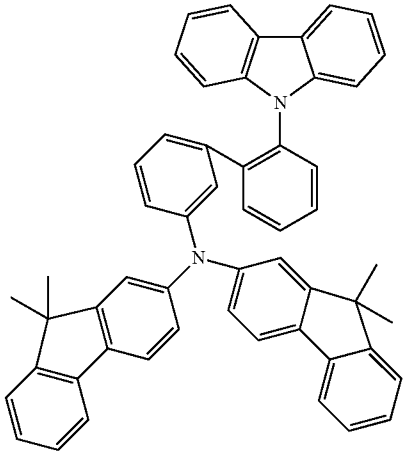
P-64
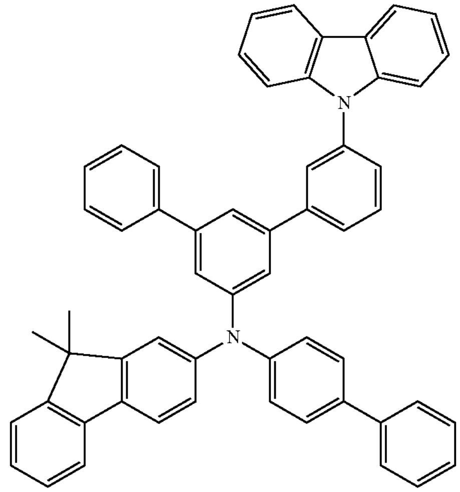

-continued
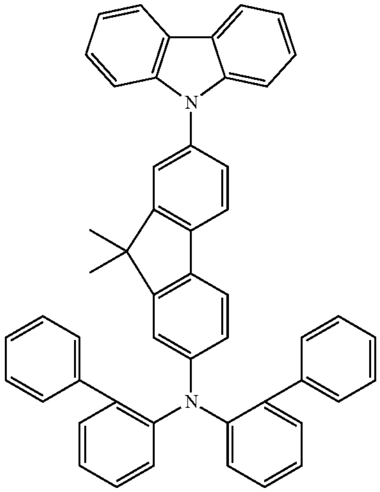
P-65
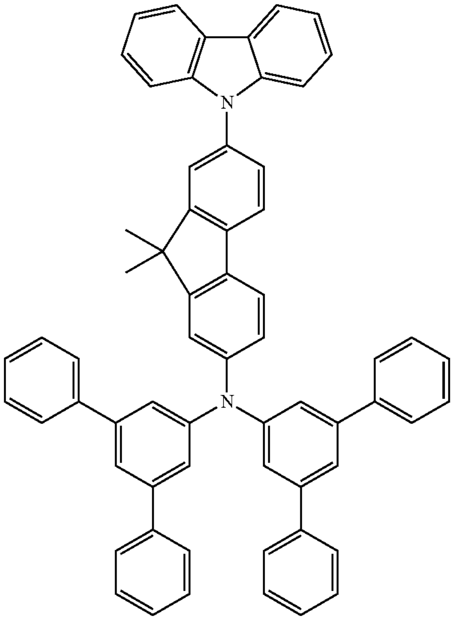
P-66
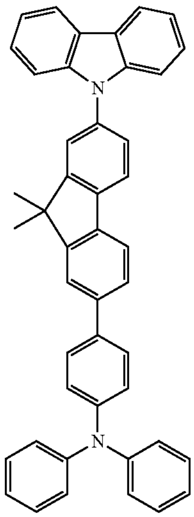
P-67
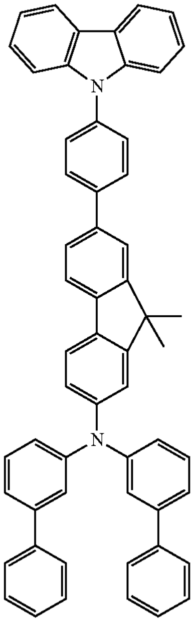
P-68

-continued
P-69
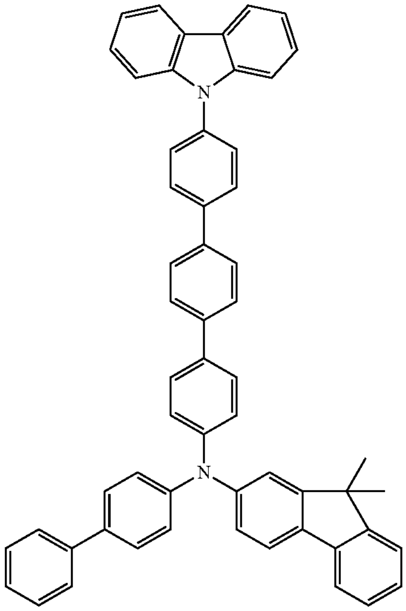
P-70
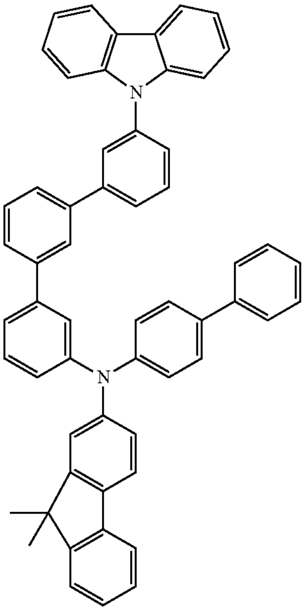
P-71
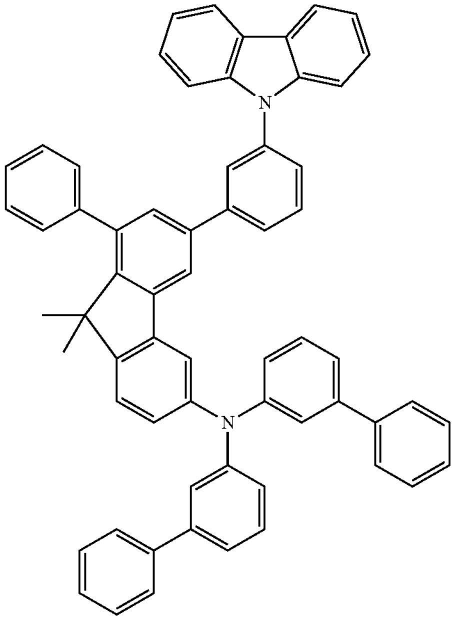
P-72
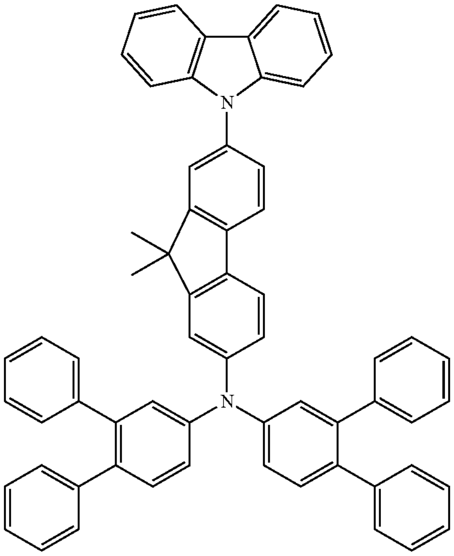

-continued
P-73
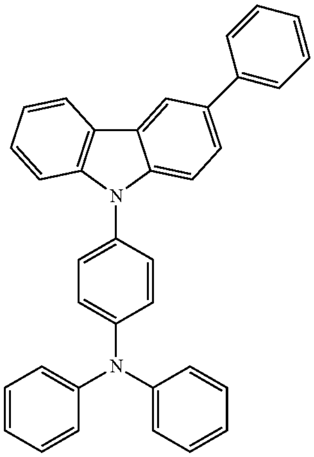
P-74
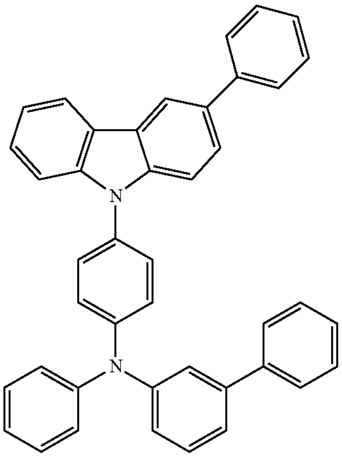
P-75
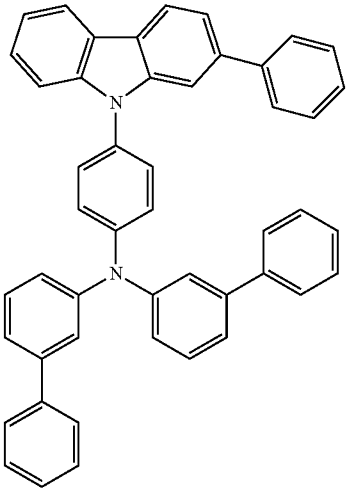
P-76
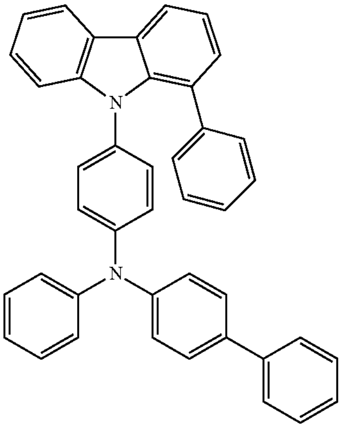
P-77
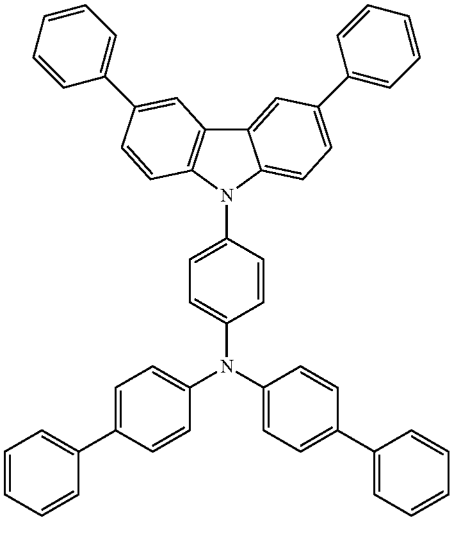
P-78
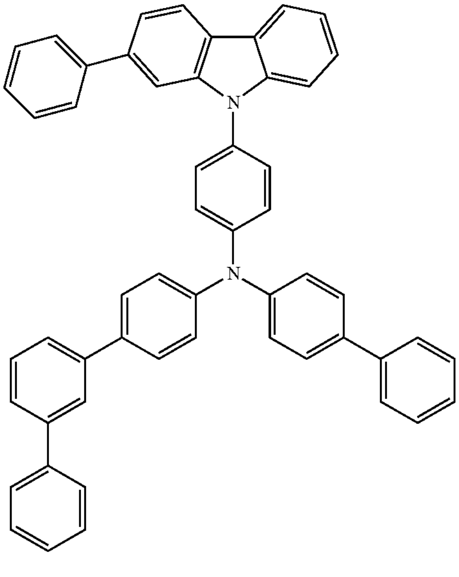

-continued
P-79
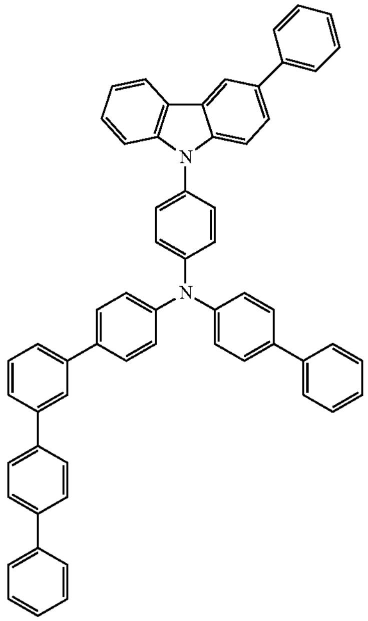
P-80
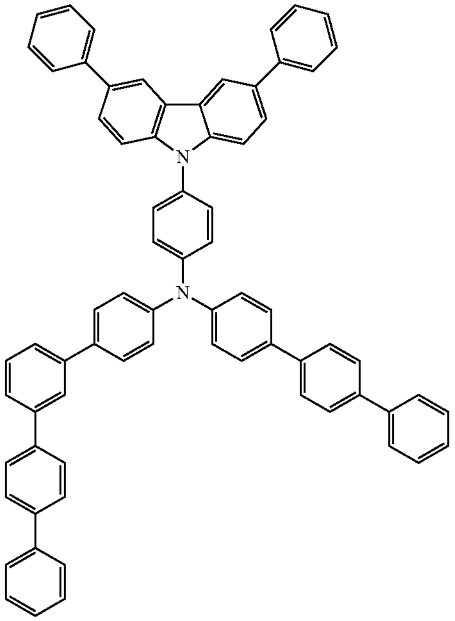
P-81
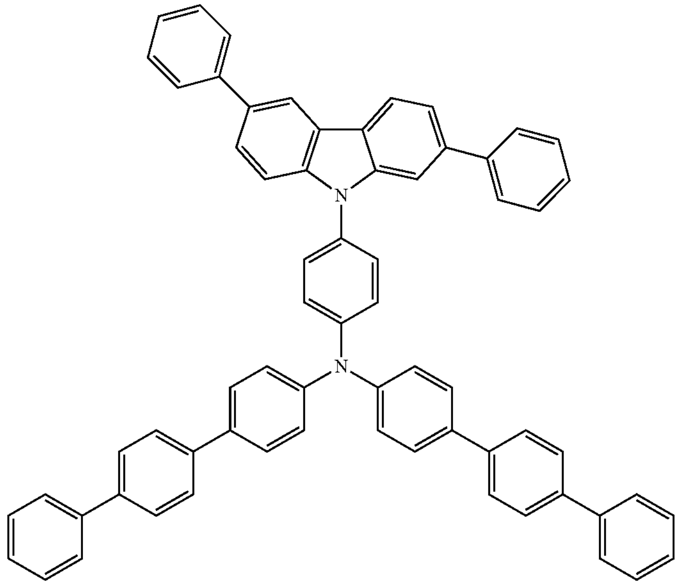

-continued
P-82
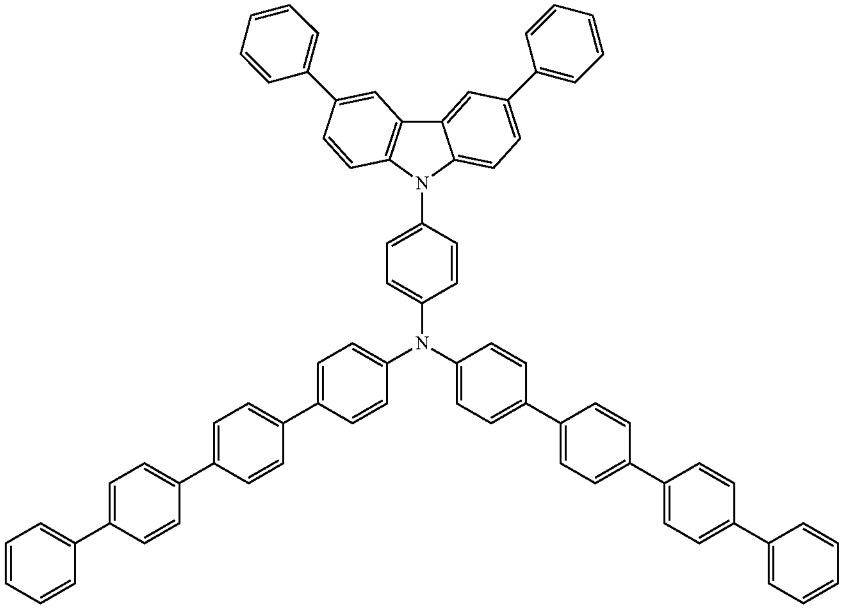
P-83
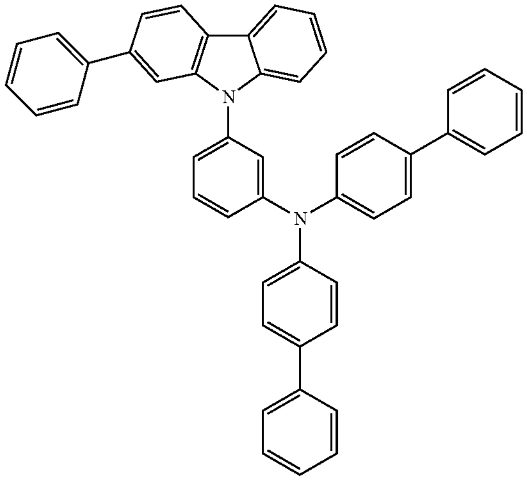
P-84
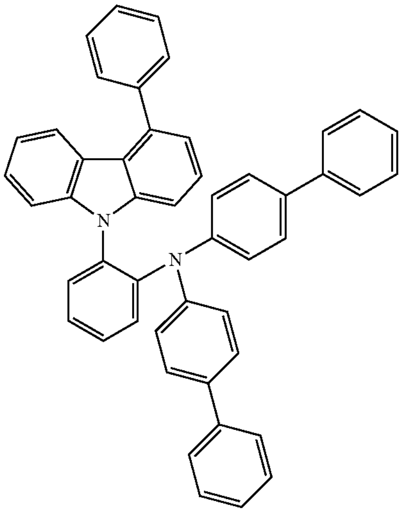
P-85
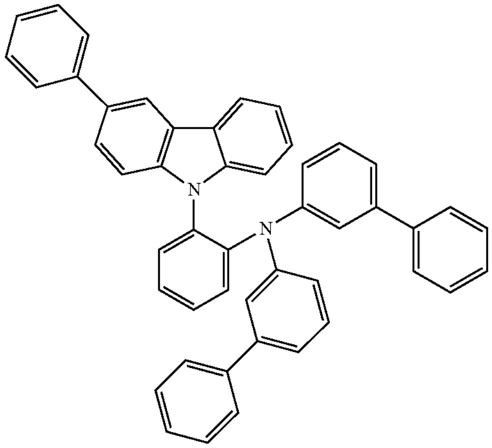
P-86
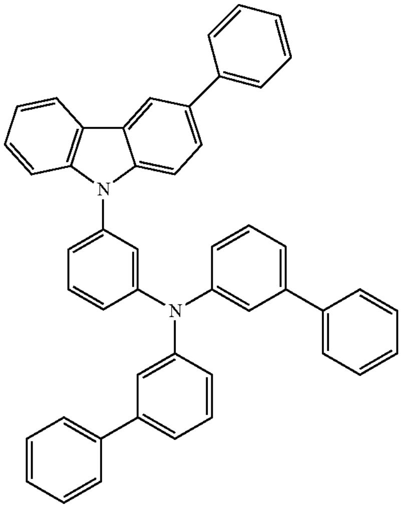

-continued
P-87
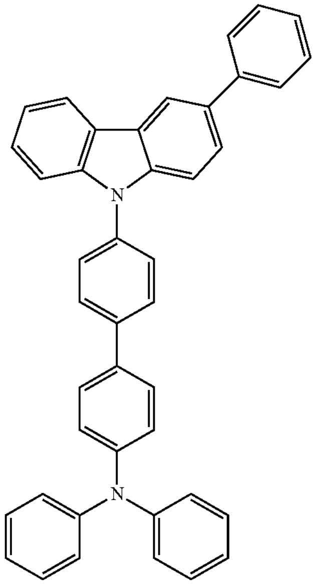
P-88
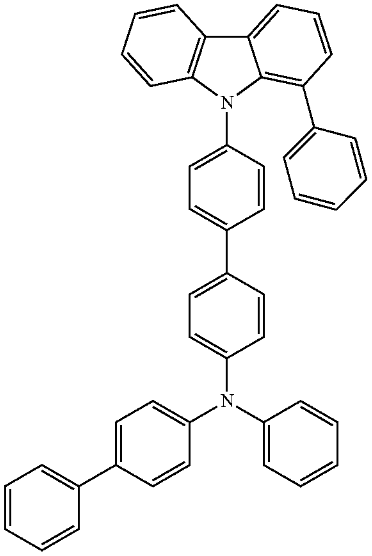
P-89
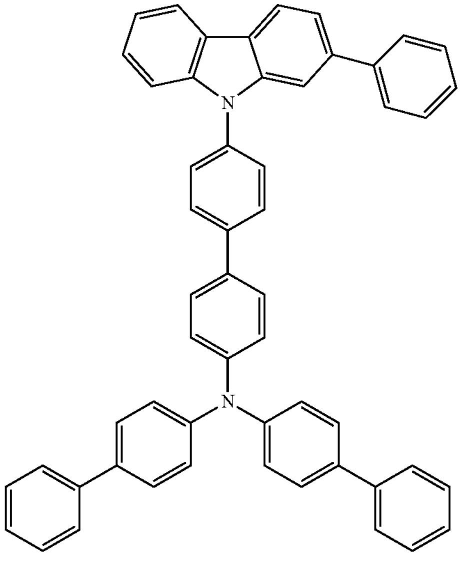
P-90
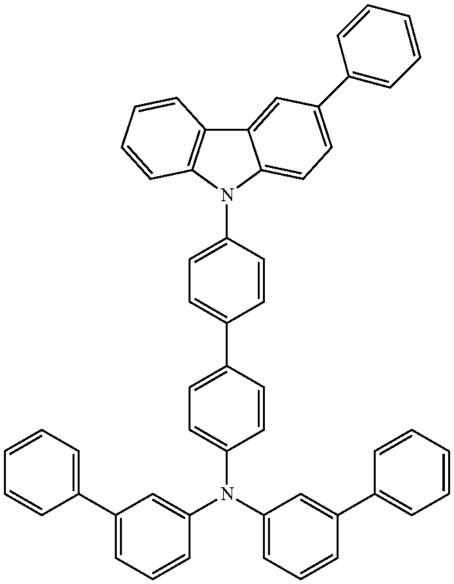

-continued
P-91
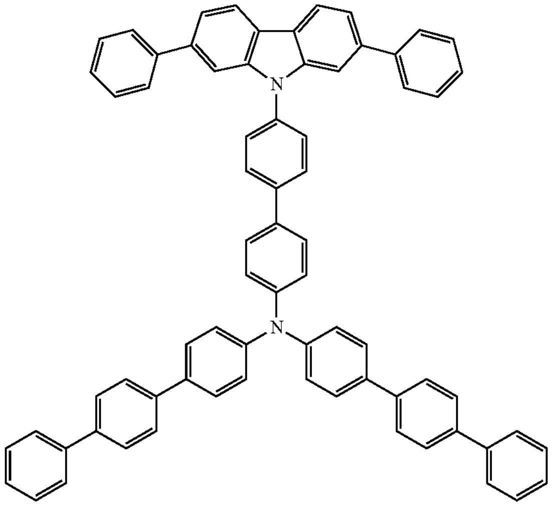
P-92
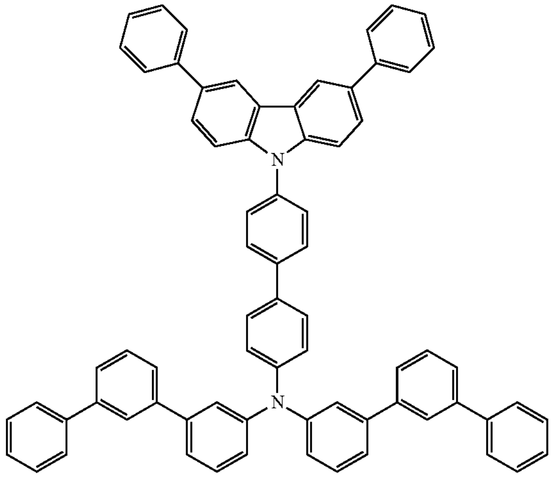
P-93
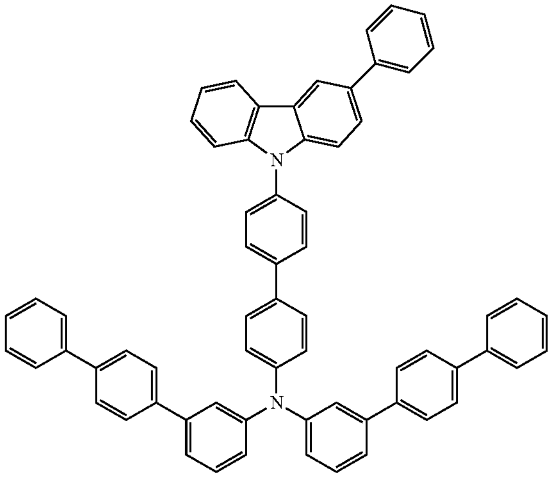
P-94
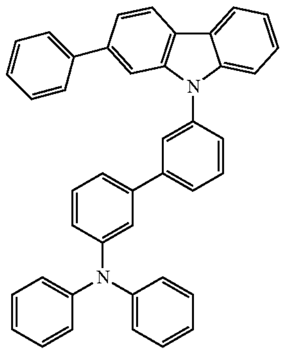
P-95
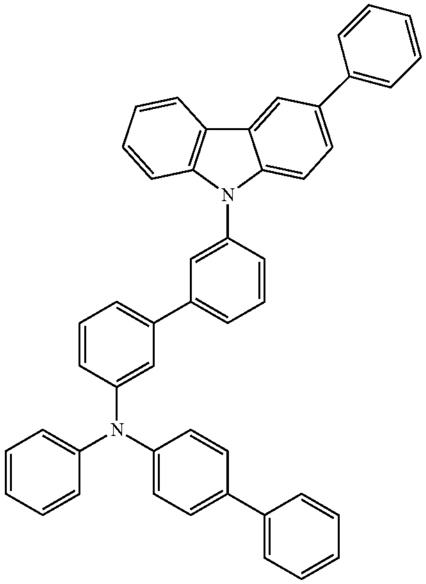
P-96
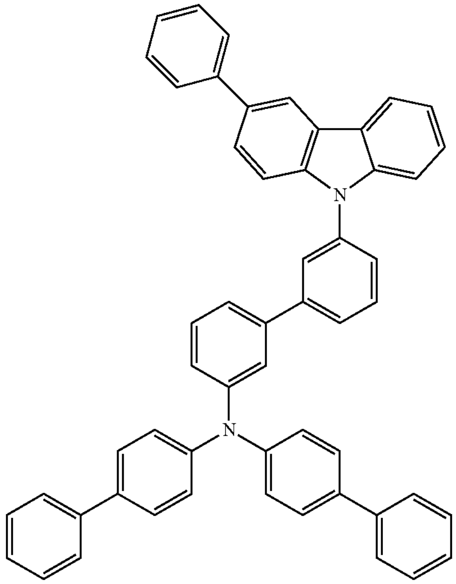

-continued
P-97
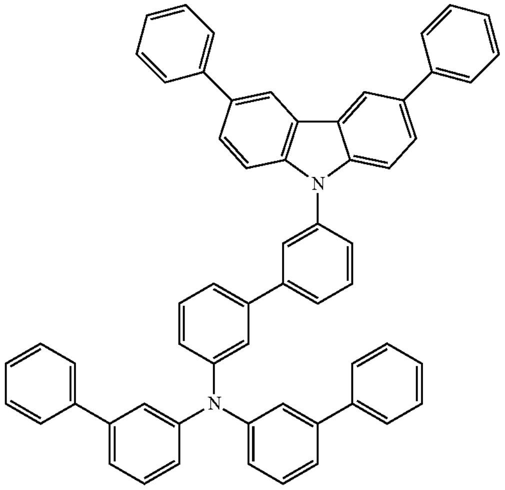
P-98
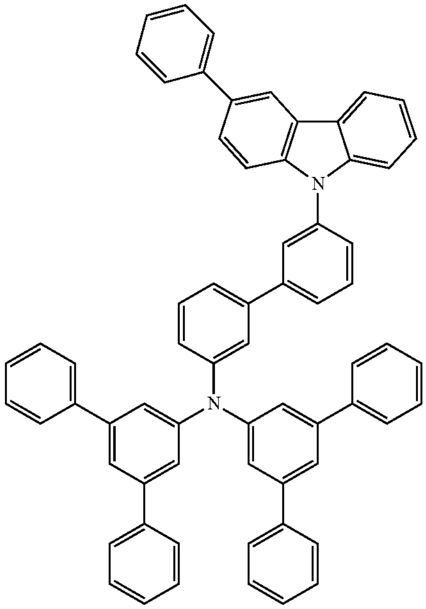
P-99
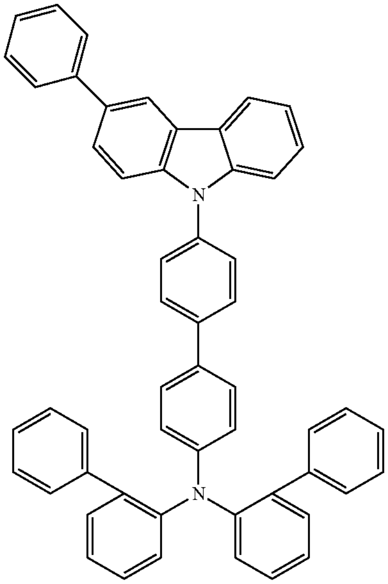
P-100
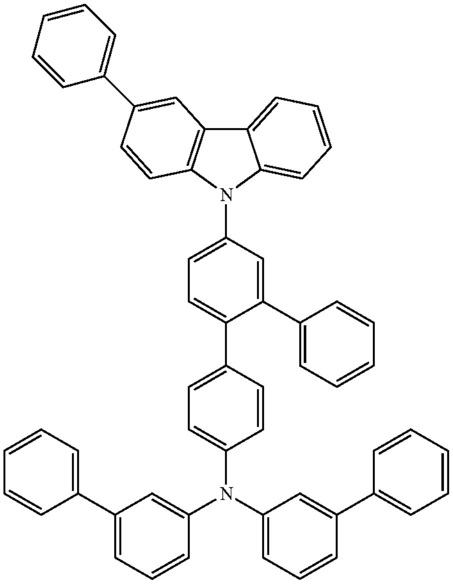

-continued
P-101
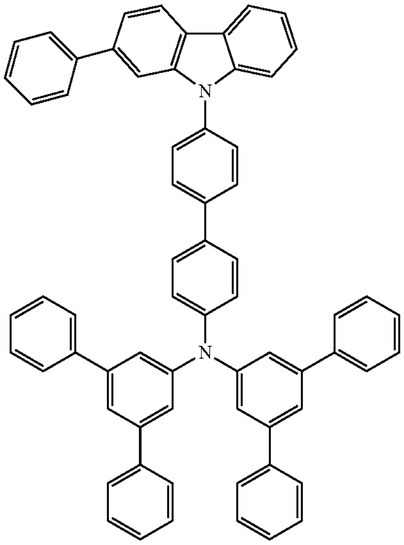
P-102
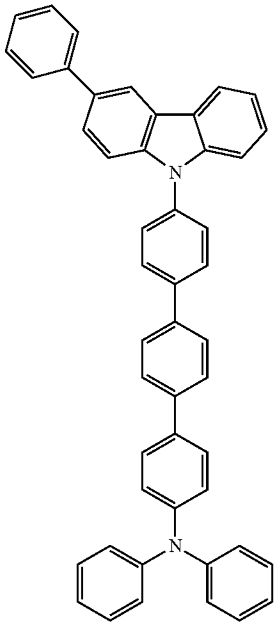
P-103
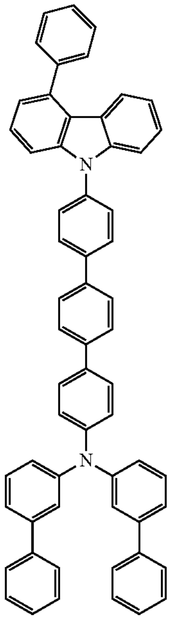
P-104
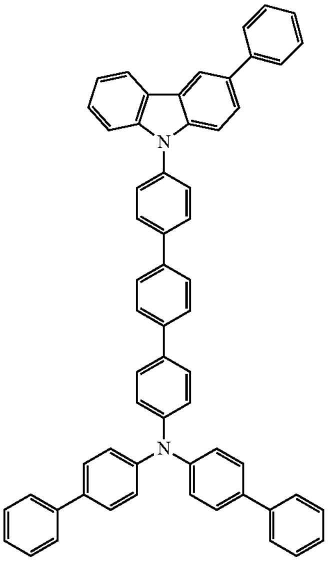

-continued
P-105
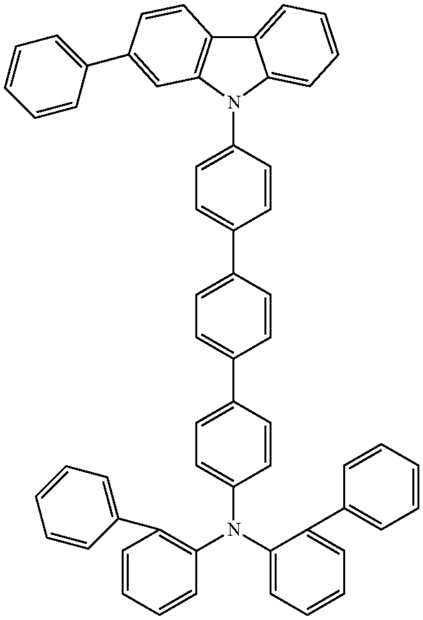
P-106
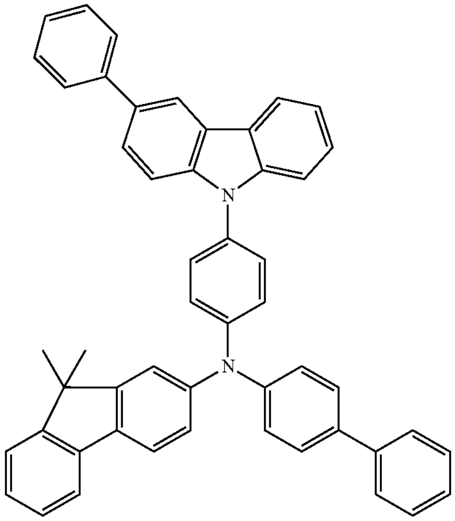
P-107
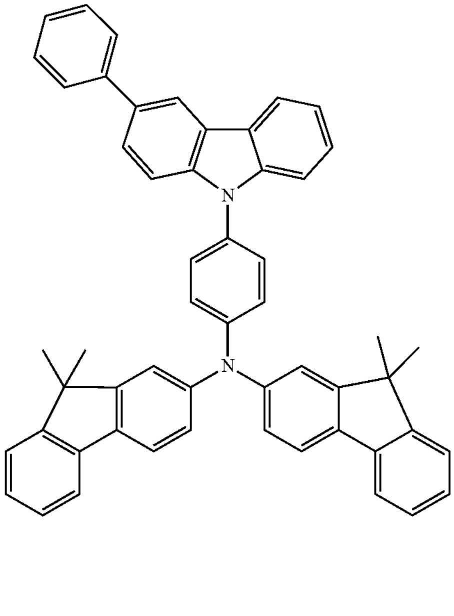
P-108
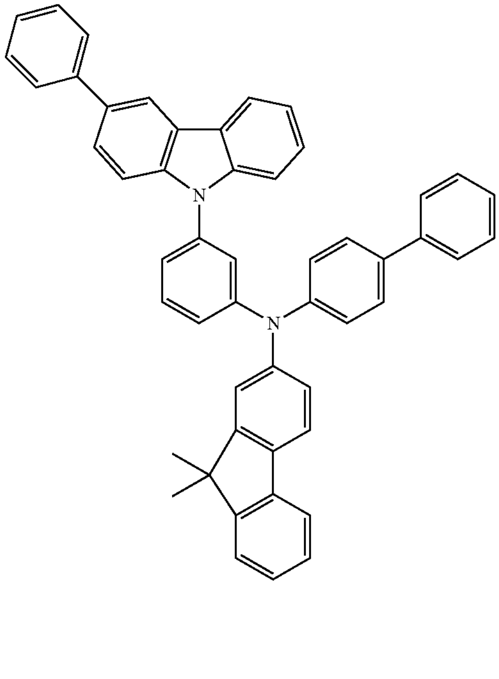

-continued
P-109
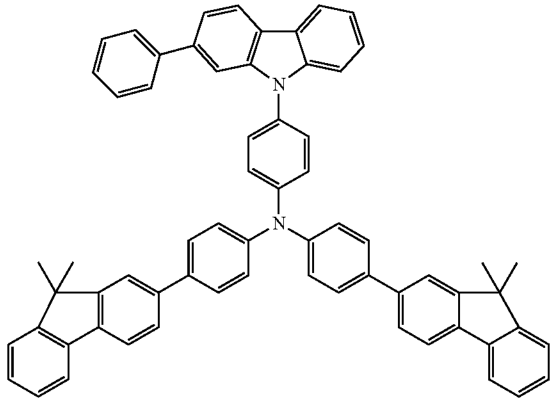
P-110
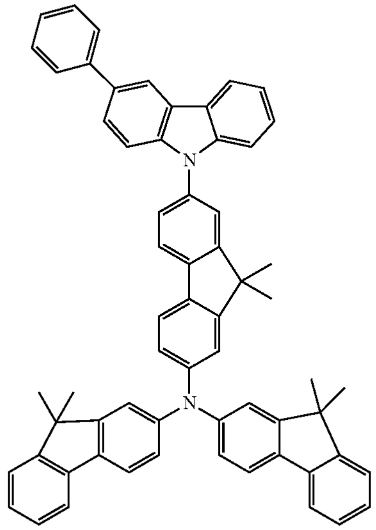
P-111
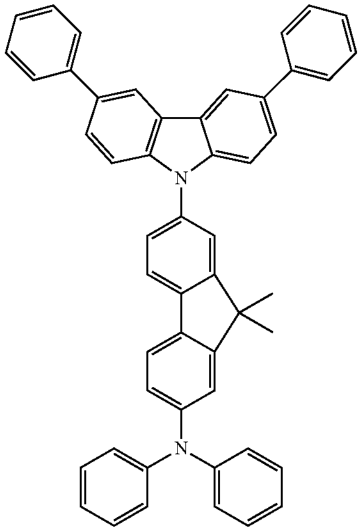
P-112
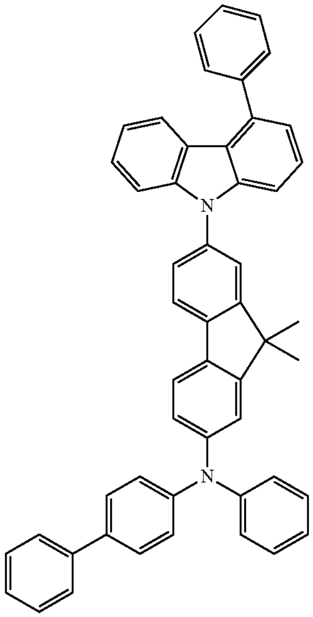

-continued
P-113
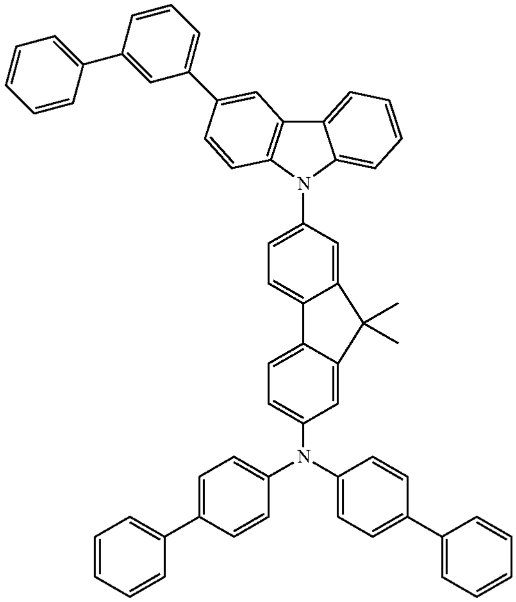
P-114
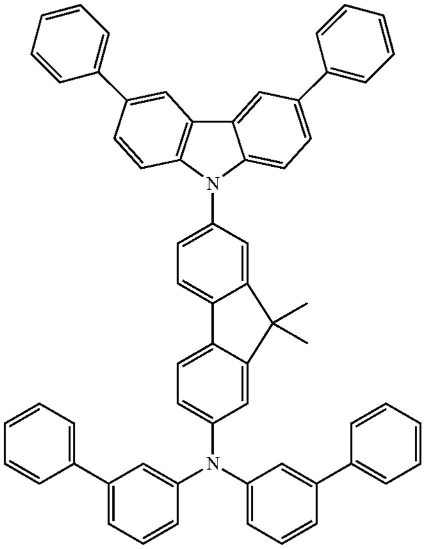
P-115
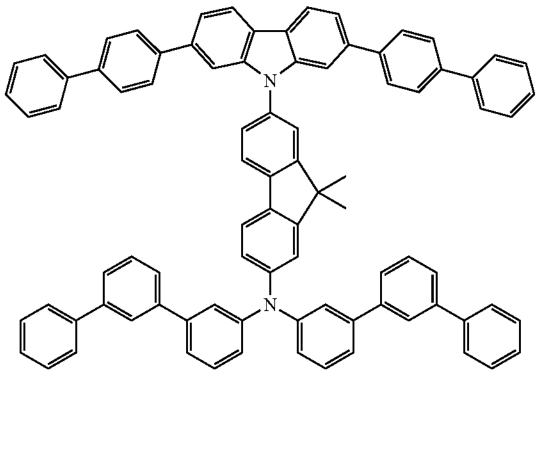
P-116
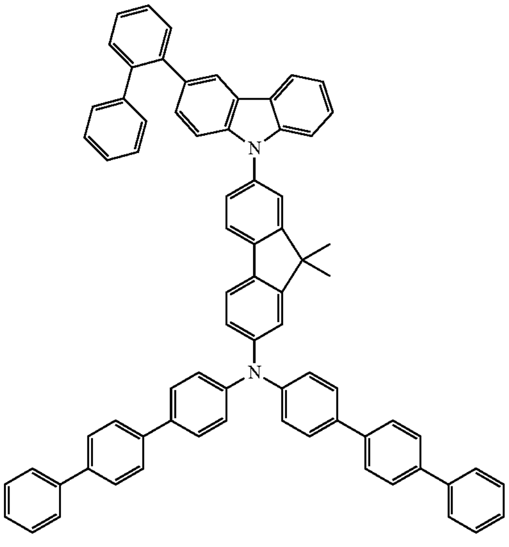

-continued

P-117

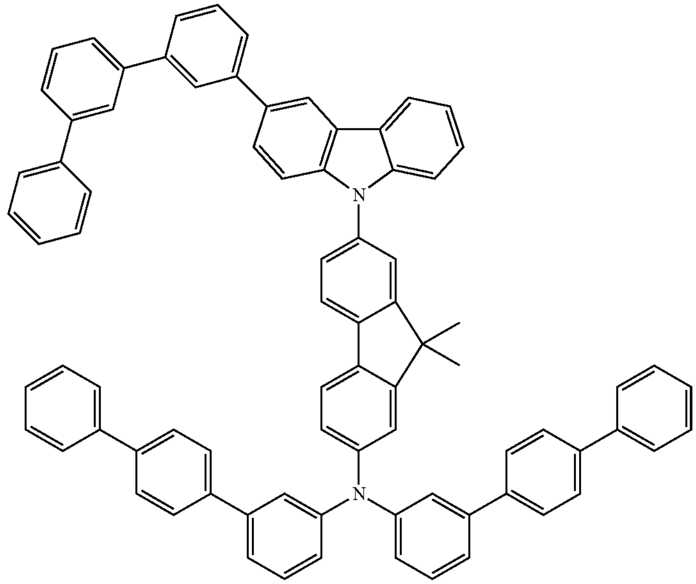

An organic optoelectronic device according to an embodiment of the present invention may simultaneously include the auxiliary electron transport layer 35 including the first compound having strong electron characteristics and the auxiliary hole transport layer 33 including a second compound having strong hole transport characteristics by reducing a HOMO energy level difference between the hole transport layer 31 and the light-emitting layer 32 and thus, adjusting hole injection characteristics. When these used together, efficiency may be improved by adjusting a charge balance through hole injection-adjusting capability of the auxiliary hole transport layer 33 and electron injection-adjusting capability of the auxiliary electron transport layer 35, and a life-span may be also improved by applying the auxiliary hole transport layer 33 and the auxiliary electron transport layer 35 and thus, preventing accumulation of charges on each interface of the organic layers and accordingly, reducing degradation of a device and stabilizing it.

Specifically, a first compound expressed by one of Chemical Formula 1-i to Chemical Formula 1-ix and a second compound expressed by one of Chemical Formula 2-i to Chemical Formula 2-iii may be used together.

More specifically, a first compound expressed by one of compounds of Group 1 and a second compound expressed by one of Chemical Formula 2-i to Chemical Formula 2-iii may be used together.

The auxiliary hole transport layer 33 and the auxiliary electron transport layer 35 may be applied on a hole transport layer by a deposition or inkjet process with a thickness of 0.1 nm to 20.0 nm, for example 0.2 nm to 10.0 nm, 0.3 nm to 5 nm, 0.3 nm to 2 nm, or 0.4 nm to 1.0 nm.

The organic layer 30 may further include a hole injection layer 37 between the anode 10 and the hole transport layer 31 and/or an electron injection layer 36 between the cathode 20 and the electron transport layer 34 as needed.

The organic light emitting diode may be applied to an organic light emitting diode (OLED) display.

In the present invention, the organic optoelectronic device may be selected from an organic light emitting diode, an organic photoelectric device, an organic solar cell, an organic transistor, an organic photo conductor drum, and an organic memory device.

Hereinafter, the embodiments are illustrated in more detail with reference to examples. These examples, however, are not in any sense to be interpreted as limiting the scope of the invention.

SYNTHESIS OF FIRST COMPOUND

Synthesis Example 1

Synthesis of Intermediate I-1

[Reaction Scheme 1]

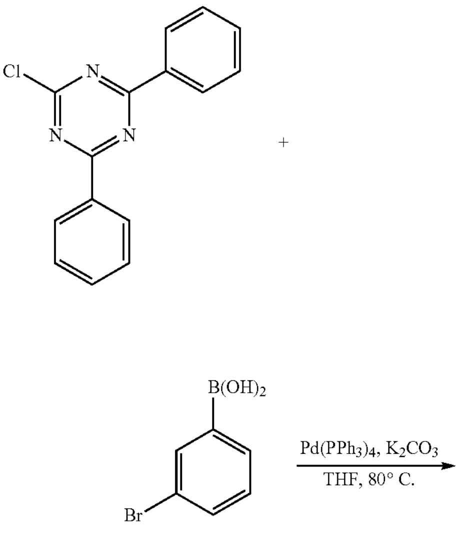

-continued

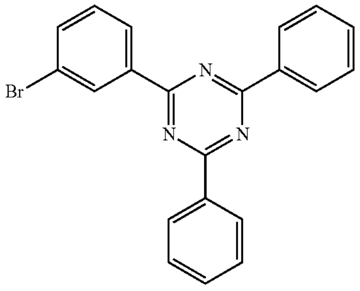

I-1

A compound, 2-chloro-4,6-diphenyl-1,3,5-triazine (50 g, 187 mmol, TCI) was dissolved in THF (1 L) under a nitrogen environment, (3-bromophenyl)boronic acid (45 g, 224.12 mmol) and tetrakis(triphenylphosphine)palladium (2.1 g, 1.87 mmol) were added thereto, and the mixture was stirred. Potassium carbonate saturated in water (64 g, 467 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. The obtained residue was separated and purified through column chromatography to obtain Compound I-1 (69 g, 95%).

HRMS (70 eV, EI+): m/z calcd for $C_{21}H_{14}BrN_3$: 387.0371, found: 387.

Elemental Analysis: C, 65%; H, 4%

Synthesis Example 2

Synthesis of Intermediate I-2

[Reaction Scheme 2]

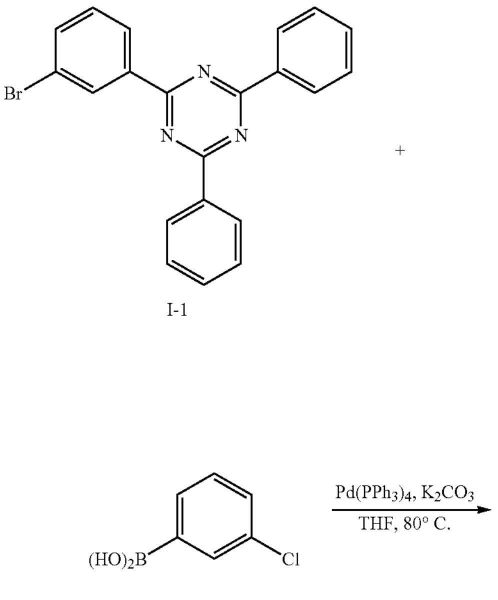

-continued

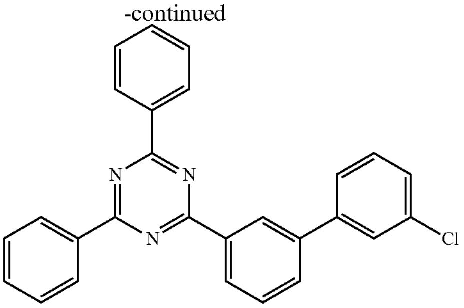

I-2

Intermediate I-2 (51 g, 95%) was obtained according to the same method as the method of synthesizing Intermediate I-1 by using Intermediate I-1 and 3-chlorophenyl boronic acid (TCI).

HRMS (70 eV, EI+): m/z calcd for $C_{27}H_{18}ClN_3$: 419.1189, found: 419.

Elemental Analysis: C, 77%; H, 4%

Synthesis Example 3

Synthesis of Intermediate I-3

[Reaction Scheme 3]

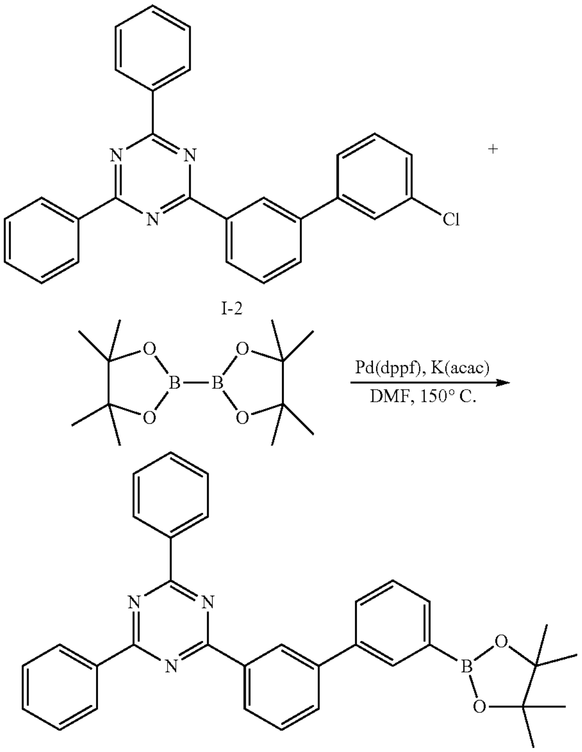

I-3

Intermediate I-2 (100 g, 238 mmol) was dissolved in dimethylforamide (DMF) (1 L) under an nitrogen environment, bis(pinacolato)diboron (72.5 g, 285 mmol), (1,1-bis (diphenylphosphine)ferrocene)dichloropalladium (II) (2 g, 2.38 mmol), and potassium acetate (58 g, 595 mmol) were added thereto, and the mixture was heated and refluxed at 150° C. for 48 hours. When the reaction was complete, water was added to the reaction solution, and the mixture was filtered and dried in a vacuum oven. The obtained residue was separated and purified through column chromatography to obtain Compound I-3 (107 g, 88%).

HRMS (70 eV, EI+): m/z calcd for $C_{33}H_{30}BN_3O_2$: 511.2431, found: 511.

Elemental Analysis: C, 77%; H, 6%

Synthesis Example 4

Synthesis of Intermediate I-4

[Reaction Scheme 4]

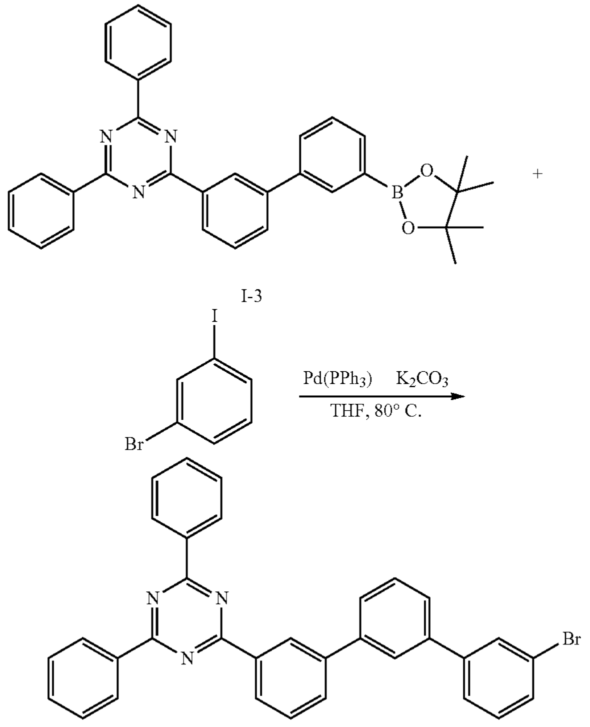

I-3

I-4

Compound I-3 (50 g, 98 mmol) was dissolved in THF (1 L) under a nitrogen environment, 1-bromo-3-iodobenzene (33 g, 117 mmol, Aldrich Corp.) and tetrakis(triphenylphosphine)palladium (1 g, 0.98 mmol) were added thereto, and the mixture was stirred. Potassium carbonate saturated in water (34 g, 245 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. The obtained residue was separated and purified through column chromatography to obtain Compound I-4 (50 g and 95%).

HRMS (70 eV, EI+): m/z calcd for $C_{30}H_{27}BO_2$: 539.0997, found: 539.

Elemental Analysis: C, 73.34; H, 4.10

Synthesis Example 5

Synthesis of Intermediate I-5

[Reaction Scheme 5]

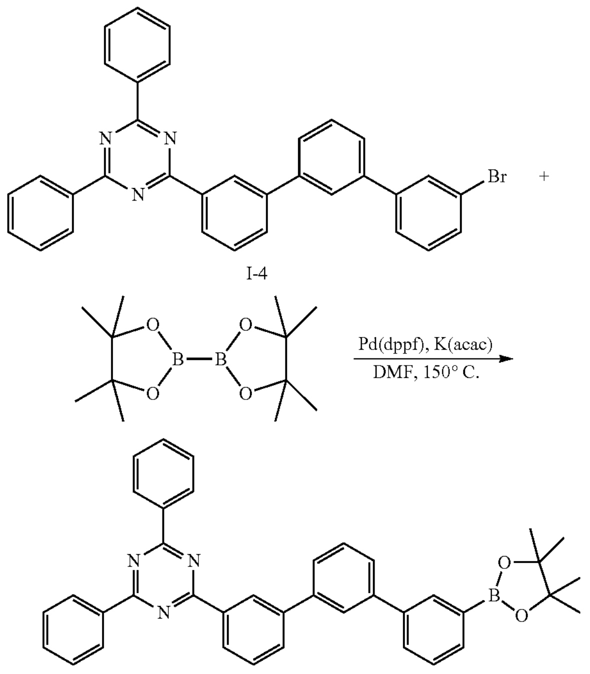

I-4

I-6

Intermediate I-5 (95 g, 88%) was obtained according to the same method as the method of synthesizing Intermediate I-3.

HRMS (70 eV, EI+): m/z calcd for $C_{39}H_{34}BN_3O_2$: 587.2744, found: 587.

Elemental Analysis: C, 80%; H, 6%

Synthesis Example 6

Synthesis of Intermediate I-6

[Reaction Scheme 6]

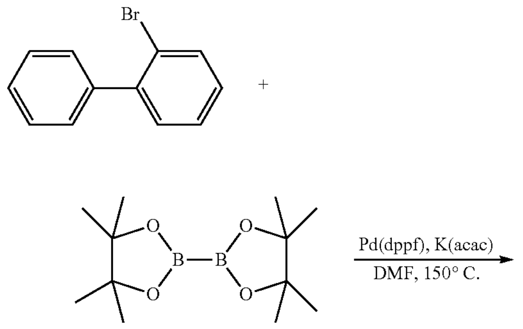

-continued

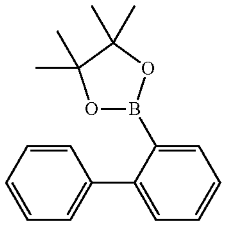

I-6

2-bromo-1,1'-biphenyl (20 g, 85.8 mmol) was dissolved in dimethylforamide (DMF) (1 L) under a nitrogen environment, bis(pinacolato)diboron (26 g, 103 mmol), (1,1'-bis (diphenylphosphine)ferrocene)dichloropalladium (II) (0.7 g, 0.85 mmol), and potassium acetate (58 g, 595 mmol) were added thereto, and the mixture was heated and refluxed at 150° C. for 5 hours. When the reaction was complete, water was added to the reaction solution, and the mixture was filtered and dried in a vacuum oven. The obtained residue was separated and purified through flash column chromatography to obtain Compound I-6 (19 g and 83%).

HRMS (70 eV, EI+): m/z calcd for C18H21BO2: 280.1635, found: 280.

Elemental Analysis: C, 77%; H, 7%

Synthesis Example 7

Synthesis of Intermediate I-7

[Reaction Scheme 7]

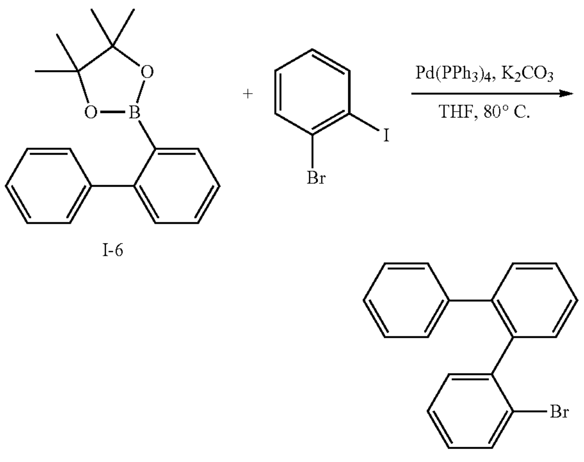

I-6

I-7

Compound I-6 (20 g, 71 mmol) was dissolved in THF (1 L) under a nitrogen environment, 1-bromo-2-iodobenzene (22 g, 78 mmol) and tetrakis(triphenylphosphine)palladium (0.8 g, 0.71 mmol) were added thereto, and the mixture was stirred. Potassium carbonate saturated in water (25 g, 177 mmol) was added thereto, and the mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. The obtained residue was separated and purified through flash column chromatography to obtain Compound I-7 (19 g and 87%).

HRMS (70 eV, EI+): m/z calcd for $C_{18}H_{13}Br$: 308.0201, found: 308.

Elemental Analysis: C, 70%; H, 4%

Synthesis Example 8

Synthesis of Intermediate I-8

[Reaction Scheme 8]

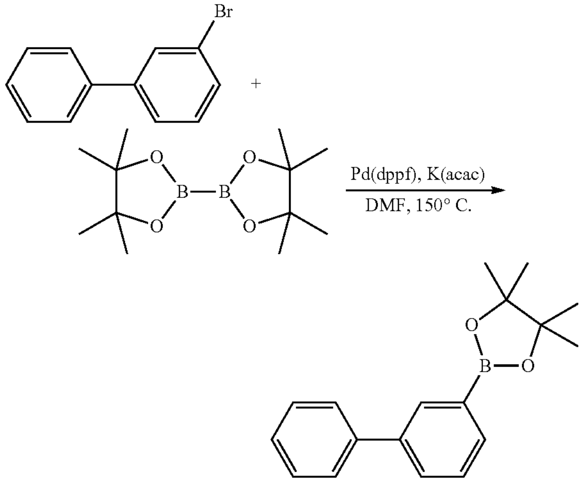

I-8

3-bromo-1,1'-biphenyl (20 g, 85.8 mmol) was dissolved in dimethylforamide (DMF) (1 L) under a nitrogen environment, bis(pinacolato)diboron (26 g, 103 mmol), (1,1'-bis (diphenylphosphine)ferrocene)dichloropalladium(II) (0.7 g, 0.85 mmol), and potassium acetate (58 g, 595 mmol) were added thereto, and the mixture was heated and refluxed at 150° C. for 5 hours. When the reaction was complete, water was added to the reaction solution, and the mixture was filtered and dried in a vacuum oven. The obtained residue was separated and purified through flash column chromatography to obtain Compound I-8 (20 g and 85%).

HRMS (70 eV, EI+): m/z calcd for $C_{18}H_{21}BO_2$: 280.1635, found: 280.

Elemental Analysis: C, 77%; H, 7%

Synthesis Example 9

Synthesis of Intermediate I-9

[Reaction Scheme 9]

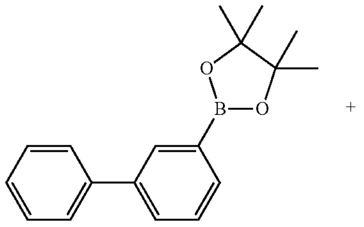

I-8

-continued

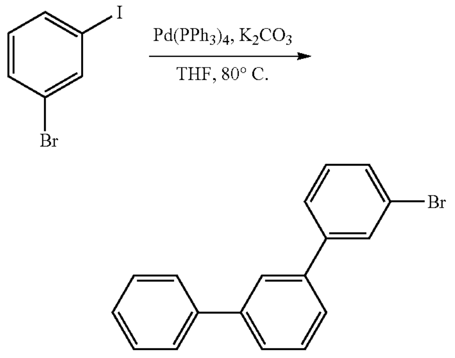

I-9

Compound I-8 (20 g, 71 mmol) was dissolved in THF (1 L) under a nitrogen environment, 1-bromo-3-iodobenzene (22 g, 78 mmol, TCI) and tetrakis(triphenylphosphine)palladium (0.8 g, 0.71 mmol) were added thereto, and the mixture was stirred. Potassium carbonate saturated in water (25 g, 177 mmol) was added thereto, and the mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-9 (20 g and 91%).

HRMS (70 eV, EI+): m/z calcd for $C_{18}H_{13}Br$: 308.0201, found: 308.

Elemental Analysis: C, 70%; H, 4%

Synthesis Example 10

Synthesis of Intermediate I-10

[Reaction Scheme 10]

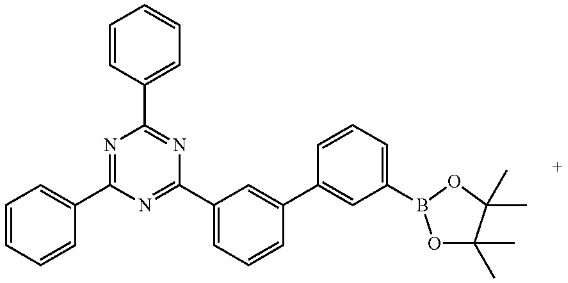

I-3

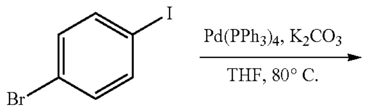

-continued

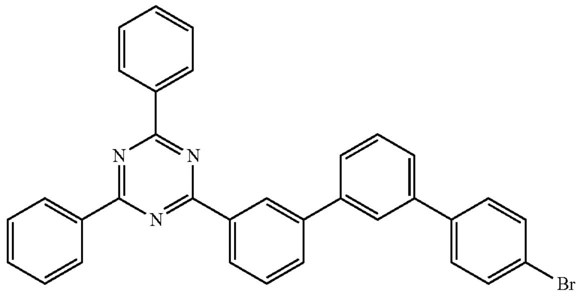

I-10

Compound I-3 (50 g, 98 mmol) was dissolved in THF (1 L) under a nitrogen environment, 1-bromo-4-iodobenzene (33 g, 117 mmol) and tetrakis(triphenylphosphine)palladium (1 g, 0.98 mmol) were added thereto, and the mixture was stirred. Potassium carbonate saturated in water (34 g, 245 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-10 (50 g and 95%).

HRMS (70 eV, EI+): m/z calcd for $C_{30}H_{27}BO_2$: 539.0997, found: 539 540.

Elemental Analysis: C, 73.34; H, 4.10

Synthesis Example 11

Synthesis of Intermediate I-11

[Reaction Scheme 11]

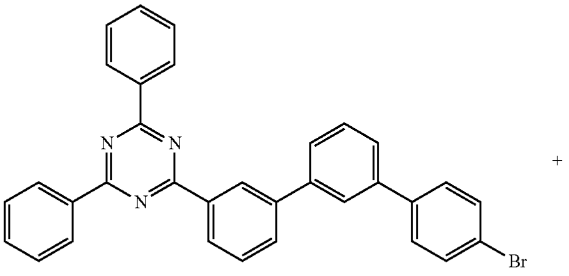

I-10

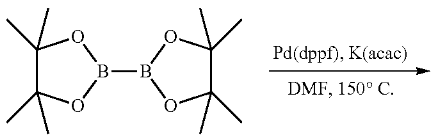

-continued

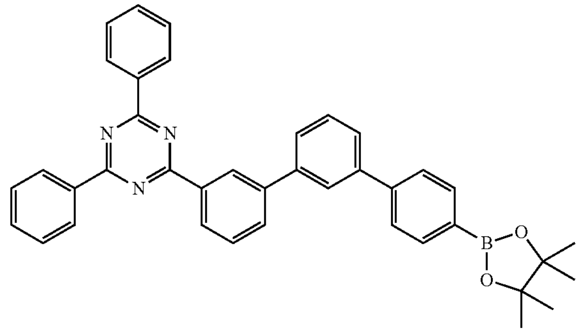

I-11

Compound I-10 (100 g, 185 mmol) was dissolved in dimethylforamide (DMF) (1 L) under a nitrogen environment, bis(pinacolato)diboron (56 g, 222 mmol), (1,1'-bis (diphenylphosphine)ferrocene)dichloropalladium (II) (1.5 g, 1.85 mmol), and potassium acetate (45 g, 595 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain Compound I-11 (95 g and 88%).

HRMS (70 eV, EI+): m/z calcd for $C_{39}H_{34}BN_3O_2$: 587.2744, found: 587.

Elemental Analysis: C, 80%; H, 6%

Synthesis Examples 12 to 16

Synthesis of Intermediate I-12 (Having Pyridine Core)

[Reaction Scheme 12]

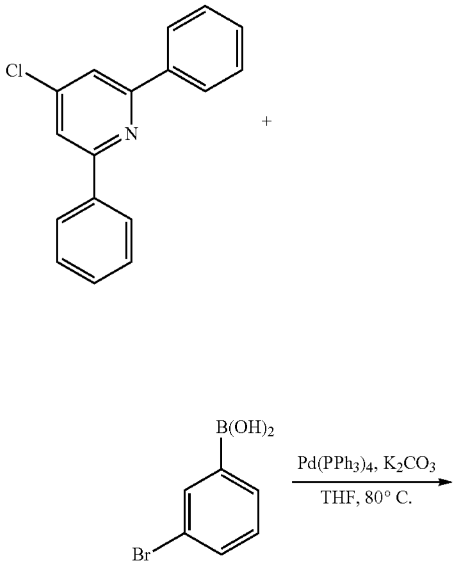

-continued

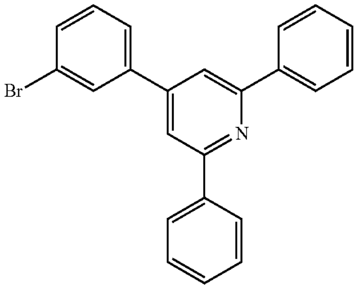

I-12

[Reaction Scheme 13]

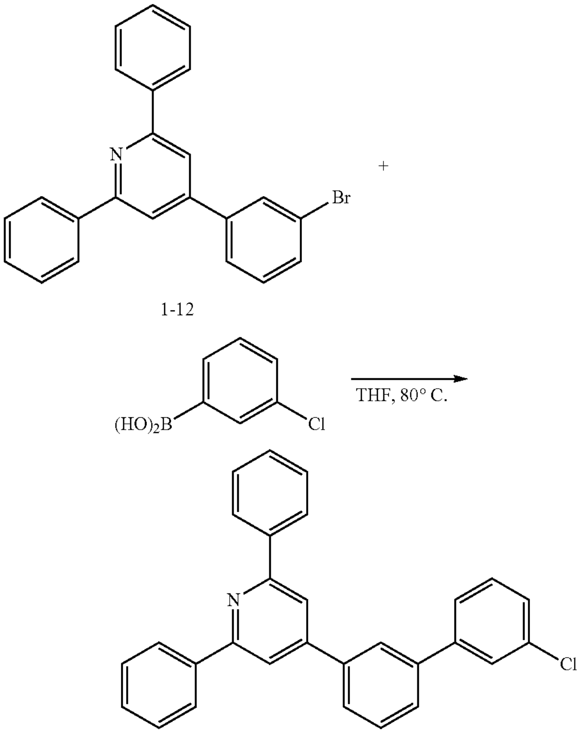

1-12

1-13

[Reaction Scheme 14]

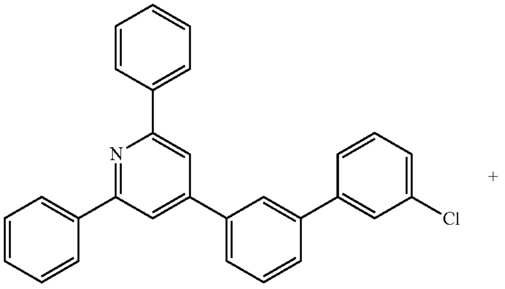

I-13

-continued

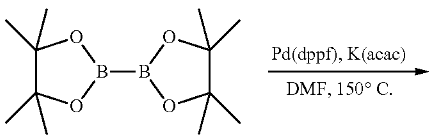

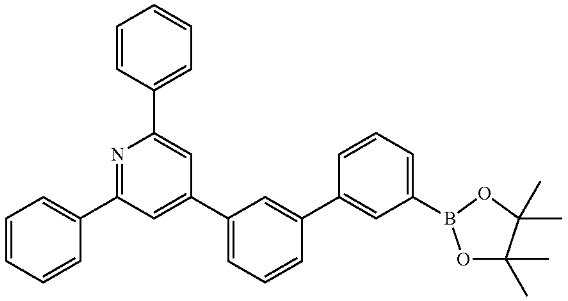

I-14

[Reaction Scheme 15]

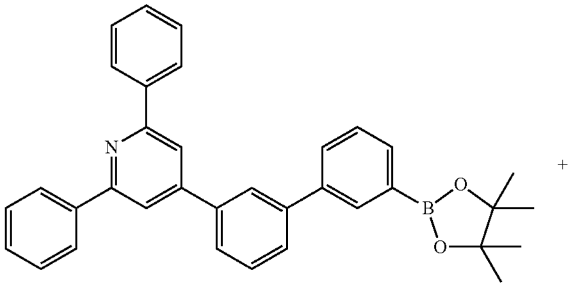

I-14

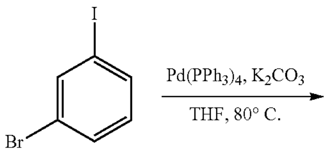

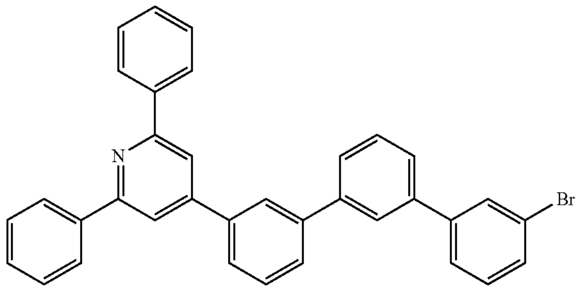

I-15

[Reaction Scheme 16]

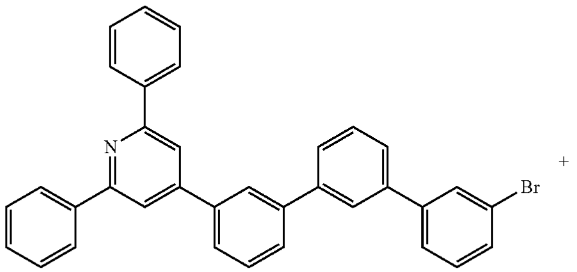

I-15

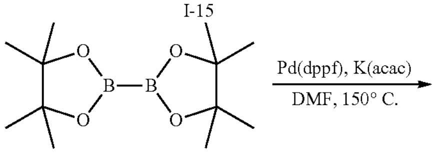

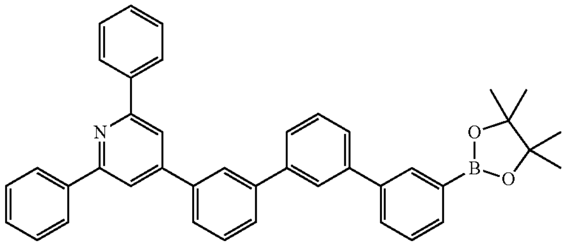

I-16

Intermediates I-12 to I-16 were obtained according to the same method as the method of synthesizing Intermediates I-1 to I-5, I-10, and I-11 except for using 4-chloro-2,6-diphenylpyridine (TCI) instead of the 2-chloro-4,6-diphenyl-1,3,5-triazine.

HRMS (70 eV, EI+): m/z calcd for $C_{41}H_{36}BNO_2$: 585.2839, found: 585.

Elemental Analysis: C, 84%; H, 6%

Synthesis Example 17 to 21

Synthesis of Intermediate I-17 (Having Pyrimidine Core)

[Reaction Scheme 17]

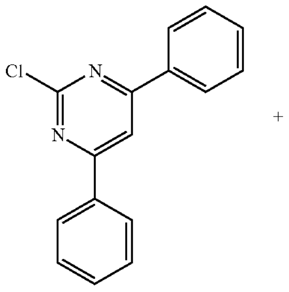

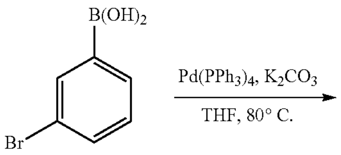

-continued
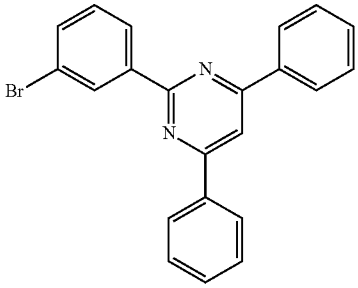
I-17
[Reaction Scheme 18]
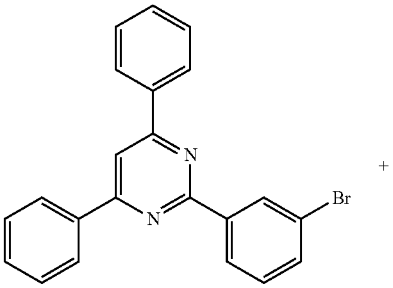
1-17
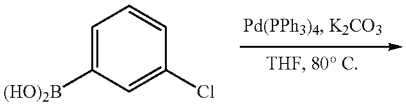
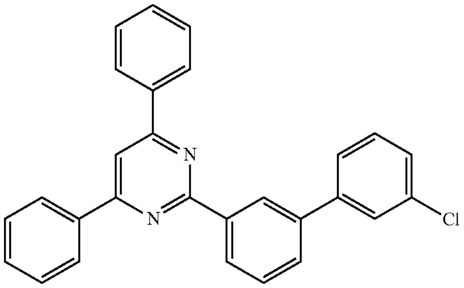
1-18
[Reaction Scheme 19]
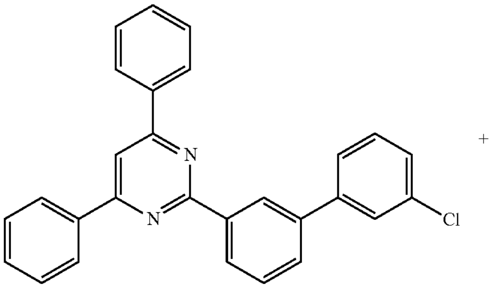
I-18
-continued
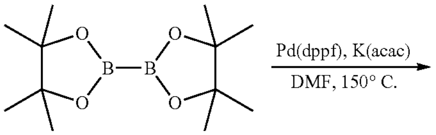
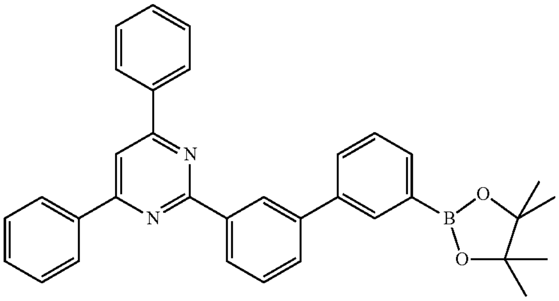
I-19
[Reaction Scheme 20]
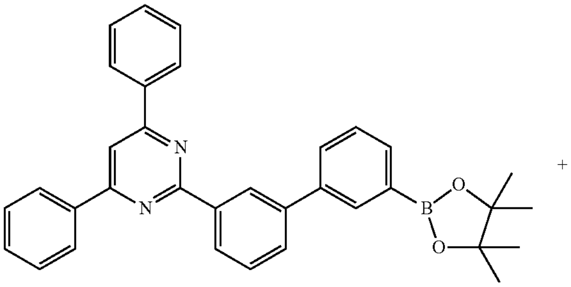
I-19
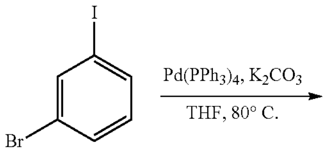
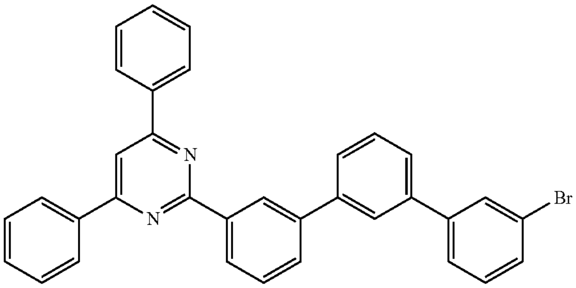
I-20

[Reaction Scheme 21]

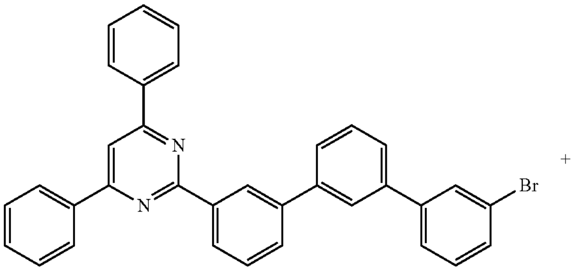

I-20

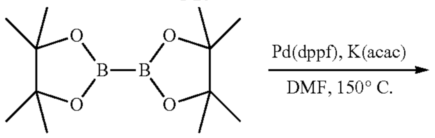

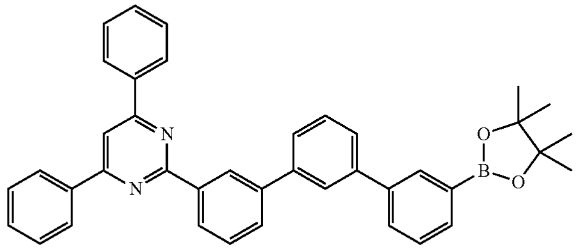

I-21

Intermediates I-17 to I-21 were obtained according to the same method as the method of synthesizing Intermediates I-1 to I-5, I-10, and I-11 except for using 2-chloro-4,6-diphenyl-1,3-pyrimidine (TCI) instead of the 2-chloro-4,6-diphenyl-1,3,5-triazine.

HRMS (70 eV, EI+): m/z calcd for $C_{40}H_{35}BN_2O_2$: 586.2792, found: 586.

Elemental Analysis: C, 82%; H, 6%

Synthesis Examples 22 to 26

Synthesis of Intermediate I-22 (Having Phenylene Core)

[Reaction Scheme 22]

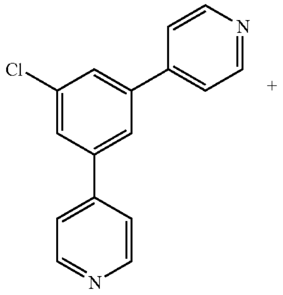

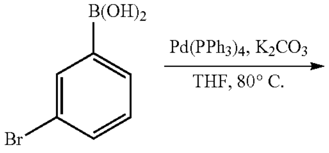

-continued

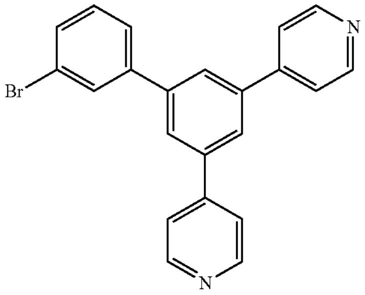

I-22

HRMS (70 eV, EI+): m/z calcd for $C_{40}H_{35}BN_2O_2$: 586.2792, found: 586.

Elemental Analysis: C, 82%; H, 6%

[Reaction Scheme 23]

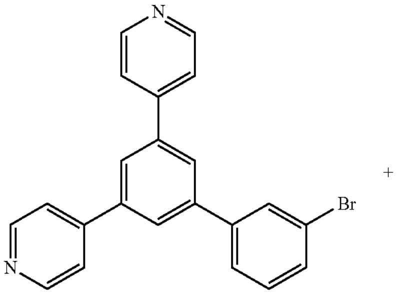

I-22

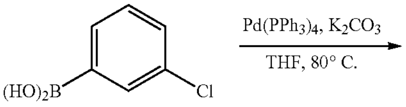

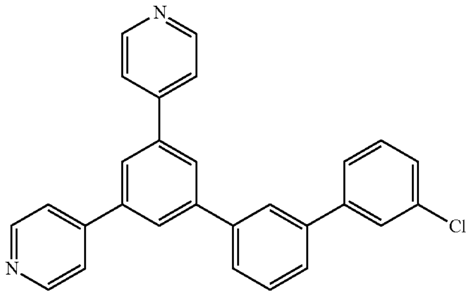

I-23

[Reaction Scheme 24]
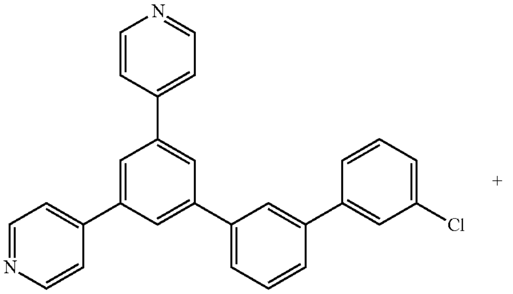
I-23
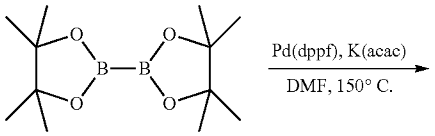
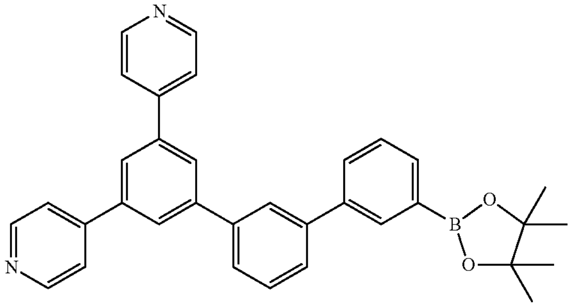
I-24
[Reaction Scheme 25]
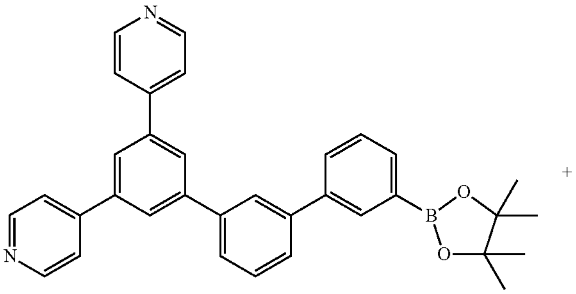
I-24
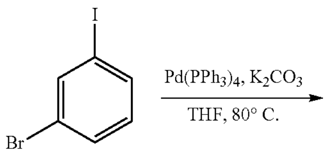
-continued
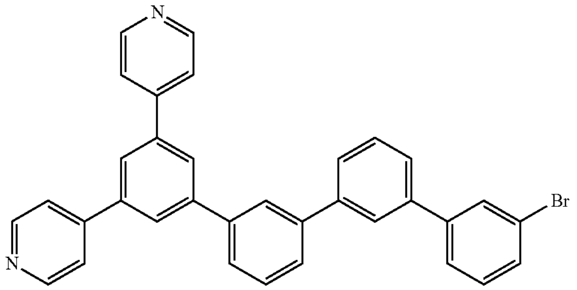
I-25
[Reaction Scheme 26]
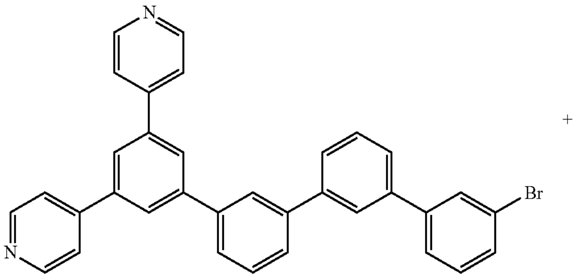
I-25
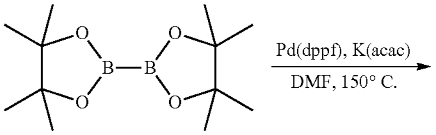
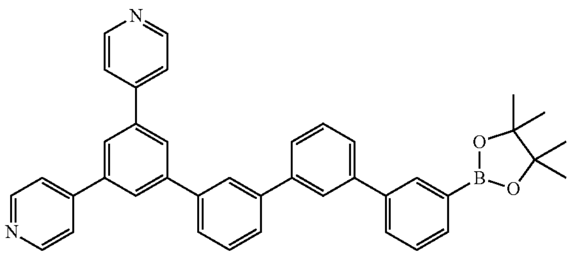
I-26
Intermediates I-22 to I-26 were obtained according to the same method as the method of synthesizing Intermediates I-1 to I-5, I-10, and I-11 except for using 4,4'-(5-bromo-1,3-phenylene)dipyridine (refer to Synthesis Example 2 of Japan Patent Laid-Open Publication No. 2008-127326) instead of the 2-chloro-4,6-diphenyl-1,3,5-triazine.

Synthesis Example 27

Synthesis of Intermediate I-27

[Reaction Scheme 27]

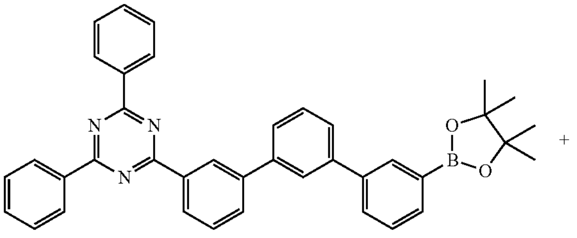

I-5

Compound I-5 (50 g, 85 mmol) was dissolved in THF (10 under a nitrogen environment, 1-bromo-3-iodobenzene (29 g, 102 mmol) and tetrakis(triphenylphosphine)palladium (1 g, 0.85 mmol) were added thereto, and the mixture was stirred. Potassium carbonate saturated in water (30 g, 212 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-27 (50 g and 95%).

HRMS (70 eV, EI+): m/z calcd for $C_{39}H_{26}BrN_3$: 615.1310, found 616.

Elemental Analysis: C, 76%; H, 4%

Synthesis Example 28

Synthesis of Intermediate I-28

[Reaction Scheme 28]

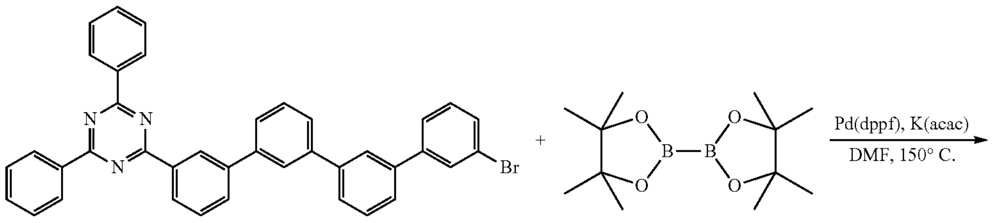

I-27

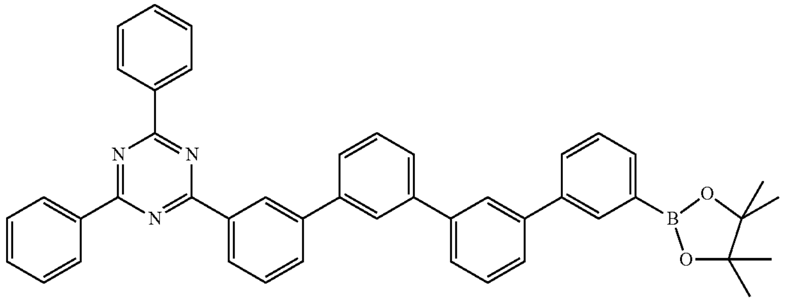

I-28

-continued

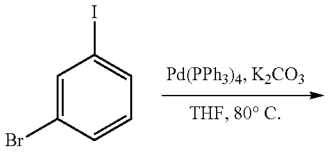

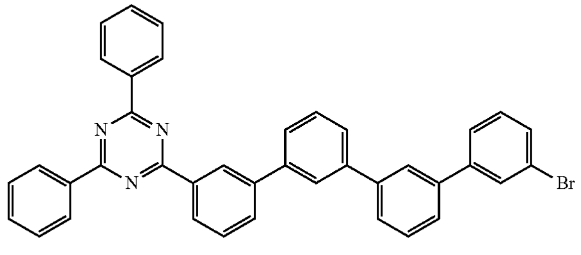

I-27

Intermediate I-27 (100 g, 162 mmol) was dissolved in dimethylforamide (DMF, 1 L) under a nitrogen environment, bis(pinacolato)diboron (49 g, 194 mmol), (1,1'-bis (diphenylphosphine)ferrocene)dichloropalladium (II) (1.3 g, 1.62 mmol), and potassium acetate (40 g, 405 mmol) were added thereto, and the mixture was heated and refluxed at 150° C. for 12 hours. When the reaction was complete, water was added to the reaction solution, and the mixture was filtered and dried in a vacuum oven. This obtained residue was separated and purified through flash column chromatography to obtain Compound I-28 (86 g and 80%).

HRMS (70 eV, EI+): m/z calcd for $C_{45}H_{38}BN_3O_2$: 663.3057, found: 663.

Elemental Analysis: C, 81%; H, 6%

Synthesis Example 29

Synthesis of Intermediate I-29

[Reaction Scheme 29]

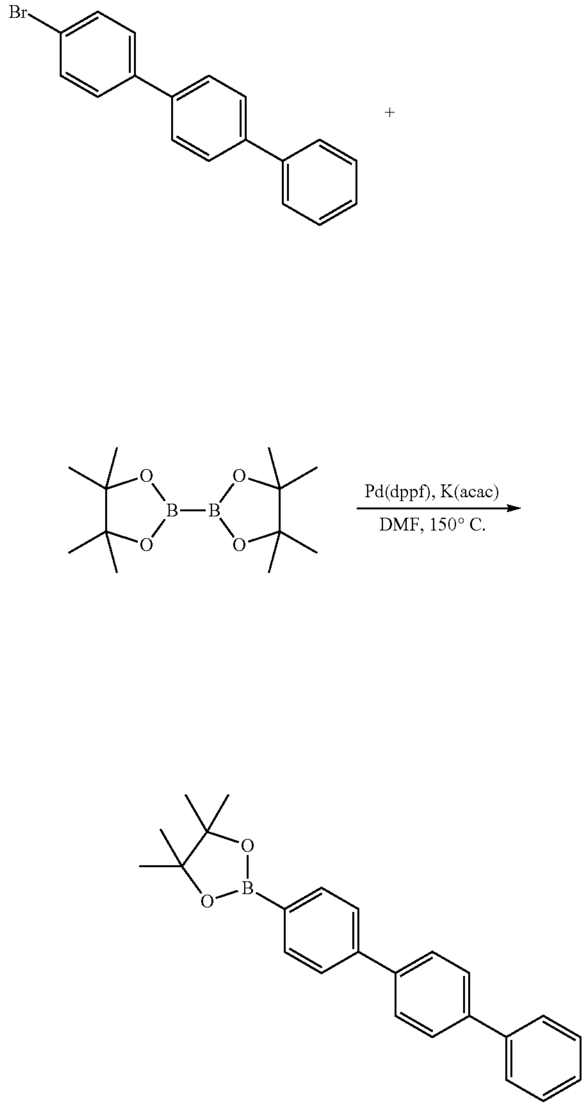

I-29

4-bromo-p-terphenyl (50 g, 162 mmol, TCI) was dissolved in dimethylforamide (DMF, 1 L) under a nitrogen environment, bis(pinacolato)diboron (49 g, 194 mmol), (1,1'-bis(diphenylphosphine)ferrocene)dichloropalladium (II) (1.3 g, 1.62 mmol), and potassium acetate (40 g, 405 mmol) were added thereto, and the mixture was heated and refluxed at 150° C. for 12 hours. When the reaction was complete, water was added to the reaction solution, and the mixture was filtered and dried in a vacuum oven. This obtained residue was separated and purified through flash column chromatography to obtain Compound I-29 (47 g and 82%).

HRMS (70 eV, EI+): m/z calcd for $C_{24}H_{25}BO_2$: 356.1948, found: 356.

Elemental Analysis: C, 81%; H, 7%

Synthesis Example 30

Synthesis of Intermediate I-30

[Reaction Scheme 30]

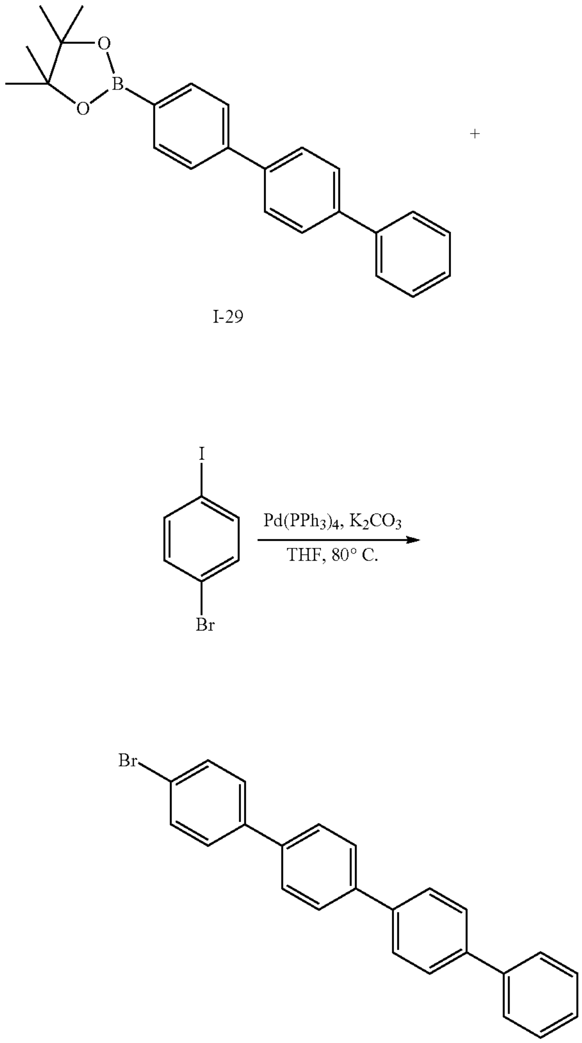

I-29

I-30

Compound I-29 (50 g, 140 mmol) was dissolved in THF (1 L) under a nitrogen environment, 1-bromo-4-iodobenzene (47 g, 168 mmol) and tetrakis(triphenylphosphine)palladium (1.6 g, 1.4 mmol) were added thereto, and the mixture was stirred. Potassium carbonate saturated in water (48 g, 350 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-30 (44 g and 89%).

HRMS (70 eV, EI+): m/z calcd for $C_{24}H_{17}Br$: 384.0514, found: 384.

Elemental Analysis: C, 75%; H, 4%

Synthesis Example 31

Synthesis of Intermediate I-31

[Reaction Scheme 31]

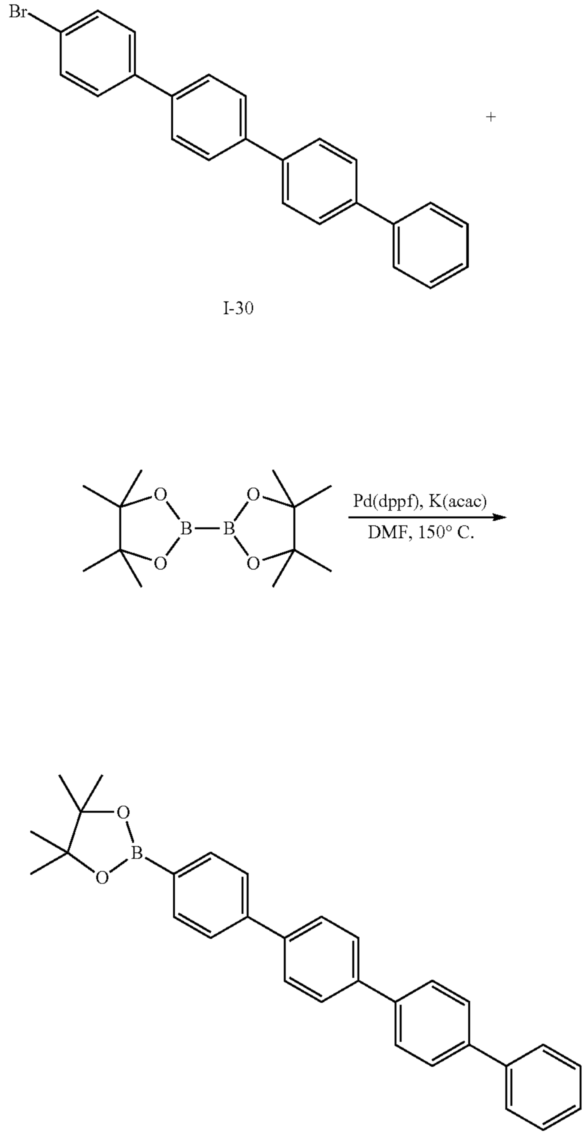

I-30

I-31

Compound I-30 (20 g, 52 mmol) was dissolved in dimethylforamide (DMF, 1 L) under a nitrogen environment, bis(pinacolato)diboron (16 g, 62.5 mmol), (1,1'-bis(diphenylphosphine)ferrocene)dichloropalladium (II) (0.4 g, 0.52 mmol), and potassium acetate (13 g, 130 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain Compound I-31 (19 g and 85%).

HRMS (70 eV, EI+): m/z calcd for $C_{30}H_{29}BO_2$: 432.2261, found: 432.

Elemental Analysis: C, 83%; H, 7%

Synthesis Example 32

Synthesis of Intermediate I-32

[Reaction Scheme 32]

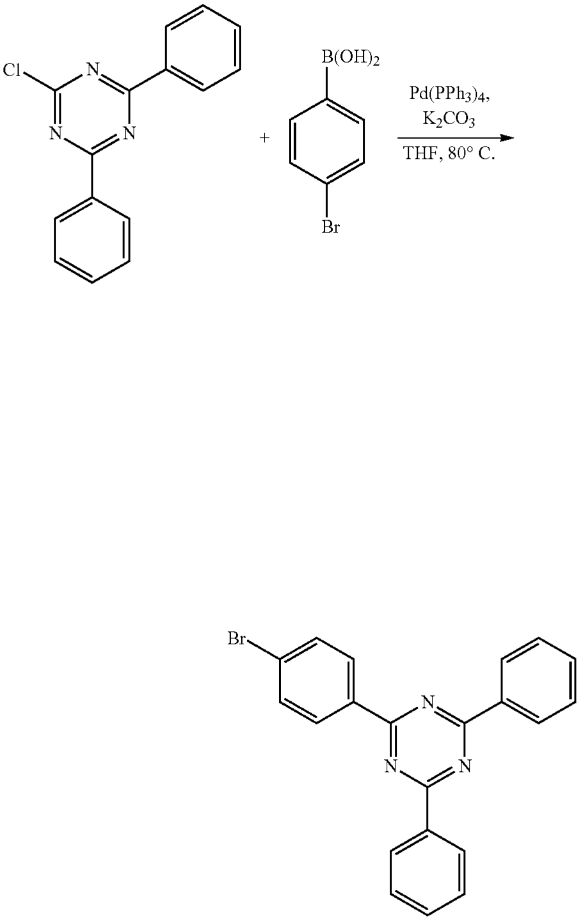

I-32

The compound, 2-chloro-4,6-diphenyl-1,3,5-triazine (50 g, 187 mmol) was dissolved in THF (1 L) under a nitrogen environment, (4-bromophenyl)boronic acid (45 g, 224.12 mmol, Aldrich Corporation), and tetrakis(triphenylphosphine)palladium (2.1 g, 1.87 mmol) were added thereto, and the mixture was stirred. Potassium carbonate saturated in water (64 g, 467 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-32 (70 g and 96%).

HRMS (70 eV, EI+): m/z calcd for $C_{21}H_{14}BrN_3$: 387.0371, found: 387.

Elemental Analysis: C, 65%; H, 4%

Synthesis Example 33

Synthesis of Intermediate I-33

[Reaction Scheme 33]

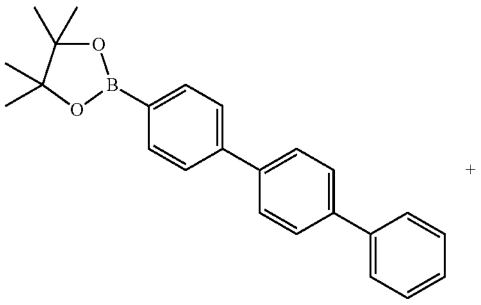

I-29

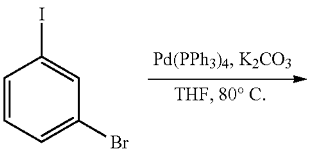

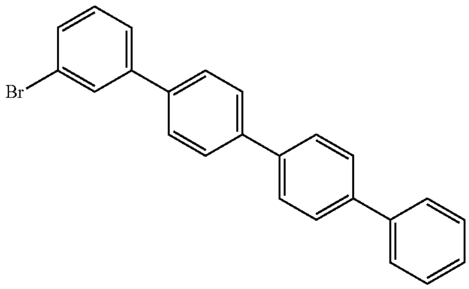

I-33

Compound I-29 (50 g, 140 mmol) was dissolved in THF (1 L) under a nitrogen environment, 1-bromo-3-iodobenzene (47 g, 168 mmol) and tetrakis(triphenylphosphine)palladium (1.6 g, 1.4 mmol) were added thereto, and the mixture was stirred. Potassium carbonate saturated in water (48 g, 350 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-33 (46 g and 90%).

HRMS (70 eV, EI+): m/z calcd for $C_{24}H_{17}Br$: 384.0514, found: 384.

Elemental Analysis: C, 75%; H, 4%

Synthesis Example 34

Synthesis of Intermediate I-34

[Reaction Scheme 34]

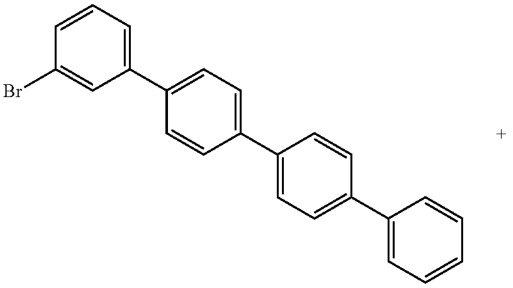

I-33

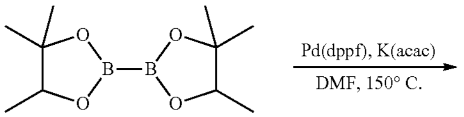

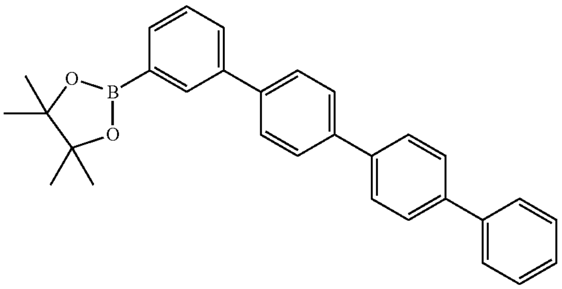

I-34

Compound I-33 (20 g, 52 mmol) was dissolved in dimethylforamide (DMF, 1 L) under a nitrogen environment, bis(pinacolato)diboron (16 g, 62.5 mmol), (1,1'-bis(diphenylphosphine)ferrocene)dichloropalladium (II) (0.4 g, 0.52 mmol), and potassium acetate (13 g, 130 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain Compound I-34 (21 g and 83%).

HRMS (70 eV, EI+): m/z calcd for $C_{30}H_{29}BO_2$: 432.2261, found: 432.

Elemental Analysis: C, 83%; H, 7%

Synthesis Example 35

Synthesis of Intermediate I-35

[Reaction Scheme 35]

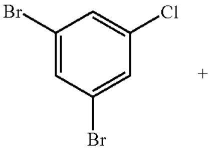

-continued

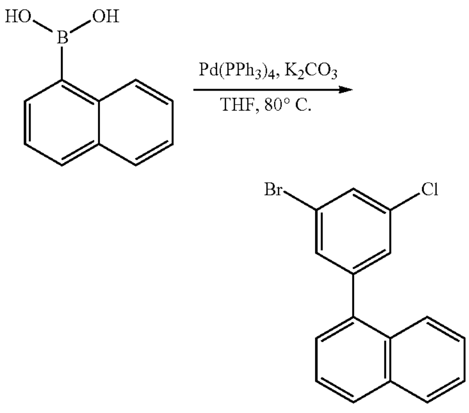

I-35

The compound, 1,3-dibromo-5-chlorobenzene (50 g, 185 mmol, TCI) was dissolved in THF (1 L) under a nitrogen environment, naphthalene-1-boronic acid (32 g, 185 mmol, Aldrich Corporation) and tetrakis(triphenylphosphine)palladium (2 g, 1.8 mmol) were added thereto, and the mixture was stirred. Potassium carbonate saturated in water (64 g, 462 mmol) was added thereto, and the mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-35 (32 g and 56%).

HRMS (70 eV, EI+): m/z calcd for $C_{16}H_{10}BrCl$: 315.9654, found: 316.

Elemental Analysis: C, 61%; H, 3%

Synthesis Example 36

Synthesis of Intermediate I-36

[Reaction Scheme 36]

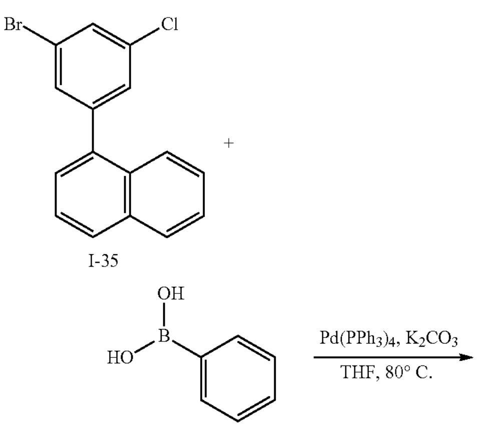

I-35

-continued

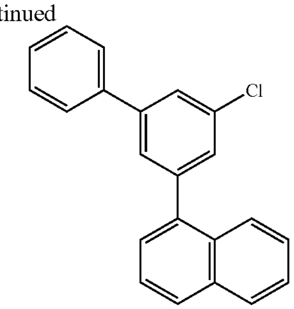

I-36

Compound I-35 (30 g, 95 mmol) was dissolved in THF (1 L) under a nitrogen environment, phenylboronic acid (14 g, 114 mmol, Aldrich Corporation) and tetrakis(triphenylphosphine)palladium (1 g, 0.95 mmol) were added thereto, and the mixture was stirred. Potassium carbonate saturated in water (33 g, 237 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-36 (32 g and 75%).

HRMS (70 eV, EI+): m/z calcd for $C_{22}H_{15}Cl$: 314.0862, found 314.

Elemental Analysis: C, 84%; H, 5%

Synthesis Example 37

Synthesis of Intermediate I-37

[Reaction Scheme 37]

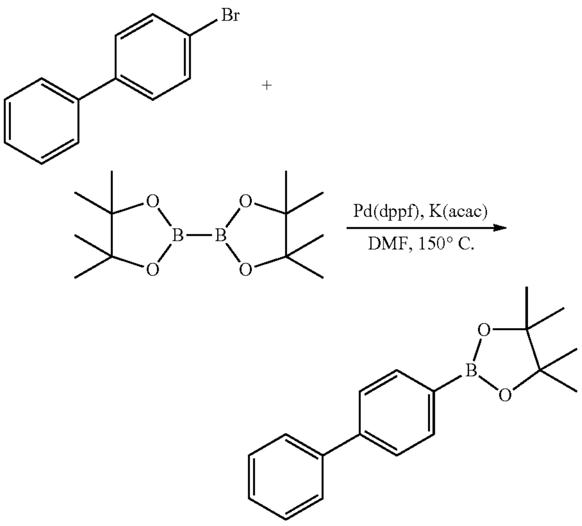

I-37

4-bromo-1,1'-biphenyl (20 g, 86 mmol, TCI) was dissolved in dimethylformamide (DMF, 1 L) under a nitrogen environment, bis(pinacolato)diboron (26 g, 103 mmol), (1,1'-bis(diphenylphosphine)ferrocene)dichloropalladium (II) (0.7 g, 0.86 mmol), and potassium acetate (21 g, 215 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain Compound I-37 (20 g and 85%).

HRMS (70 eV, EI+): m/z calcd for $C_{18}H_{21}BO_2$:280.1635, found: 280.

Elemental Analysis: C, 77%; H, 8%

Synthesis Example 38

Synthesis of Intermediate I-38

[Reaction Scheme 38]

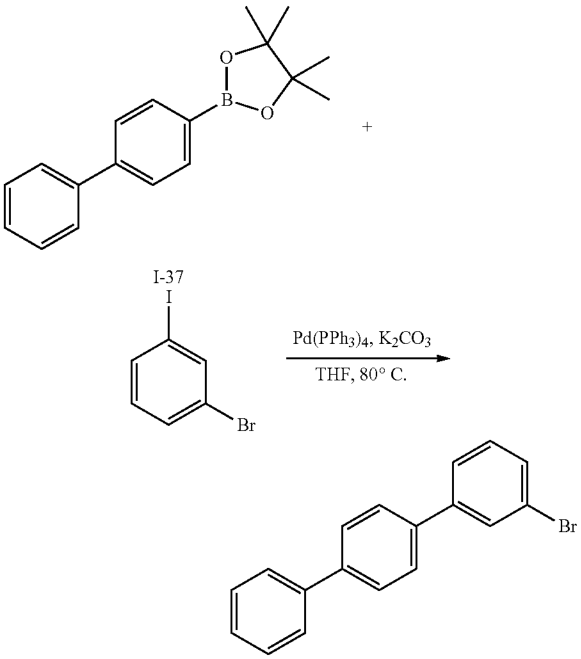

I-37

I-38

Compound I-37 (20 g, 71 mmol) was dissolved in THF (1 L) under a nitrogen environment, 1-bromo-3-iodobenzene (24 g, 85 mmol) and tetrakis(triphenylphosphine)palladium (0.8 mg, 0.7 mmol) were added thereto, and the mixture was stirred. Potassium carbonate saturated in water (24.5 g, 177 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-38 (30 g and 90%).

HRMS (70 eV, EI+): m/z calcd for $C_{18}H_{13}Br$:309.1998, found 309.

Elemental Analysis: C, 70%; H, 4%

Synthesis Example 39

Synthesis of Intermediate I-39

[Reaction Scheme 39]

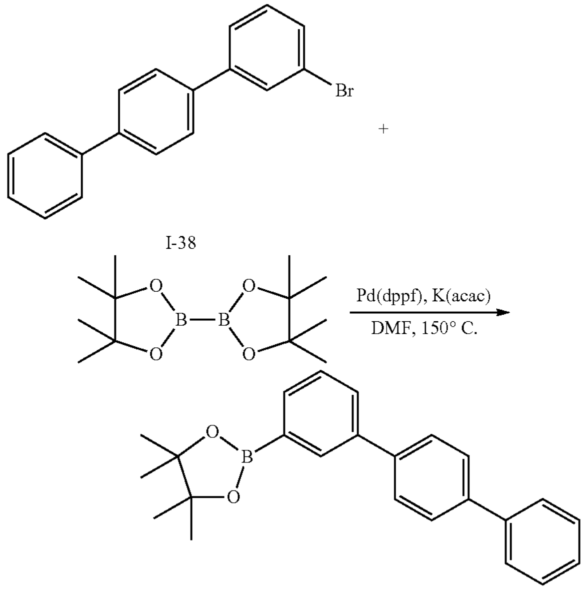

I-38

I-39

Compound I-38 (25 g, 81 mmol) was dissolved in dimethylforamide (DMF, 1 L) under a nitrogen environment, bis(pinacolato)diboron (25 g, 97 mmol), (1,1'-bis(diphenylphosphine)ferrocene)dichloropalladium (II) (0.7 g, 0.81 mmol), and potassium acetate (20 g, 203 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain Compound I-39 (27 g and 93%).

HRMS (70 eV, EI+): m/z calcd for $C_{24}H_{25}BO_2$:356.1948, found: 356.

Elemental Analysis: C, 81%; H, 7%

Synthesis Example 40

Synthesis of Intermediate I-40

[Reaction Scheme 40]

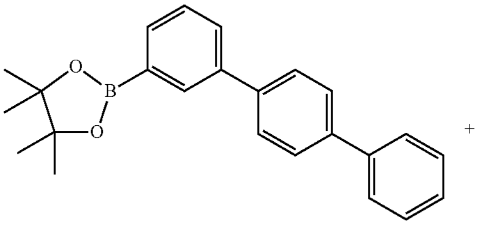

I-39

-continued

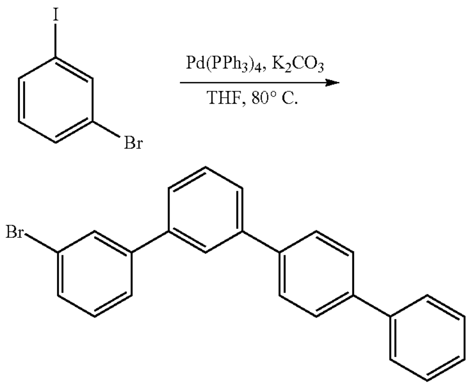

I-40

Compound I-39 (50 g, 140 mmol) was dissolved in THF (1 L) under a nitrogen environment, 1-bromo-3-iodobenzene (47 g, 168 mmol) and tetrakis(triphenylphosphine)palladium (1.6 g, 1.4 mmol) were added thereto, and the mixture was stirred. Potassium carbonate saturated in water (48 g, 350 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-40 (44 g and 89%).

HRMS (70 eV, EI+): m/z calcd for $C_{24}H_{17}Br$:384.0514, found: 384.

Elemental Analysis: C, 75%; H, 4%

Synthesis Example 41

Synthesis of Intermediate I-41

[Reaction Scheme 41]

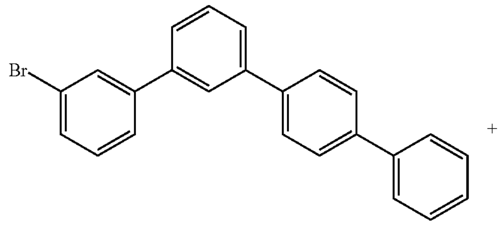

I-40

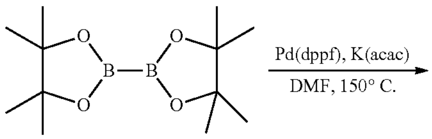

-continued

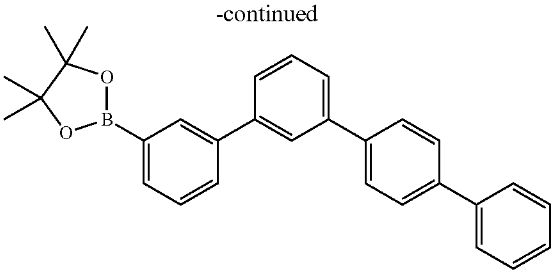

I-41

Compound I-40 (20 g, 52 mmol) was dissolved in dimethylforamide DMF, 1 L) under a nitrogen environment, bis(pinacolato)diboron (16 g, 62.5 mmol), (1,1'-bis(diphenylphosphine)ferrocene)dichloropalladium (II) (0.4 g, 0.52 mmol), and potassium acetate (13 g, 130 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain Compound I-41 (19 g and 85%).

HRMS (70 eV, EI+): m/z calcd for $C_{30}H_{29}BO_2$: 432.2261, found: 432.

Elemental Analysis: C, 83%; H, 7%

Synthesis Example 42

Synthesis of Intermediate I-42

[Reaction Scheme 42]

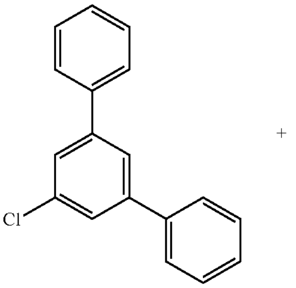

I-48

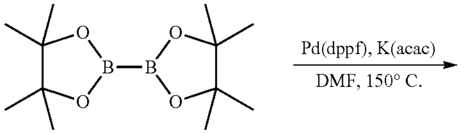

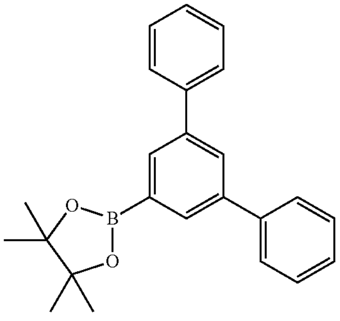

I-42

Compound I-48 (27.8 g, 105.00 mmol) was dissolved in dimethylforamide (DMF, 1 L) under a nitrogen environment, bis(pinacolato)diboron (32.0 g, 126.01 mmol), (1,1'-bis(diphenylphosphine)ferrocene)dichloropalladium (II) (0.86 g, 1.05 mmol), and potassium acetate (25.8 g, 262.51 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain Compound I-42 (33 g and 88%).

HRMS (70 eV, EI+): m/z calcd for $C_{24}H_{25}BO_2$: 356.1948, found: 356.

Elemental Analysis: C, 81%; H, 7%

Synthesis Example 43

Synthesis of Intermediate I-43

[Reaction Scheme 43]

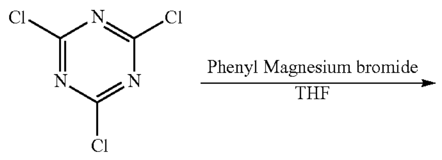

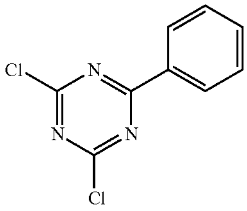

I-43

Cyanuric chloride (50 g, 271.13 mmol, TCI) was dissolved in THF (1 L) under a nitrogen environment, and the solution was cooled down to −10° C. Then, 3.0 M phenyl Magnesium bromide (90 ml, 271.13 mmol) was slowly added thereto in a dropwise fashion, and the mixture was slowly heated up to room temperature. The resultant was stirred for 30 minutes. When a reaction was complete, the reaction solution was washed with a HCl solution, and a solvent of an organic layer was removed. This obtained residue was separated and purified through flash column chromatography to obtain Compound I-43 (33 g and 85%).

HRMS (70 eV, EI+): m/z calcd for $C_9H_5Cl_2N_3$: 224.9861, found: 225.

Elemental Analysis: C, 48%; H, 2%

Synthesis Example 44

Synthesis of Intermediate I-44

[Reaction Scheme 44]

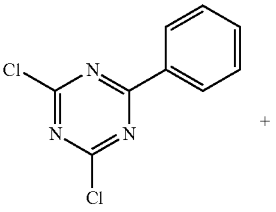

I-43

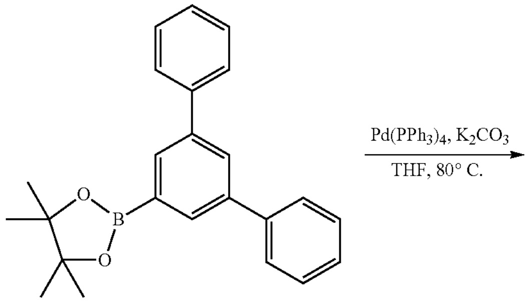

I-42

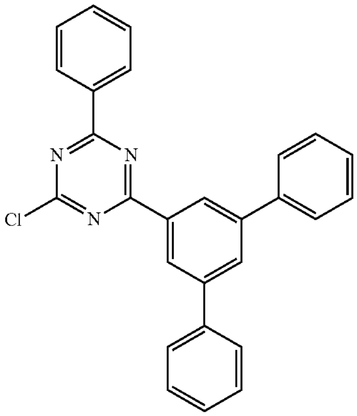

I-44

Compound I-42 (50 g, 140 mmol) was dissolved in THF (1 L) under a nitrogen environment, Compound I-43 (31 g, 140 mmol) and tetrakis(triphenylphosphine)palladium (1.6 g, 1.4 mmol) were added thereto, and the mixture was stirred. Potassium carbonate saturated in water (48 g, 350 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-44 (32 g and 70%).

HRMS (70 eV, EI+): m/z calcd for $C_{27}H_{18}ClN_3$: 419.1189, found: 419.

Elemental Analysis: C, 77%; H, 4%

Synthesis Example 45

Synthesis of Intermediates I-45 and I-48

[Reaction Scheme 45]

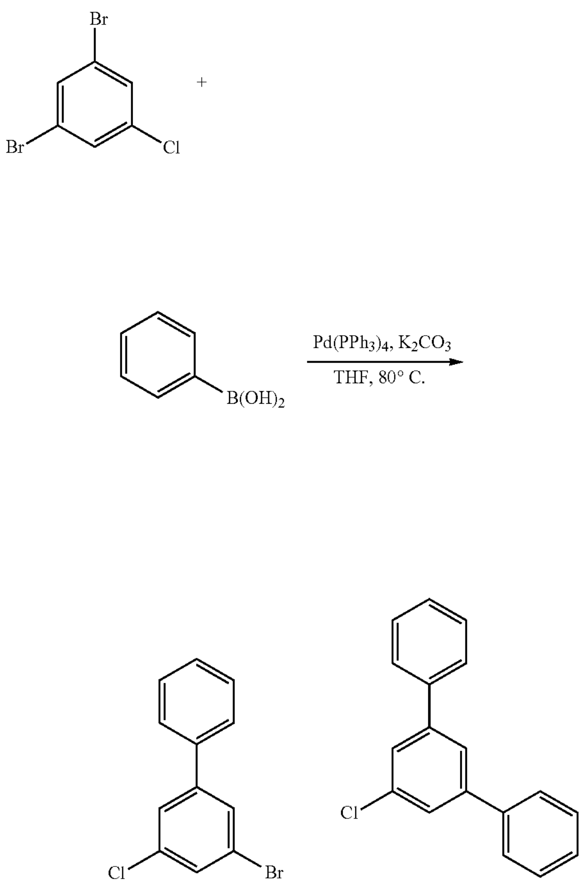

I-45 or I-48

The compound, 1,3-dibromo-5-chlorobenzene (100 g, 370 mmol, TCI) was dissolved in THF (2 L) under a nitrogen environment, phenylboronic acid (47.3 g, 388 mmol, Aldrich Corporation) and tetrakis(triphenylphosphine)palladium (1.5 g, 1.36 mmol) were added thereto, and the mixture was stirred. Potassium carbonate saturated in water (127 g, 925 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-45 (49 g and 50%).

HRMS (70 eV, EI+): m/z calcd for $C_{12}H_8BrCl$: 265.9498, found: 266.

Elemental Analysis: C, 54%; H, 3%

Compound I-48 was obtained according to the same method as above except for increasing twice the equivalent of the phenyl boronic acid.

HRMS (70 eV, EI+): m/z calcd for $C_{18}H_{13}Cl$: 264.0706, found: 264.

Elemental Analysis: C, 82%; H, 5%

Synthesis Example 46

Synthesis of Intermediate I-46

[Reaction Scheme 46]

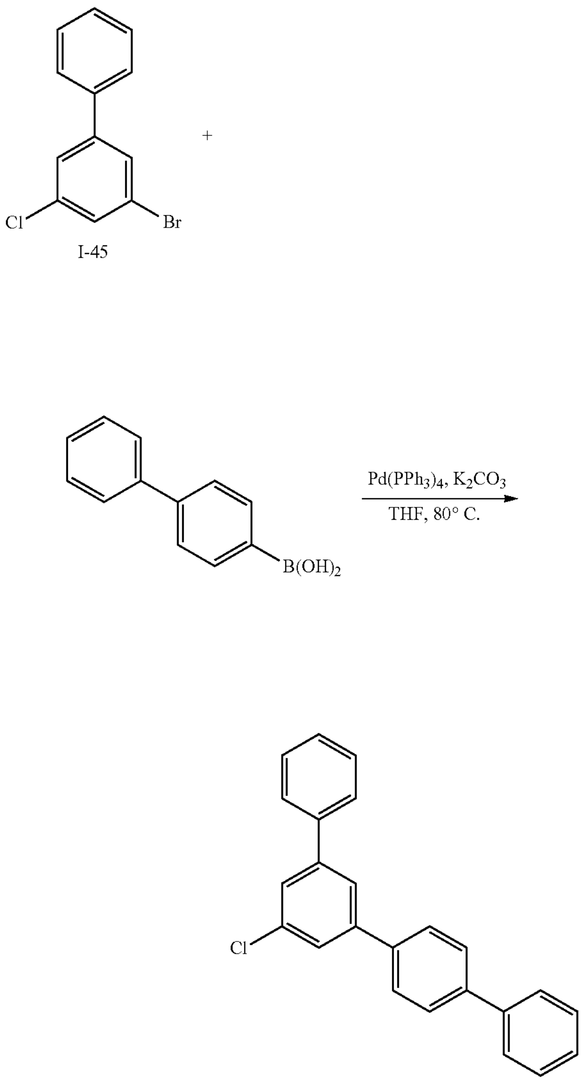

I-45

I-46

Compound I-45 (20 g, 75 mmol) was dissolved in THF (1 L) under a nitrogen environment, 4-biphenylboronic acid (17.7 g, 90 mmol, TCI) and tetrakis(triphenylphosphine) palladium (863 mg, 0.74 mmol) were added thereto, and the mixture was stirred. Potassium carbonate saturated in water (26 g, 186.87 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound I-46 (49 g and 80%).

HRMS (70 eV, EI+): m/z calcd for $C_{24}H_{17}Cl$: 340.1019, found: 340.

Elemental Analysis: C, 85%; H, 5%

Synthesis Example 47

Synthesis of Intermediate I-47

[Reaction Scheme 47]

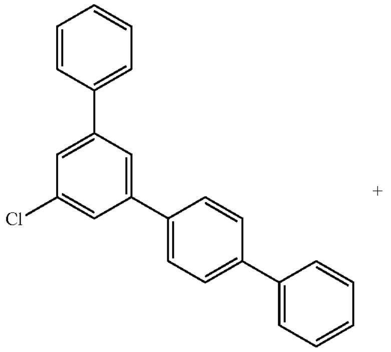

I-46

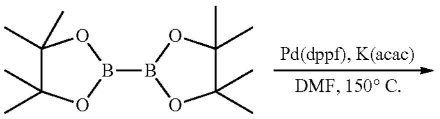

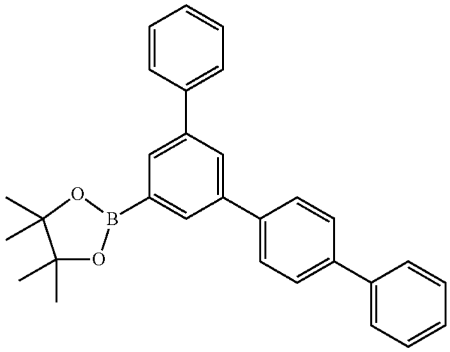

I-47

Compound I-46 (17.5 g, 51 mmol) was dissolved in dimethylforamide (DMF, 1 L) under a nitrogen environment, bis(pinacolato)diboron (15.6 g, 61.6 mmol), (1,1'-bis (diphenylphosphine)ferrocene)dichloropalladium (II) (2.5 g, 3.06 mmol), and potassium acetate (15 g, 153 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain Compound I-47 (20 g and 90%).

HRMS (70 eV, EI+): m/z calcd for $C_{30}H_{29}BO_2$: 432.2261, found: 432.

Elemental Analysis: C, 83%; H, 7%

SYNTHESIS OF FINAL COMPOUND

Synthesis Example 49

Synthesis of Compound A-1

[Reaction Scheme 49]

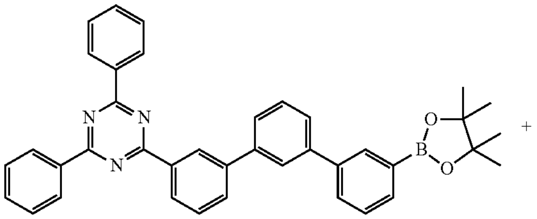

I-5

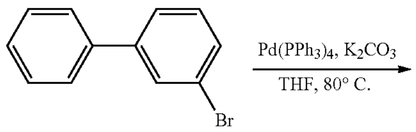

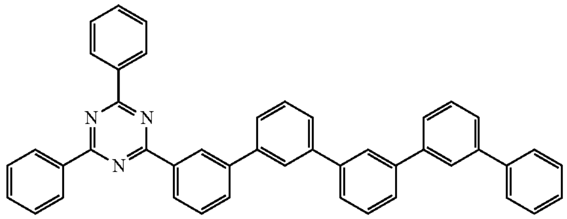

Compound I-5 (20 g, 34 mmol) was dissolved in tetrahydrofuran (THF, 0.2 L) under a nitrogen environment, 3-biphenylboronic acid (9.5 g, 40 mmol, TCI) and tetrakis (triphenylphosphine)palladium (0.39 g, 0.34 mmol) were added thereto, and the mixture was stirred. Potassium carbonate saturated in water (12 g, 85 mmol) was added thereto, and the obtained mixture was heated and refluxed at 80° C. for 20 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound A-1 (24 g and 70%). A molecular weight of Compound A-1 was 613.2518.

HRMS (70 eV, EI+): m/z calcd for $C_{45}H_{31}N_3$: 613.2518, found: 613.

Elemental Analysis: C, 88%; H, 5%

Synthesis Example 50

Synthesis of Compound B-1

[Reaction Scheme 50]

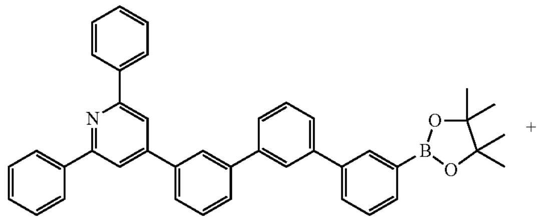

I-16

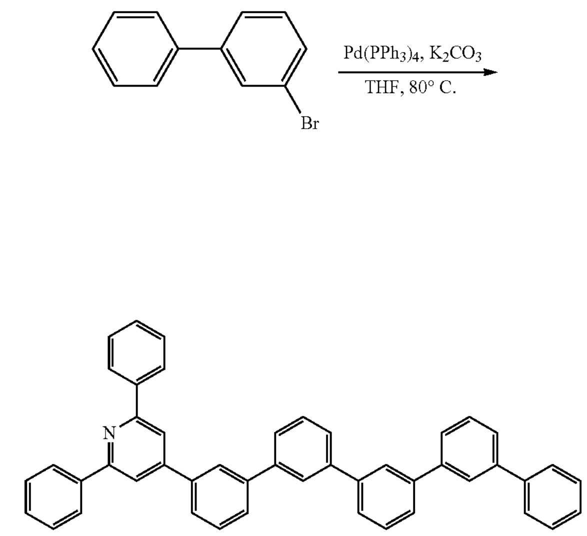

Compound I-16 (20 g, 34 mmol) was dissolved in tetrahydrofuran (THF, 0.2 L) under a nitrogen environment, 3-bromo-1,1'-biphenyl (9.5 g, 40 mmol) and tetrakis(triphenylphosphine)palladium (0.39 g, 0.34 mmol) were added thereto, and the mixture was stirred. Potassium carbonate saturated in water (12 g, 85 mmol) was added thereto, and the obtained mixture was heated and refluxed at 80° C. for 20 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound B-1 (15 g and 72%). A molecular weight of Compound B-1 was 611.2613.

HRMS (70 eV, EI+): m/z calcd for $C_{47}H_{33}N$: 611.2613, found: 611.

Elemental Analysis: C, 92%; H, 5%

Synthesis Example 51

Synthesis of Compound B-2

[Reaction Scheme 51]

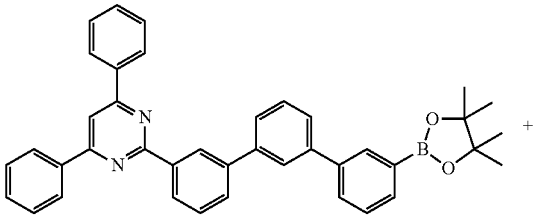

I-21

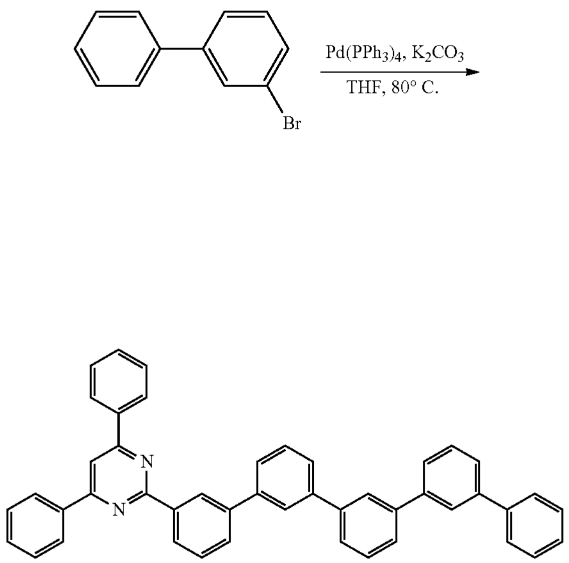

Compound I-21 (20 g, 34 mmol) was dissolved in tetrahydrofuran (THF, 0.2 L) under a nitrogen environment, 3-bromo-1,1'-biphenyl (9.5 g, 40 mmol) and tetrakis(triphenylphosphine)palladium (0.39 g, 0.34 mmol) were added thereto, and the mixture was stirred. Potassium carbonate saturated in water (12 g, 85 mmol) was added thereto, and the obtained mixture was heated and refluxed at 80° C. for 20 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound B-2 (16 g and 75%). A molecular weight of Compound B-2 was 612.2565.

HRMS (70 eV, EI+): calcd for $C_{46}H_{32}N_2$: 612.2565, found: 612.

Elemental Analysis: C, 90%; H, 5%

Synthesis Example 52

Synthesis of Compound A-2

[Reaction Scheme 52]

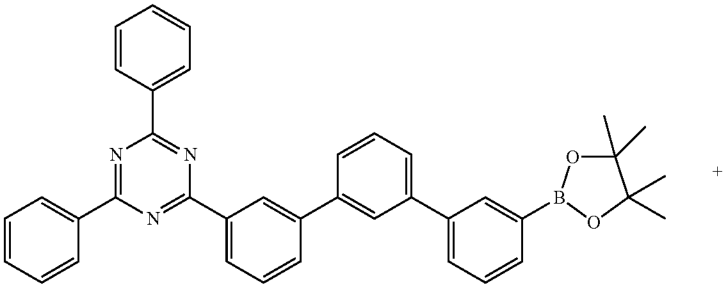

I-5

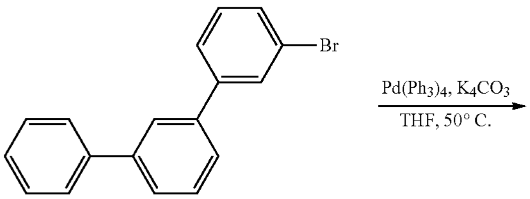

I-9

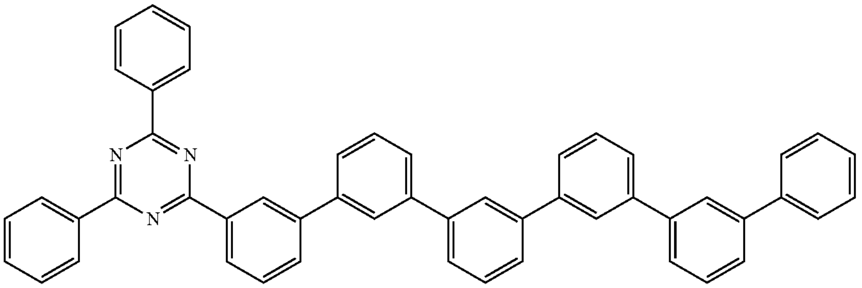

Compound I-5 (20 g, 34 mmol) was dissolved in tetrahydrofuran (THF, 0.2 L) under a nitrogen environment, Compound I-9 (13 g, 41 mmol) and tetrakis(triphenylphosphine)palladium (0.39 g, 0.34 mmol) were added thereto, and the mixture was stirred. Potassium carbonate saturated in water (12 g, 85 mmol) was added thereto, and the obtained mixture was heated and refluxed at 80° C. for 20 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound A-2 (19 g and 75%). A molecular weight of Compound A-2 was 689.2831.

HRMS (70 eV, EI+): m/z calcd for $C_{51}H_{35}N_3$: 689.2831, found: 689.

Elemental Analysis: C, 89%; H, 5%

Synthesis Example 53

Synthesis of Compound A-3

[Reaction Scheme 53]

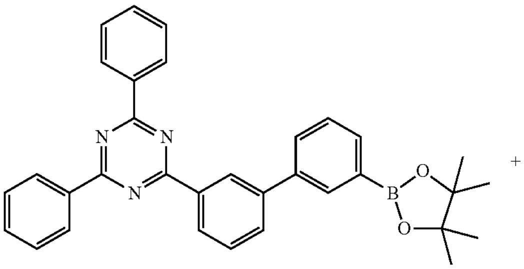

I-3

-continued

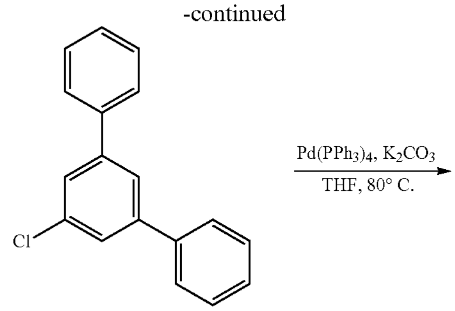

I-48

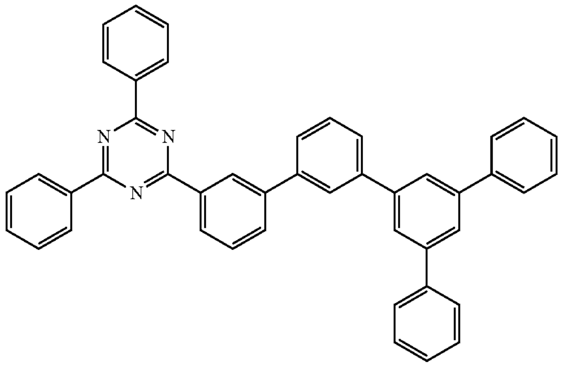

Compound I-3 (20 g, 39.1 mmol) was dissolved in tetrahydrofuran (THF, 0.2 L) under a nitrogen environment, Compound I-48 (12.45 g, 47 mmol) and tetrakis(triphenylphosphine)palladium (0.45 g, 0.39 mmol) were added thereto, and the mixture was stirred. Potassium carbonate saturated in water (13.5 g, 98 mmol) was added thereto, and the obtained mixture was heated and refluxed at 80° C. for 20 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound A-3 (20 g and 83%). A molecular weight of Compound A-3 was 613.2518.

HRMS (70 eV, EI+): m/z calcd for $C_{45}H_{31}N_3$: 613.2518, found: 613.

Elemental Analysis: C, 88%; H, 5%

Synthesis Example 54

Synthesis of Compound A-4

[Reaction Scheme 54]

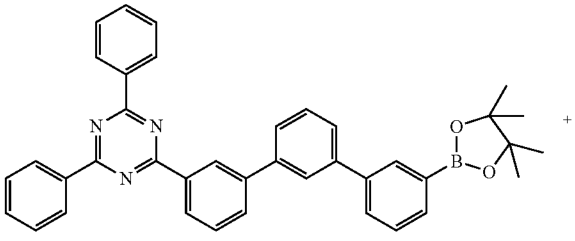

I-5

-continued

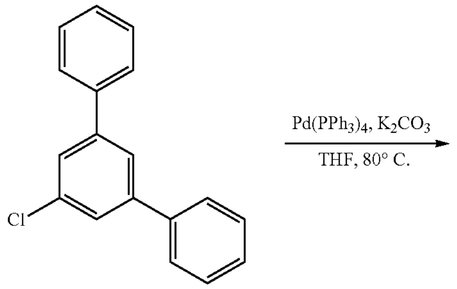

I-48

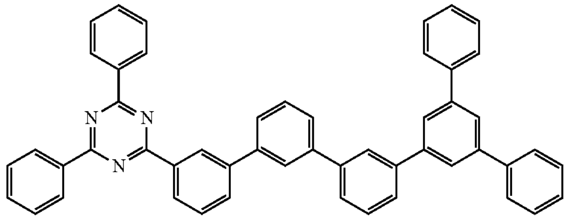

Compound I-5 (20 g, 34 mmol) was dissolved in tetrahydrofuran (THF, 0.2 L) under a nitrogen environment, Compound I-48 (10.8 g, 41 mmol) and tetrakis(triphenylphosphine)palladium (0.40 g, 0.34 mmol) were added thereto, and the mixture was stirred. Potassium carbonate saturated in water (12 g, 85 mmol) was added thereto, and the obtained mixture was heated and refluxed at 80° C. for 20 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound A-4 (19 g and 80%). A molecular weight of Compound A-4 was 689.2831.

HRMS (70 eV, EI+): m/z calcd for $C_{51}H_{35}N_3$: 689.2831, found: 689.

Elemental Analysis: C, 89%; H, 5%

Synthesis Example 55

Synthesis of Compound A-5

[Reaction Scheme 55]

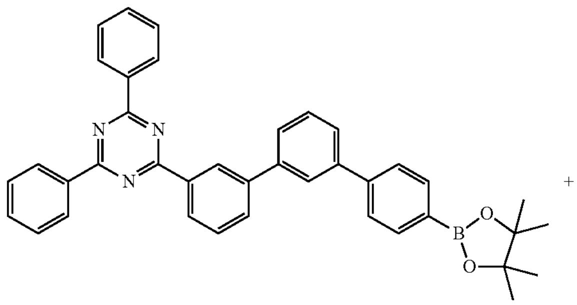

I-11

-continued

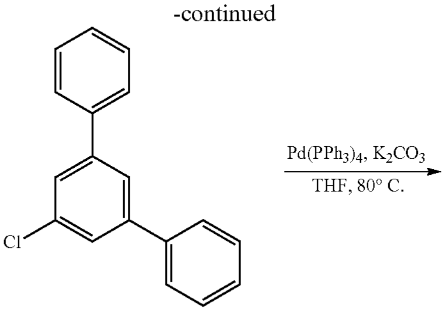

I-48

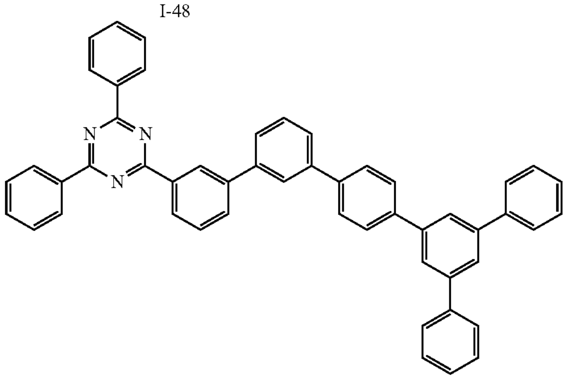

Compound I-11 (20 g, 34 mmol) was dissolved in tetrahydrofuran (THF, 0.2 L) under a nitrogen environment, Compound I-48 (10.8 g, 41 mmol) and tetrakis(triphenylphosphine)palladium (0.40 g, 0.34 mmol) were added thereto, and the mixture was stirred. Potassium carbonate saturated in water (12 g, 85 mmol) was added thereto, and the obtained mixture was heated and refluxed at 80° C. for 20 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound A-5 (20 g and 85%). A molecular weight of Compound A-5 was 689.2831.

HRMS (70 eV, EI+): m/z calcd for $C_{51}H_{35}N_3$: 689.2831, found: 689.

Elemental Analysis: C, 89%; H, 5%

Synthesis Example 56

Synthesis of Compound A-8

[Reaction Scheme 56]

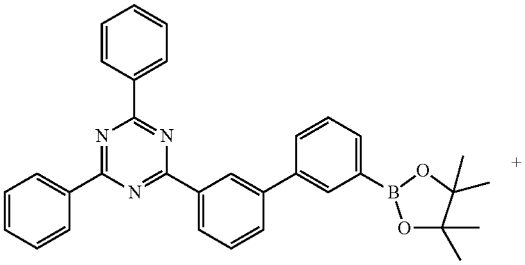

I-3

-continued

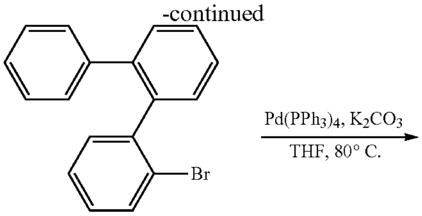

I-7

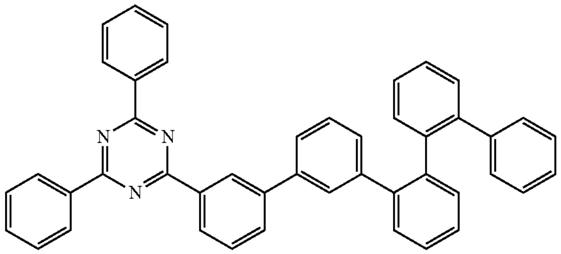

Compound I-3 (20 g, 39 mmol) was dissolved in tetrahydrofuran (THF, 0.2 L) under a nitrogen environment, Compound I-7 (14.5 g, 47 mmol) and tetrakis(triphenylphosphine)palladium (0.45 g, 0.39 mmol) were added thereto, and the mixture was stirred. Potassium carbonate saturated in water (13.5 g, 97 mmol) was added thereto, and the obtained mixture was heated and refluxed at 80° C. for 20 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound A-8 (17 g and 70%). A molecular weight of Compound A-8 was 613.2518.

HRMS (70 eV, EI+): m/z calcd for $C_{45}H_{31}N_3$: 613.2518, found: 613.

Elemental Analysis: C, 88%; H, 5%

Synthesis Example 57

Synthesis of Compound A-9

[Reaction Scheme 57]

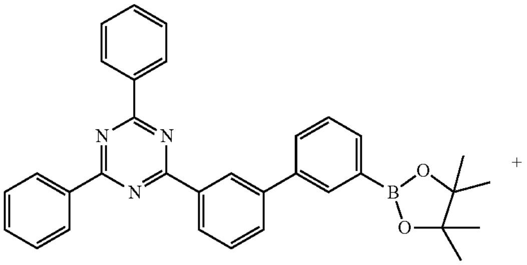

I-3

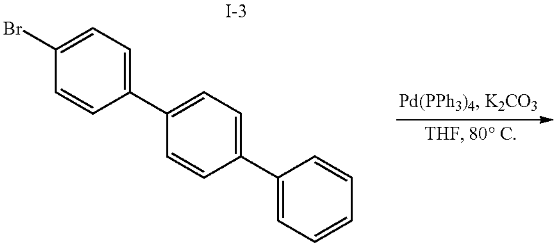

-continued

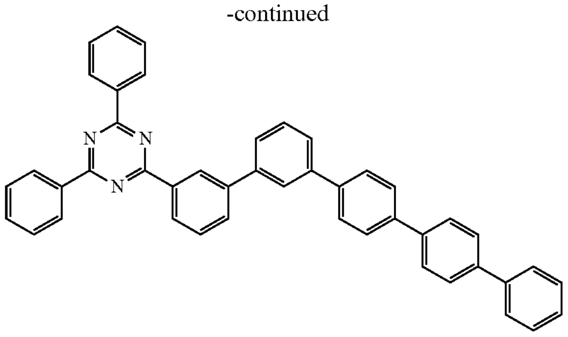

Compound I-3 (20 g, 39 mmol) was dissolved in tetrahydrofuran (THF, 0.2 L) under a nitrogen environment, 4-bromo-p-terphenyl (14.5 g, 47 mmol, TCI) and tetrakis (triphenylphosphine)palladium (0.45 g, 0.39 mmol) were added thereto, and the mixture was stirred. Potassium carbonate saturated in water (13.5 g, 97 mmol) was added thereto, and the obtained mixture was heated and refluxed at 80° C. for 20 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound A-9 (19 g and 79%). A molecular weight of Compound A-9 was 613.2518.

HRMS (70 eV, EI+): m/z calcd for $C_{45}H_{31}N_3$: 613.2518, found: 613.

Elemental Analysis: C, 88%; H, 5%

Synthesis Example 58

Synthesis of Compound A-6

[Reaction Scheme 58]

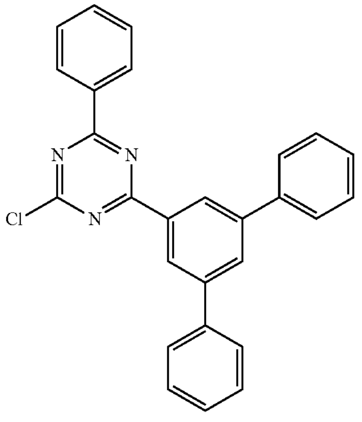

+

I-44

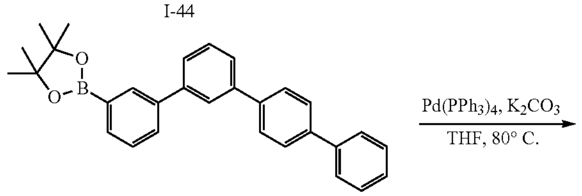

I-41

-continued

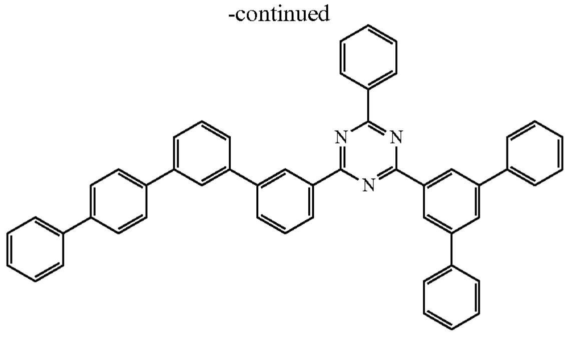

Compound I-44 (32 g, 76 mmol) was dissolved in THF (1 L) under a nitrogen environment, Compound I-41 (33 g, 76 mmol) and tetrakis(triphenylphosphine)palladium (0.88 g, 0.76 mmol) were added thereto, and the mixture was stirred. Potassium carbonate saturated in water (26 g, 190 mmol) was added thereto, and the obtained mixture was heated and refluxed at 80° C. for 12 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound A-6 (32 g and 80%). A molecular weight of Compound A-6 was 689.2831.

HRMS (70 eV, EI+): m/z calcd for $C_{51}H_{35}N_3$:689.2831, found 689.

Elemental Analysis: C, 89%; H, 5%

Synthesis Example 59

Synthesis of Compound A-72

[Reaction Scheme 59]

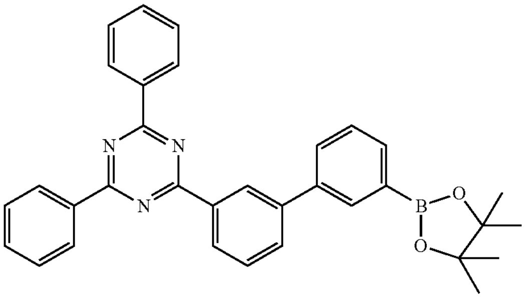

+

I-3

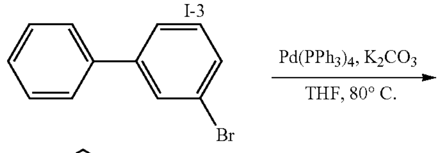

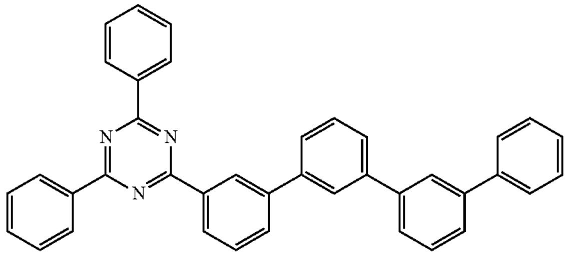

Compound I-3 (20 g, 39 mmol) was dissolved in tetrahydrofuran (THF, 0.2 L) under a nitrogen environment, 3-bromo-1,1'-biphenyl (11 g, 47 mmol) and tetrakis(triphenylphosphine)palladium (0.45 g, 0.39 mmol) were added thereto, and the mixture was stirred. Potassium carbonate saturated in water (13.5 g, 97 mmol) was added thereto, and the obtained mixture was heated and refluxed at 80° C. for 20 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound A-72 (16 g and 78%). A molecular weight of Compound A-72 was 537.2205.

HRMS (70 eV, EI+): m/z calcd for $C_{39}H_{27}N_3$: 537.2205, found: 537.

Elemental Analysis: C, 87%, H, 5%

Synthesis Example 60

Synthesis of Compound A-73

[Reaction Scheme 60]

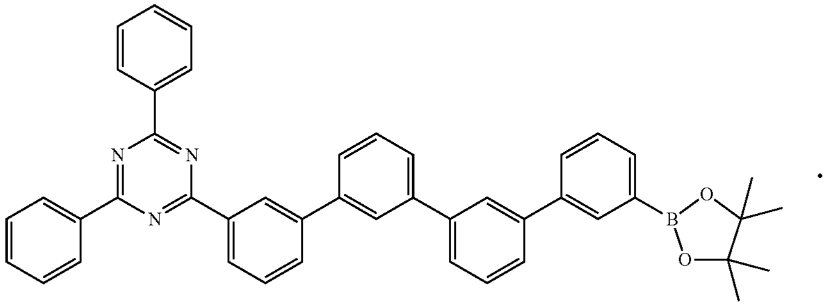

I-28

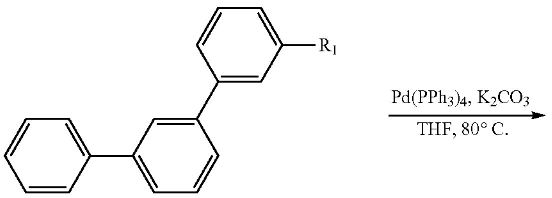

I-9

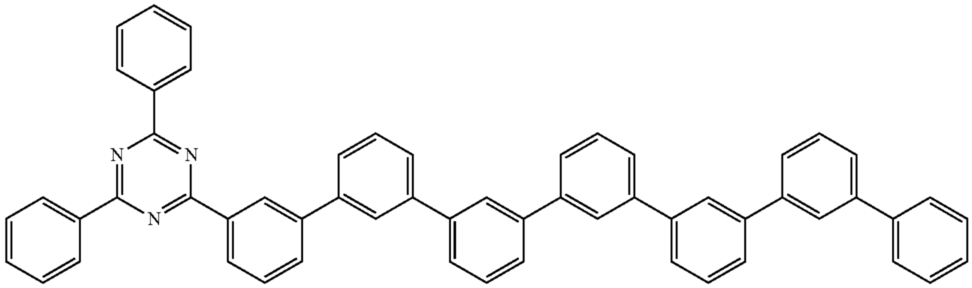

Compound I-28 (20 g, 30 mmol) was dissolved in tetrahydrofuran (THF, 0.2 L) under a nitrogen environment, Compound I-9 (11 g, 36 mmol) and tetrakis(triphenylphosphine)palladium (0.35 g, 0.30 mmol) were added thereto, and the mixture was stirred. Potassium carbonate saturated in water (10 g, 75 mmol) was added thereto, and the obtained mixture was heated and refluxed at 80° C. for 20 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound A-73 (14.5 g, 70%). A molecular weight of Compound A-73 was 765.3144.

HRMS (70 eV, EI+): m/z calcd for $C_{51}H_{35}N_3$: 765.3144, found: 765.

Elemental Analysis: C, 89%; H, 5%

Synthesis Example 61

Synthesis of Compound A-74

[Reaction Scheme 61]

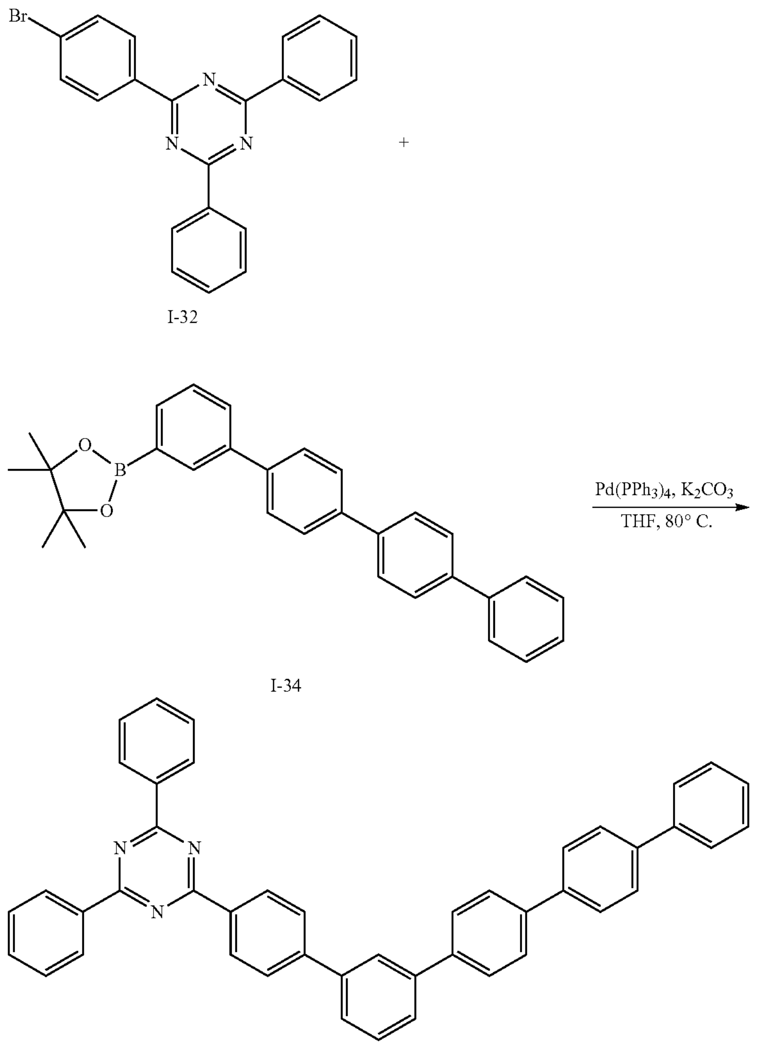

I-32

I-34

Compound I-32 (20 g, 51 mmol) was dissolved in tetrahydrofuran (THF, 0.2 L) under a nitrogen environment, Compound I-34 (26.5 g, 61.2 mmol) and tetrakis(triphenylphosphine)palladium (0.6 g, 0.51 mmol) were added thereto, and the mixture was stirred. Potassium carbonate saturated in water (17.5 g, 127 mmol) was added thereto, and the obtained mixture was heated and refluxed at 80° C. for 20 hours. When the reaction was complete, water was dichloromethane (DCM) and then, filtered after removing moisture with anhydrous $MgSO_4$ and concentrated under a reduced pressure. This obtained residue was separated and purified through flash column chromatography to obtain Compound A-74 (22.5 g, 75%). A molecular weight of Compound A-74 was 613.2518.

HRMS (70 eV, EI+): m/z calcd for $C_{45}H_{31}N_3$: 613.2518, found: 613.

Elemental Analysis: C, 88%; H, 5%

Synthesis Example 62

Synthesis of Compound A-19

[Reaction Scheme 62]

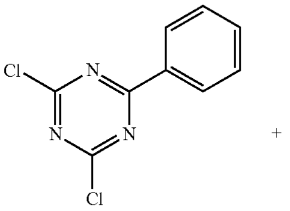

I-43

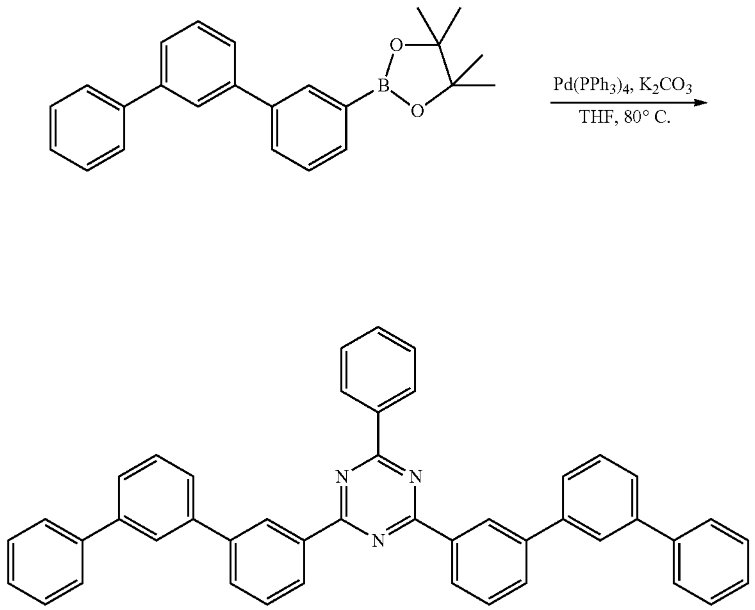

Intermediate I-43 (5.0 g, 22.12 mmol), 2-([1,1':3',1"-terphenyl]-3-yl)-4,4,5,5-tetramethyl-1,3,2-dioxaborolane (18.12 g, 50.87 mmol), potassium carbonate (7.64 g, 55.30 mmol), and tetrakis(triphenyl phosphine) palladium (0) (1.28 g, 1.11 mmol) were added to tetrahydrofuran (THF, 100 mL) and water (30 mL) in a 250 mL flask and then, heated and refluxed under a nitrogen current for 10 hours. The obtained mixture was added to methanol (500 mL) to crystallize a solid, the solid was filtered, dissolved in monochlorobenzene, filtered with silica gel/Celite, and then, recrystallized with methanol after removing an appropriate amount of an organic solvent to obtain Compound A-19 (11.3 g, 83%). An elemental analysis of Compound A-19 is as follows.

calcd $C_{45}H_{31}N_3$: C, 88.06; H, 5.09; N, 6.85, found: C, 87.94; H, 5.12; N, 6.76.

Synthesis Example 63

Synthesis of Compound A-20

[Reaction Scheme 63]

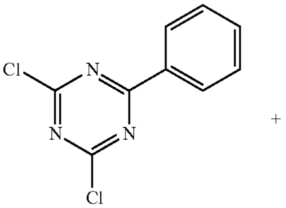

I-43

-continued

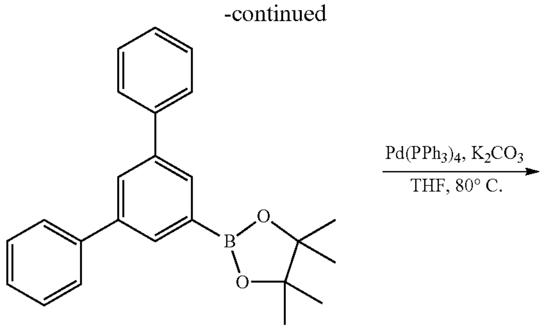

I-42

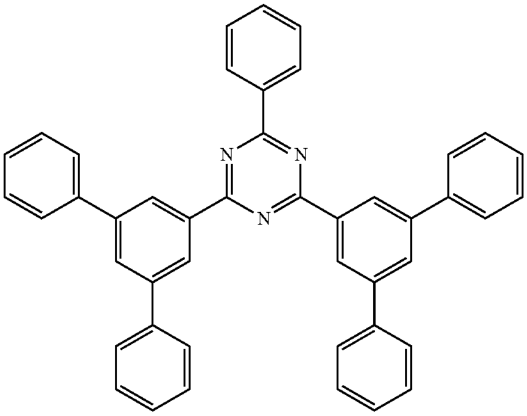

Intermediate I-43 (5.0 g, 22.12 mmol), Intermediate I-42 (18.12 g, 50.87 mmol), potassium carbonate (7.64 g, 55.30 mmol), and tetrakis(triphenyl phosphine) palladium (0) (1.28 g, 1.11 mmol) were added to tetrahydrofuran (THF, 100 mL) and water (30 mL) in a 250 mL flask and then, heated and refluxed under a nitrogen stream for 10 hours. The obtained mixture was added to methanol (500 mL) to crystallize a solid, and the solid was filtered, dissolved in monochlorobenzene, filtered with silica gel/Celite, and then, recrystallized with methanol after removing an appropriate amount of an organic solvent to obtain Compound A-20 (8.5 g, 63%). An elemental analysis of Compound A-20 was as follows.

calcd. $C_{45}H_{31}N_3$: C, 88.06; H, 5.09; N, 6.85, found: C, 88.16; H, 5.23; N, 6.63.

Synthesis Example 64

Synthesis of Compound A-23

[Reaction Scheme 64]

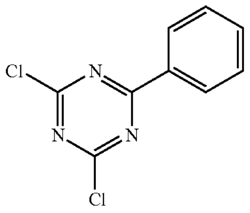

I-43

+

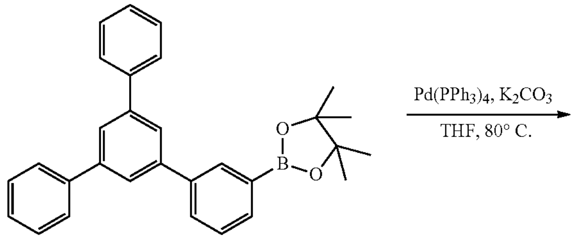

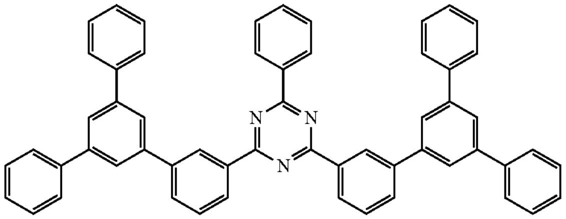

Intermediate I-46 (5.0 g, 22.12 mmol), 4,4,5,5-tetramethyl-2-(5'-phenyl-[1,1':3',1"-terphenyl]-3-yl)-1,3,2-dioxaborolane (21.99 g, 46.60 mmol), potassium carbonate (7.64 g, 55.30 mmol), and tetrakis(triphenyl phosphine) palladium (0) (1.28 g, 1.11 mmol) were added to tetrahydrofuran (THF, 100 mL) and water (30 mL) in a 250 mL flask and then, heated and refluxed under a nitrogen stream for 10 hours. The obtained mixture was added to methanol (500 mL) to crystallize a solid, and the solid was filtered, dissolved in monochlorobenzene, filtered with silica gel/Celite, and then, recrystallized with methanol after removing an appropriate amount of an organic solvent to obtain Compound A-23 (13.0 g, 77%). An elemental analysis of Compound A-23 was as follows.

calcd. $C_{57}H_{39}N_3$: C, 89.38; H, 5.13; N, 5.49, found: C, 89.21; H, 5.04; N, 5.53.

Synthesis Example 65

Synthesis of Compound A-25

[Reaction Scheme 65]

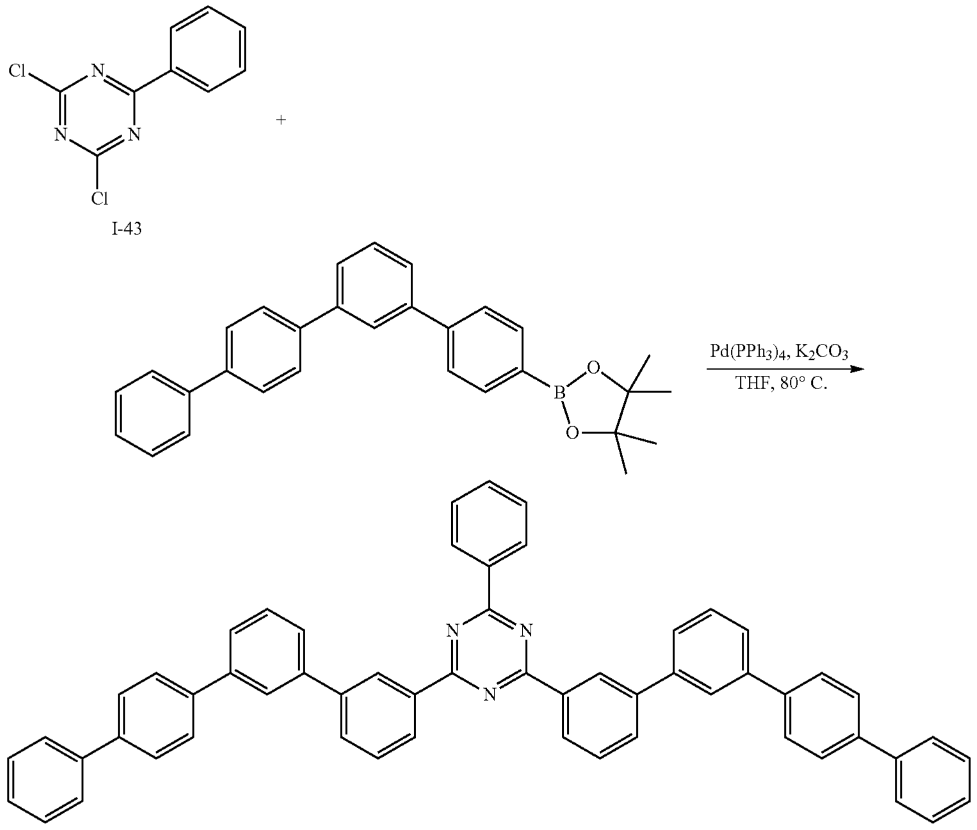

I-43

Intermediate I-43 (5.0 g, 22.12 mmol), 2-([1,1':3',1":4",1'"-quaterphenyl]-4-yl)-4,4,5,5-tetramethyl-1,3,2-dioxaborolane (21.99 g, 46.60 mmol), potassium carbonate (7.64 g, 55.30 mmol), and tetrakis(triphenyl phosphine) palladium (0) (1.28 g, 1.11 mmol) were added to tetrahydrofuran (THF, 100 mL) and water (30 mL) in a 250 mL flask and then, heated and refluxed under a nitrogen stream for 10 hours. The obtained mixture was added to methanol (500 mL) to crystallize a solid, and the solid was dissolved in monochlorobenzene, filter with silica gel/Celite and then, recrystallized with methanol after removing an appropriate amount of an organic solvent to obtain Compound A-25 (14.2 g, 84%). An elemental analysis of Compound A-25 was as follows.

calcd. $C_{57}H_{39}N_3$: C, 89.38; H, 5.13; N, 5.49, found: C, 89.48; H, 5.33; N, 5.41.

Synthesis Example 66

Synthesis of Compound A-43

[Reaction Scheme 66]

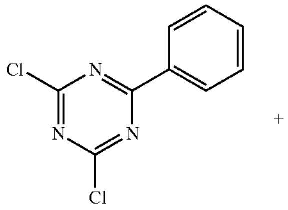

I-43

-continued

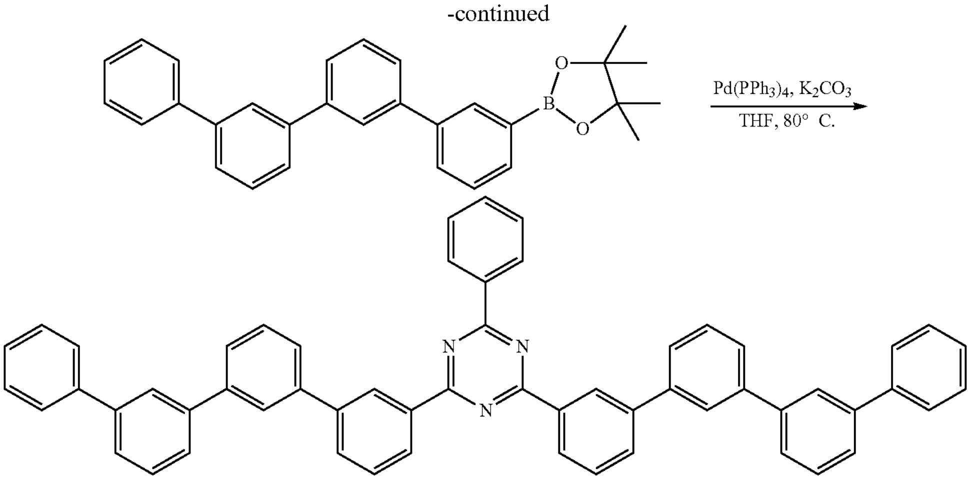

Intermediate I-43 (5.0 g, 22.12 mmol), 2-([1,1':3',1":3",1'"-quaterphenyl]-3-yl)-4,4,5,5-tetramethyl-1,3,2-dioxaborolane (21.99 g, 46.60 mmol), potassium carbonate (7.64 g, 55.30 mmol), and tetrakis(triphenyl phosphine) palladium (0) (1.28 g, 1.11 mmol) were added to tetrahydrofuran (THF, 100 mL) and water 30 mL in a 250 mL flask and then, heated and refluxed under a nitrogen stream for 10 hours. The obtained mixture was added to methanol (500 mL) to crystallize a solid, and the solid was filtered, dissolved in monochlorobenzene, filtered with silica gel/Celite, and then, recrystallized after removing an appropriate amount of an organic solvent to obtain Compound A-43 (12.2 g, 72%). An elemental analysis of Compound A-43 was as follows.

calcd. $C_{57}H_{39}N_3$: C, 89.38; H, 5.13; N, 5.49, found: C, 89.71; H, 5.46; N, 5.24.

Synthesis Example 67

Synthesis of Compound A-68

[ReactionScheme 67]

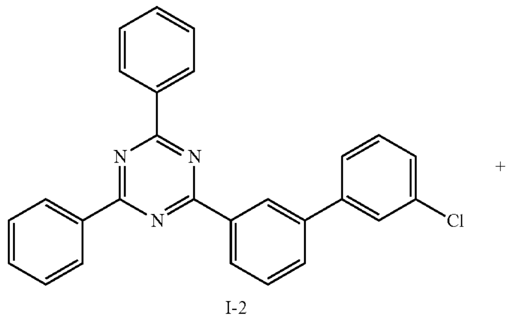

I-2

-continued

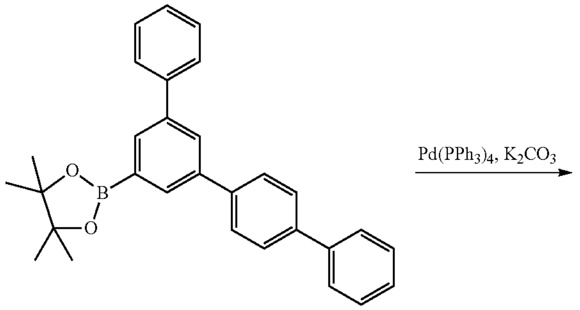

I-47

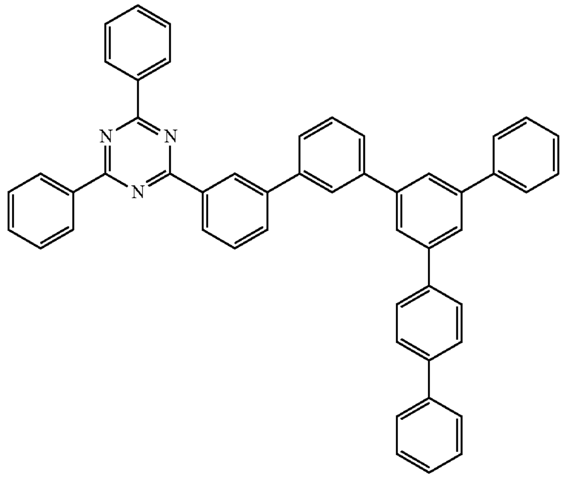

Compound I-2 (20 g, 47.63 mmol) was dissolved in tetrahydrofuran (THF, 0.2 L) under a nitrogen environment, Compound I-47 (24.71 g, 57.16 mmol) and tetrakis(triphenylphosphine)palladium (0.55 g, 0.48 mmol) were added thereto, and the mixture was stirred. Potassium carbonate saturated in water (13 g, 97 mmol) was added thereto, and the mixture was heated and refluxed at 80° C. for 20 hours. When the reaction was complete, water was added to the reaction solution, and the mixture was extracted with dichloromethane (DCM) and then, filtered after removing moisture with anhydrous $MgSO_4$ and concentrated under a reduced pressure. This obtained residue was separated and purified through flash column chromatography to obtain Compound A-68 (23.66 g, 72%). A molecular weight of Compound A-68 was 689.86.

HRMS (70 eV, EI+): m/z calcd for $C_{51}H_{35}N_3$: 689.28, found: 689.

Elemental Analysis: C, 89%; H, 5%

SYNTHESIS OF SECOND COMPOUND

Synthesis Example 68

Synthesis of Intermediate PI-1

[Reaction Scheme 68]

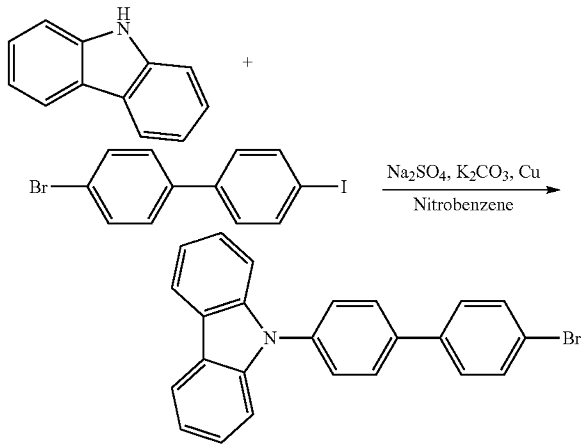

PI-1

9H-carbazole (60.00 g, 358.83 mmol) as a starting material was dissolved in nitrobenzene in a round-bottomed flask, 4-bromo-4'-iodo-1,1'-biphenyl (154.58 g, 430.60 mmol), $Na_2SO_4$ (50.95 g, 358.83 mmol), $K_2CO_3$ (49.52 g, 358.83 mmol), and Cu (6.84 g, 107.65 mmol) were added thereto, and the mixture was stirred at 200° C. Whether the reaction was complete or not was checked by using TLC, and the nitrobenzene was distillated and removed under a reduced pressure and extracted with $CH_2Cl_2$ and water. An organic layer therefrom was dried and concentrated with $MgSO_4$, and a compound produced therefrom was treated with silica gel column and recrystallized to obtain PI-1 (104.33 g, 261.95 mmol, 73%).

HRMS (70 eV, EI+): m/z calcd for $C_{24}H_{16}BrN$: 397.05, found: 397.

Elemental Analysis: C, 72%, H, 4%

Synthesis Example 69

Synthesis of Intermediate PI-2

[Reaction Scheme 69]

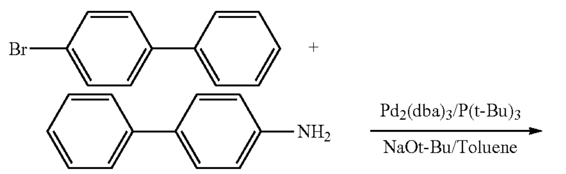

-continued

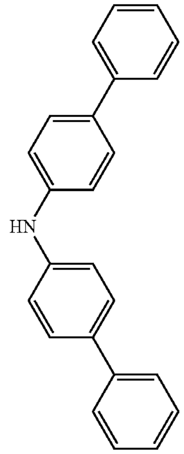

4-bromo-1-1'-biphenyl (50.00 g, 214.49 mmol) as a starting material was dissolved in toluene in a round flask, [1,1'-biphenyl]-4-amine (72.60 g, 428.98 mmol), $Pd_2(dba)_3$ (4.59 g, 5.0 mmol), 50% $P(t\text{-}Bu)_3$ (4.92 ml, 10.0 mmol), and NaOt-Bu (61.84 g, 643.47 mmol) were added thereto, and the mixture was stirred at 40° C. Whether the reaction was complete or not was checked by using TLC, an organic layer extracted by using $CH_2Cl_2$ and water was dried and concentrated with $MgSO_4$ to obtain a compound, and the compound was treated through silica-gel column and recrystallized to obtain PI-2 (51.71 g, 160.87 mmol, 75%).

HRMS (70 eV, EI+): m/z calcd for $C_{24}H_{19}N$: 321.15, found: 321.

Elemental Analysis: C, 90%; H, 6%

Synthesis Example 70

Synthesis of Compound P-17

[Reaction Scheme 70]

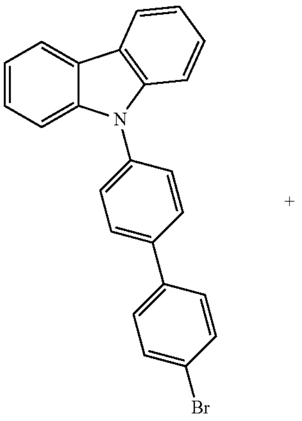

PI-1

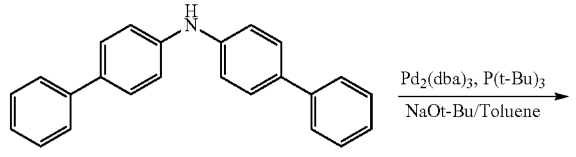

PI-2

-continued

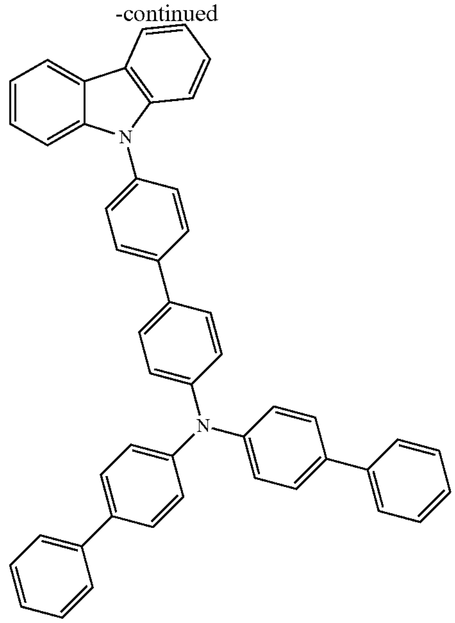

P-17

The PI-1 (53.59 g, 134.06 mmol) was dissolved in toluene in a round-bottomed flask, the PI-2 (51.71 g, 160.87 mmol), $Pd_2(dba)_3$ (4.59 g, 5.0 mmol), 50% $P(t-Bu)_3$ (4.92 ml, 10.0 mmol), and NaOt-Bu (61.84 g, 643.47 mmol) were added thereto, and the mixture was stirred at 100° C. Whether the reaction was complete or not was checked by using TLC, an organic layer extracted by $CH_2Cl_2$ and water was dried and concentrated with $MgSO_4$ to produce a compound, and the compound was treated with silica-gel column and recrystallized to obtain P-17 (71.08 g, 111.27 mmol, 83%).

HRMS (70 eV, EI+): m/z calcd for $C_{48}H_{34}N_2$: 638.27, found: 638.

Elemental Analysis: C, 90%; H, 5%

Manufacture of Organic Light Emitting Diode

EXAMPLE 1

A glass substrate coated with ITO (indium tin oxide) to be 1500 Å thick was ultrasonic wave-washed with a distilled water. Subsequently, the glass substrate was ultrasonic wave-washed with a solvent such as isopropyl alcohol, acetone, methanol, and the like, moved to a plasma cleaner, cleaned by using oxygen plasma for 10 minutes, and then, moved to a vacuum depositor. This ITO transparent electrode was used as an anode, a 700 Å-thick hole injection layer (HIL) was formed thereon by vacuum-depositing N4,N4'-diphenyl-N4,N4'-bis(9-phenyl-9H-carbazol-3-yl)biphenyl-4,4'-diamine) (Compound A), and a hole transport layer was formed on the hole injection layer (HIL) by depositing 1,4,5,8,9,11-hexaazatriphenylene-hexacarbonitrile (HAT-CN) (Compound B) to be 50 Å thick and then, N-(biphenyl-4-yl)-9,9-dimethyl-N-(4-(9-phenyl-9H-carbazol-3-yl)phenyl)-9H-fluoren-2-amine) (Compound C) to be 700 Å thick. On the hole transport layer, a 50 Å-auxiliary hole transport layer was formed by vacuum-depositing Compound P-17 according to Synthesis Example 70. Subsequently, on the auxiliary hole transport layer, a 200 Å-thick light-emitting layer was formed by depositing BH113 and BD370 available from SFC as a blue fluorescent light emitting host of a dopant doped in an amount of 5 wt %. A 50 Å-thick auxiliary electron transport layer was formed by vacuum-depositing Compound 61 according to Synthesis Example 65 on the light-emitting layer.

Subsequently, on the auxiliary electron transport layer, a 310 Å-thick electron transport layer was formed by simultaneously vacuum-depositing (8-(4-(4-(naphthalen-2-yl)-6-(naphthalen-3-yl)-1,3,5-triazin-2-yl)phenyl)quinoline) (Compound E) and Liq in a ratio of 1:1, and a cathode was formed by sequentially vacuum-depositing Liq to be 15 Å thick and Al to be 1200 Å thick on the electron transport layer, manufacturing an organic light emitting diode.

The organic light emitting diode had a six-layered organic thin film structure and specifically, a structure of ITO/A (700 Å)/B (50 Å)/C (700 Å)/auxiliary hole transport layer [P-17 50 Å]/EML [BH113:BD370 (95:5 wt %)] 200 Å/auxiliary electron transport layer [Compound 61 (50 Å)]/E:Liq=1:1 (310 Å) /Liq (15 Å/Al (1200 Å).

EXAMPLE 2

An organic light emitting diode was manufactured according to the same method as Example 1 except for using Compound 152 according to Synthesis Example 67 instead of Compound 61 for the auxiliary electron transport layer.

REFERENCE EXAMPLE 1

An organic light emitting diode was manufactured according to the same method as Example 1 except for depositing Compound C to form a 750 Å-thick hole transport layer without forming the auxiliary electron transport layer.

COMPARATIVE EXAMPLE 1

An organic light emitting diode was manufactured according to the same method as Example 1 except for depositing Compound C to form a 750 Å-thick hole transport layer without forming the auxiliary hole transport layer and depositing Compound E:Liq=1:1 to form a 360 Å-thick electron transport layer instead of Compound E:Liq=1:1 to form the 310 Å-thick electron transport layer without forming the auxiliary electron transport layer.

COMPARATIVE EXAMPLE 2

An organic light emitting diode was manufactured according to the same method as Example 1 except for depositing Compound E:Liq=1:1 to form a 360 Å-thick electron transport layer instead of Compound E:Liq=1:1 to form the 310 Å-thick electron transport layer without forming the auxiliary electron transport layer.

Evaluation

Luminous efficiency of each organic light emitting diode according to Examples 1 and 2, Reference Example 1, and Comparative Examples 1 and 2 were measured.

Specific measurement methods were as follows, and the results were provided in Table 1.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), the measured current value was divided by area to provide the results.

(2) Measurement of Luminance Change Depending on Voltage Change Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 $mA/cm^2$) were calculated by using the luminance, current density, and voltages (V) from the items (1) and (2).

(4) Roll-Off

Efficiency roll-off was calculated as a percentage through (Max measurement−Measurement at 6000 $cd/m^2$/Max measurement) among the measurements of (3).

TABLE 1

| | Auxiliary hole transport layer | Auxiliary electron transport layer | Driving voltage (V) | Luminous efficiency (cd/A) | External quantum efficiency |
|---|---|---|---|---|---|
| Example 1 | P-17 | Compound 61 | 4.16 | 7.4 | 50.3 |
| Example 2 | P-17 | Compound 152 | 3.99 | 7.7 | 52.7 |
| Reference Example 1 | Compound C | Compound 61 | 4.23 | 6.2 | 41.4 |
| Comparative Example 1 | Compound C | — | 4.38 | 5.9 | 39.5 |
| Comparative Example 2 | P-17 | — | 4.30 | 7.0 | 46.7 |

Referring to Table 1, the organic light emitting diodes according to Examples 1 and 2 shows a low driving voltage and simultaneously, remarkably improved luminous efficiency and external quantum efficiency characteristics compared with the organic light emitting diodes according to Reference Example 1 and Comparative Examples 1 and 2.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

[Description of Symbols]

| | |
|---|---|
| 10: anode | 20: cathode |
| 30: organic layer | 31: hole transport layer |
| 32: light-emitting layer | 33: auxiliary hole transport layer |
| 34: electron transport layer | 35: auxiliary electron transport layer |
| 36: electron injection layer | 37: hole injection layer |

What is claimed is:

1. An organic optoelectronic device, comprising an anode and a cathode facing each other, a light-emitting layer located between the anode and cathode, a hole transport layer located between the anode and light-emitting layer, an auxiliary hole transport layer located between the hole transport layer and light-emitting layer, an electron transport layer located between the cathode and light-emitting layer, and an auxiliary electron transport layer between the electron transport layer and light-emitting layer, wherein the auxiliary electron transport layer includes at least one type of a first compound expressed by Chemical Formula 1, and the auxiliary hole transport layer includes at least one type of a second compound expressed by Chemical Formula 2:

[Chemical Formula 1]

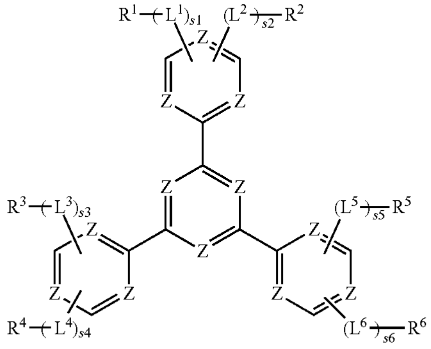

wherein, in Chemical Formula 1,

Z is independently N, C, or $CR^a$, at least one of Z is N, $R^1$ to $R^6$ and $R^a$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof, $L^1$ to $L^6$ are independently a single bond, a substituted or unsubstituted C6 to C30 arylene group, a substituted or unsubstituted heteroarylene group, or a combination thereof, and s1 to s6 are independently an integer ranging from 0 to 5,

[Chemical Formula 2]

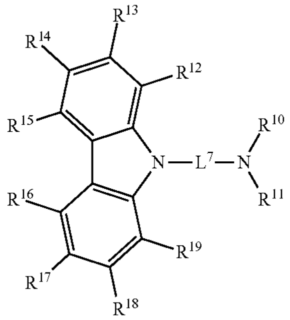

wherein, in Chemical Formula 2, $R^{10}$ to $R^{19}$ are independently hydrogen, deuterium, a substituted or unsubstituted C6 to C30 aryl group, a substituted or unsubstituted C2 to C30 heteroaryl group, or a combination thereof, and $L^7$ is a substituted or unsubstituted C2 to C10 alkenylene group, a substituted or unsubstituted C6 to C30 arylene group, a substituted or unsubstituted C2 to C30 heteroaryl group, or a combination thereof, and "substituted" refers replacement of at least one hydrogen by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, a fluorenyl group, or a cyano group.

2. The organic optoelectronic device of claim 1, wherein the first compound is expressed by one of Chemical Formula 1-i to Chemical Formula 1-ix:

[Chemical Formula 1-i]

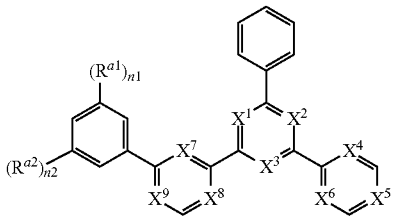

[Chemical Formula 1-ii]

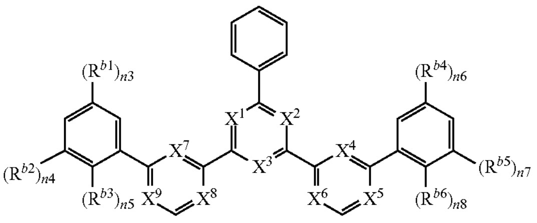

[Chemical Formula 1-iii]

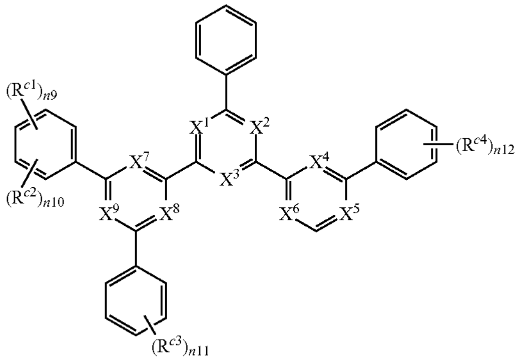

[Chemical Formula 1-iv]

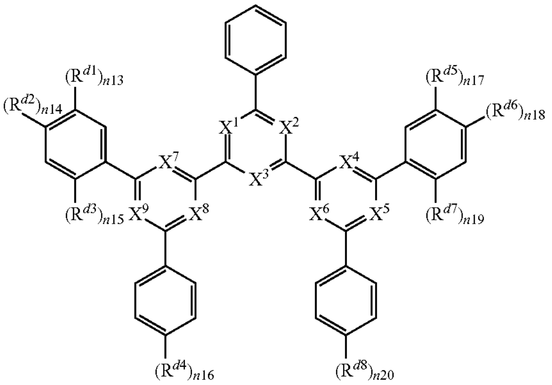

[Chemical Formula 1-v]

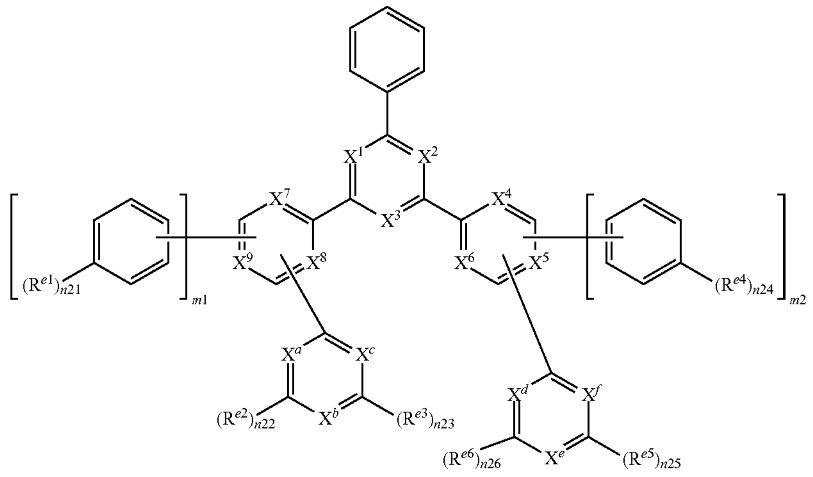

[Chemical Formula 1-vi]

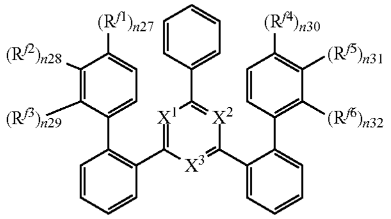

[Chemical Formula 1-vii]

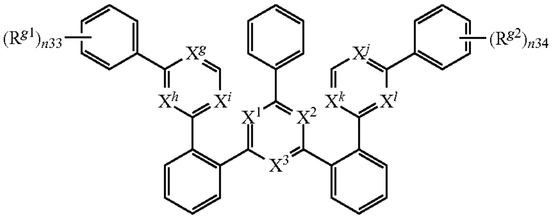

-continued

[Chemical Formula 1-viii]

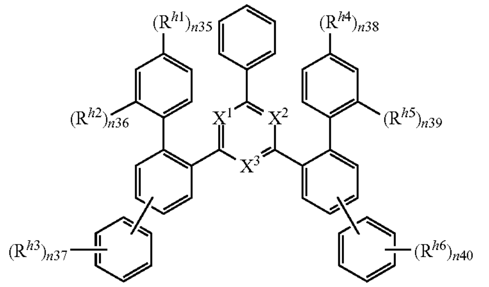

[Chemical Formula 1-ix]

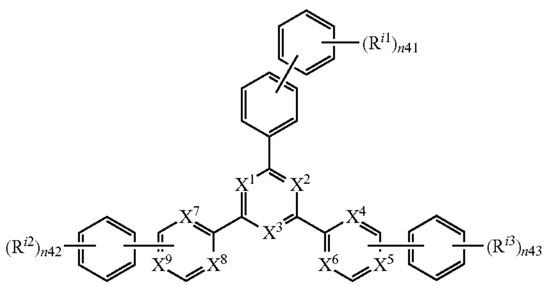

wherein in Chemical Formula 1-i, $R^{a1}$ and $R^{a2}$ are independently a substituted or unsubstituted C1 to C10 alkyl group, a substituted or unsubstituted C6 to C30 aryl group, a substituted or unsubstituted C2 to C30 heteroaryl group, or a combination thereof, n1 and n2 are independently an integer of 0 or 1, provided that n1 and n2 are not simultaneously 0, wherein, in Chemical Formula 1-ii, $R^{b1}$ to $R^{b6}$ are independently a substituted or unsubstituted C1 to C10 alkyl group, a substituted or unsubstituted C6 to C30 aryl group, a substituted or unsubstituted C2 to C30 heteroaryl group, or a combination thereof, and n3 to n8 are independently an integer of 0 or 1, but n3 to n5 are not 0 simultaneously and n6 to n8 are not 0 simultaneously, wherein in Chemical Formula 1-iii, $R^{c1}$ to $R^{c4}$ are independently a substituted or unsubstituted C1 to C10 alkyl group, a substituted or unsubstituted C6 to C30 aryl group, a substituted or unsubstituted C2 to C30 heteroaryl group, or a combination thereof, n9 to n12 are independently an integer of 0 or 1, wherein in Chemical Formula 1-iv, $R^{d1}$ to $R^{d8}$ are independently a substituted or unsubstituted C1 to C10 alkyl group, a substituted or unsubstituted C6 to C30 aryl group, a substituted or unsubstituted C2 to C30 heteroaryl group, or a combination thereof, n13 to n20 are independently an integer of 0 or 1, In Chemical Formula 1-v, $X^a$ to $X^f$ are independently N or CH, at least one of $X^a$ to $X^c$ is N, at least one of $X^d$ to $X^f$ is N, $R^{e1}$ to $R^{e6}$ are independently a substituted or unsubstituted C1 to C10 alkyl group, a substituted or unsubstituted C6 to C30 aryl group, a substituted or unsubstituted C2 to C30 heteroaryl group, or a combination thereof, n21 to n26, ml and m2 are independently an integer of 0 or 1, wherein in Chemical Formula 1-vi, $R^{f1}$ to $R^{f6}$ are independently a substituted or unsubstituted C1 to C10 alkyl group, a substituted or unsubstituted C6 to C30 aryl group, a substituted or unsubstituted C2 to C30 heteroaryl group, or a combination thereof, n27 to n32 are independently an integer of 0 or 1, but n27 to n29 are not 0 simultaneously and n30 to n32 are not 0 simultaneously, wherein, in Chemical Formula 1-vii, $X^g$ to $X^l$ are independently N or CH, at least one of $X^g$ to $X^i$ is N, at least one of $X^g$ to $X^i$ is N, $R^{g1}$ and $R^{g2}$ are independently a substituted or unsubstituted C1 to C10 alkyl group, a substituted or unsubstituted C6 to C30 aryl group, a substituted or unsubstituted C2 to C30 heteroaryl group, or a combination thereof, and n33 and n34 are independently an integer of 0 or 1, wherein in Chemical Formula 1-viii, $R^{h1}$ to $R^{h6}$ are independently a substituted or unsubstituted C1 to C10 alkyl group, a substituted or unsubstituted C6 to C30 aryl group, a substituted or unsubstituted C2 to C30 heteroaryl group, or a combination thereof, and n35 to n40 are independently an integer of 0 or 1, wherein in Chemical Formula 1-ix, $R^{i1}$ $R^{i3}$ are independently a substituted or unsubstituted C1 to C10 alkyl group, a substituted or unsubstituted C6 to C30 aryl group, a substituted or unsubstituted C2 to C30 heteroaryl group, or a combination thereof, and n41 to n43 are independently an integer ranging of 0 or 1, in Chemical Formulae 1-i to 1-v and 1-ix, $X^1$ to $X^9$ is CH or N, at least one of the $X^1$ to $X^9$ is N, and in Chemical Formulae 1-vi, 1-vii, and 1-viii, $X^1$ to $X^3$ is CH or N, at least one of the $X^1$ to $X^3$ is N, and "substituted" refers to replacement of at least one hydrogen by deuterium. a halogen. a hydroxy group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, a fluorenyl group, or a cyano group.

3. The organic optoelectronic device of claim 1, wherein the first compound is expressed by Chemical Formula Y:

[Chemical Formula Y]

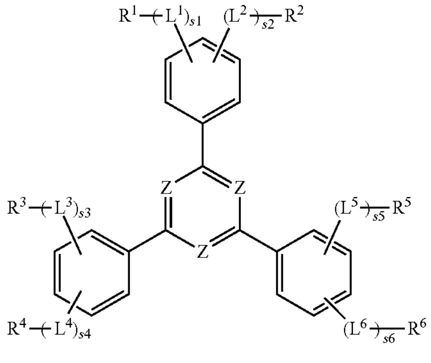

wherein, in Chemical Formula Y,

Z is independently N or CH, at least one of Z is N, $R^1$ to $R^6$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof, $L^1$ to $L^6$ are independently a single bond, a substituted or unsubstituted C6 to C30 arylene group, a substituted or unsubstituted heteroarylene group, or a combination thereof, and s1 to s6 are independently an integer of 0 to 5, "substituted" refers to replacement of at least one hydrogen by deuterium, halogen, a hydroxy group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, a fluorenyl group, or a cyano group.

4. The organic optoelectronic device of claim 1, wherein the first compound is expressed by Chemical Formula Z:

[Chemical Formula Z]

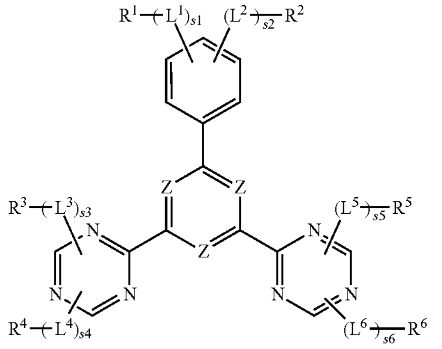

wherein, in Chemical Formula Z,

Z is independently N or CH, at least one of Z is N, $R^1$ to $R^6$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof, $L^1$ to $L^6$ are independently a single bond, a substituted or unsubstituted C6 to C30 arylene group, a substituted or unsubstituted heteroarylene group, or a combination thereof, and s1 to s6 are independently an integer ranging from 0 to 5, "substituted" refers to replacement of at least one hydrogen by deuterium, halogen, a hydroxy group, an amino group. a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, a fluorenyl group, or a cyano group.

5. The organic optoelectronic device of claim 1, wherein the second compound is expressed by one of Chemical Formula 2-i to Chemical Formula 2-iii:

[Chemical Formula 2-i]

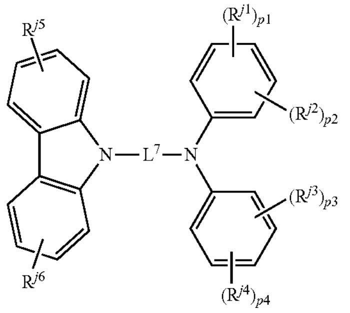

[Chemical Formula 2-ii]

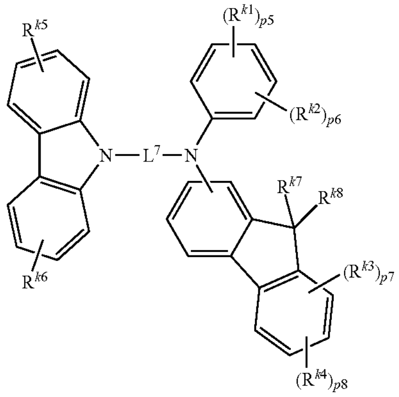

[Chemical Formula 2-iii]

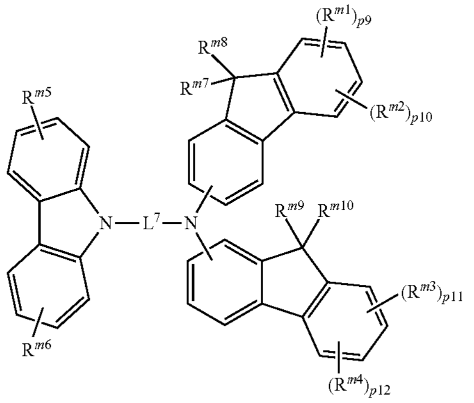

wherein, in Chemical Formula 2-i, $L^7$ is a substituted or unsubstituted C6 to C30 arylene group, a substituted or unsubstituted C2 to C30 hetero arylene group, or a combination thereof, and $R^{j1}$ $R^{j6}$ are independently a substituted or unsubstituted C1 to C10 alkyl group, a substituted or unsubstituted C1 to C30 aryl group, a substituted or unsubstituted C2 to C30 hetero arylene group, or a combination thereof, p1 to p4 are independently an integer of 0 to 5, provided that $0 \le p1+p2 \le 5$, and $0 \le p3+p4 \le 5$, wherein, in Chemical Formula 2-ii, $L^7$ is a substituted or unsubstituted C6 to C30 arylene group, a substituted or unsubstituted C2 to C30 heteroarylene group, or a combination thereof, $R^{k1}$ to $R^{k6}$ are independently a substituted or unsubstituted C1 to C10 alkyl group, a substituted or unsubstituted C6 to C30 aryl group, a substituted or unsubstituted C2 to C30 hetero arylene group, or a combination thereof, $R^{k7}$ and $R^{k8}$ are independently hydrogen or a substituted or unsubstituted C1 to C10 alkyl group, a substituted or unsubstituted C6 to C30 aryl group, a substituted or unsubstituted C2 to C30 hetero arylene group, or a combination thereof, p5 and p6 are independently an integer of 0 to 5, provided that $0 \le p5+p6 \le 5$, and p7 and p8 are independently an integer of 0 to 4, provided that $0 \le p7+p8 \le 4$, wherein, in Chemical Formula 2-iii, $L^7$ is a substituted or unsubstituted C6 to C30 arylene group, a substituted or unsubstituted C2 to C30 hetero arylene group, or a combination thereof, $R^{m1}$ to $R^{m6}$ are independently a substituted or unsubstituted C1 to C10 alkyl group, a substituted or unsubstituted C6 to C30 aryl group, a substituted or unsubstituted C2 to C30 hetero arylene group, or a combination thereof, $R^{m7}$ to $R^{m10}$ are independently hydrogen or a substituted or unsubstituted C1 to C10 alkyl group, a substituted or unsubstituted C6 to C30 aryl group, a substituted or unsubstituted C2 to C30 hetero arylene group, or a combination thereof, and p9 to p12 are independently an integer ranging from 0 to 4, provided that $0 \le p9+p10 \le 4$ and $0 \le p11+p12 \le 4$, "substituted" refers replacement of at least one hydrogen by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, a fluorenyl group, or a cyano group.

6. The organic optoelectronic device of claim 5, wherein $L^7$ is one of linking groups of Group A:

[Group A]

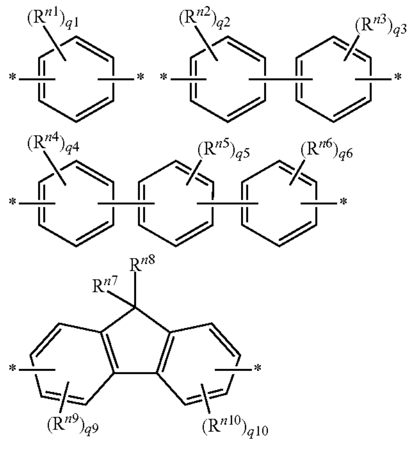

-continued

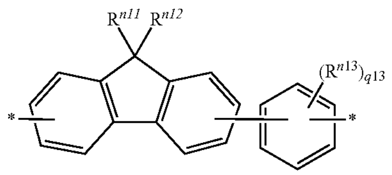

wherein, in Group A, $R^{n1}$ to $R^{n13}$ are independently hydrogen, a substituted or unsubstituted C1 to C10 alkyl group, or a substituted or unsubstituted C6 to C20 aryl group, q1 to q6 and q13 are independently an integer ranging from 0 to 4, and q9 and q10 are independently an integer ranging from 0 to 3, "substituted" refers replacement of at least one hydrogen by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, a fluorenyl group, or a cyano group.

7. The organic optoelectronic device of claim 5, wherein in [Chemical Formula 2-i], [Chemical Formula 2-ii], and [Chemical Formula 2-iii], the C6 to C30 arylene group is a phenylene group, a biphenylene group, a terphenylene group, a tetraphenylene group, a fluorenylene group, or a combination thereof, and the C6 to C30 aryl group is a phenyl group, a biphenyl group, a terphenyl group, a tetraphenyl group, a fluorenyl group, or a combination thereof.

8. The organic optoelectronic device of claim 1, wherein the auxiliary electron transport layer is a first compound expressed by Chemical Formula 1-i or 1-ii, and the auxiliary hole transport layer includes a second compound expressed by Chemical Formula 2-i:

[Chemical Formula 1-i]

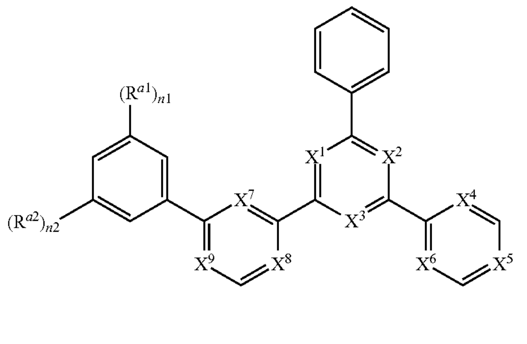

-continued

[Chemical Formula 1-ii]

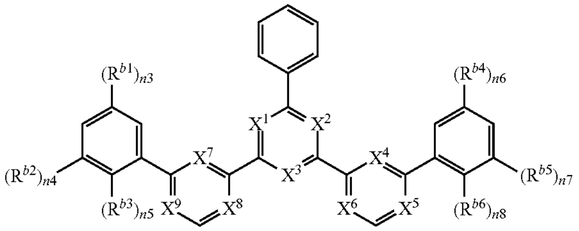

wherein, in Chemical Formula 1i, $R^{a1}$ and $R^{a2}$ are independently a substituted or unsubstituted C1 to C10 alkyl group, a substituted or unsubstituted C6 to C30 aryl group, a substituted or unsubstituted C2 to C30 heteroaryl group, or a combination thereof, n1 and n2 are independently an integer of 0 or 1, provided that n1 and n2 are not simultaneously 0, and $X^1$ to $X^9$ are CH or N, provided that at least one of $X^1$ to $X^9$ is N, wherein, in Chemical Formula 1ii, $R^{b1}$ to $R^{b6}$ are independently a substituted or unsubstituted C1 to C10 alkyl group, a substituted or unsubstituted C6 to C30 aryl group, a substituted or unsubstituted C2 to C30 heteroaryl group, or a combination thereof, n3 to n8 are independently an integer of 0 or 1, but n3 to n5 are not 0 simultaneously and n6 to n8 are not 0 simultaneously, and $X^1$ to $X^9$ are CH or N, provided that at least one of $X^1$ to $X^9$ is N,

[Chemical Formula 2-i]

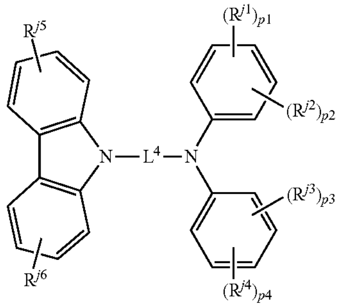

wherein in Chemical Formula 2-i, $L^7$ is a substituted or unsubstituted C6 to C30 arylene group, $R^{j1}$ to $R^{j6}$ are independently a substituted or unsubstituted C1 to C10 alkyl group, a substituted or unsubstituted C6 to C30 aryl group, a substituted or unsubstituted C2 to C30 heteroaryl group, or a combination thereof, and p1 to p4 are independently an integer of 0 to 5, provided that $0 \leq p1+p2 \leq 5$, and $0 \leq p3+p4 \leq 5$, "substituted" refers replacement of at least one hydrogen by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, a fluorenyl group, or a cyano group.

9. The organic optoelectronic device of claim 1, wherein the first compound is one of compounds of Group 1:

[Group 1]

[A-1]

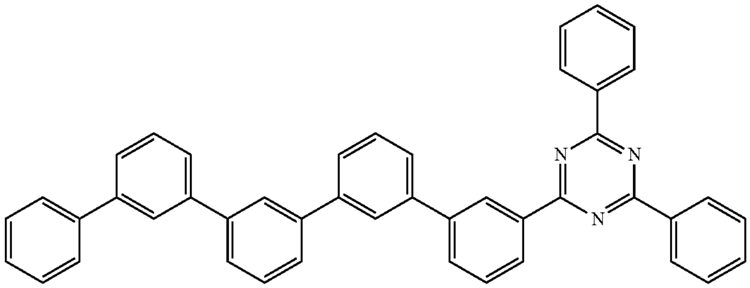

[A-2]

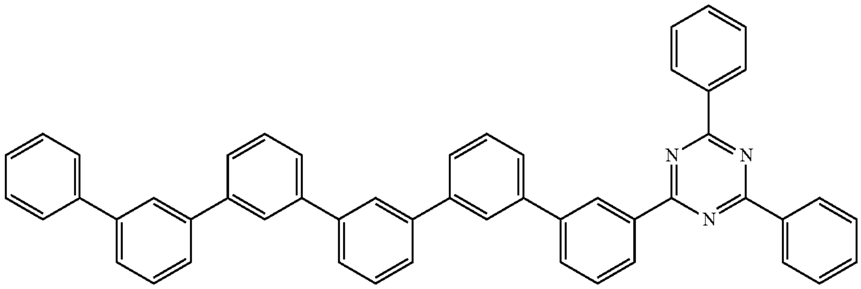

-continued
[A-3]
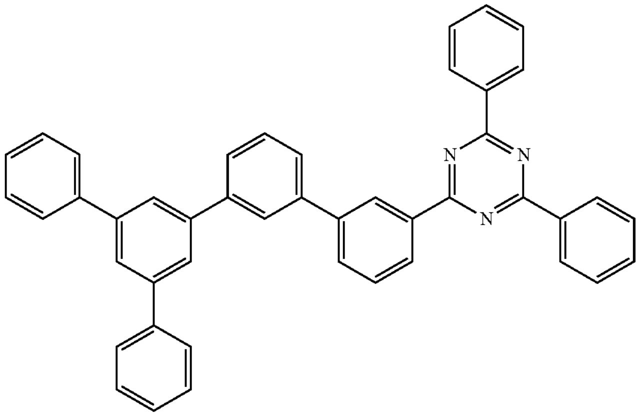
[A-4]
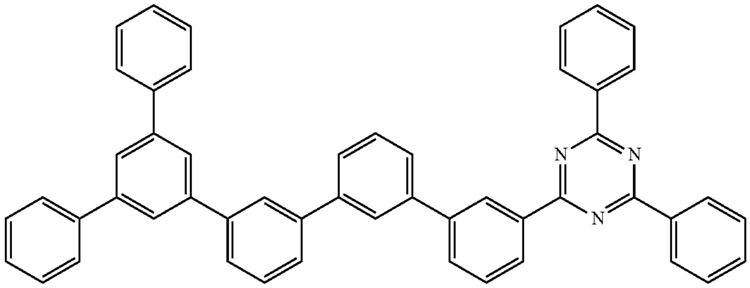
[A-5]
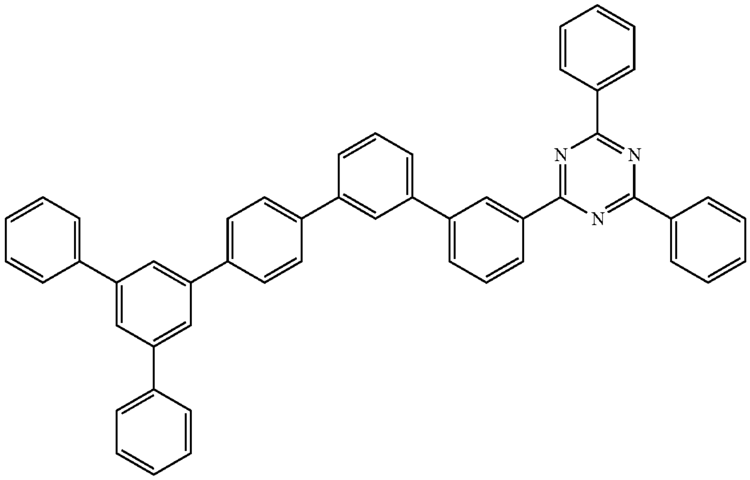
[A-6]
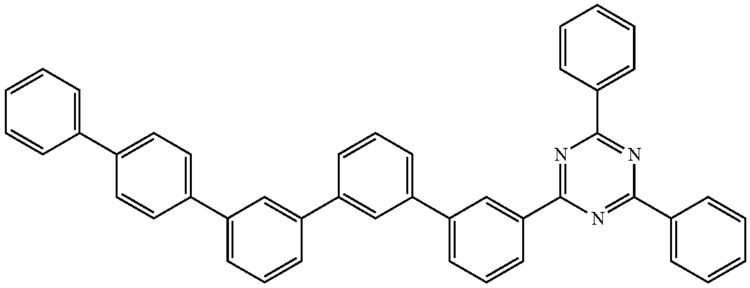

-continued
[A-7]
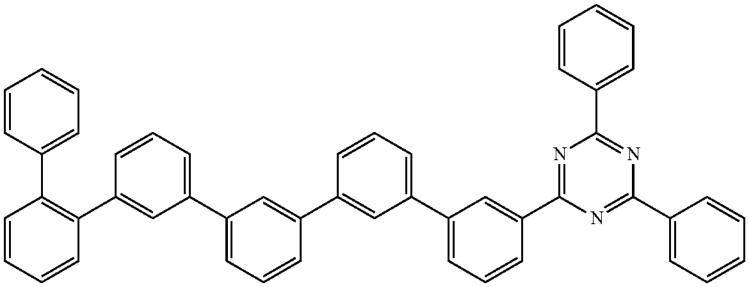
[A-8]
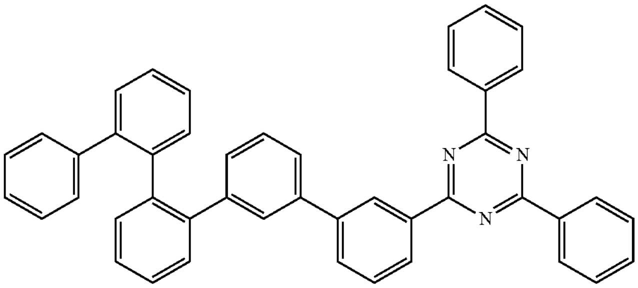
[A-9]
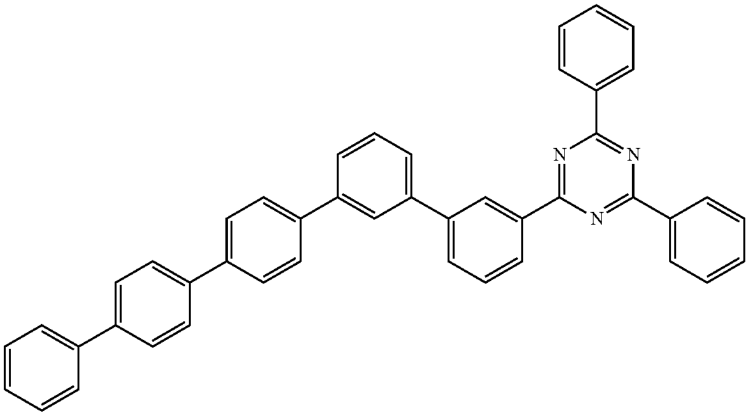
[A-10]
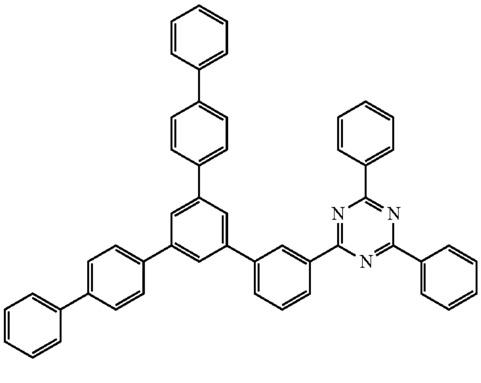
[A-11]
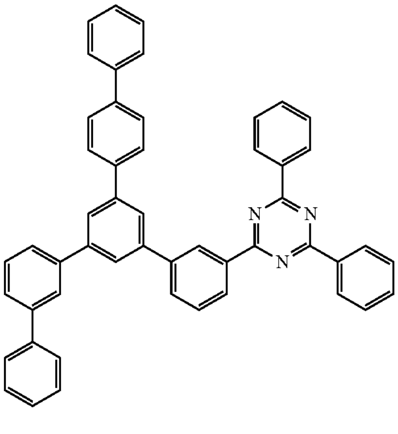

-continued
[A-12]
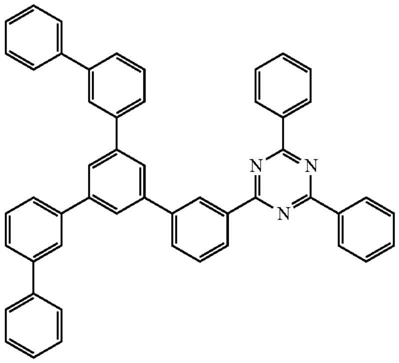
[A-13]
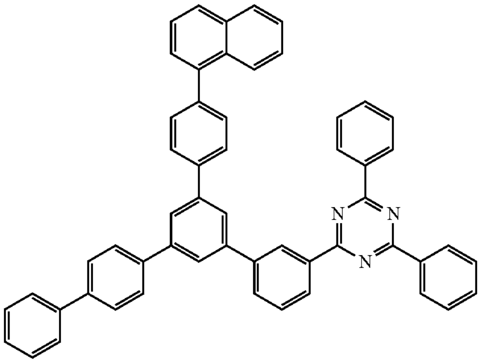
[A-14]
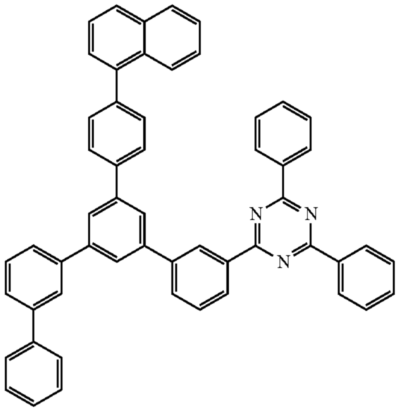
[A-15]
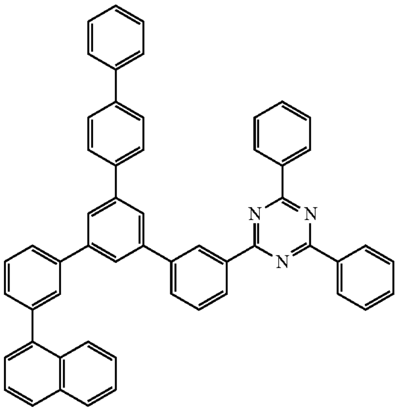
[A-16]
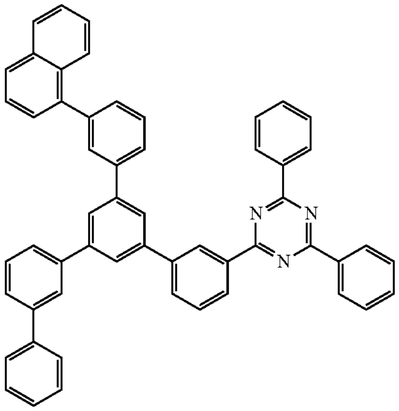
[A-17]
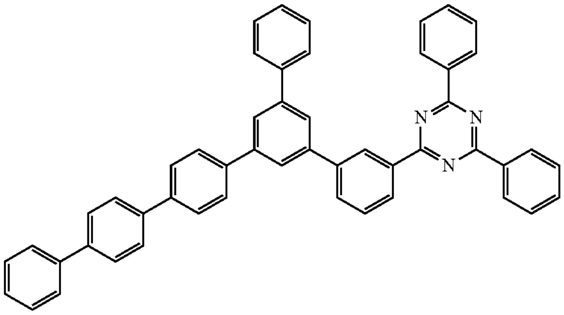

-continued
[A-18]
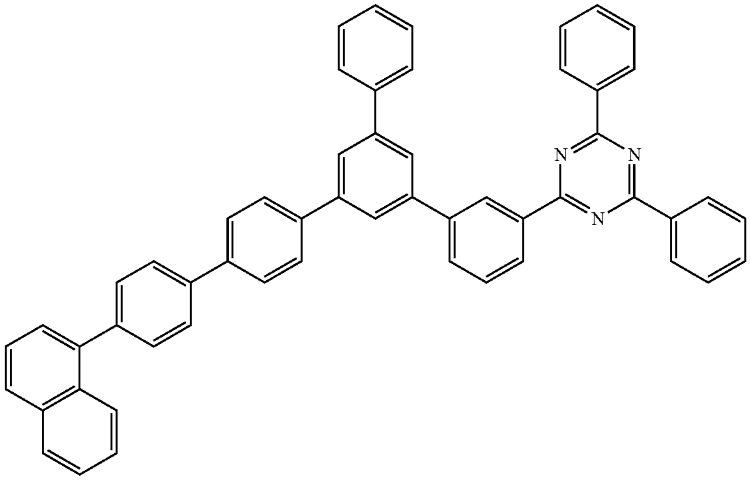
[A-19]
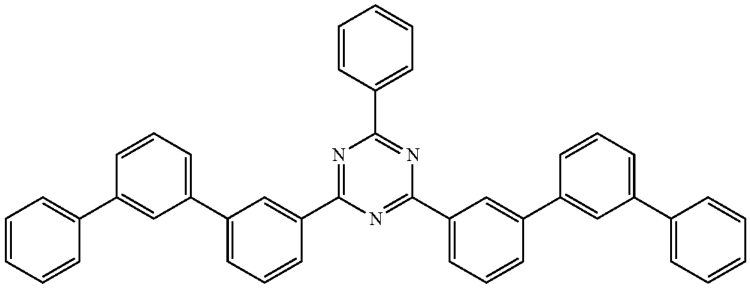
[A-20]
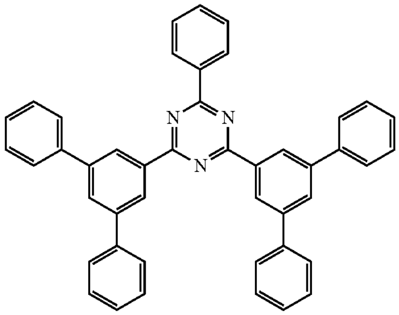
[A-21]
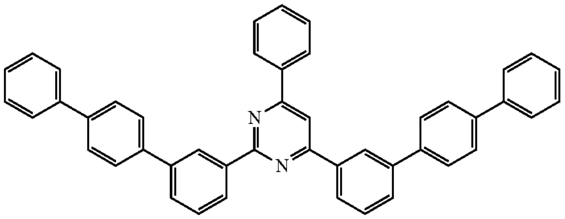
[A-22]
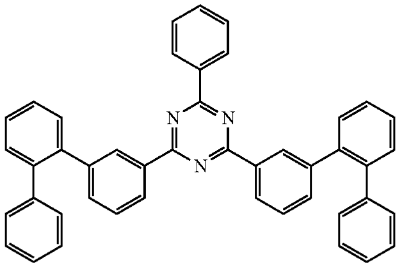
[A-23]
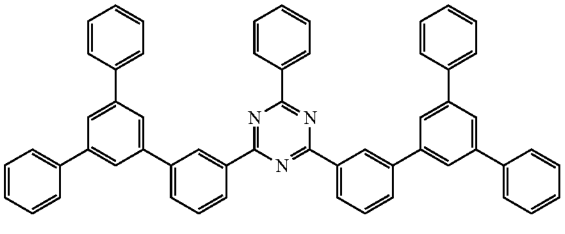

-continued
[A-24]
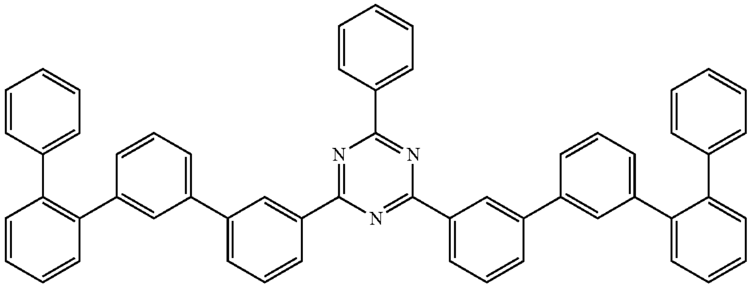
[A-25]
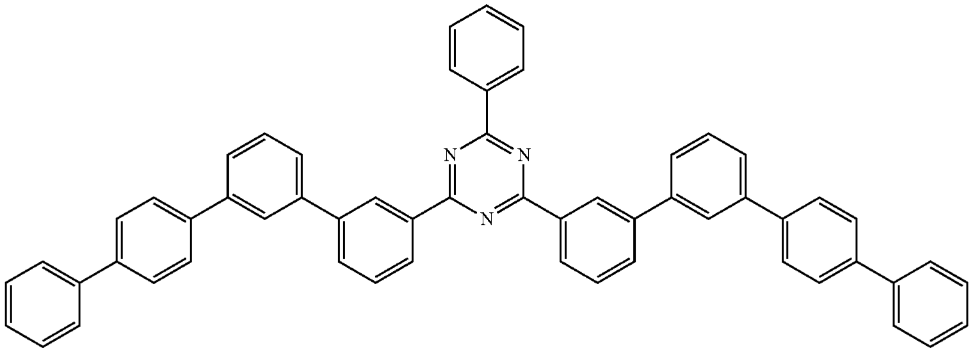
[A-26]
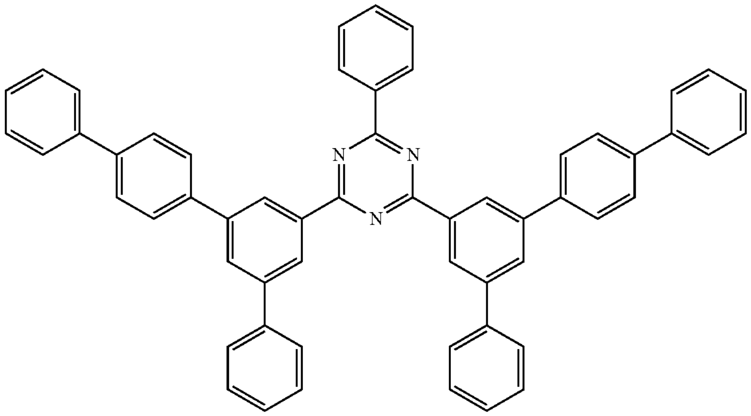
[A-27]
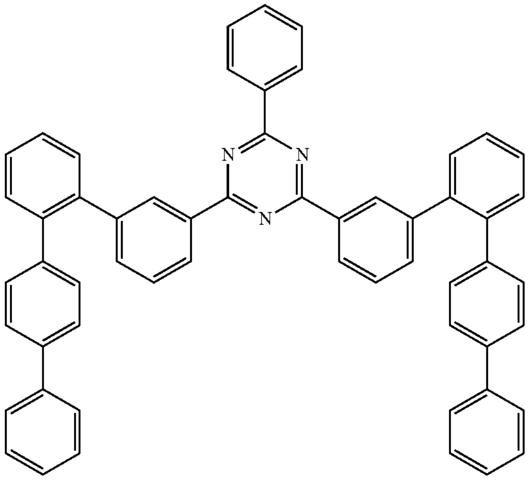

-continued
[A-28]
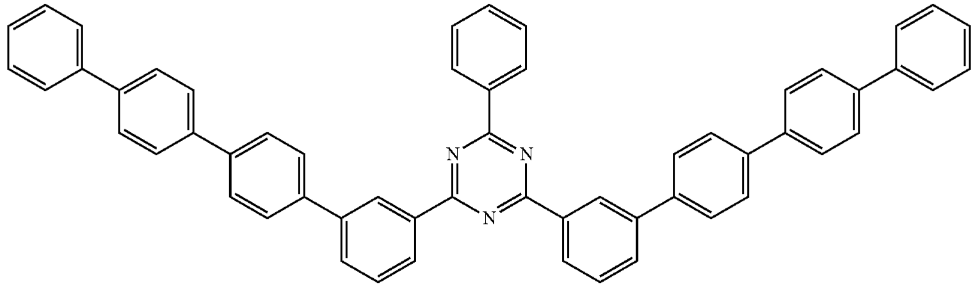
[A-29]
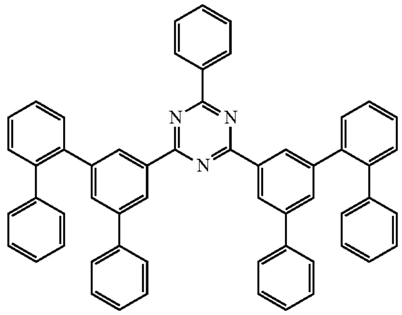
[A-30]
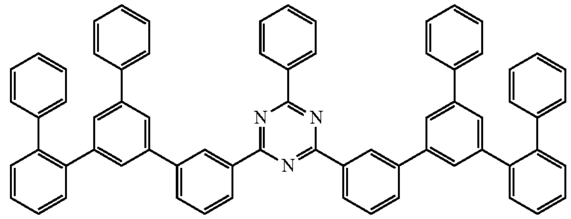
[A-31]
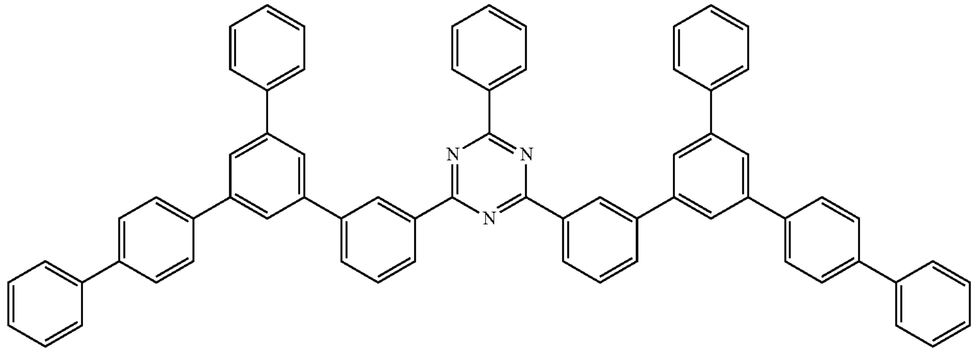
[A-32]
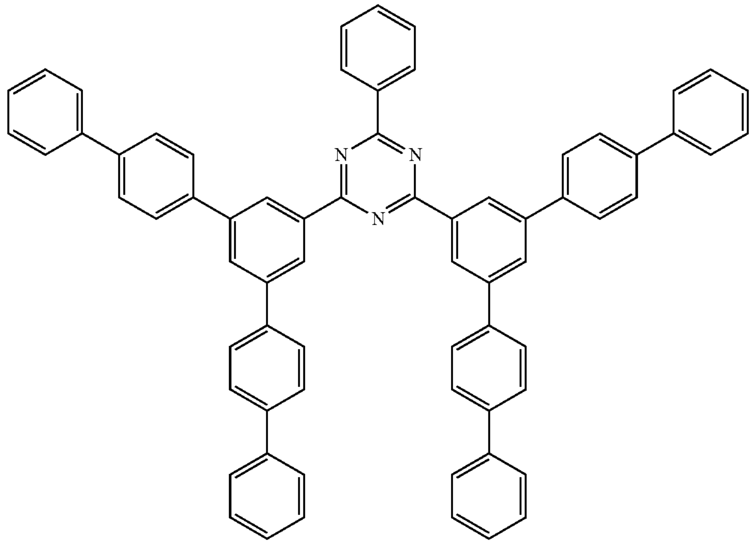

-continued
[A-33]
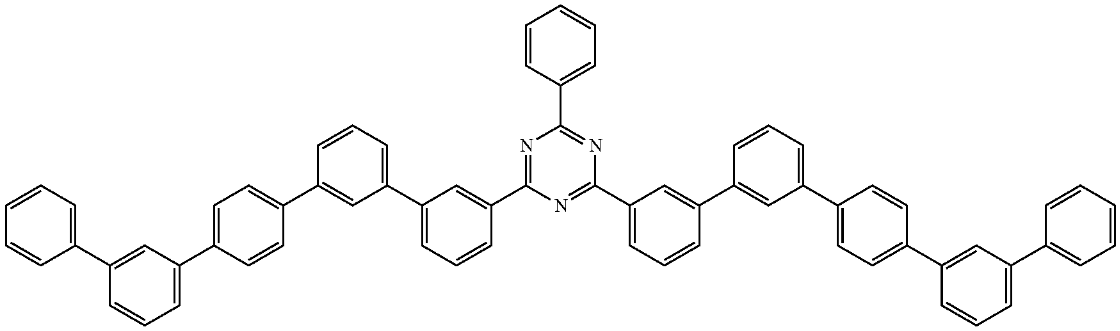
[A-34]
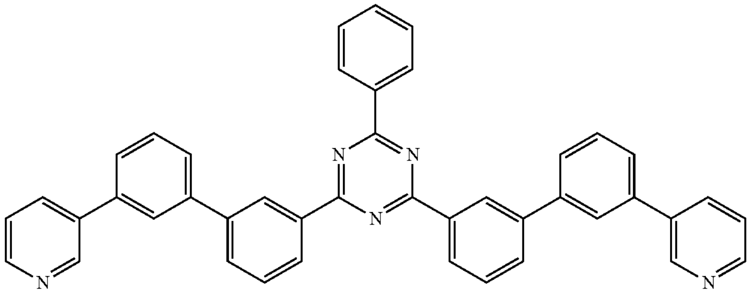
[A-35]
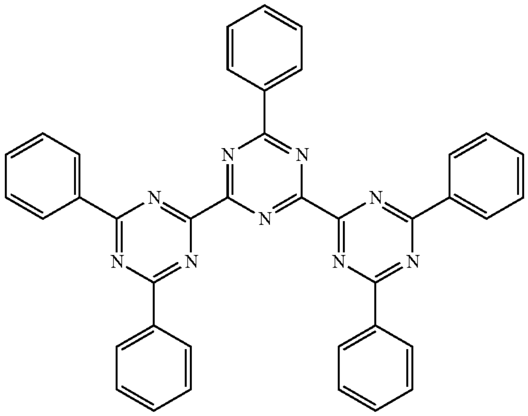
[A-36]
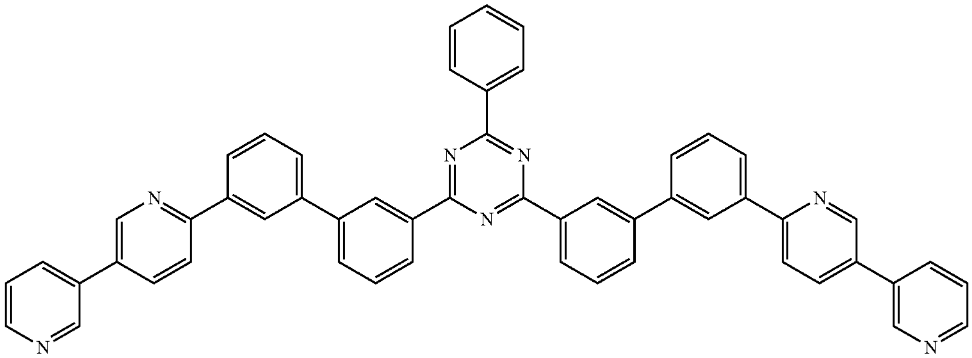

-continued
[A-37]
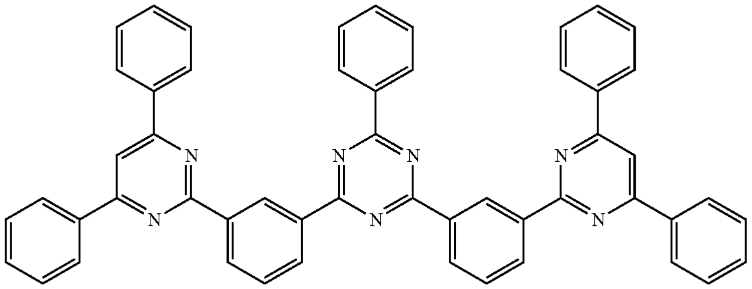
[A-38]
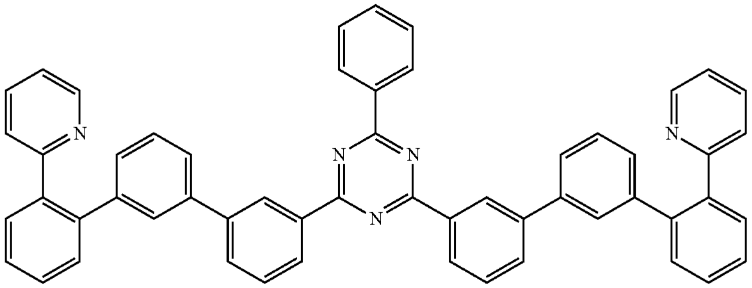
[A-39]
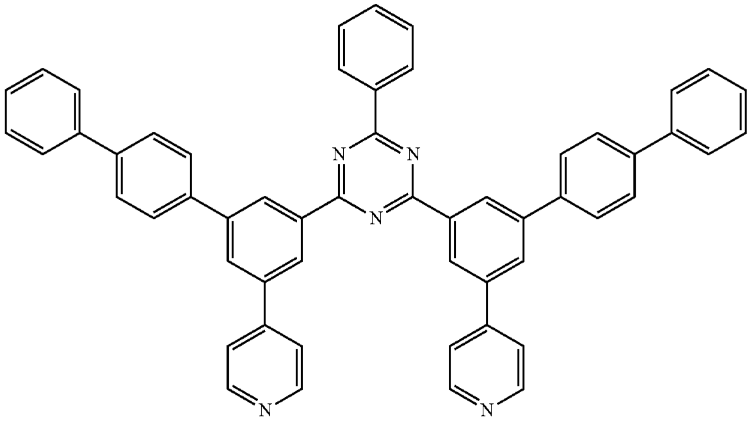
[A-40]
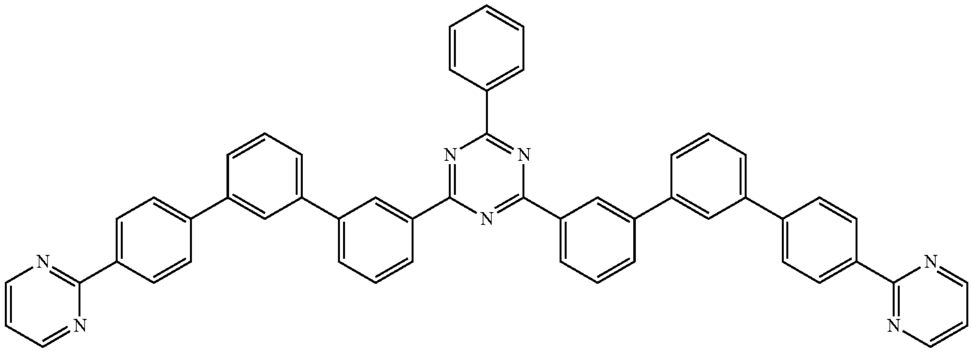

-continued
[A-41]
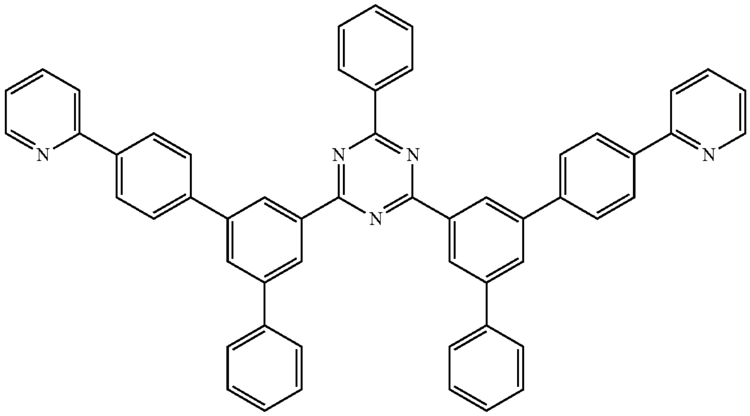
[A-42]
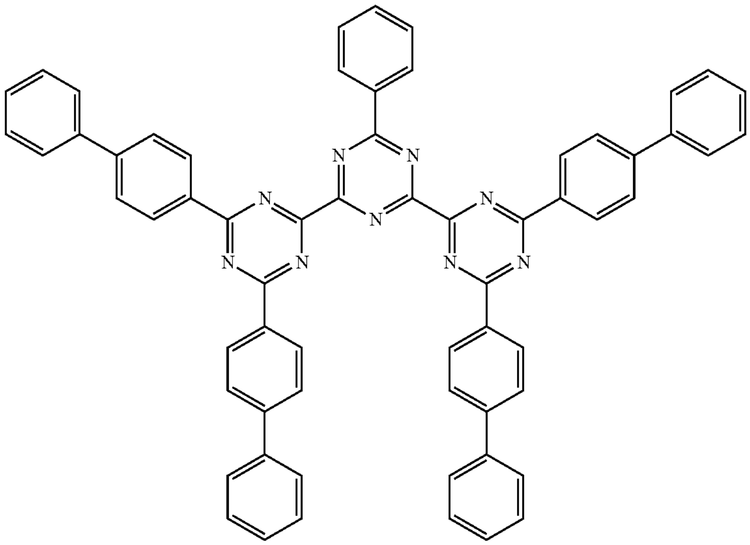
[A-43]
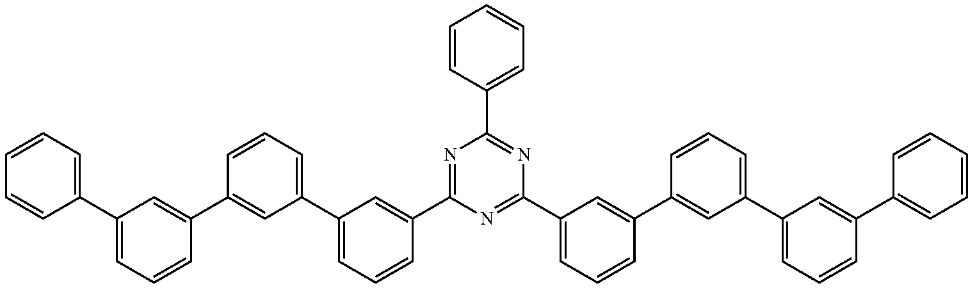
[A-44]
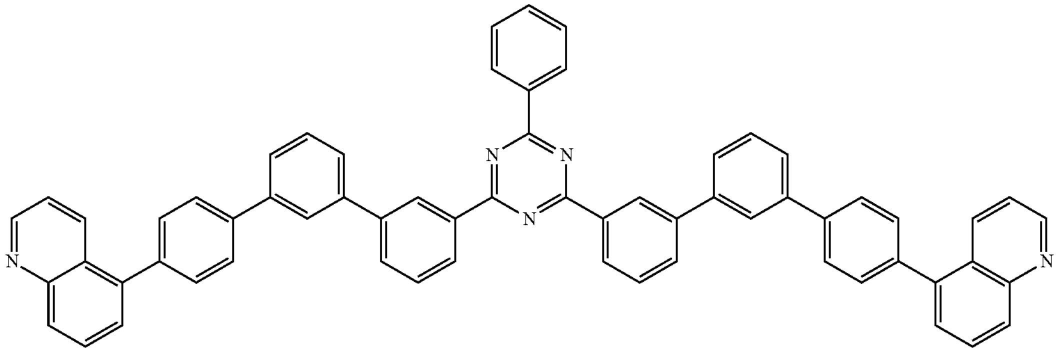

-continued
[A-45]
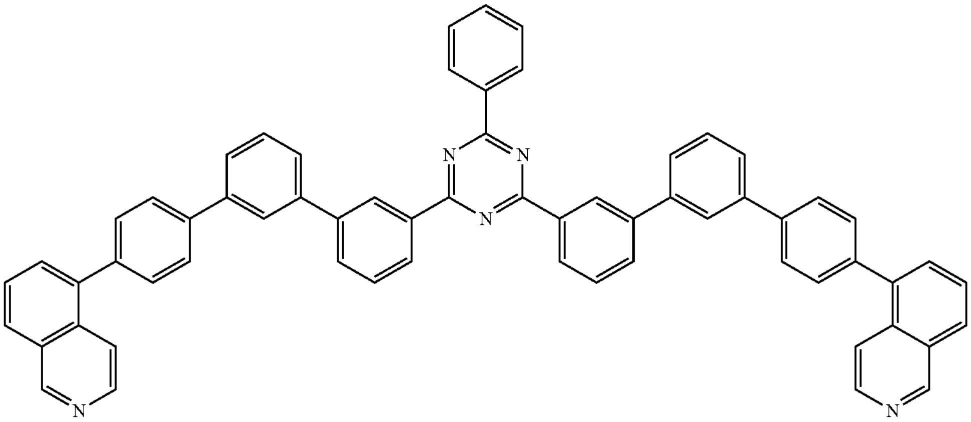
[A-46]
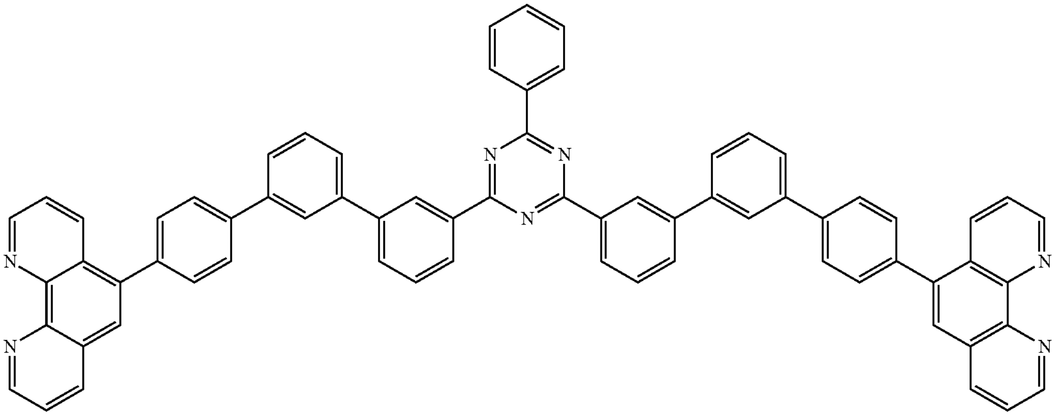
[A-47]
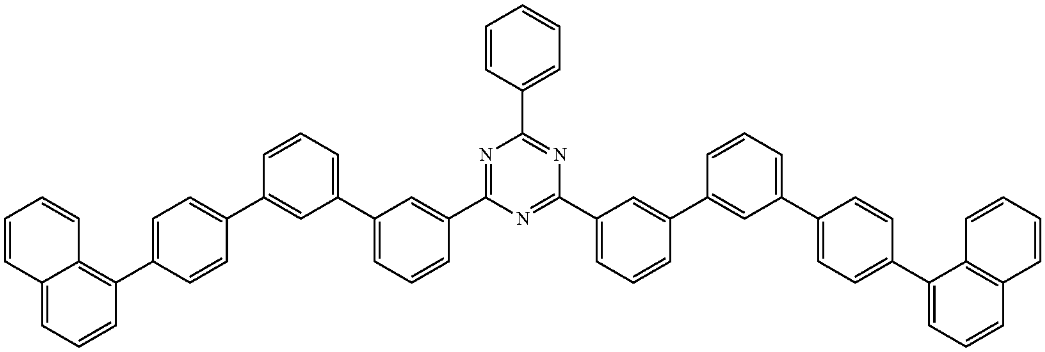
[A-48]
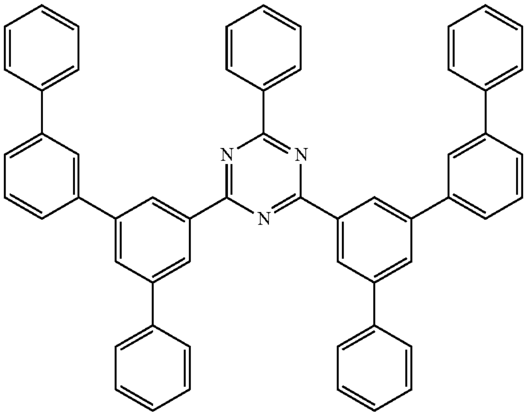

-continued
[A-49]
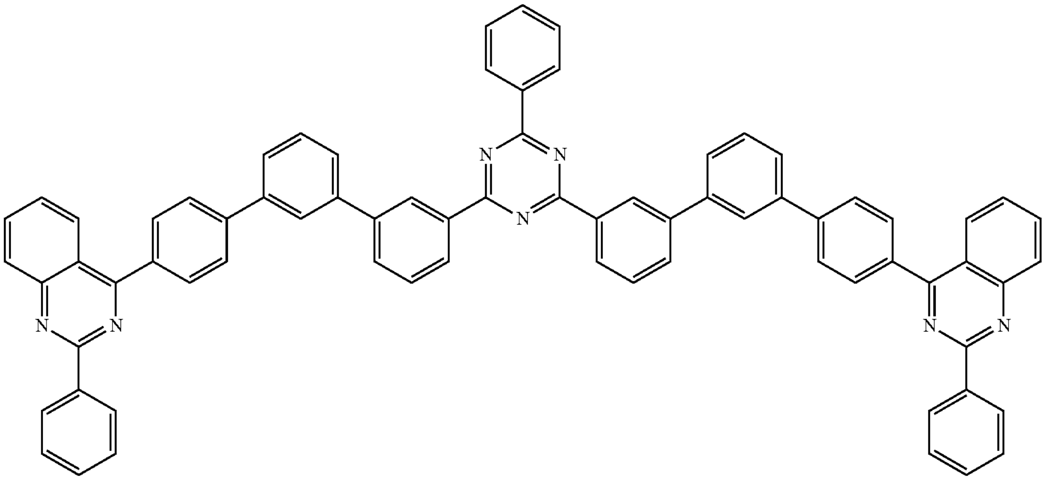
[A-50]
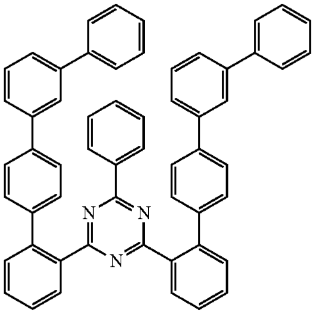
[A-51]
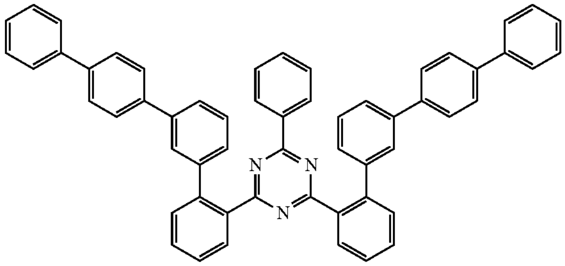
[A-52]
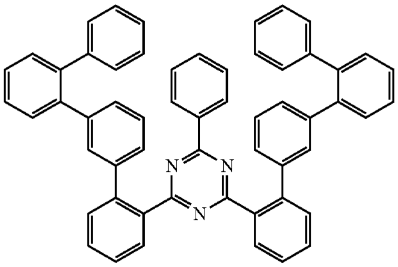
[A-53]
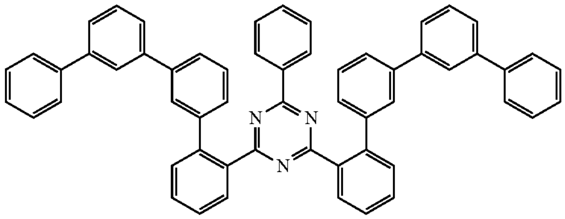
[A-54]
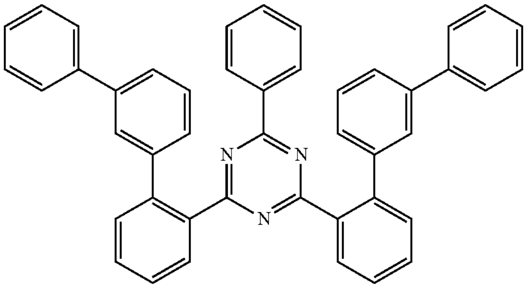
[A-55]
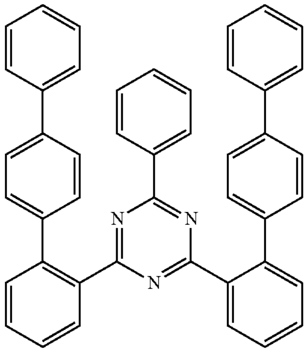

-continued
[A-56]
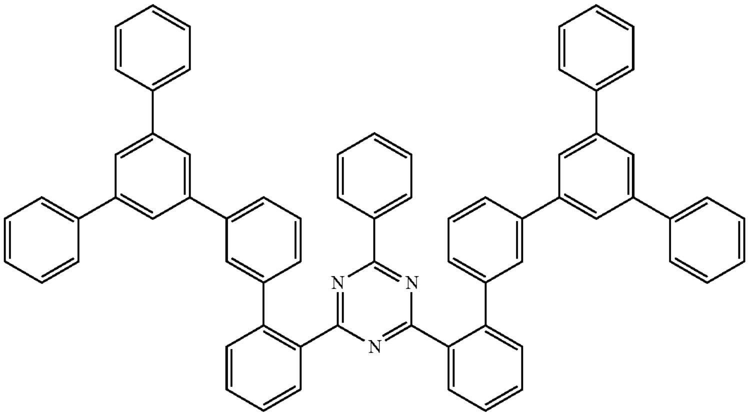
[A-57]
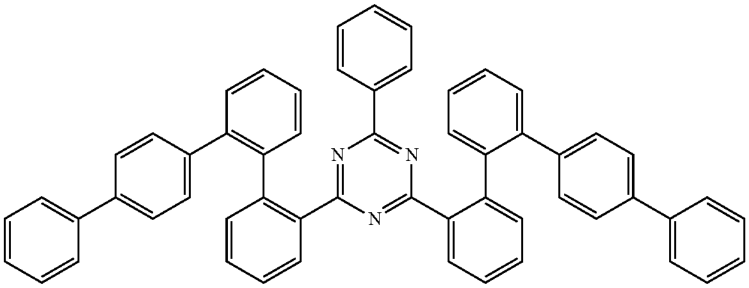
[A-58]
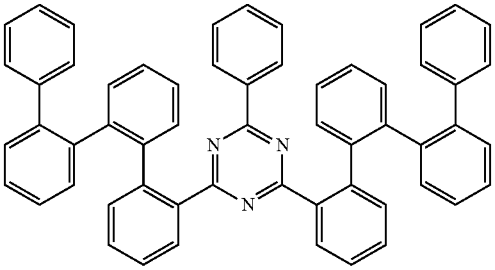
[A-59]
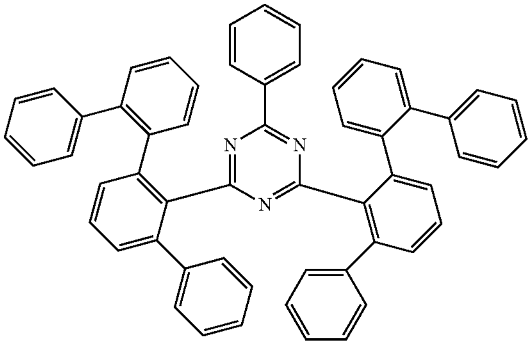
[A-60]
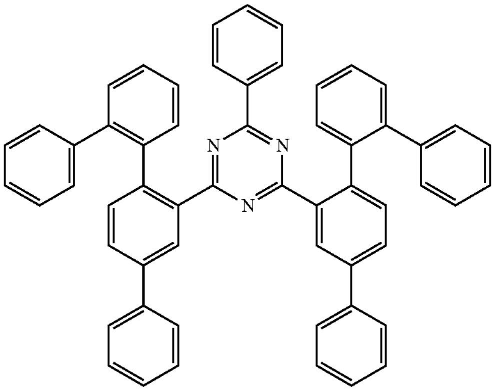
[A-61]
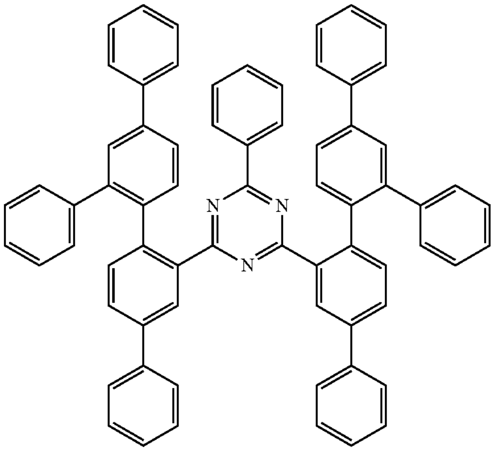

-continued
[A-62]
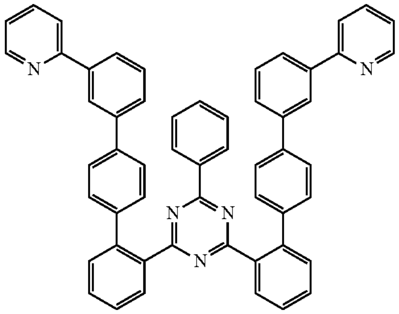
[A-63]
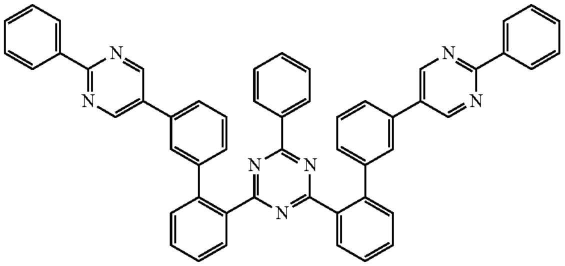
[A-64]
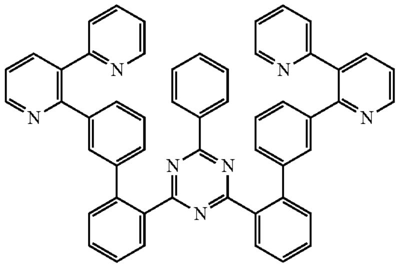
[A-65]
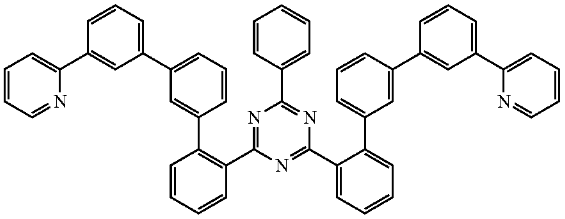
[A-66]
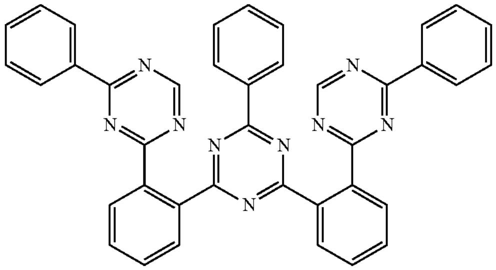
[A-67]
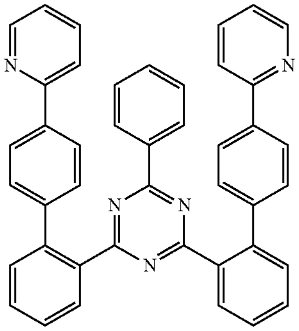
[A-68]
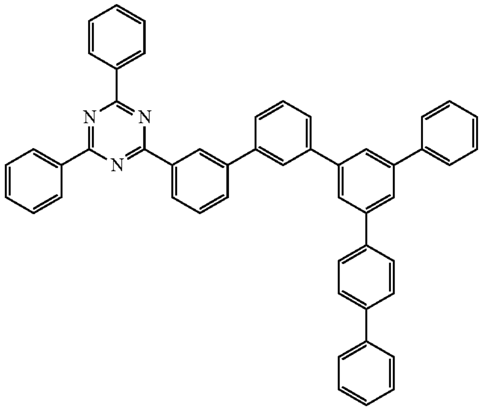
[A-69]
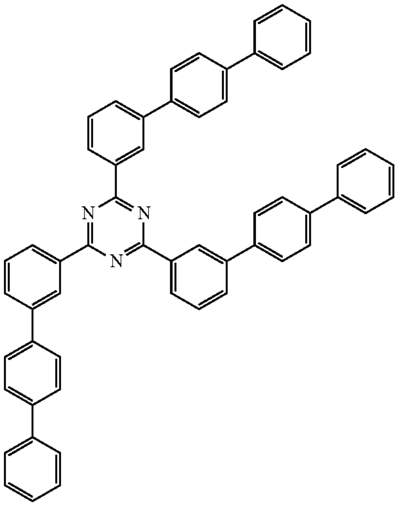

-continued
[A-70]
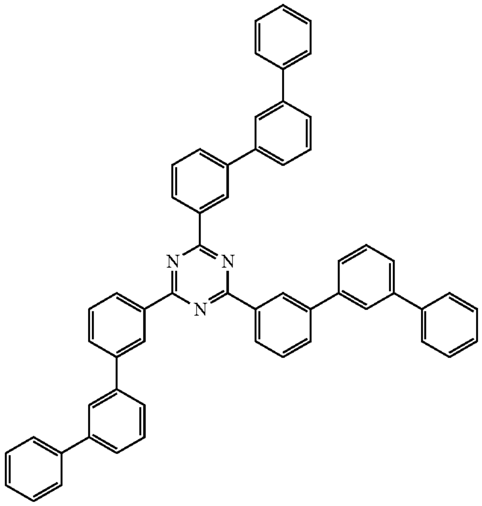
[A-71]
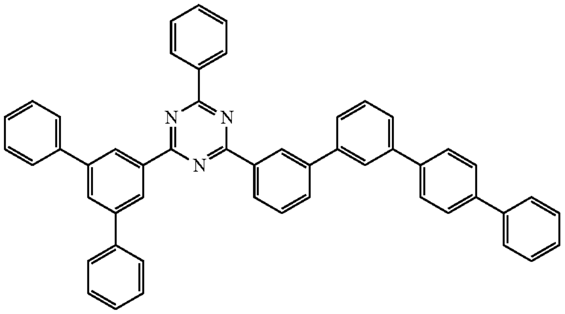
[A-72]
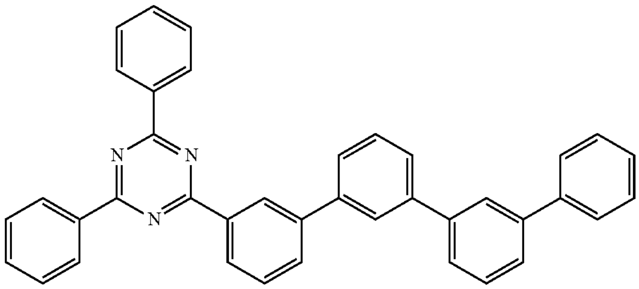
[A-73]
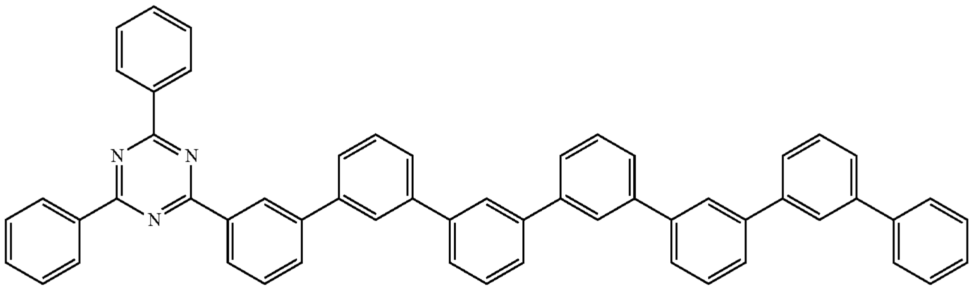

-continued
[A-74]
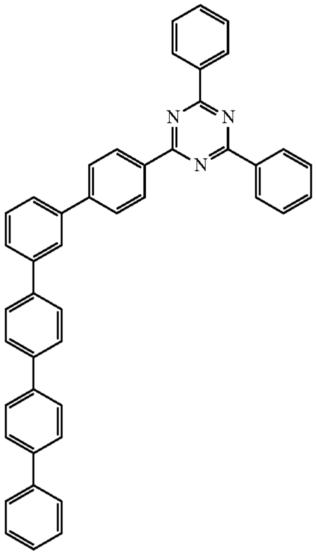
[B-1]
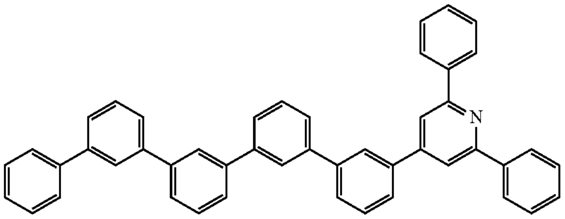
[B-2]
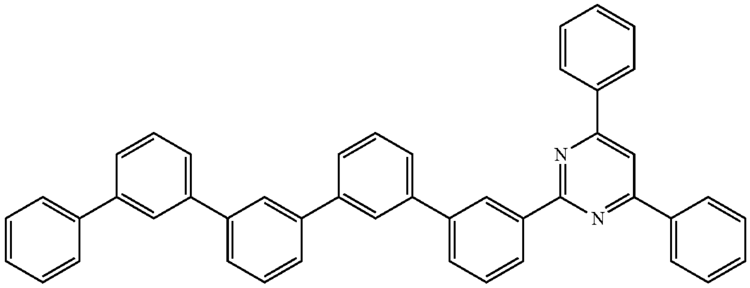
[B-3]
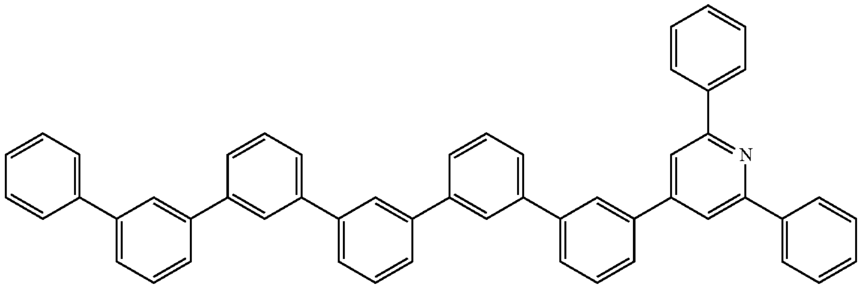
[B-4]
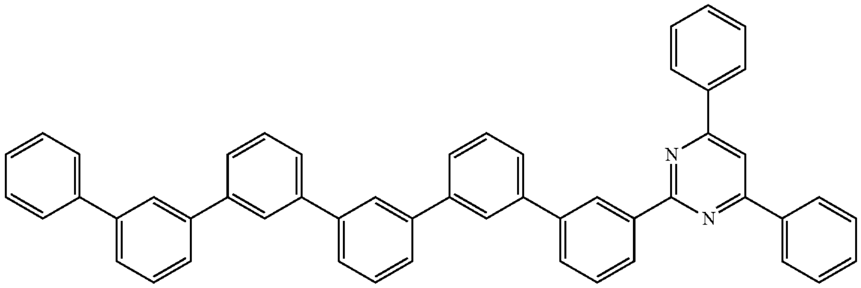

-continued
[B-5]
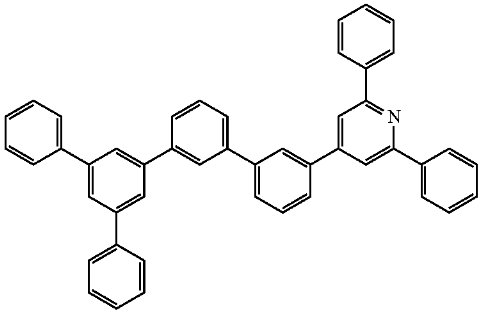
[B-6]
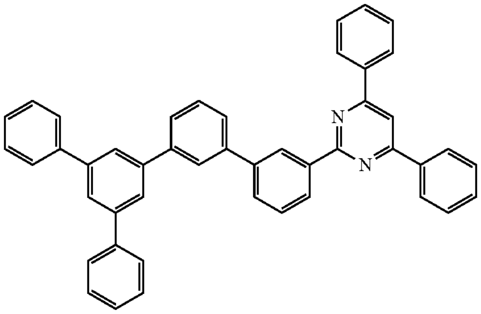
[B-7]
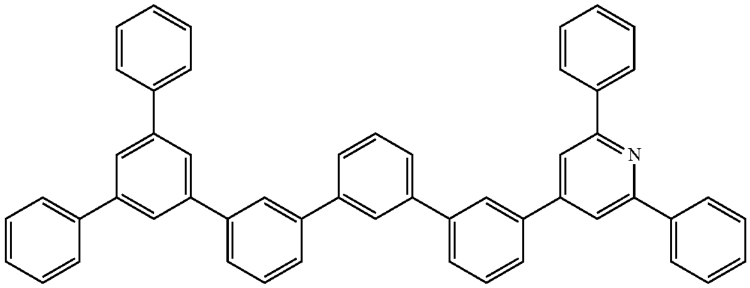
[B-8]
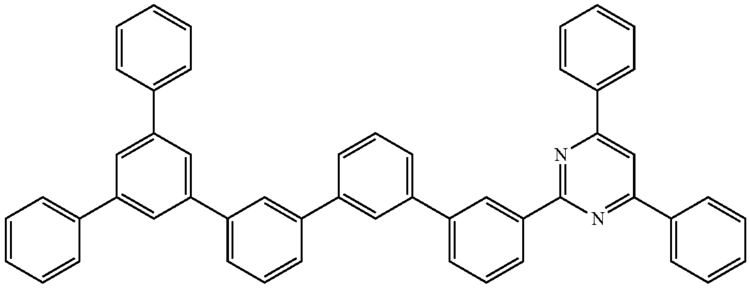
[B-9]
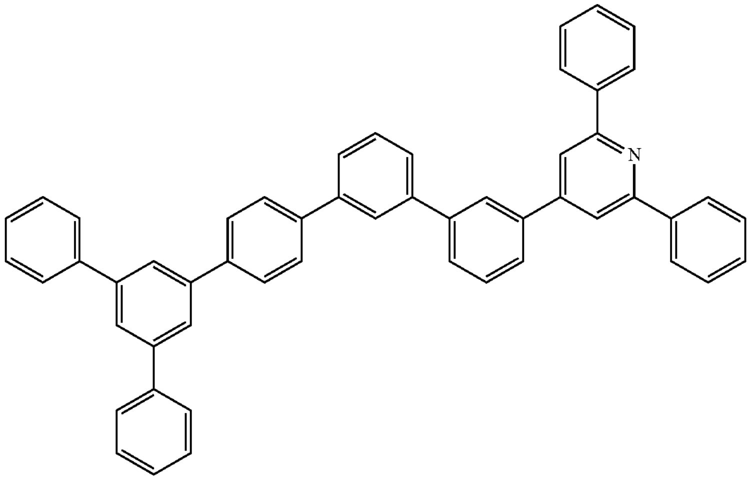

-continued
[B-10]
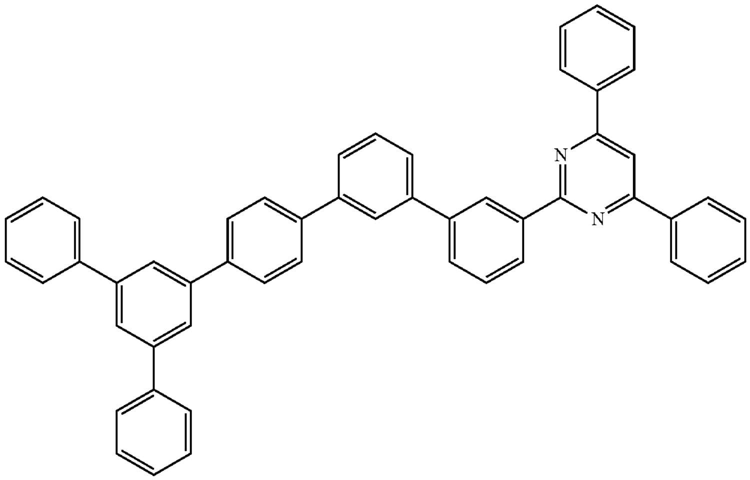
[B-11]
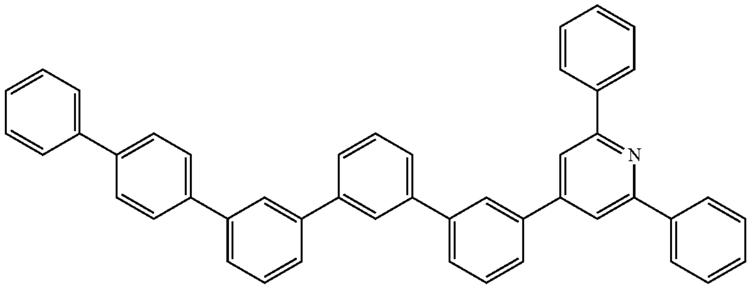
[B-12]
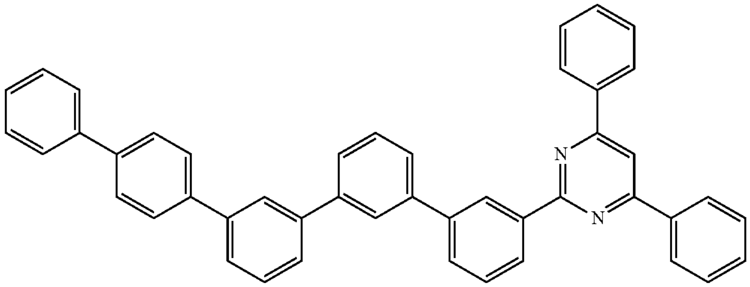
[B-13]
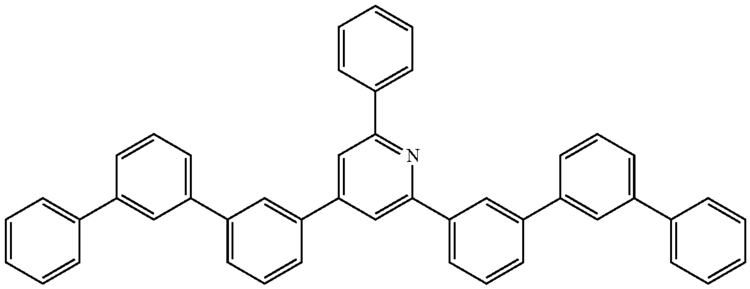

-continued
[B-14]
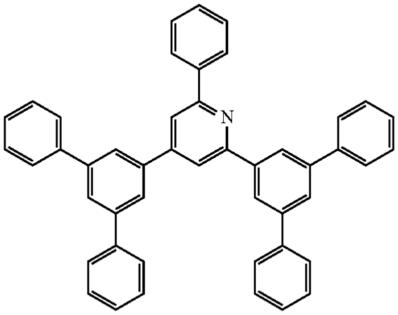
[B-15]
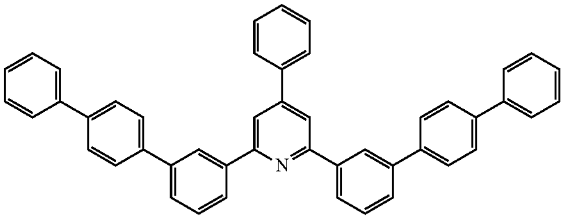
[B-16]
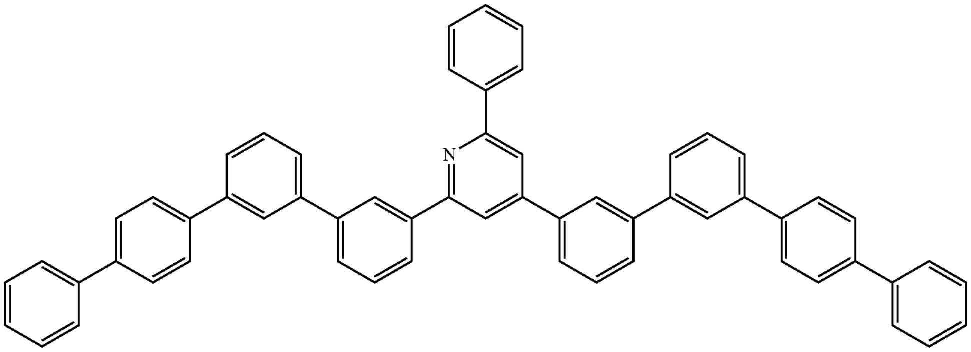
[B-17]
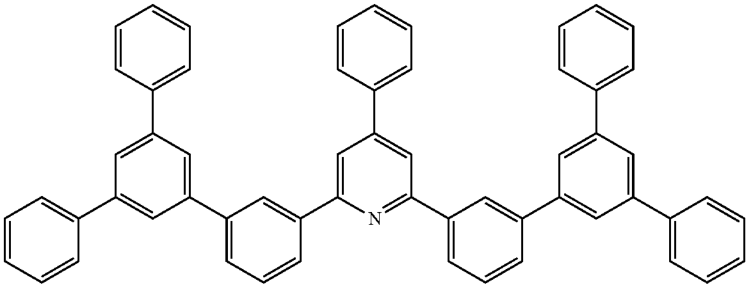
[B-18]
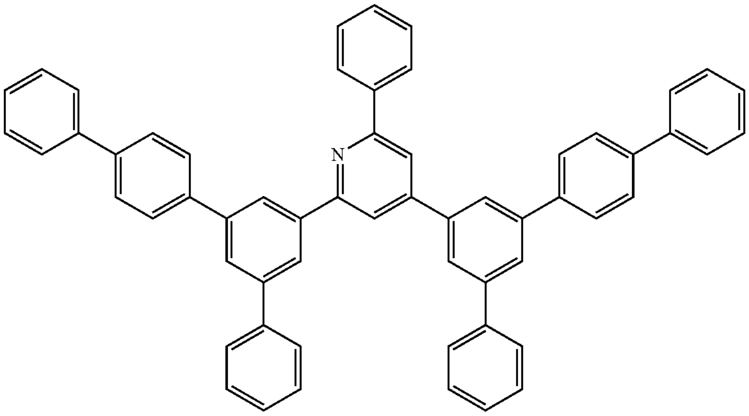

-continued
[B-19]
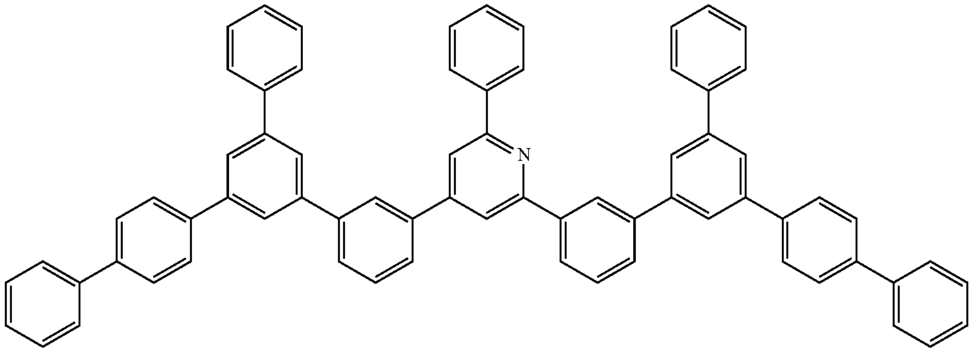
[B-20]
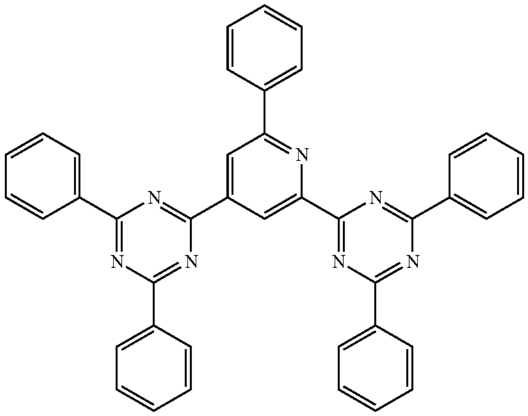
[B-21]
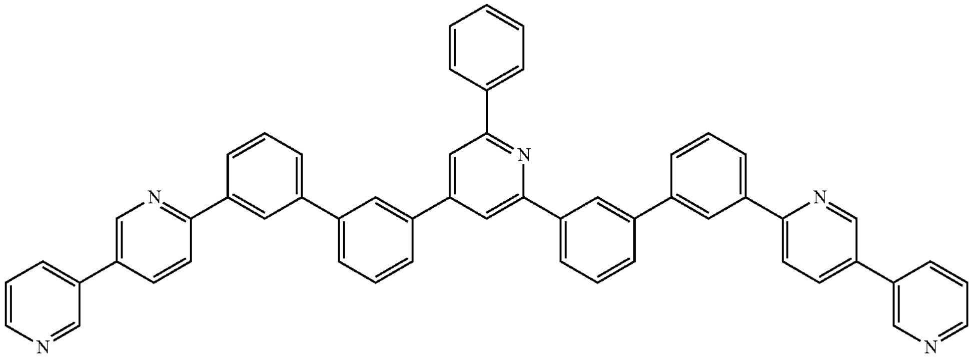
[B-22]
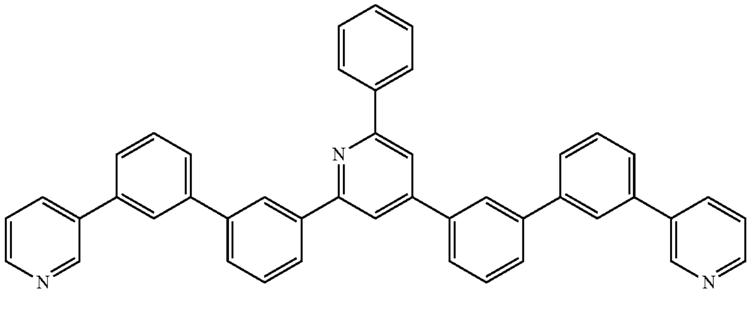

-continued
[B-23]
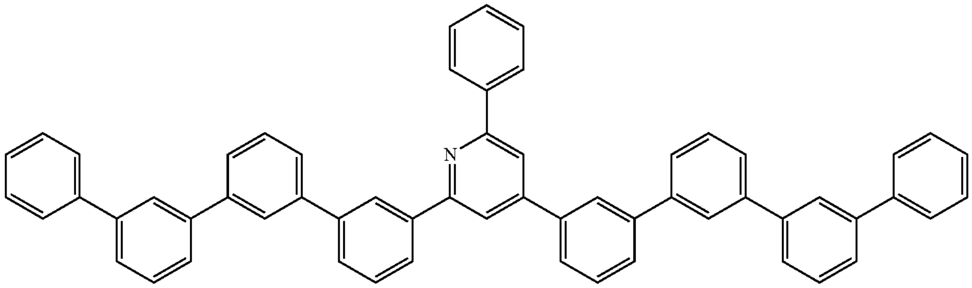
[B-24]
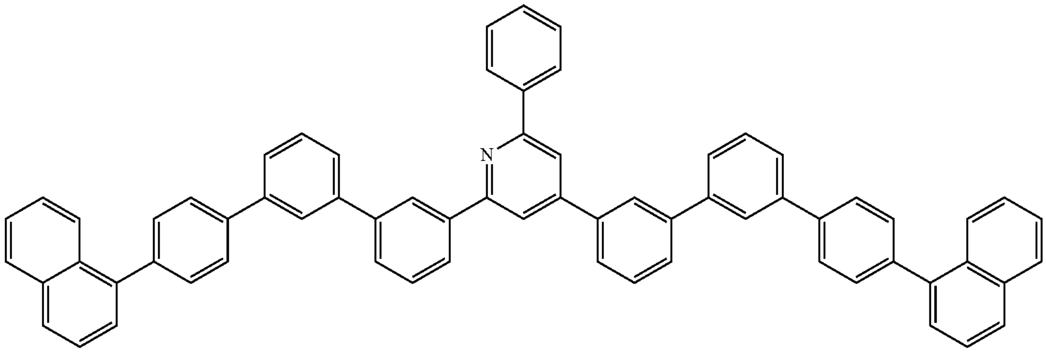
[B-25]
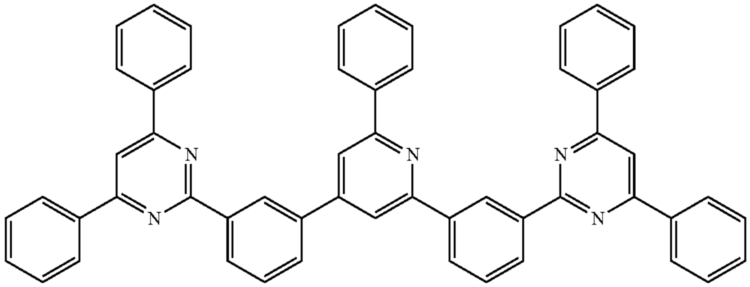
[B-26]
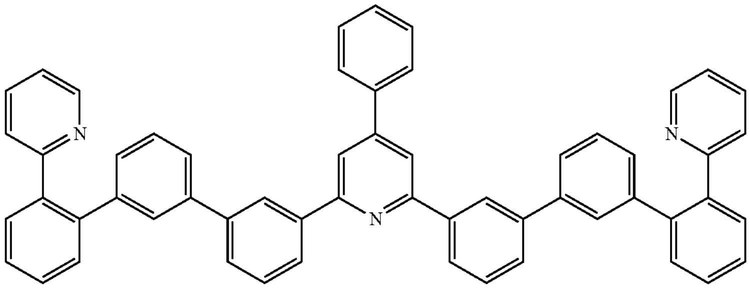

-continued
[B-27]
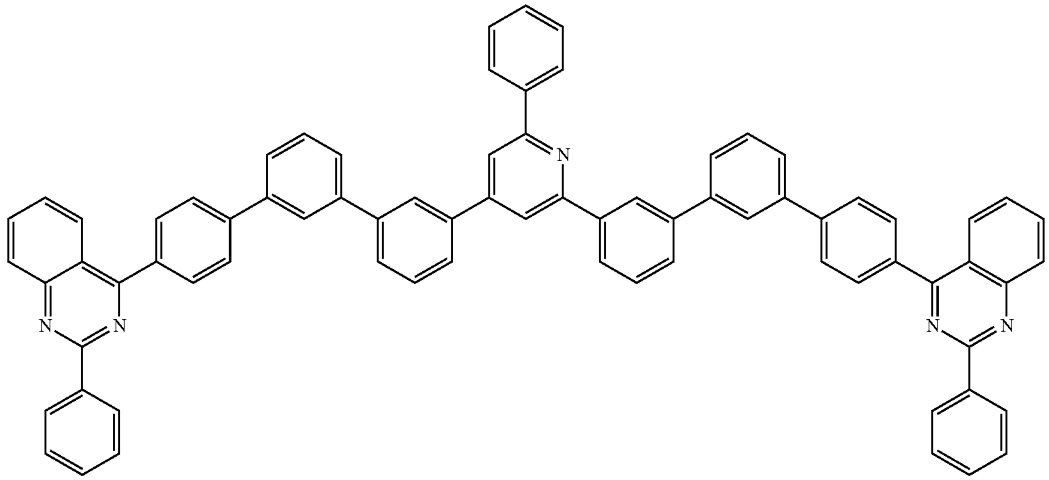
[B-28]
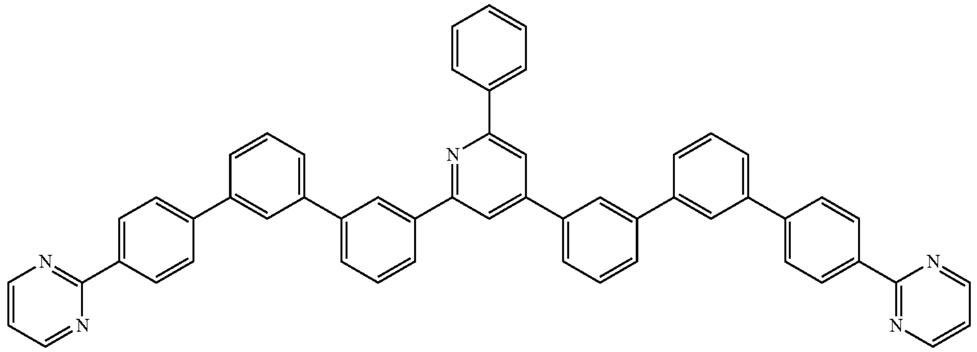
[B-29]
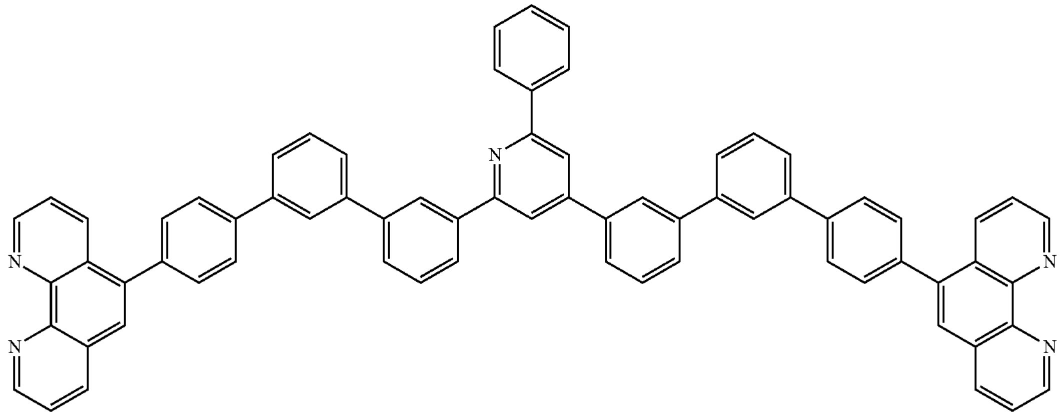
[B-30]
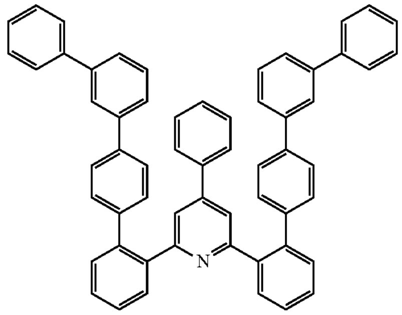
[B-31]
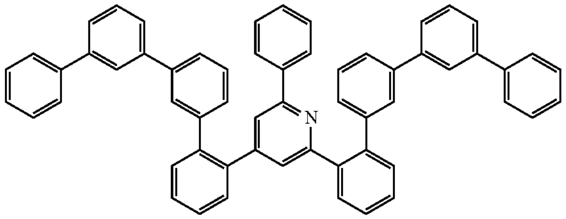

-continued
[B-32]
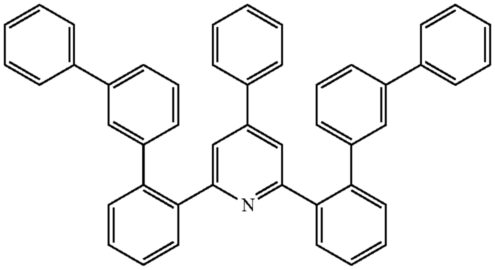
[B-33]
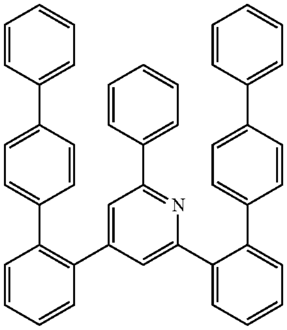
[B-34]
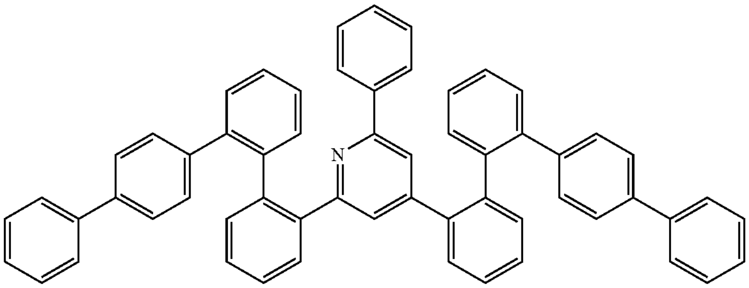
[B-35]
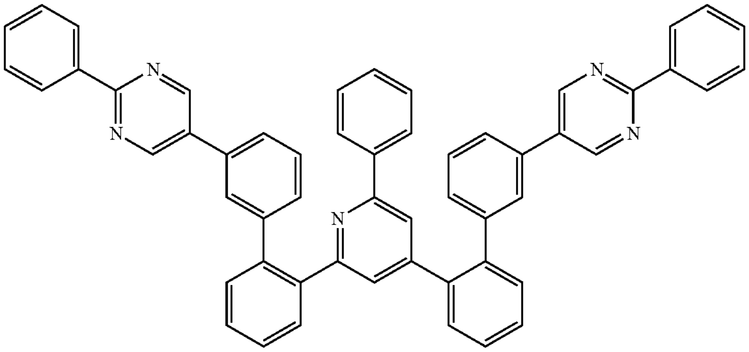
[B-36]
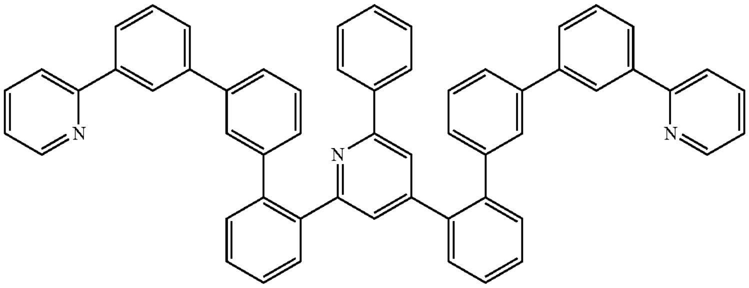
[B-37]
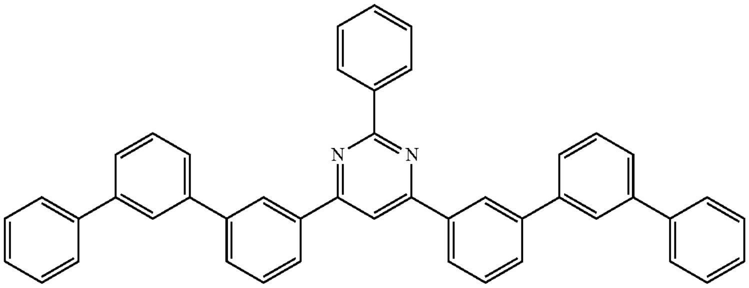

-continued
[B-38]
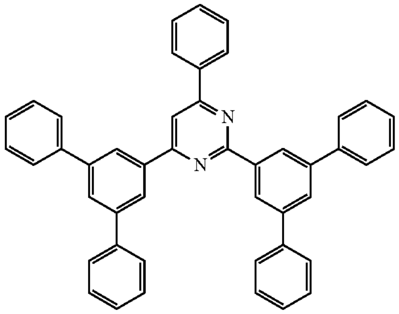
[B-39]
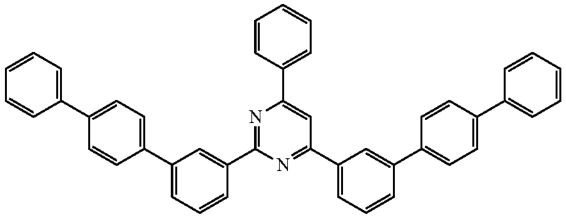
[B-40]
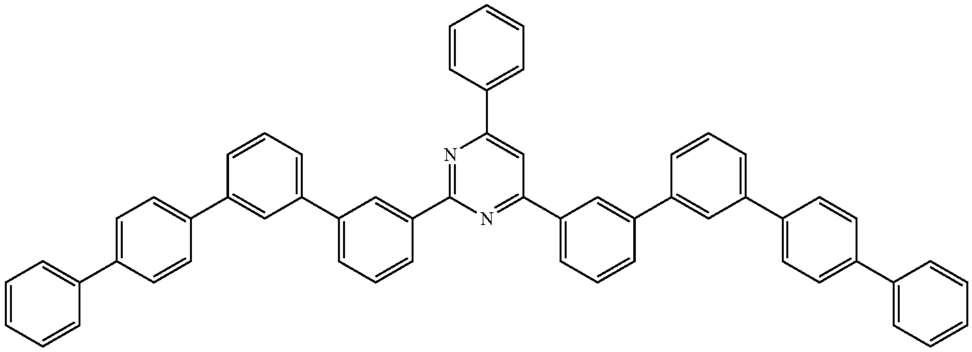
[B-41]
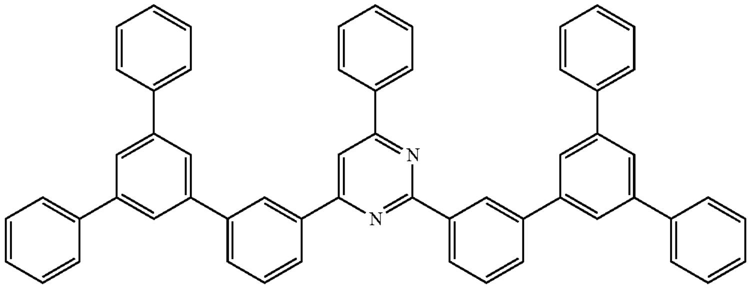
[B-42]
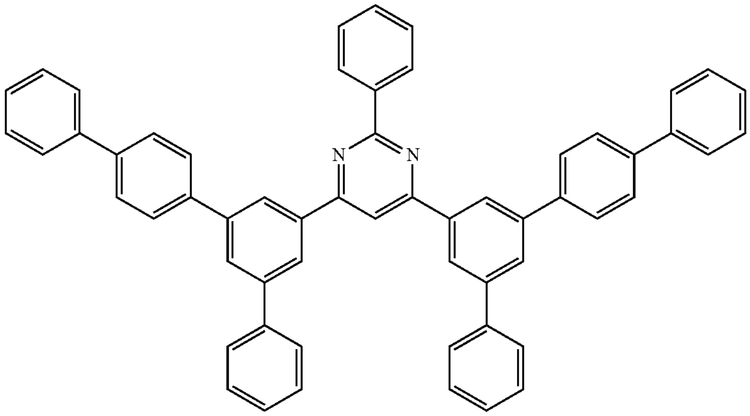

-continued
[B-43]
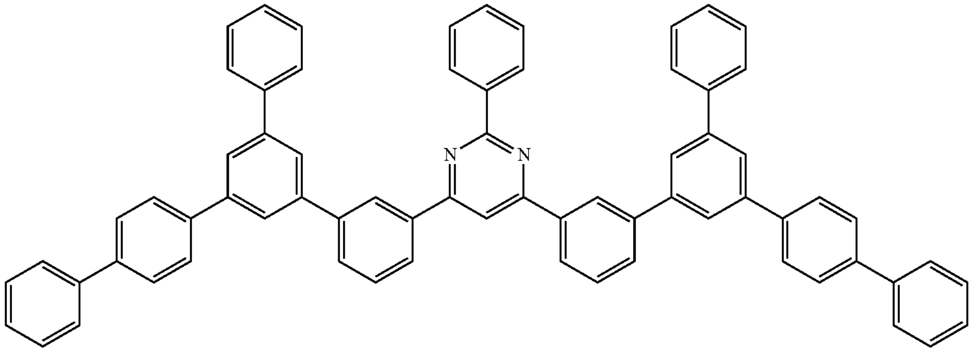
[B-44]
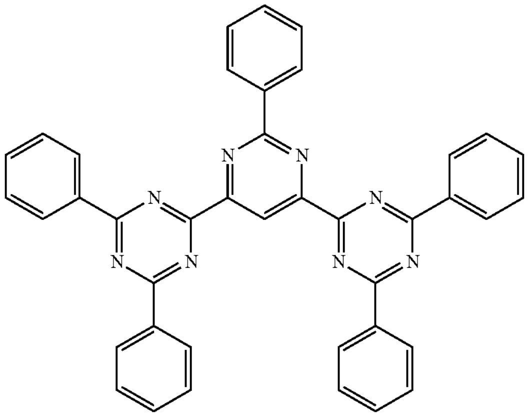
[B-45]
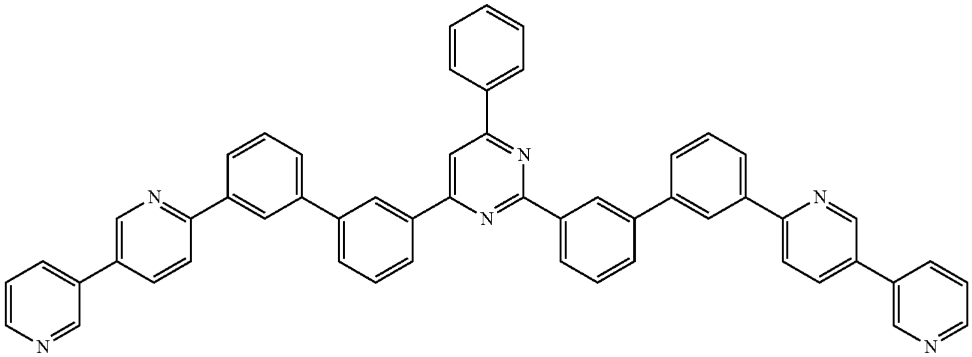
[B-46]
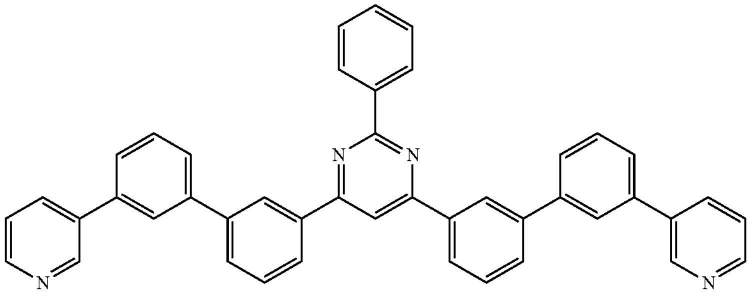

-continued
[B-47]
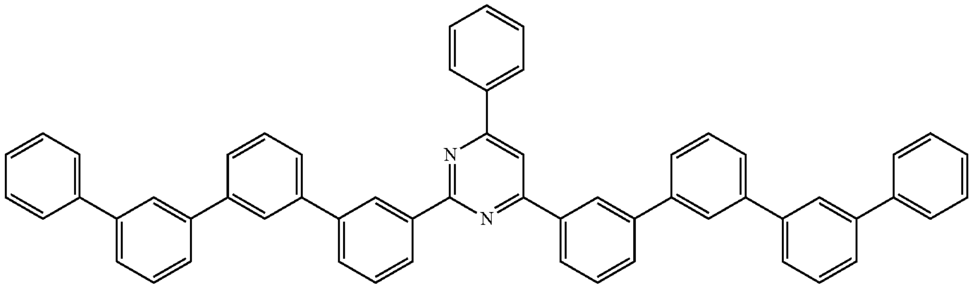
[B-48]
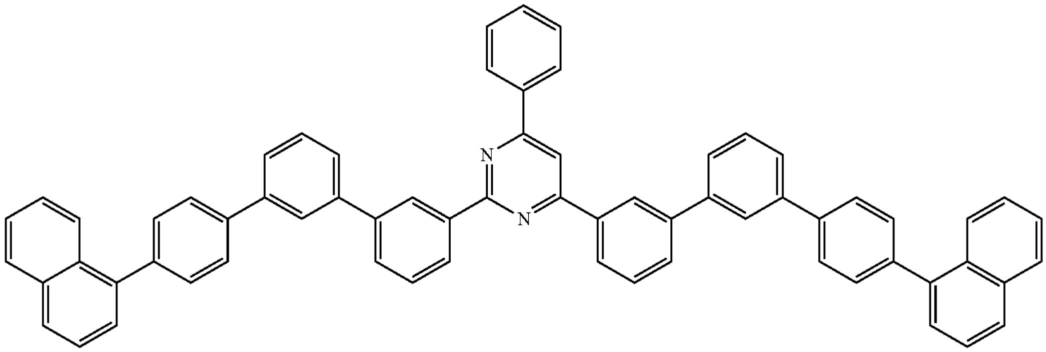
[B-49]
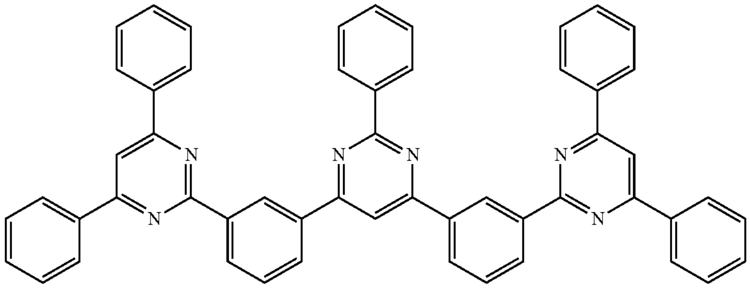
[B-50]
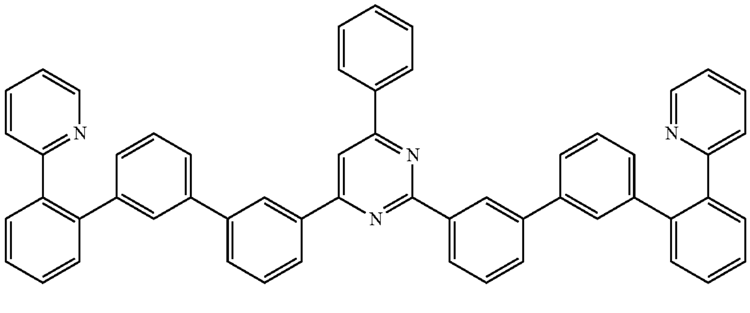

-continued
[B-51]
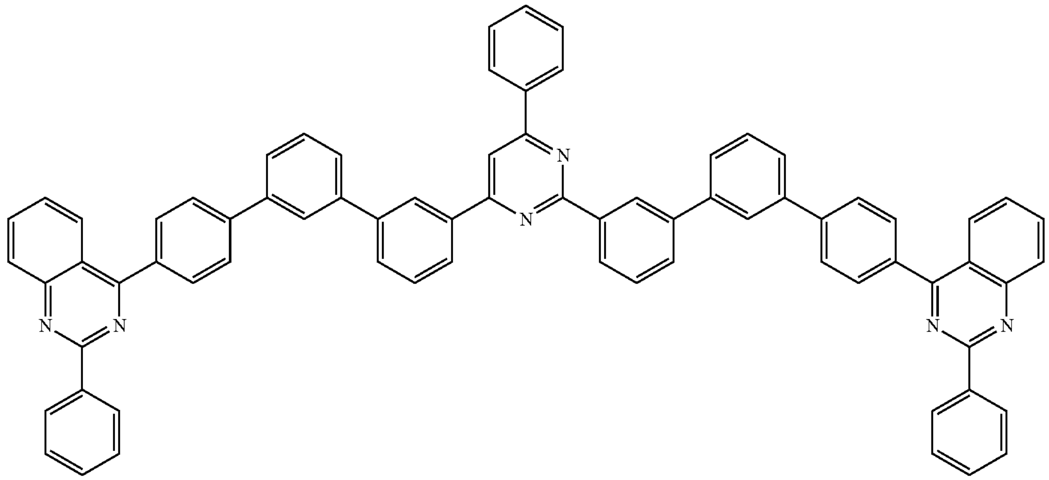
[B-52]
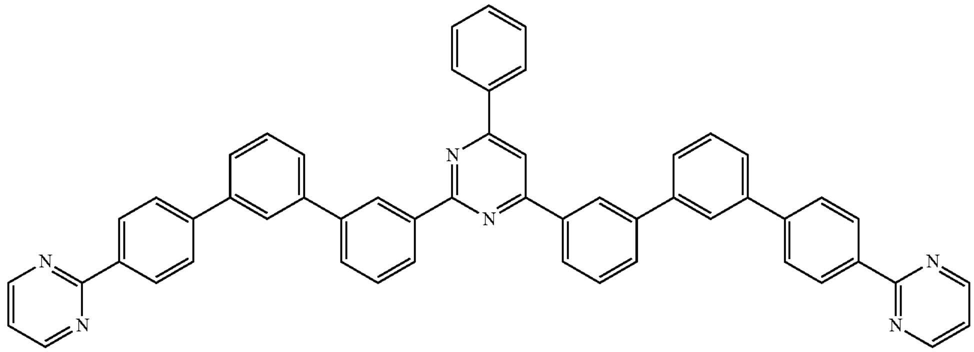
[B-53]
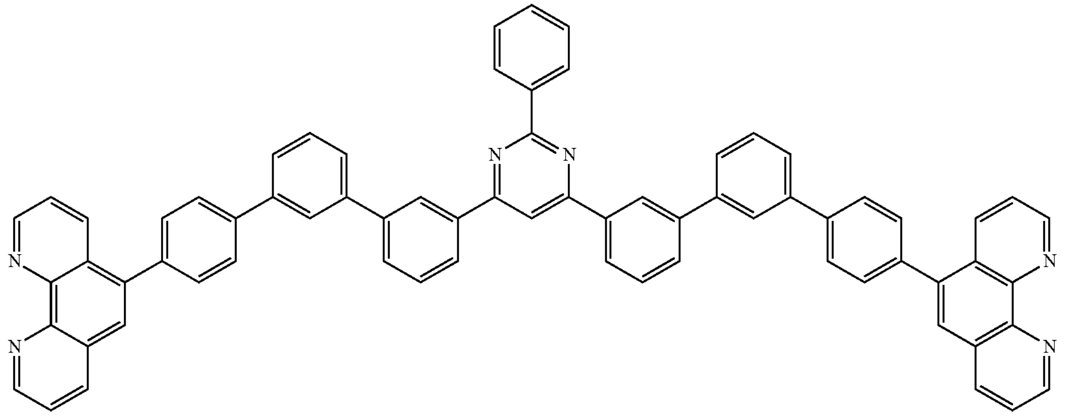
[B-54]
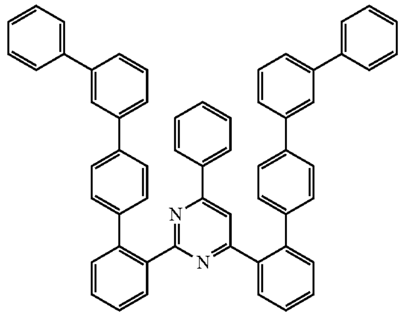
[B-55]
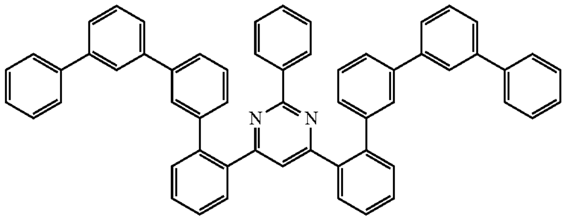

-continued
[B-56]
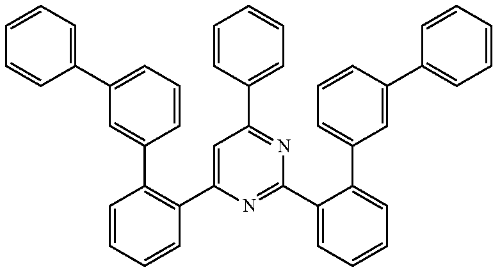
[B-57]
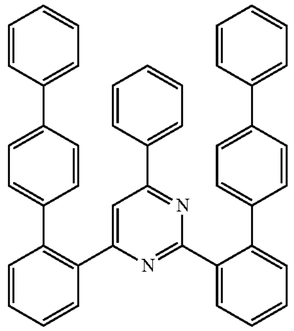
[B-58]
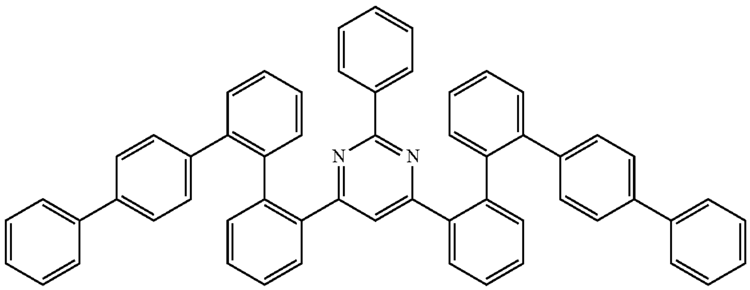
[B-59]
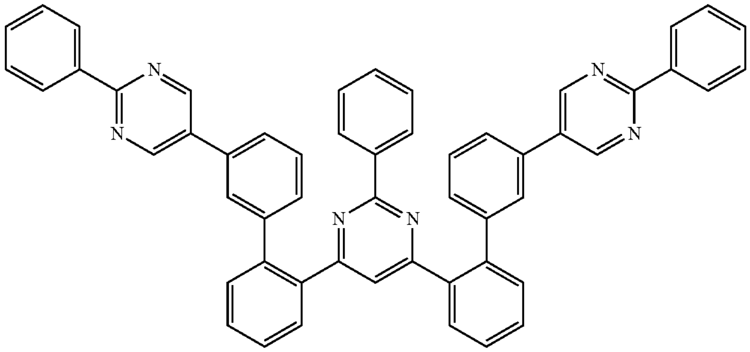
[B-60]
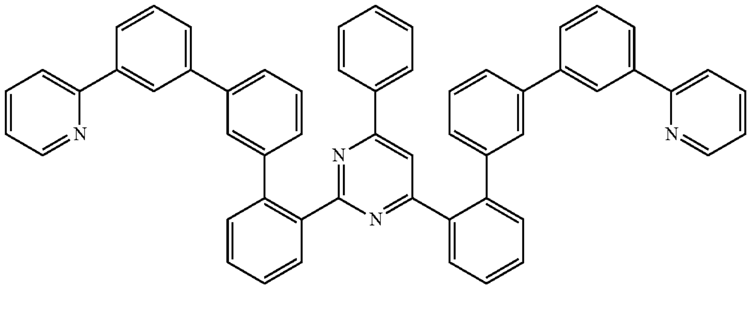

-continued
[B-61]
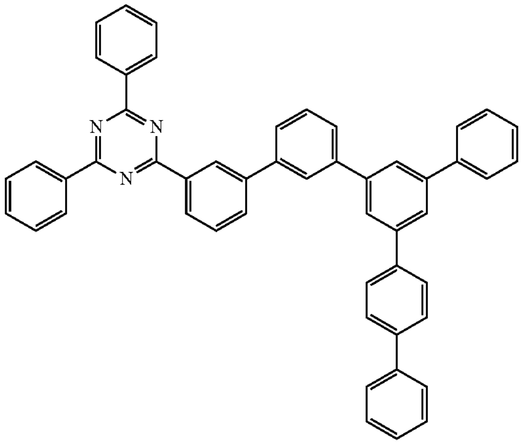
[B-62]
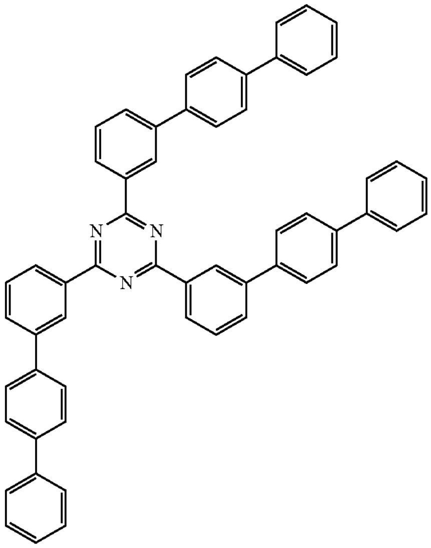
[B-63]
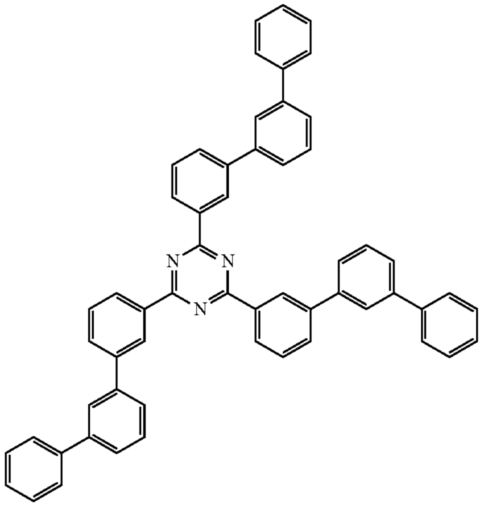
[B-64]
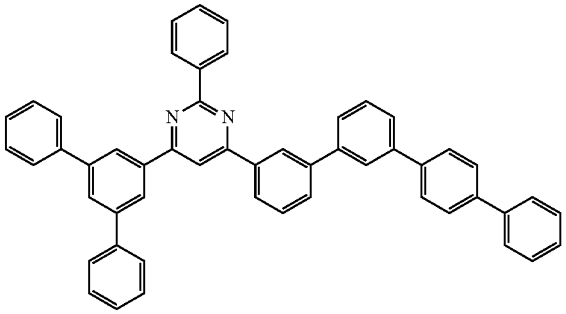
[B-65]
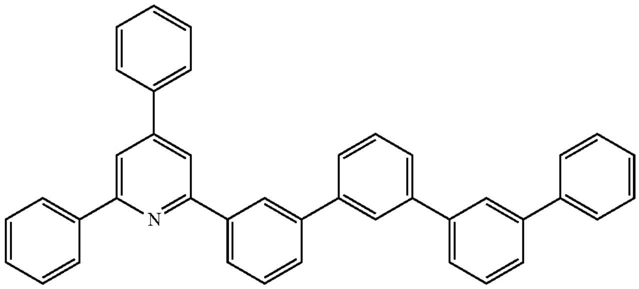

-continued

[B-66]

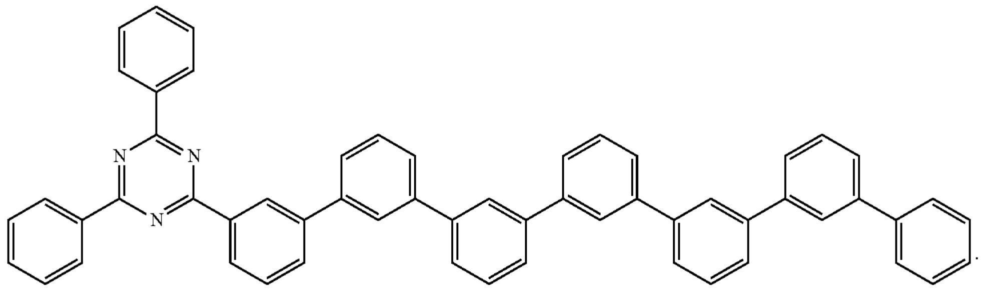

10. The organic optoelectronic device of claim 1, wherein the auxiliary hole transport layer contacts the hole transport layer and the light-emitting layer respectively, and the auxiliary electron transport layer contacts the electron transport layer and the light-emitting layer respectively.

11. The organic optoelectronic device of claim 1, wherein the light-emitting layer further includes a fluorescent dopant.

12. The organic optoelectronic device of claim 1, wherein in [Chemical Formula 2], the C6 to C30 arylene group is a phenylene group, a biphenylene group, a terphenylene group, a tetraphenylene group, a fluorenylene group, or a combination thereof, and the C6 to C30 aryl group is a phenyl group, a biphenyl group, a terphenyl group, a tetraphenyl group, a fluorenyl group, or a combination thereof.

13. A display apparatus comprising the organic optoelectronic device of claim 1.

14. The organic optoelectronic device of claim 1, wherein the organic optoelectronic device is selected from an organic light emitting diode, an organic photoelectric device, an organic solar cell, an organic transistor, an organic photo conductor drum, and an organic memory device.

* * * * *